(12) United States Patent
Beerli et al.

(10) Patent No.: US 8,476,286 B2
(45) Date of Patent: *Jul. 2, 2013

(54) QUINAZOLINE DERIVATIVES WHICH PROMOTE THE RELEASE OF PARATHYROID HORMONE

(75) Inventors: René Beerli, Binningen (CH); Ruben A Tommasi, Whitehouse Station, NJ (US); Sven Weiler, Lörrach (DE); Leo Widler, Muenchenstein (CH)

(73) Assignee: Novartis AG, Basel (CH)

( * ) Notice: Subject to any disclaimer, the term of this patent is extended or adjusted under 35 U.S.C. 154(b) by 1267 days.

This patent is subject to a terminal disclaimer.

(21) Appl. No.: 10/480,559

(22) PCT Filed: Jun. 14, 2002

(86) PCT No.: PCT/EP02/06606
§ 371 (c)(1),
(2), (4) Date: Dec. 12, 2003

(87) PCT Pub. No.: WO02/102782
PCT Pub. Date: Dec. 27, 2002

(65) Prior Publication Data
US 2004/0180912 A1    Sep. 16, 2004

(30) Foreign Application Priority Data

Jun. 15, 2001 (GB) .................................. 0114701.6
Jun. 15, 2001 (GB) .................................. 0114702.4

(51) Int. Cl.
*A61K 31/517* (2006.01)
*C07D 239/82* (2006.01)
*C07D 239/80* (2006.01)
*C07D 229/34* (2012.01)

(52) U.S. Cl.
USPC .......... 514/266.31; 544/286; 580/19; 580/22; 580/36; 562/443

(58) Field of Classification Search
USPC .................. 514/266.2, 266.3, 266.31, 266.4, 514/253.04; 544/283, 286, 284, 288; 558/309; 560/19, 22, 36; 562/443
See application file for complete search history.

(56) References Cited

U.S. PATENT DOCUMENTS

| | | | |
|---|---|---|---|
| 1,181,570 A | | 5/1916 | Churchward |
| 1,195,066 A | | 8/1916 | Morton |
| 1,248,428 A | | 11/1917 | Roberts |
| 1,313,789 A | | 8/1919 | Bulman |
| 3,305,553 A | | 2/1967 | Hoefle et al. |
| 3,767,797 A | * | 10/1973 | Inaba et al. ............. 514/266.21 |
| 3,793,324 A | | 2/1974 | Denzer .................... 544/250 |
| 3,812,257 A | * | 5/1974 | Yamamoto et al. ....... 514/266.21 |
| 3,910,911 A | * | 10/1975 | Ishizumi et al. ............. 544/286 |
| 3,923,803 A | * | 12/1975 | Inaba et al. ................. 544/286 |
| 3,925,548 A | | 12/1975 | Oh |
| 3,926,993 A | | 12/1975 | Ishizumi et al. |
| 3,953,446 A | | 4/1976 | Ishizumi et al. |
| 3,997,564 A | | 12/1976 | Cooke et al. |
| 4,067,868 A | | 1/1978 | Ishizumi et al. |
| 4,171,441 A | | 10/1979 | Smith |
| 4,202,974 A | | 5/1980 | Yamamoto et al. |
| 4,236,006 A | | 11/1980 | Gamboni et al. |
| 4,387,223 A | | 6/1983 | Yamamoto et al. |
| 5,773,663 A | | 6/1998 | Curtze et al. |
| 5,856,503 A | | 1/1999 | Aebi et al. |
| 6,008,230 A | | 12/1999 | Oku et al. |
| 6,031,803 A | | 2/2000 | Kubota et al. |
| 6,211,244 B1 | | 4/2001 | Van Wagenen et al. |
| 2004/0180912 A1 | * | 9/2004 | Beerli et al. ............. 514/266.31 |
| 2006/0079685 A1 | | 4/2006 | Altmann et al. |

FOREIGN PATENT DOCUMENTS

| | | |
|---|---|---|
| CA | 1046063 | 1/1979 |
| CA | 1046063 A1 | 1/1979 |

(Continued)

OTHER PUBLICATIONS

Hino et al. "Preparation of Phenylquinazoline Derivatives as Anticonvulsants and Antiepileptics" Chemical Abstract No. 108:112476 and JP 62145073A2, Heterocycles, vol. 108, pp. 635, Dainippon Pharmaceutical Co., ltd.

Masai et al., "13C Nuclear Magnetic Resonance Studies of Anti-Inflamatory 2(1H)-Quinazolinones", Chemical Abstract No. 86:61720, Chem Pharm Bull, vol. 25, No. 11, pp. 3018-3022, (1977).

Maeda et al., "Quantitative Determination of Quinazolinone Derivatives", Japan, Kokai 76 25 193 (Sumitomo Chemical Co., Ltd.) Chemical Abstract No. 85:87535 and JP 51025193A2.

(Continued)

*Primary Examiner* — Paul V. Ward
(74) *Attorney, Agent, or Firm* — John B. Alexander

(57) ABSTRACT

Use of compound of formula (I), wherein, is, or, and wherein the symbols are as defined, or a pharmaceutically-acceptable and -cleavable ester, or acid addition salt thereof, for the preparation of a medicament for promoting the release of parathyroid hormone, e.g. for preventing or treating bone conditions which are associated with increased calcium depletion or resorption or in which stimulation of bone formation and calcium fixation in the bone is desirable.

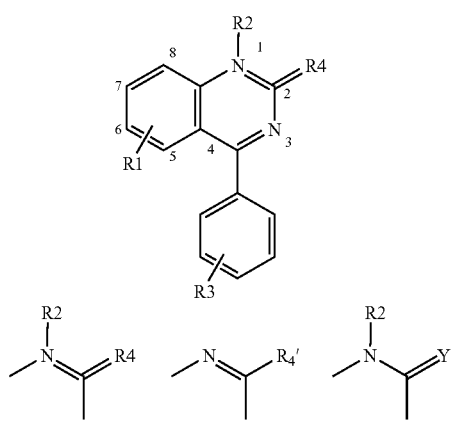

3 Claims, No Drawings

FOREIGN PATENT DOCUMENTS

| | | |
|---|---|---|
| EP | 0 634 169 | 1/1995 |
| EP | 1052254 A1 | 11/2000 |
| GB | 1 181 570 | 2/1970 |
| GB | 1 195 066 | 6/1970 |
| GB | 1 248 428 | 10/1971 |
| GB | 1464033 A | 2/1973 |
| GB | 1 313 789 | 4/1973 |
| GB | 1353789 A | 4/1973 |
| JP | 1973040787 A | 6/1973 |
| JP | 1975046680 A | 4/1975 |
| JP | 1976008287 A | 1/1976 |
| JP | 57095966 | 6/1982 |
| JP | 1999209350 A | 8/1999 |
| JP | 2001302515 | 10/2001 |
| WO | 00/43374 A1 | 7/2000 |
| WO | 02/24683 A1 | 3/2002 |
| WO | 02/102782 A2 | 12/2003 |

OTHER PUBLICATIONS

Yamamoto et al., "Quinazolinones", Japan, Kokai 73 40, 787, Chemical Abstract No. 79:66396 and JP 50013271B4 (Sumitomo Chemical Co., Ltd.).

Russell R.K. et al., European Journal of Medicinal Chemistry vol. 27, No. 3, 1992, pp. 227-284, XP002935850.

Chemical Abstract, XP 002280288 & Oyo Yakuri vol. 18, No. 1, 1979, pp. 9-22.

Chemical Abstract XP 002280289 & S. Mardente et al. Therapeutic drug Monitoring, vol. 3, No. 4, 1981, pp. 351-356.

Chemical Abstract & M.I. Jaeda et al., Journal of chemical technology and biotechnology, vol. 58, No. 4, 1993, pp. 391-394.

Chemical Abstract XP 002280291 & JP 55 143959 A Apr. 22, 2004.

Database Crossfire Beilstein XP 002280292 & B. Berger et al., Acta Crystallogr. Sect. C: Cryst. Struct. Commun, vol. 50, 1994, pp. 773-775.

Merck Index 11th Edition (1989), No. 4120 "Fluproquazone".

Miyagishi, Akira et al., Pharmacometrics, 979, vol. 18, No. 1, p. 9-22. Apr. 22, 2004.

Masai, et al., Chemical Pharma Bulletin, vol. 25, No. 11, pp. 3018-3022 (1977).

Hino, et al, "Preparation of Phenylquinazoline Derivatives as Anticonvulsants and Antiepileptics" Chemical Abstract No. 108:112476 and JP62145073A2, Heterocycles, vol.108, pp. 635, Dainippon Pharmaceutical Co., Ltd. (1999).

Maeda, et al., "Quantitative Determination of Quinazolinone Derivatives", Japan, Kokai 76 25 193 (Sumitomo Chemical Co., Ltd.) Chemical Abstract No. 85:87535 and JP 51025193A2 (1999).

Yamamoto, et al, "Quinazolinones", Japan, Kokai 73 40, 787, Chemical Abstract No. 79:66396 and JP 50013271B4 (Sumitomo Chemical Co., Ltd.) (1997).

Takiura, et al, XP009000437, "Chemical and Pharmaceutical Bulletin", Chem. Pharm. Bull., vol. 25, No. 10, pp. 3018-3022, (1977).

Coombs, et al., XP002043570, "Synthesis and Antiinflammatory Activity of 1-Aklyl-4-aryl-2(1H)- quinazolinones and Quinazolinethiones", vol, 16, No. 11 pp. 1237-1245, (1973).

Gehring et al., XP009000431, "Structures and Dynamics of Hydrogen Chelates", Helvetica Chimica Acta, vol. 81, pp. 236-250, (1998).

\* cited by examiner

QUINAZOLINE DERIVATIVES WHICH PROMOTE THE RELEASE OF PARATHYROID HORMONE

This invention relates to bicyclic compounds, in particular to 4-aryl-2(1H)-quinazolinone derivatives and 2-substituted-4-aryl-quinazoline derivatives and to new pharmaceutical uses thereof.

4-Aryl-2(1H)-quinazolinone derivatives have been described and proposed for therapeutic use as anti-inflammatory, analgesic and antipyretic agents; for example, described in the following published patents and patent applications: GB 1,181,570 (Roussel Uclaf), DE OS 1,805,501A (Sandoz), U.S. Pat. No. 3,925,548 (Sandoz), DE OS 1,935,404A, U.S. Pat. Nos. 4,067,868, 3,953,446, CH 612 186 and U.S. Pat. No. 4,387,223 (Sumitomo). Biarison (1-isopropyl-7-methyl-4-phenyl-2(1H)-quinazolinone) has been marketed as an anti-inflammatory and analgesic agent by Sandoz.

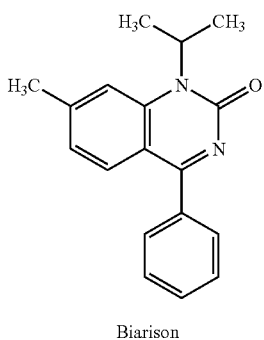 [SMILES: Cc1ccc2c(-c3ccccc3)nc(=O)n(C(C)C)c2c1]

Biarison

Similarly 2-substituted-4-aryl-quinazolines have been described and proposed for use as anti-inflammatory analgesic and antipyretic agents. Thus, for example, EP 0 567 107 A (Takeda) describes the preparation of quinoline and quinazoline derivatives and their use as antinflammatory agents, in particular for treating arthritis. Takeda also propose (EP 0 634 169A) similar quinoline and quinazoline derivatives for use in inhibiting bone resorption and treating osteoporosis, and further propose such compounds for use as immunosuppressants for treatment of various autoimmune diseases.

We have now found that certain 4-aryl-2(1H)-quinazolinone derivatives and 2-substituted-4-aryl-quinazoline derivatives have additional desirable activities which indicate that these derivatives may be useful in additional pharmaceutical applications.

Accordingly the invention provides use of a compound of formula I

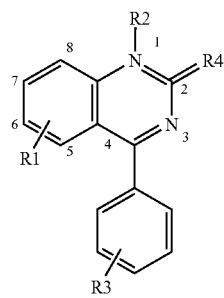

I

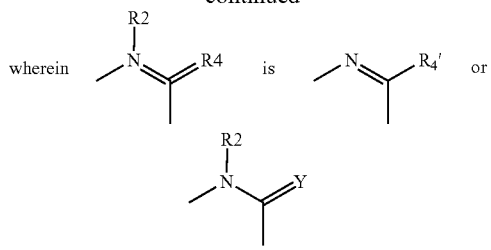

wherein Y is O or S;

R1 represents from 1 to 3 substituents independently selected from OH, SH, halo, $NO_2$, optionally substituted (lower alkyl, lower alkoxy, lower alkenyl, lower alkenyloxy, lower alkynyl, lower alkynyloxy, lower alkanoyl, lower alkylsulphone, lower alkylsulphoxide or amino);

R2 is H or optionally substituted (lower alkyl, aryl, aryl-lower alkyl, cycloalkyl, cycloalkyl-lower alkyl or carbonyl lower alkyl);

R3 represents from 1 to 3 substituents selected from halo, optionally substituted (lower alkyl, cycloalkyl, lower alkoxy or amino);

R4' which is cyano, halo, azide (—N=N=N) or optionally substituted (lower alkyl, lower alkoxy, lower thioalkoxy, aryloxy, aryl lower alkoxy or amino), or a pharmaceutically-acceptable and -cleavable ester, or acid addition salt thereof, for the preparation of a medicament for promoting the release of parathyroid hormone.

It is now well established that controlled treatment of patients with parathyroid hormone (PTH) and analogues and fragments thereof can have a pronounced anabolic effect on bone formation. Thus compounds which promote PTH release, such as the compounds for use in the present invention may be used for preventing or treating conditions of bone which are associated with increased calcium depletion or resorption or in which stimulation of bone formation and calcium fixation in the bone is desirable.

Thus in a further aspect the invention includes a method for preventing or treating bone conditions which are associated with increased calcium depletion or resorption or in which stimulation of bone formation and calcium fixation in the bone is desirable in which an effective amount of a compound of formula I as defined above, or a pharmaceutically-acceptable and -cleavable ester, or acid addition salt thereof is administered to a patient in need of such treatment.

In a yet further aspect the invention includes a pharmaceutical composition for preventing or treating bone conditions which are associated with increased calcium depletion or resorption or in which stimulation of bone formation and calcium fixation in the bone is desirable comprising a compound of formula I as defined above, or a pharmaceutically-acceptable and -cleavable ester, or acid addition salt thereof, in admixture with a pharmaceutically acceptable excipient, diluent or carrier.

Above and elsewhere in the present description the following terms have the following meanings.

Halo or halogen denote I, Br, Cl or F.

The term "lower" referred to above and hereinafter in connection with organic radicals or compounds respectively defines such as branched or unbranched with up to and including 7, preferably up to and including 4 and advantageously one or two carbon atoms.

A lower alkyl group is branched or unbranched and contains 1 to 7 carbon atoms, preferably 1-4 carbon atoms. Lower alkyl represents; for example, methyl, ethyl, propyl, butyl, isopropyl isobutyl, or tertiary butyl.

Halo-substituted lower alkyl is $C_1$-$C_7$ lower alkyl substituted by up to 6 halo atoms.

A lower alkoxy group is branched or unbranched and contains 1 to 7 carbon atoms, preferably 1-4 carbon atoms. Lower alkoxy represents for example methoxy, ethoxy, propoxy, butoxy, isopropoxy, isobutoxy or tertiary butoxy.

A lower alkene, alkenyl or alkenyloxy group is branched or unbranched and contains 2 to 7 carbon atoms, preferably 1-4 carbon atoms and contains at least one carbon-carbon double bond. Lower alkene lower alkenyl or lower alkenyloxy represents for example vinyl, prop-1-enyl, allyl, butenyl, isopropenyl or isobutenyl and the oxy equivalents thereof.

A lower alkyne, alkynyl or alkynyloxy group is branched or unbranched and contains 2 to 7 carbon atoms, preferably 1-4 carbon atoms and contains at least one carbon-carbon triple bond. Lower alkyne or alkynyl represents for example ethynyl, prop-1-ynyl, propargyl (propargyl), butynyl, isopropynyl or isobutynyl and the oxy equivalents thereof.

In the present description, oxygen containing substituents, e.g. alkoxy, alkenyloxy, alkynyloxy, carbonyl, etc. encompass their sulphur containing homologues, e.g. thioalkoxy, thioalkenyloxy, thioalkynyloxy, thiocarbonyl, sulphone, sulphoxide etc.

Aryl represents carbocyclic or heterocyclic aryl.

Carbocyclic aryl represents monocyclic, bicyclic or tricyclic aryl, for example phenyl or phenyl mono-, di- or tri-substituted by one, two or three radicals selected from lower alkyl, lower alkoxy, aryl, hydroxy, halogen, cyano, trifluoromethyl, lower alkylenedioxy and oxy-$C_2$-$C_3$-alkylene; or 1- or 2-naphthyl; or 1- or 2-phenanthrenyl. Lower alkylenedioxy is a divalent substituent attached to two adjacent carbon atoms of phenyl, e.g. methylenedioxy or ethylenedioxy. Oxy-$C_2$-$C_3$-alkylene is also a divalent substituent attached to two adjacent carbon atoms of phenyl, e.g. oxyethylene or oxypropylene. An example for oxy-$C_2$-$C_3$-alkylene-phenyl is 2,3-dihydrobenzofuran-5-yl.

Preferred as carbocyclic aryl is naphthyl, phenyl or phenyl mono- or disubstituted by lower alkoxy, phenyl, halogen, lower alkyl or trifluoromethyl, especially phenyl or phenyl mono- or disubstituted by lower alkoxy, halogen or trifluoromethyl, and in particular phenyl.

Heterocyclic aryl represents monocyclic or bicyclic heteroaryl, for example pyridyl, indolyl, quinoxalinyl, quinolinyl, isoquinolinyl, benzothienyl, benzofuranyl, benzopyranyl, benzothiopyranyl, benzothiadiazolyl, furanyl, pyrrolyl, thiazolyl, oxazolyl, isoxazolyl, triazolyl, tetrazolyl, pyrazolyl, imidazolyl, thienyl, or any said radical substituted, especially mono- or di-substituted as defined above.

Preferably, heterocyclic aryl is pyridyl, indolyl, quinolinyl, pyrrolyl, thiazolyl, isoxazolyl, triazolyl, tetrazolyl, pyrazolyl, imidazolyl, thienyl, or any said radical substituted, especially mono- or di-substituted as defined above.

Cycloalkyl represents a saturated cyclic hydrocarbon optionally substituted by lower alkyl which contains 3 to 10 ring carbons and is advantageously cyclopropyl, cyclopentyl, cyclohexyl, cycloheptyl or cyclooctyl optionally substituted by lower alkyl.

R1 may represent from 1 to 3 substituents; though more preferably represent 1 or 2 substituents. The R1 substituents may be present at any of positions 5, 6, 7 or 8; for instance, at positions 5, 6 or 7, e.g. when R1 represent 2 substituents these may be present at the 5 and 6 or 6 and 7 positions. Preferably at least one of thr R1 substituents is at the 6 position.

R1 as optionally substituted (lower alkyl, lower alkoxy, lower alkenyl, lower alkenyloxy, lower alkynyl, lower alkynyloxy, lower alkanoyl or amino) may be substituted by 1 or 2 substituents independently selected from halo, e.g. Cl, lower alkyl, e.g. ethyl or methyl, lower alkenyl, lower alkynly, cyloalkyl, e.g. $C_3$-$C_6$ cycloalkyl, or cyano.

Particularly preferred significances for R1 are: propargyloxy, methoxy, ethoxy, allyloxy, 2-chloroethoxy, isopropoxy, n-propoxy, cyclopropylmethoxy, 3-chloropropoxy, 2-methyl-allyloxy, n butoxy, allyl, amino, acetonitrileoxy, methylamino, dimethylamino, propargylamino, or allylamino; in particular, e.g. as hereinafter described in the Examples.

R2 as optionally substituted (lower alkyl, aryl, aryl-lower alkyl, cycloalkyl, cycloalkyl-lower alkyl or carbonyl lower alkyl) may be substituted by up to 5, usually 1, 2 or 3 substituents, independently selected from halo, nitro, cyano, amino, OH, SH, lower alkyl, lower alkoxy, lower thioalkoxy, lower alkoxycarbonyl, lower alkylsulphonyl, lower alkoxysulphonyl, lower alkylcarbonyloxy, trifluoromethyl, optionally halo-substituted aryl, optionally oxo-substitued pyrrolidinyl or —X-A-Z, wherein
- —X— is —CO—O—, —O—, —CH$_2$—O—, —CO—NR5-, —NR5-, —CH$_2$—NR5-, —CO—CH$_2$—, —S—, —SO—NR5-, —SO$_2$—NR5-, —NR5—CO— or —O—CO—, where R5 is H or optionally substituted (lower alkyl, lower alkenyl, lower alkoxy-lower alkyl, aryl lower alkyl or optionally mono-or di-lower alkyl-substituted amino lower alkyl),
- -A- is $C_1$-$C_{10}$ alkyl, preferably $C_3$-$C_8$ alkyl optionally interrupted by one or more, e.g. up to 4, preferably 1, 2 or 3, of —O—, —S— or —NR5-, and
- Z is H, halo, lower alkoxy, lower alkoxy-lower alkoxy, —NR5R5', —N$^+$R5R5'R5", —COOH, imidazolyl, optionally R5 substituted-piperazinyl, —CH(COOH)$_2$, —SO$_3^-$, —NR5-(CH$_2$)$_n$—CH$_2$—NR5R5', —NR5-(CH$_2$)$_n$—CH$_2$—OR5, morpholino or tetrahydropyranyl,
- where R5, R5' and R5" are independently H or optionally substituted (lower alkyl, lower alkoxy-lower alkyl or aryl lower alkyl, e.g. indolylethyl), or
- R5, R5' or R5" may be linked together in an optionally substituted N-heterocyclic ring containing from 3 to 8 ring atoms one or more of which may comprise a further heteroatom selected from O, S or —NR5-, wherein R5 is as defined above.

R2 as aryl-lower alkyl or cycloalkyl-lower alkyl is preferably arylmethyl, e.g. furanylmethyl, pyridylmethyl, naphthylmethyl or quinolinylmethyl, or especially benzyl, or cycloalkyl-methyl, e.g. $C_3$-$C_6$ cycloalkyl-methyl, all optionally substituted as described above, preferably by —X-A-Z. In X-A-Z:
- —X is preferably —CO—O—, —O—, —CH$_2$—O—, —CO—NR5-, —NR5-, —CH$_2$—NR5-, —CO—CH$_2$— or —NR5—CO—;
- A is preferably —CH$_2$—CH$_2$—O—CH$_2$—CH$_2$—, CH$_2$—CH$_2$—CH$_2$—O—CH$_2$—CH$_2$—, —CH$_2$—N(CH$_3$)—CH$_2$—CH$_2$—CH$_2$—, or $C_3$-$C_6$ alkylene, and
- Z is preferably an acidic or basic group selected from —NR5R5', —N$^+$R5R5'R5", —COOH, imidazolyl, morpholino, optionally R5 substituted-piperazinyl, —CH(COOH)$_2$ or —SO$_3^-$, wherein R, R' and R" are as defined above.

R2 as carbonyl lower alkyl is preferably lower alkyoxycarbonylmethyl, e.g. ethoxycarbonylmethyl, or arylcarbonylmethyl, e.g. phenylcarbonylmethyl or aminocarbonylmethyl.

Preferred significances for R2 include: methyl, ethyl, isopropyl, 3-chloropropyl, isobutyl, benzyl, cyclopentyl, phenylcarbonylmethyl, cyanomethyl, ethoxycarbonylmethyl, 2-hydroxybenzyl, 2-methylbenzyl, 2-nitrobenzyl, 2-aminobenzyl, 2-chlorobenzyl, 2-fluoro-benzyl, 2-(6-chlorohexyloxy)-benzyl, 2-(6-dimethylamino-hexyloxy)-benzyl, 2-(6-imidazol-1-yl-hexyloxy)-benzyl, 3-hydroxy-benzyl, 3-chlorobenzyl, 3-fluorobenzyl, 3-methoxybenzyl, 3-methoxycarbonylbenzyl, 3-(7-piperidin-1-yl-heptyloxy)-benzyl, 4-(3-dimethylamino-propyl)-N-methyl-carbamoyl)-benzyl, 4-nitrobenzyl, 4-bromobenzyl, 4-chlorobenzyl, 4-fluorobenzyl, 4-aminobenzyl, 4-hydroxybenzyl, 4-methoxybenzyl, 4-trifluoromethylbenzyl, 4-t-butylbenzyl, 4-methylthiobenzyl, 4-methoxycarbonylbenzyl, 4-methoxycarbonyl-2-methoxybenzyl, 4-methylsulphonylbenzyl, 4-methylcarbonyloxybenzyl, 2,6-difluorobenzyl, 2,4-difluorobenzyl, 3,4-difluorobenzyl, 3,4-dichlorobenzyl, 2,4,6-trifluorobenzyl, 2,3,4,5,6-pentafluorobenzyl, 5-nitrofuran-2-ylmethyl, 2-cyanobenzyl, 3-cyanobenzyl, 4-cyanobenzyl, 5-cyanobenzyl, 4-cyanomethoxybenzyl, 7-fluoroquinolin-2-ylmethyl, naphth-2-ylmethyl, 3-pyridylmethyl, 4-pyridylmethyl, 3-[4-[4-(2-methoxy-ethyl)-piperazin-1-yl]-butyl]carbonylaminobenzyl, 3-(2-oxo-pyrrolidin-1-yl)-benzyl, 3[(3-dimethylmino-propyl)-N-methyl-aminocarbonylamino]benzyl, 3-(4-allyl-piperazin-1-yl)acetamido-benzyl, 3-(4-methyl-piperazin-1-yl)acetamido-benzyl, 3-(4-(2-methoxy-ethyl)-piperazin-1-yl)acetamido-benzyl, 3-(4-(2-methoxy-ethyl)-piperazin-1-yl)-N-methylacetamido-benzyl, 3-(4-(3-dimethylamino-propyl)-piperazin-1-yl)acetamido-benzyl, 3-(2-(4-methyl-piperazin-1-yl)-acetamido)-benzyl, 3-(4-(4-(3-dimethylamino-propyl)-piperazin-1-yl)butyramido)-benzyl, 3-(4-[(2-methoxy-ethyl)-N-methyl-amino]-butyramido)-benzyl, 3(4-morpholin4-yl-butyramido)-benzyl, 3-(4-methyl-piperazin-1-yl)butyramido-benzyl, phenylethyl, benzo[1,2,5]thiadiazol-5-ylmethyl, thiazol-2-ylmethyl, 3-[2 (2-methoxy-ethoxy)-ethoxy]-benzyl, 3-(2-{2-[2-(2-methoxy-ethoxy)-ethoxy]-ethoxy}-ethoxy)-benzyl, 4-(2-{2-[2(2-methoxy-ethoxy)-ethoxy]-ethoxy}-ethoxy)-benzyl, 3-(2-methoxy-ethoxy)-benzyl, 3-{2-[2-(2-methoxy-ethoxy)-ethoxy]-ethoxy}-benzyl, 3-[2-(tetrahydro-pyran-2-yloxy)-ethoxy]-benzyl, 3-(2-hydroxy-ethoxy)-benzyl, 2-{2-[2-(2-methoxy-ethoxy)-ethoxy]-ethoxy}-benzyl, 2-methanesulphonylbenzyl, 2-hydroxy-2-phenyl-ethyl, 2-acetyl-2-phenyl-ethyl, 2-oxo-2-phenyl-ethyl, 2-(4-Fluorophenyl)-2-oxo-ethyl, cyclohexylmethyl, 3-(2-(2-dimethylamino-ethoxy)-ethyloxycarbonyl)-benzyl, in particular, e.g. as hereinafter described in the Examples.

R3 represents 1, 2 or 3; for instance, 1 substituent, in the 2-position or 3-position or more preferably in the 4-position, selected from halo, optionally substituted (lower alkyl or amino) in which lower alkyl is preferably unsubstituted and amino is preferably mono-or di-substituted by lower alkyl.

Preferred significances for R3 include: methyl, ethyl, isopropyl, t-butyl or chloro. Most preferably R3 is isopropyl in the 4-position.

R4 as lower alkyl is preferably unsubstituted, e.g. as methyl or ethyl, or halo-substituted e.g. as trifluoromethyl.

R4 as lower alkoxy (including thioalkoxy) is preferably $C_1$-$C_4$alkoxy, e.g. methoxy, ethoxy, isopropoxy or butoxy, optionally substituted, preferably by a single substituent selected from OH or aryl, e.g. phenyl or pyridyl.

R4 as aryloxy is preferably phenoxy or pyridyloxyaryl, e.g. 3-pyridyloxy.

R4 as amino may be unsubstituted, substituted by optionally halo-substituted mono- or di-lower alkyl, disubstituted to form an optionally mono- or di-lower alkyl substituted 5-7 membered heterocyclic ring optionally containing a further heteroatom selected from O, S, N or NR, where R is H or lower alkyl.

Preferred significances for R4 include: chloro, fluoro, cyano, methyl, —N=N=N, trifluoromethyl, methoxy, isopropoxy, thio-isopropoxy, 3-pyridoxy, 4-methyl-3-pyridoxy, phenoxy, 2,2,2-trifluoroethylamino, 2-hydroxyethoxy, 3,5-dimethylmorpholino, 2-methylbenzyloxy, 3-pyridylmethoxy, in particular, e.g. as hereinafter described in the Examples.

In preferred embodiments the invention provides use of a compound of formula II or III

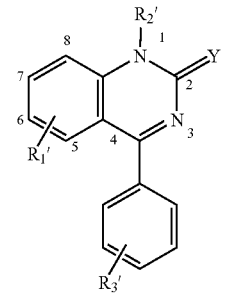

II

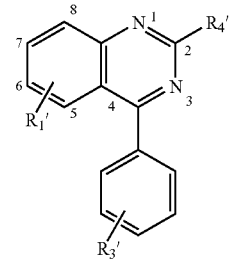

III wherein
Y is O or S;
R1' represents from 1 or 2 substituents independently selected from H, OH, halo, $NO_2$, optionally substituted (lower alkyl, lower alkoxy, lower alkenyl, lower alkenyloxy, lower alkynyl, lower alkynyloxy, lower alkanoyl or amino) wherein the optional substituents are 1 or 2 substituents independently selected from halo, e.g. Cl, lower alkyl, e.g. ethyl or methyl, lower alkenyl, e.g. allyl, loweralkynyl, e.g. propargyl, cycloalkyl, e.g. $C_3$-$C_6$ cycloalkyl or cyano;
R2' is H or optionally substituted (lower alkyl, aryl, aryllower alkyl, cycloalkyl, cycloalkyl-lower alkyl or carbonyl lower alkyl) may be substituted by up to 5, usually 1, 2 or 3 substituents, independently selected from halo, nitro, cyano, amino, OH, SH, lower alkyl, lower alkoxy, lower thioalkoxy, lower alkoxycarbonyl, lower alkylsulphonyl, lower alkoxysulphonyl, lower alkylcarbonyloxy, trifluoromethyl, optionally halo-substituted aryl, optionally oxo-substitued pyrrolidinyl or —X-A-Z, wherein
—X— is —CO—O—, —O—, —$CH_2$—, —CO—NR5-, —NR5-, —$CH_2$—NR5-, —CO—$CH_2$—, —S—, —SO—NR5-, —$SO_2$—NR5-, —NR5-CO— or —O—CO—, where R5 is H or optionally substituted (lower alkyl, lower alkenyl, lower alkoxy-lower alky, aryl lower alkyl or optionally mono- or di-lower alkyl-substituted amino lower alkyl),
-A- is $C_1$-$C_{10}$ alkyl, preferably $C_3$-$C_8$ alkyl optionally interrupted by one or more, e.g. up to 4, preferably 1, 2 or 3, of —O—, —S— or —NR5-, and
Z is H, halo, lower alkoxy, lower alkoxy-lower alkoxy, —NR5R5', —$N^+$R5R5'R5'', —COOH, Imidazolyl, optionally R5 substituted-piperazinyl, —CH(COOH)$_2$, —SO$_3^-$, —NR5-(CH$_2$)$_n$—CH$_2$—NR5R5', —NR5-(CH$_2$)$_n$—CH$_2$—OR5, morpholino or tetrahydropyranyl, where R5, R5' and R5" are independently H or optionally substituted (lower alkyl, lower alkoxy-lower alkyl or aryl lower alkyl, e.g. indolylethyl), or R5, R5' or R5" may be linked together in an optionally substituted N-heterocyclic ring containing from 3 to 8 ring atoms one or more of which may comprise a further heteroatom selected from O, S or —NR5-, wherein R5 is as defined above;

R3' represents 1 substituent, in the 4-position, selected from optionally substituted (lower alkyl or amino) in which lower alkyl is preferably unsubstituted and amino is preferably mono- or di-substituted by lower alkyl;

R4' is halo, cyano, unsubstituted lower alkyl, or (C$_1$-C$_4$ alkoxy, phenoxy or pyridyloxy), optionally substituted by a single substituent selected from OH or aryl, e.g. phenyl or pyridyl, or unsubstituted amino, amino substituted by optionally halo-substituted mono- or di-lower alkyl, or amino bi-substituted to form an optionally mono- or di-lower alkyl substituted 5-7 membered heterocyclic ring optionally containing a further heteroatom selected from O, S, N or NR, where R is H or lower alkyl, or a pharmaceutically-acceptable and -cleavable ester, or acid addition salt thereof, for the preparation of a medicament for promoting the release of parathyroid hormone.

The compounds of formula I include many compounds which are novel and such novel compounds are included per se within the scope of the invention Thus the invention includes compounds of formula IV

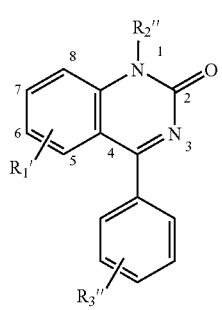

IV wherein R1' is as previously defined, R3" is lower alkyl and R2' is optionally substituted lower alkyl, e.g. isopropyl, aryl-lower alkyl, e.g. benzyl, cycloalkyl-lower alkyl, e.g. cyclohexylmethyl, aryl, e.g. phenyl, or cycloalkyl, e.g. cyclopentyl or cyclohexyl;

provided that the compound of formula IV is not 1-benzyl-4-phenyl-6-nitro-2(1H)-quinazolinone, 1-(2-pyridylmethyl)-4-phenyl-6-nitro-2(1H)-quinazolinone, 1-(2-furylmethyl)-4-phenyl-6-nitro-2(1H)-quinazolinone or 1-(2-thienylmethyl)-4-phenyl-6-nitro-2(1H)-quinazolinone, or a pharmaceutically-acceptable and -cleavable ester, or acid addition salt thereof.

Preferably R2" is optionally substituted aryl-methyl, especially benzyl. The optional substituents may be as defined above.

In a further embodiment the invention also includes compounds of formula V

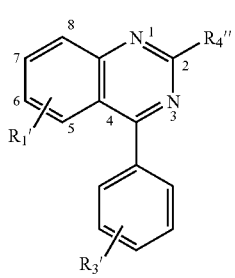

V wherein R1' and R2' are as previously defined and

R4" is halo, cyano, methyl, ethyl, trifluoromethyl or (C$_1$-C$_4$alkoxy, phenoxy or pyridyloxy), optionally substituted by a single substituent selected from OH or aryl, e.g. phenyl or pyridyl, or unsubstituted amino, amino substituted by optionally halo-substituted mono- or di-lower alkyl, or amino bi-substituted to form an optionally mono- or di-lower alkyl substituted 5-7 membered heterocyclic ring optionally containing a further heteroatom selected from O, S, N or NR, where R is H or lower alkyl, or a pharmaceutically-acceptable and -cleavable ester, or acid addition salt thereof.

In particular the invention includes the compounds of formula IV as hereinafter described in the Examples.

Particularly preferred compounds of formula IV include:

6-Propargylamino-1-benzyl-4-(4-isopropyl-phenyl)-1.H.-quinazolin-2-one;

6-Allylamino-1-benzyl-4-(4-isopropyl-phenyl)-1.H.-quinazolin-2-one;

1-Benzyl-4-(4-isopropyl-phenyl)-6-methoxy-1.H.-quinazolin-2-one;

6-allyloxy-1-isopropyl-4-(4-isopropyl-phenyl)-1.H.-quinazolin-2-one;

1-Isopropyl-4-(4-isopropyl-phenyl)-6-propargyloxy-1.H.-quinazolin-2-one;

5-allyl-6-hydroxy-1-isopropyl-4-(4-isopropyl-phenyl)-1.H.-quinazolin-2-one;

3-[4-(4-Isopropyl-phenyl)-2-oxo-6-prop-2-ynyloxy-2H-quinazolin-1-ylmethyl]-benzoic acid 2-(2-dimethylamino-ethoxy)-ethyl ester (trifluoroacetic acid salt);

1-(2-Fluoro-benzyl)-4-(4-isopropyl-phenyl)-6,7-dimethoxy-1H-quinazolin-2-one;

1-benzyl-4-(4-isopropyl-phenyl)-6-propargyloxy-1.H.-quinazolin-2-one;

6-Allyloxy-1-benzyl-4-(4-isopropyl-phenyl)-1.H.-quinazolin-2-one;

Acetic acid 4-[4-(4-isopropyl-phenyl)-2-oxo-6-propargyloxy-2.H.-quinazolin-1-ylmethyl]-phenyl ester;

1-Benzo[1,2,5]thiadiazol-5-ylmethyl-4-(4-isopropyl-phenyl)-6-propargyloxy-1H-quinazolin-2-one;

1-(2-Hydroxy-benzyl)-4-(4-isopropyl-phenyl)-6-prop-2-ynyloxy-1H-quinazolin-2-one;

1-(2-Hydroxy-benzyl)-4-(4-isopropyl-phenyl)-6,7-dimethoxy-1H-quinazolin-2-one;

1-(3-Hydroxy-benzyl)-4-(4-isopropyl-phenyl)-6-prop-2-ynyloxy-1H-quinazolin-2-one;

1-[2-(6-Imidazol-1-yl-hexyloxy)-benzyl]-4-(4-isopropyl-phenyl)-6-prop-2-ynyloxy-1H-quinazolin-2-one;

4-(4-Isopropyl-phenyl)-1-[3-(7-piperidin-1-yl-heptyloxy)-benzyl]-6-prop-2-ynyloxy-1H-quinazolin-2-one (trifluoroacetic acid salt);

4-(4-Isopropyl-phenyl)-1-{3-[2-(2-methoxy-ethoxy)-ethoxy]-benzyl}-6-prop-2-ynyloxy-1H-quinazolin-2-one;

4-(4-Isopropyl-phenyl)-1-[3-(2-{2-[2-(2-methoxy-ethoxy)-ethoxy]-ethoxy}-ethoxy)-benzyl]-6-prop-2-ynyloxy-1H-quinazolin-2-one;

4-(4-isopropyl-phenyl)-1-[3-(2-methoxy-ethoxy)-benzyl]-6-prop-2-ynyloxy-1H-quinazolin-2-one;

4-(4-isopropyl-phenyl)-1-(3-{2-[2-(2-methoxy-ethoxy)-ethoxy]-ethoxy}-benzyl)-6-prop-2-ynyloxy-1H-quinazolin-2-one;

4-(4-Isopropyl-phenyl)-1-{2-[2-(2-methoxy-ethoxy)-ethoxy]-benzyl}-6-prop-2-ynyloxy-1H-quinazolin-2-one;

1-[3-(2-hydroxy-ethoxy)-benzyl]-4-(4-isopropyl-phenyl)-6-prop-2-ynyloxy-1H-quinazolin-2-one;

4-(4-isopropyl-phenyl)-1-(2-{2-[2-(2-methoxy-ethoxy)-ethoxy]-ethoxy}-benzyl)-6-prop-2-ynyloxy-1H-quinazolin-2-one;

Methanesulfonic acid 2-[4-(4-isopropyl-phenyl)-2-oxo-6-prop-2-ynyloxy-2H-quinazolin-1-ylmethyl]-phenyl ester;

2-[(3-Dimethylamino-propyl)-methyl-amino]-N-{3-[4-(4-isopropyl-phenyl)-2-oxo-6-propargyloxy-2H-quinazolin-1-ylmethyl]-phenyl}-acetamide;

4-(4-Isopropyl-phenyl)-1-[3-(2-oxo-pyrrolidin-1-yl)-benzyl]-6-propargyloxy-1H-quinazolin-2-one;

2-[(3-Dimethylmino-propyl)-methyl-amino]-N-{3-[4-(4-isopropyl-phenyl)-2-oxo-6-propargyloxy-2H-quinazolin-1-ylmethyl]-phenyl}-acetamide;

N-{3-[4-(4-Isopropyl-phenyl)-2-oxo-6-propargyloxy-2H-quinazolin-1-ylmethyl]-phenyl}-2-(4-methyl-piperazin-1-yl)-acetamide;

N-{3-[4-(4-Isopropyl-phenyl)-2-oxo-6-propargyloxy-2H-quinazolin-1-ylmethyl]-phenyl}-2-[4-(2-methoxy-ethyl)-piperazin-1-yl]-acetamide;

4-[4-(3-Dimethylamino-propyl)-piperazin-1-yl]-N-{3-[4-(4-isopropyl-phenyl)-2-oxo-6-propargyloxy-2H-quinazolin-1-ylmethyl]-phenyl}-butyramide;

N-{3-[4-(4-Isopropyl-phenyl)-2-oxo-6-propargyloxy-2H-quinazolin-1-ylmethyl]-phenyl}-4-[(2-methoxy-ethyl)-methyl-amino]-butyramide;

N-{3-[6-Allyloxy-4-(4-isopropyl-phenyl)-2-oxo-2H-quinazolin-1-ylmethyl]-phenyl}-4-(4-methyl-piperazin-1-yl)-butyramide;

1-benzyl-4-(3-chloro-4-isopropyl-phenyl)-6-prop-2-ynyloxy-1H-quinazolin-2-one;

1-cyclohexylmethyl-4-(4-isopropyl-phenyl)-6,7-dimethoxy-1H-quinazolin-2-one;

{2-[2-(3,5-Dimethoxy-phenyl)-2-methyl-propylamino]-4,5-dimethoxy-phenyl}-(4-isopropyl-phenyl)-methanone;

1-(2-Hydroxy-benzyl)-4-(4-isopropyl-phenyl)-6-methoxy-1.H.-quinazolin-2-one;

1-[2-(4-Fluoro-phenyl)-2-oxo-ethyl]-4-(4-isopropyl-phenyl)-6-prop-2-ynyloxy-1H-quinazolin-2-one, or a pharmaceutically-acceptable and -cleavable ester, or acid addition salt thereof.

As hereinafter described compounds of formula II may be prepared by cyclisation of a compound of formula VII

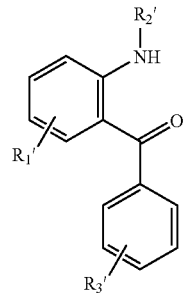

wherein R1', R2' And R3' are as defined above. Compounds of formula VII have activity as promoters of PTH release and are included within the present invention for use as PTH release promoters and where novel as compounds per se.

Accordingly the invention provides (use of) a compound of formula VII'

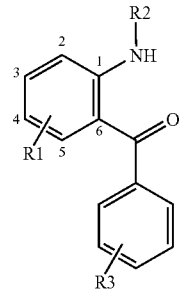

wherein R1, R2 and R3 are as defined above for formula I;

or R1 as a substituent at the 2-position is joined to R2 to provide an optionally substituted N-containing hydrocarbyl ring having from 4 to 8 ring members and optionally including a further heteroatom selected form O, S or NR5 where R5 is H or optionally substituted (lower alkyl, lower alkoxy-lower alkyl or aryl lower alkyl);

or a pharmaceutically-acceptable and -cleavable ester, or acid addition salt thereof, (for the preparation of a medicament for promoting the release of parathyroid hormone).

Similarly the invention includes methods and pharmaceutical compositions for preventing or treating bone conditions, which are associated with increased calcium depletion or resorption or in which stimulation of bone formation and calcium fixation in the bone is desirable using the compounds of formula VII' and esters and salts thereof.

In the compounds of formula VII' R1, R2 and R3 have preferred significances as for the compounds of formula I. Preferably The R1 substituents may be present at any of positions 2, 3, 4 or 5 of the anilino ring; for instance, at positions 2, 3 or 4, e.g. when R1 represent 2 substituents these may be present at the 3 and 4 or 4 and 5 positions. Preferably at least one of the R1 substituents is at the 4 position.

Thus in preferred embodiments the invention provides (use of) a compound of formula VII

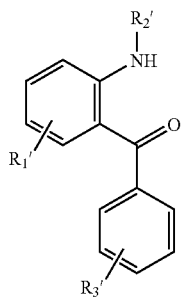

VII wherein R1', R2' And R3' are as defined above for formula II; or a pharmaceutically-acceptable and -cleavable ester, or acid addition salt thereof, (for the preparation of a medicament for promoting the release of parathyroid hormone).

The compounds of formula VII' include many compounds which are novel and such novel compounds are included per se within the scope of the invention Thus the invention includes compounds of formula VII"

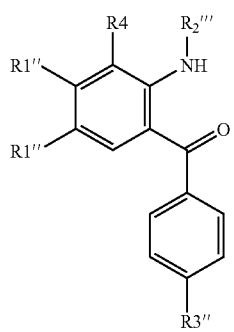

VII"

wherein
each R1" is independently H, lower alkoxy, lower alkenyloxy, lower alkynyloxy, lower alkylamino, lower alkenylamino or lower alkynylamino;
R2''' is lower alkyl, arylmethyl, cycloalkylmethyl, or arylmethyl or cycloalkylmethyl substituted by up to 5 substituents selected independently from halo, nitro, cyano, OH, SH, lower-alkyl, lower alkoxy, lower thioalkoxy, lower alkoxycarbonyl, lower alkoxysulphonyl, lower alkoxycarbonyloxy, tribluoromethyl, phenyl or —X-A-Z,
wherein —X—, -A-, -Z are as defined above;
R3" is optionally substituted (lower alkyl or amino),
or a pharmaceutically-acceptable and -cleavable ester, or acid addition salt thereof.

In particular the invention includes the compounds of formula VII" as hereinafter described in the Examples.

The compounds of formula I, II, III, IV, V, VII'and VII" and as listed above are hereinafter referred to as Agents of the Invention.

The Agents of the Invention which comprise free hydroxyl groups may also be used in the form of pharmaceutically acceptable, physiologically cleavable esters, and as such and where novel are included within the scope of the invention. Such pharmaceutically acceptable esters are preferably prodrug ester derivatives, such being convertible by solvolysis or cleavage under physiological conditions to the corresponding Agents of the Invention which comprise free hydroxyl groups. Suitable pharmaceutically acceptable prodrug esters are those derived from a carboxylic acid, a carbonic acid monoester or a carbamic acid, advantageously esters derived from an optionally substituted lower alkanoic acid or an arylcarboxylic acid.

Agents of the Invention may also exist in the form of pharmaceutically acceptable salts, and as such and where novel are included within the scope of the invention. Pharmaceutically acceptable salts include acid addition salts with conventional acids, for example, mineral acids, e.g., hydrochloric acid, sulfuric or phosphoric acid, or organic acids, for example, aliphatic or aromatic carboxylic or sulfonic acids, e.g., acetic, trifluoroacetic, propionic, succinic, glycolic, lactic, malic, tartaric, citric, ascorbic, maleic, fumaric, hydroxymaleic, pyruvic, pamoic, methanesulfonic, toluenesulfonic, naphthalenesulfonic, sulfanilic or cyclohexylsulfamic acid; also amino acids, such as arginine and lysine. For compounds of the invention having acidic groups, for example, a free carboxy group, pharmaceutically acceptable salts also represent metal or ammonium salts, such as alkali metal or alkaline earth metal salts, e.g., sodium, potassium, magnesium or calcium salts, as well as ammonium salts, which are formed with ammonia or suitable organic amines.

Agents of the Invention of formula II and III may be prepared as follows:
Agents of the invention of formula II

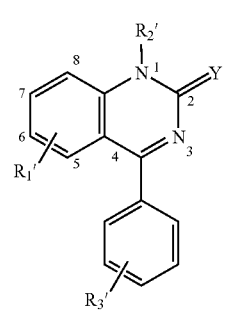

II wherein R1', R2' and R3' are as defined above may be prepared by cyclising a compound of formula VII

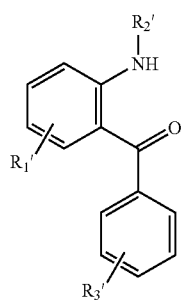

VII with a condensation reagent such as chlorosulfonyl isocyanate (ClSO$_2$NCO) or sodium cyanate or sodium thiocyanate and acetic acid, and thereafter, if required converting the R1', R2' or R3' residues into an alternative R1', R2' or R3' residues to give alternative compound of formula II. For example, the benzophenone of formula VII in solution is treated with a solution of chlorosulfonyl isocyanate, e.g. in benzene, with cooling, e.g. at 0° C.

Agents of the Invention of formula II in which R1' is nitro may be converted to Agents of formula II in which R1' is amino by reduction of the nitro group, e.g. with Raney Nickel in EtOH/THF solution or Iron in AcOH solution. Agents of the Invention of formula II in which R1' is amino may be converted into corresponding Agents of the Invention in which R1' is amino mono- or di-substituted by lower alkenyl, lower alkyl or lower alkynyl by interaction with the corresponding halide, e.g. bromide, in the presence of an appropriate base and other appropriate reagents, e.g. for monoalkylation in the presence of TMSCl as intermediate protecting group to provide in situ mono protection and Hünig's base in CH$_2$Cl$_2$, or K$_2$CO$_3$/DMF.

Benzophenone compounds of formula VII, in which R1' is an activating group, e.g. NO$_2$ in the 6 position, may be prepared by amination of a corresponding chloro precursor of formula VIII

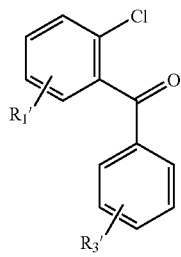

VIII wherein R1' and R3' are as defined above, with the corresponding amine, R2'NH$_2$; for instance by heating the compound of formula VIII with the amine, e,g, to 65° C. for 10 h in a sealed tube.

The compound of formula VIII may be obtained by oxidation of the corresponding alcohol of formula IX

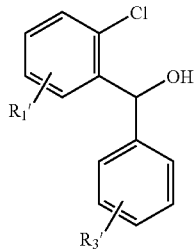

IX wherein R1' and R3' are as defined above, e.g. with Jones reagent.

The alcohol of formula IX may be obtained by coupling of the 2-chlorobenzaldehyde compound of formula X with the corresponding organometallic compound of formula XI

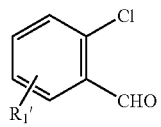

X

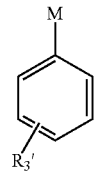

XI wherein R1' and R3' are as defined above and M is e.g. MgBr, Li or Ti (OR)$_3$; e.g. as hereinafter described in the Examples.

Alternatively Benzophenone compounds of formula VII may be prepared by treatment of the corresponding amine of formula XXX

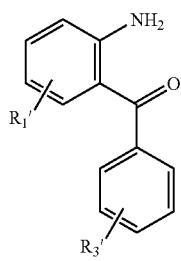

XXX with the corresponding bromide, R2'Br and a suitable base such as K$_2$CO$_3$.

Alternatively, compounds of formula VII may be prepared by reduction amination of the corresponding aldehyde with the amine XXX, using Ti(I-Opr)$_4$ as dehydrating agent and NaBH(Oac)$_3$ as the reducing agent, the amine XXX being obtainable from the the corresponding nitro derivative by reduction, e.g. with Raney Nickel, and the nitro derivative being obtainable by nitration e.g. with fuming nitric acid, of the corresponding benzophenone of formula XXXI

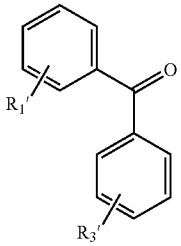

XXXI wherein R3' is as previously defined and R1" is an activating group.

The compound of formula XXXI may in turn be obtained by the oxidation, e.g. with Jones reagent, of the corresponding alcohol which may in turn be obtained by coupling an organometallic compound derived from the corresponding bromide of formula XXXIII and aldehyde of formulae XXXII respectively; for instance as described in the Examples

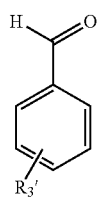

XXXII

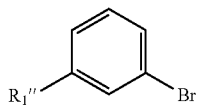

XXXIII

The amine of formula XXX may be prepared alternatively directly by coupling of a 2-aminonitrile of formula XV with an R3'-substituted bromide of formula XXXIV,

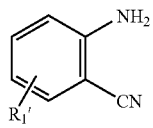

XV

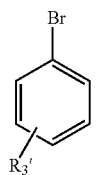

XXXIV for instance, involving addition of the 2-aminonitrile compound to the addition product of the bromide and BuLi, typically with cooling, e.g. as hereinafter described in the Examples.

Alternatively Agents of the Invention of formula II may be obtained by cyclisation of a compound of formula XII

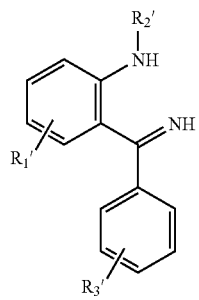

XII wherein R1', R2' and R3' are as defined above, with phosgene; for instance, as hereinafter described in the Examples, and thereafter, if required converting the R1', R2' or R3' residues into an alternative R1', R2' or R3' residues to give an alternative compound of formula II.

For example, compounds of formula II in which R1' represents di-lower alkoxy, e.g. 6,7-dimethoxy, may be converted to the corresponding dihydroxy compound, e.g. by treatment with BBr3, and the dihydroxy compound may in turn be converted to the corresponding di-alkenyloxy compound by treatment with the corresponding alkenyl bromide, e.g. allylbromide.

In a further alternative particular embodiment quinazoline thione Agents of the Invention may be prepared by a variant of the procedure described immediately above, in which thiophosgene is used in place of phosgene The imine compound of formula XII may be obtained by coupling of the corresponding nitrile of formula XIII with the corresponding Grignard reagent or phenyl lithium compound of formula XIV, e.g. the latter prepared from butyllithium and the corresponding bromobenzene compound

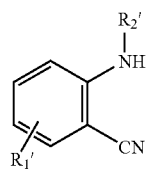

XIII

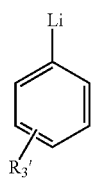

XIV and the nitrile of formula XIII may be obtained from the corresponding 2-aminonitrile of formula XV by reaction with the R2' iodide or bromide; for instance as described in the Examples.

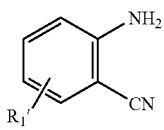

XV

In a further alternative Agents of the Invention of formula II may be obtained by oxidation of a compound of formula XVII;

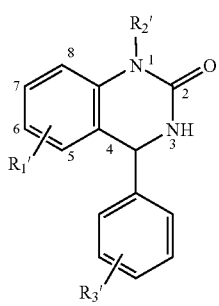

XVII for instance, in the presence of sodium periodate and a trace of ruthenium trichloride hydrate.

The 3,4-dihydro-1.H.-quinazolin-2-one of formula XVII may be obtained by coupling of a phenylurea compound of formula XVIII with an aldehyde of formula XIX;

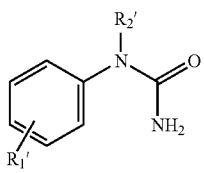

XVIII

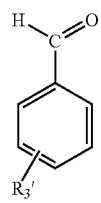

XIX for instance as described in the Examples. The urea of formula XVIII may be obtained by treatment of the precursor of formula XX

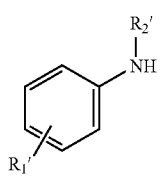

XX with sodium cyanate in acetic acid, and the compound of formula XX may be obtained by treatment of the corresponding amine with the corresponding R2' halide; for instance as described in the Examples.

In a yet further alternative Agents of the Invention of formula II, in which R2' is optionally substituted benzyl may be prepared by alkylation of an Agent of the Invention of formula XXXXII

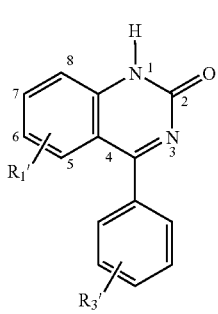

XXXXII at the 1-position with the corresponding optionally substituted benzylhalide; for instance, in the presence of e.g. LiHMDS and NaI, in solution, e.g. THF/DMF, with mild heating. The Agent of formula XXXXII may be prepared by treatment of the corresponding compound of formula III in which R4' is chloro with HCl in dioxane with heating. The compound of formula III in which R4' is chloro may be prepared by coupling of the corresponding R3'-substituted benzene boronic acid with the corresponding R1'-substituted 2,4-dichloroquinazoline of formula XXXXIII

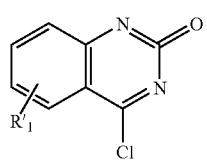

XXXXIII typically in the presence of a catalyst, such as palladium(II) acetate, and $K_2CO_3$ solution with heating; for instance, as hereinafter described in the Examples. The dichloro compound of formula XXXXIII may be prepared from the corresponding 2,4-dione, for instance by treatment with $POCl_3$ in the presence of N,N-diethylaniline; for instance, as described in the Examples. The 2,4-dione may in turn be prepared by cyclisation of the corresponding 2-aminobenzoic acid, e.g. by treatment with potassium cyanate in the presence of acetic acid; for instance, as hereinafter described in the Examples.

Agents of the Invention of formula III may be prepared as follows:

Thus Agents of formula III

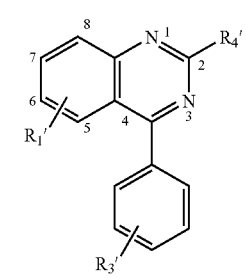

III wherein R1', R2' and R4' are as previously defined, in particular where R4' is halo, e.g. chloro, may be prepared by coupling of the corresponding 4-halo, e.g. chloro-substituted quinolene of formula XXXX

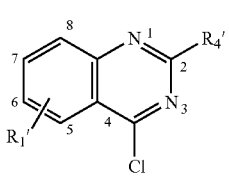

XXXX with the corresponding benzene boronic acid of formula XXXXI;

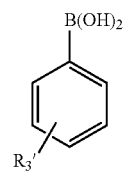

XXXXI for instance, in solution, e.g. in DMF, in the presence of, e.g. tri-O-tolylphosphine, palladium (II) acetate and aqueous $K_2CO_3$ solution.

Agents of the Invention of formula m in which R4' is halo, e.g. chloro, may be converted into further compounds of formula m by replacement of the R4' halo substituent. Thus for example, Agents in which R4' is CN may be obtained by treating the R4' halo Agent with, e.g. KCN in the presence of DABCO, in solution, e.g. DMSO/$H_2$O, with heating;

Agents in which R4' is F may be obtained by treatment with KF, e.g. in the presence of DMA, with heating;

Agents in which R4' is optionally substituted aryloxy may be obtained by treating with the corresponding hydroxy-aryl precursor, e.g. in the presence of NaH, with heating;

Agents in which R4' is optionally substituted alkoxy may be obtained by treating with the corresponding hydroxy-alkyl precursor, e.g. in the presence of NaH, with heating;

For instance as hereinafter described in the Examples.

Accordingly the Invention includes processes for the preparation of Agents of the Invention of formula II and III

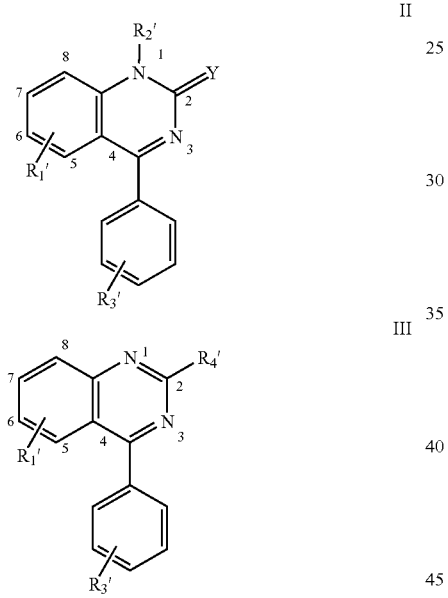

wherein the symbols are as defined above comprising a) for an Agent of the invention of formula II

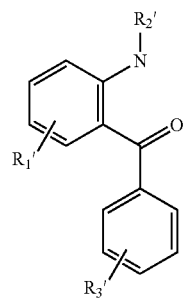

wherein R1', R2' and R3' are as defined, cyclising a compound of formula VII with a condensation reagent such as chlorosulfonyl isocyanate (ClSO$_2$NCO) or sodium cyanate or sodium thiocyanate b) for an Agent of the Invention of formula II cyclising a compound of formula XII

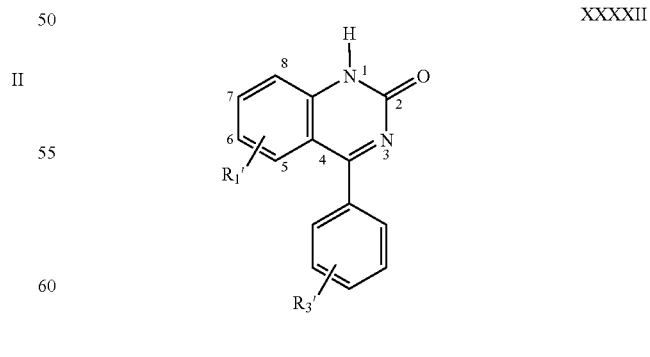

wherein R1', R2' and R3' are as defined above, with a condensation reagent such as phosgene or thiophosgene;

c) for an Agent of the Invention of formula II, in which R2' is optionally substituted benzyl, alkylation of an Agent of the Invention of formula XXXXII at the 1-position with the corresponding optionally substituted benzylhalide;

d) for an Agents of the Invention of formula II, oxidation of a compound of formula XVII;

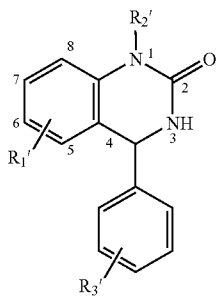

XVII for instance, in the presence of sodium periodate and a trace of ruthenium trichloride hydrate e) for an Agent of the Invention of formula III

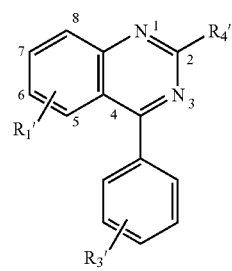

III wherein R1' and R3' as previously defined, and where R4' is halo, e.g. chloro, coupling of the corresponding 4-halo, e.g. chloro-substituted quinolene of formula XXXX

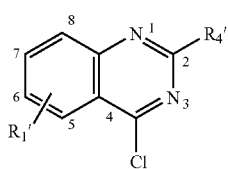

XXXX with the corresponding benzene boronic acid of formula XXXXI;

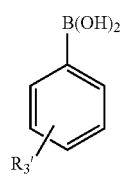

XXXXI and thereafter, if required converting the R1', R2', R3' or R4' residues into alternative R1', R2', R3' or R4' residues to give an alternative compound of formula II or III.

The preparation of Agents of the Invention of formula VII' as described above is also included within the invention.

Accordingly in a further aspect the invention provides processes for the preparation of Agents of the Invention of formula VII

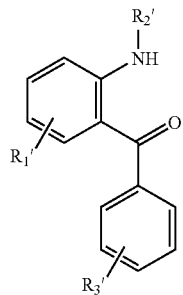

VII wherein R1', R2' and R3' are as defined above comprising a). alkylation of the corresponding aminobenzophenone compound of formula XXX

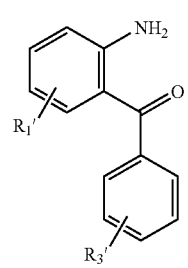

XXX wherein R1' and R3' are as defined above, or b). amination of a halo e.g. chloro, precursor of formula VIII

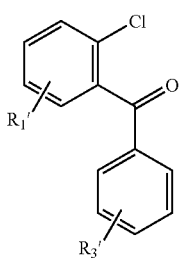

VIII wherein R1' and R3' are as defined above (for instance when R1' is an activating group, e.g. $NO_2$ in the 4-position of the anilino ring) with the corresponding amine, R2-$NH_2$, and thereafter, if required, converting R1', R2' or R3' residues into alternative R1', R2' or R3' residues to give an alternative compound of formula I.

The invention is described by way of illustration only in the following non-limiting Examples which relate to the preparation of compounds of the invention of formulae II, III and IV'.

EXAMPLES
Synthesis of 6-nitro-1-isopropyl-4-(4-isopropyl-phenyl)-1.H.-quinazolin-2-one and derivatives thereof
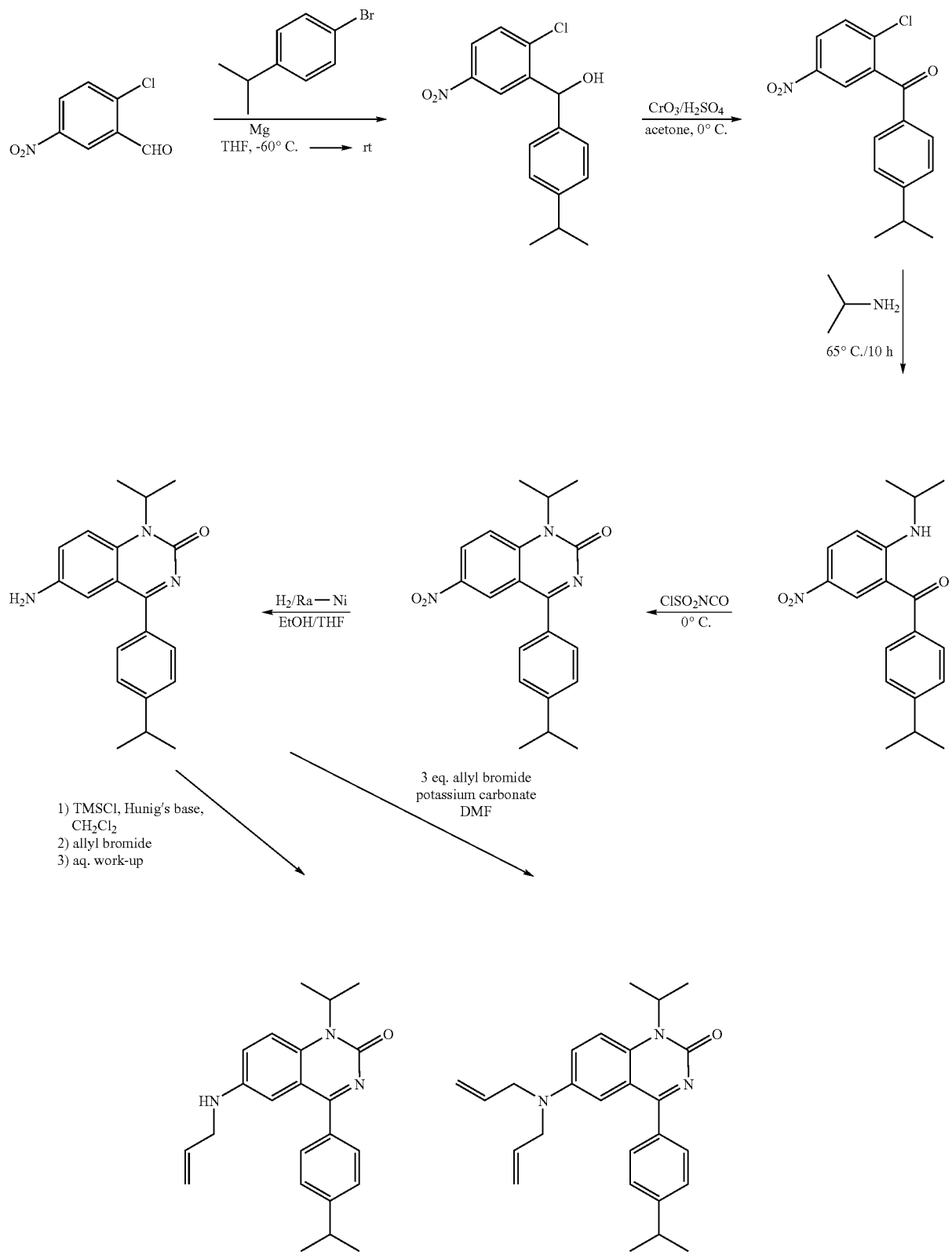

Example 1

6-Nitro-1-isopropyl-4-(4-isopropyl-phenyl)-1.H.-quinazolin-2-one

A. Synthesis of (2-chloro-5-nitro-phenyl)-(4-isopropyl-phenyl)-methanol

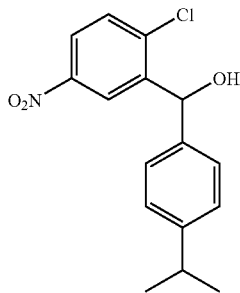 [SMILES: CC(C)c1ccc(C(O)c2cc([N+](=O)[O-])ccc2Cl)cc1]

A solution of 11.1 g (60 mmol) of 2-chloro-5-nitrobenzaldehyde in 140 ml anhydrous THF is treated at −75° C. dropwise with 86 ml 0.72 M 4-isopropyl-phenyl-magnesium bromide (prepared from 4-isopropyl-bromobenzene and magnesium). After complete addition, the mixture is allowed to come to rt. Extractive work-up with diluted HCl solution/ethyl acetate results in 20 g of a dark oil, which is purified by flash-chromatography (hexane/ethyl acetate 98:2). yield: 15 g (81%) in form of a yellow oil.

$^1$H-NMR (300 MHz, CDCl$_3$): 8.71 (d, 1H), 8.10 (dd, 1H), 7.49 (d, 1H), 7.31 (d, 2H), 7.22 (d, 2H), 6.17 (d, 1H), 2.90 (hept, 1H), 2.88 (d, OH), 1.24 (d, 6H).

B. Synthesis of 2-chloro-5-nitro-4'-isopropyl-benzophenone

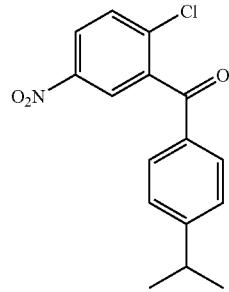 [SMILES: CC(C)c1ccc(C(=O)c2cc([N+](=O)[O-])ccc2Cl)cc1]

The alcohol prepared in step A (1.2 g, 4.14 mmol) in 10 ml acetone is treated at 0° C. with Jones reagent. Stirring is continued overnight at rt. The acetone is removed i.v. followed by extractive workup with ethyl acetate/water. yield: 1.09 g (96%) yellow solid. m.p. 86-89° C.

$^1$H-NMR (300 MHz, CDCl$_3$): 8.29 (dd, 1H), 8.23 (d, 1H), 7.73 (d, 2H), 7.67 (d, 1H), 7.36 (d, 2H), 3.00 (hept, 1H), 1.29 (d, 6H).

C. Synthesis of 2-isopropylamino-5-nitro-4'-isopropyl-benzophenone

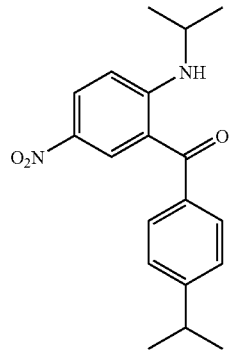 [SMILES: CC(C)Nc1ccc([N+](=O)[O-])cc1C(=O)c1ccc(C(C)C)cc1]

A mixture of 300 mg (0.95 mmol) of the compound obtained in step B in 15 ml isopropylamine is heated to 65° C. for 10 h in a sealed tube. The excess of amine is stripped off i.v. Extraction of the residue with ethyl acetate/water gives a quantitative yield of the product in form of a yellow resin, which is used without purification in the next step.

$^1$H-NMR (300 MHz, CDCl$_3$): 9.24 (broad d, NH), 8.54 (d, 1H), 8.23 (dd, 1H), 7.57 (d, 2H), 7.35 (d, 2H), 6.78 (d, 1H), 3.88 (8-line system, 1H), 3.00 (hept, 1H), 1.36 (d, 6H), 1.31 (d, 6H). MS: 327 (M+1)$^+$ D. Synthesis of 1-isopropyl-4-(4-isopropyl-phenyl)-6-nitro-1.H.-quinazolin-2-one

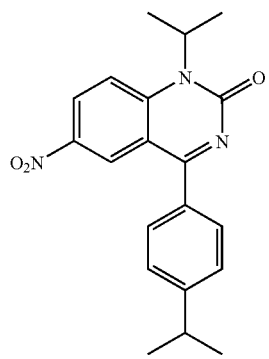

The crude benzophenone derivative obtained in step C is taken up in 10 ml benzene and treated slowly with 0.10 ml (1.2 mmol) of chlorosulfonyl isocyanate (diluted with 2 ml benzene). After 1 h at rt extractive work-up with ethyl acetate/water affords the crude product, which is purified by flash-chromatography (petroleum ether/ethyl acetate). Yield (after recrystallisation from diethyl ether): 140 mg (40%) slightly yellow solid. m.p. 208-209° C.

$^1$H-NMR (300 MHz, CDCl$_3$): 8.79 (d, 1H), 8.53 (dd, 1H), 7.71 (d, 2H), 7.67 (d, 1H), 7.43 (d, 1H), 5.14 (hept, 1H), 3.03 (hept, 1H), 1.73 (d, 6H), 1.33 (d, 6H). MS: 352 (M+1)$^+$

Example 2

Synthesis of 6-amino-1-isopropyl-4-(4-isopropyl-phenyl)-1.H.-quinazolin-2-one

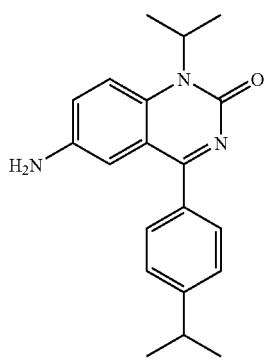 [SMILES: CC(C)c1ccc(-c2nc(=O)n(C(C)C)c3ccc([N+](=O)[O-])cc23)cc1]

Catalytic hydrogenation of a solution of 4.05 g (11.5 mmol) 6-nitro-isopropyl-4-(4-isopropyl-phenyl)-1.H.-quinazolin-2-one (step D) in 150 ml ethanol/50 ml THF over Raney Nickel (1 g) yields 3.6 g (quant.) of a red solid. m.p. 218-220° C.

$^1$H-NMR (300 MHz, CDCl$_3$): 7.65 (d, 2H), 7.42 (d, 1H), 7.34 (d, 2H), 7.08-7.13 (m, 2H), 5.18 (broad hept, 1H), 3.67 (broad, NH$_2$), 2.99 (hept, 1H), 1.67 (d, 6H), 1.30 (d, 6H). MS: 322 (M+1)$^+$

Example 3

Synthesis of 6-diallylamino-1-isopropyl-4-(4-isopropyl-phenyl)-1.H.-quinazolin-2-one

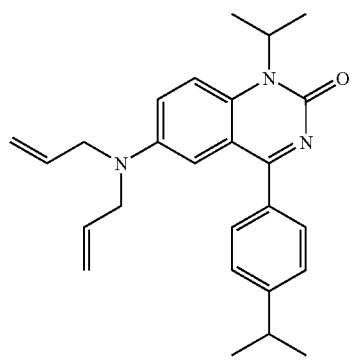 [SMILES: C=CCN(CC=C)c1ccc2c(c1)c(-c1ccc(C(C)C)cc1)nc(=O)n2C(C)C]

A mixture of 100 mg (0.311 mmol) of the amine obtained in Example 2 in 5 ml dichloromethane and 130 mg (0.93 mmol) of potassium carbonate, is treated at 0° C. with 80 µl (0.93 mmol, 3 equiv.) of allyl bromide. Stirring is continued overnight at 50° C. Work-up affords a red oil, which is purified by flash chromatography (petroleum ether/ethyl acetate). yield: 25 mg (20%) yellow oil.

$^1$H-NMR (300 MHz, CDCl$_3$): 7.66 (d, 2H), 7.45 (d, 1H), 7.32 (d, 2H), 7.15 (dd, 1H), 7.06 (d, 1H), 5.71-5.86 (m, 2H), 5.21 (hept, 1H), 5.15 (d, 2H), 5.09 (d, 2H), 3.88 (d, 4H), 2.98 (hept, 1H), 1.66 (d, 6H), 1.29 (d, 6H). MS: 402 (M+1)$^+$

Example 4

Synthesis of 6-allylamino-1-isopropyl-4-(4-isopropyl-phenyl)-1.H.-quinazolin-2-one

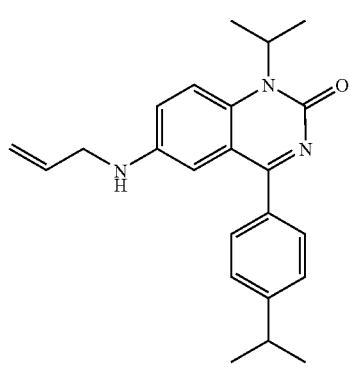 [SMILES: C=CCNc1ccc2c(c1)c(-c1ccc(C(C)C)cc1)nc(=O)n2C(C)C]

To a solution of 40 mg (0.124 mmol) of the amine obtained in Example 2 and 50 µl (0.29 mmol) diisopropyl-ethyl amine (in 2 ml dichloromethane) 16 µl (0.13 mmol) trimethylsilyl-chloride is added dropwise. After stirring for one hour at 50° C. one equivalent of allyl bromide (11 µl, 0.13 mmol) is added. The reaction is kept for 6 h at that temperature. The crude product obtained after extractive work-up with ethyl acetate/water is purified by flash chromatography (ethyl acetate/hexane). yield: 10 mg (33%). m.p. 209-211° C.

$^1$H-NMR (300 MHz, CDCl$_3$): 7.67 (d, 2H), 7.43 (d, 1H), 7.33 (d, 2H), 7.07 (dd, 1H), 6.99 (d, 1H), 5.80-5.94 (m, 1H), 5.13-5.26 (m, 3H), 3.89 (broad s, NH), 3,72 (broad d, 2H), 2.98 (hept, 1H), 1.66 (d, 6H), 1.29 (d, 6H). MS (ES+): 362 (M+1)$^+$ The compounds of the following examples are prepared by analogy to the examples described above:

Example 5

6-Dimethylamino-1-isopropyl-4-isopropyl-phenyl)-1.H.-quinazolin-2-one

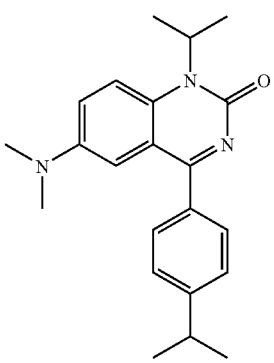 [SMILES: CC(C)c1ccc(-c2nc(=O)n(C(C)C)c3ccc(N(C)C)cc23)cc1]

¹H-NMR (300 MHz, CDCl₃): 7.73 (d, 2H), 7.51 (d, 1H), 7.35 (d, 2H), 7.23 (d, 1H), 7.12 (d, 1H) 5.23 (hept, 1H), 3.00 (hept, 1H), 2.91 (s, 6H), 1.68 (d, 6H), 1.31 (d, 6H). MS: 350 (M+1)⁺

Example 6

6-Diethylamino-1-isopropyl-4-(4-isopropyl-phenyl)-1.H.-quinazolin-2-one

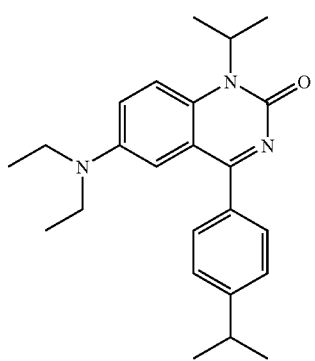 [SMILES: CCN(CC)c1ccc2c(c1)c(-c1ccc(C(C)C)cc1)nc(=O)n2C(C)C]

m.p. 170-172° C. ¹H-NMR (300 MHz, CDCl₃): 7.71 (d, 2H), 7.48 (d, 1H), 7.35 (d, 2H), 7.18 (dd, 1H), 7.04 (d, 1H), 5.23 (broad hept, 1H), 3.29 (q, 4H), 2.99 (hept, 1H), 1.30 (d, 6H), 1.12 (t, 6H). MS: 378 (M+1)⁺

Example 7

6-(Dipropylamino)-1-isopropyl-4-(4-isopropyl-phenyl)-1.H.-quinazolin-2-one

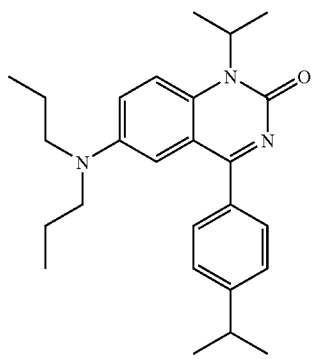 [SMILES: CCCN(CCC)c1ccc2c(c1)c(-c1ccc(C(C)C)cc1)nc(=O)n2C(C)C]

m.p. 182-184° C. ¹H-NMR (300 MHz, CDCl₃): 7.68 (d, 2H), 7.46 (d, 1H), 7.33 (d, 2H), 7.12 (dd, 1H), 6.91 (d, 1H), 5.24 (broad hept, 1H), 3.16 (t, 4H), 2.98 (hept, 1H), 1.67 (d, 6H), 1.54 (6-line system, 4H), 1.28 (d, 6H), 0.85 (t, 6H). MS: 406 (M+1)⁺

Example 8

6-(Ethylamino)-1-isopropyl-4-(4-isopropyl-phenyl)-1.H.-quinazolin-2-one

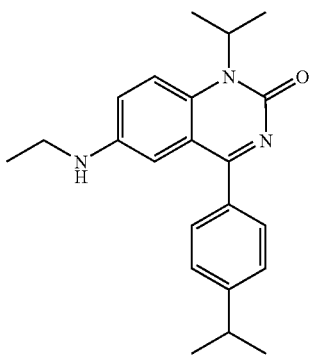 [SMILES: CCNc1ccc2c(c1)c(-c1ccc(C(C)C)cc1)nc(=O)n2C(C)C]

m.p. 225-227° C. ¹H-NMR (300 MHz, CDCl₃): 7.69 (d, 2H), 7.45 (d, 1H), 7.85 (d, 2H), 7.06 (dd, 1H), 6.99 (d, 1H), 5.21 (broad hept, 1H), 3.69 (broad s, NH), 3.10 (q, 2H), 2.99 (hept, 1H), 1.68 (d, 6H), 1.30 (d, 6H), 1.24 (t, 3H). MS: 350 (M+1)⁺

Example 9

6-Propylamino-1-isopropyl-4-(4-isopropyl-phenyl)-1.H.-quinazolin-2-one

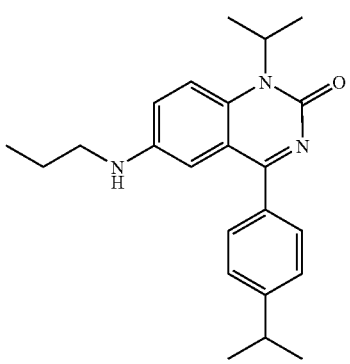 [SMILES: CCCNc1ccc2c(c1)c(-c1ccc(C(C)C)cc1)nc(=O)n2C(C)C]

m.p. 231-233° C. ¹H-NMR (300 MHz, CDCl₃): 7.69 (d, 2H), 7.44 (d, 1H), 7.34 (d, 2H), 7.05 (dd, 1H), 6.97 (d, 1H), 5.20 (broad 5-line system, 1H), 3.66 (broad, NH), 2.93-3.06 (m, 3H), 1.67 (d, 6H), 1.62 (6-line system, partially obscured by adjacent signal, 2H), 1.30 (d, 6H), 0.97 (t, 3H). MS: 364 (M+1)⁺

Example 10

1-Isopropyl-4-(4-tert.butyl-phenyl)-6-nitro-1.H.-quinazolin-2-one

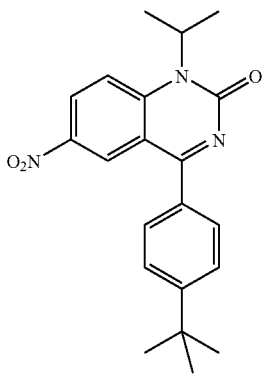

¹H-NMR (300 MHz, CDCl₃): 8.80 (d, 1H), 8.53 (dd, 1H), 7.72 (d, 2H), 7.67 (d, 1H), 7.59 (d, 2H), 5.15 (hept, 1H), 1.73 (d, 6H), 1.40 (s, 9H). MS: 366 (M+1)⁺

Example 11

6-Amino-1-benzyl-4-(4-tert.butyl-phenyl)-1.H.-quinazolin-2-one

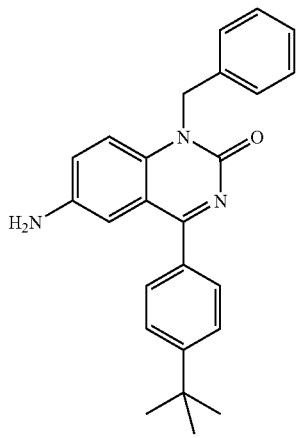 [SMILES: CC(C)(C)c1ccc(-c2nc(=O)n(Cc3ccccc3)c3ccc(N)cc23)cc1]

¹H-NMR (300 MHz, CDCl₃): 7.70 (d, 1H), 7.53 (d, 2H), 7.20-7.32 (m, 6H), 7.10-7.14 (m, 2H), 7.00 (dd, 1H), 5.52 (broad s, 2H), 3.70 (broad, NH₂), 1.38 (s, 9H). MS: 384 (M+1)⁺

Example 12

6-Dipropargylamino-1-isopropyl-4-(4-isopropyl-phenyl)-1.H.-quinazolin-2-one

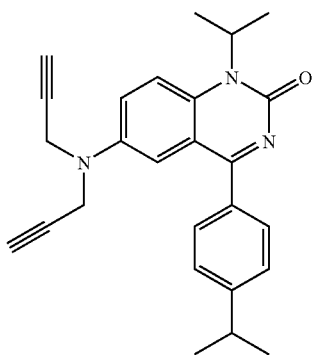 [SMILES: C#CCN(CC#C)c1ccc2c(c1)c(-c1ccc(C(C)C)cc1)nc(=O)n2C(C)C]

¹H-NMR (300 MHz, CDCl₃): 7.75 (d, 2H), 7.52-7.59 (m, 1H), 7.40-7.48 (m, 2H), 7.36 (d, 2H), 5.21 (broad hept, 1H), 4.06 (d, 4H), 3.00 (hept, 1H), 2.28 (broad s, 2H), 1.69 (d, 6H), 1.31 (d, 6H). MS: 398 (M+1)⁺

Example 13

6-Propargylamino-1-isopropyl-4-(4-isopropyl-phenyl)-1.H.-quinazolin-2-one

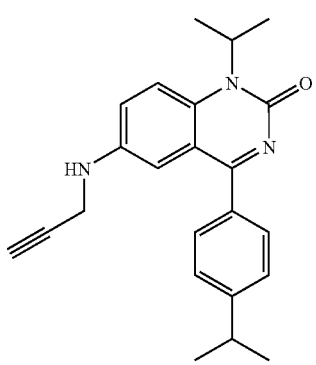 [SMILES: C#CCNc1ccc2c(c1)c(-c1ccc(C(C)C)cc1)nc(=O)n2C(C)C]

¹H-NMR (300 MHz, CDCl₃): 7.72 (d, 2H), 7.49 (d, 1H), 7.35 (d, 2H), 7.12-7.18 (m, 2H), 5.21 (broad hept, 1H), 3.87-4.00 (m, 3H), 3.00 (hept, 1H), 2.24 (broad s, 1H), 1.68 (d, 6H), 1.31 (d, 6H). MS: 360 (M+1)⁺

Example 14

6-Propargylamino-1-benzyl-4-(4-isopropyl-phenyl)-1.H.-quinazolin-2-one

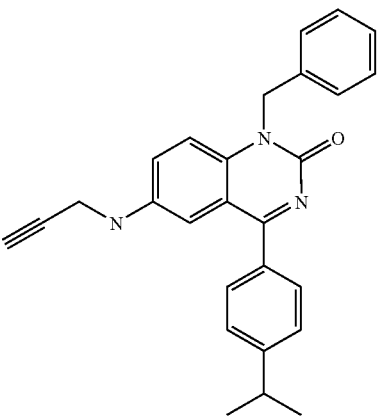 [SMILES: C#CCNc1ccc2c(c1)c(-c1ccc(C(C)C)cc1)nc(=O)n2Cc1ccccc1]

¹H-NMR (300 MHz, CDCl₃): 7.77 (d, 2H), 7.13-7.45 (m, 9H), 7.05 (d, 1H), 5.55 (broad s, 2H), 3.96 (broad s, NH), 3.89 (broad s, 2H), 3.02 (hept, 1H), 2.23 (s, 1H), 1.33 (d, 6H). MS: 408 (M+1)⁺

Example 15

6-Allylamino-1-benzyl-4-(4-isopropyl-phenyl)-1.H.-quinazolin-2-one

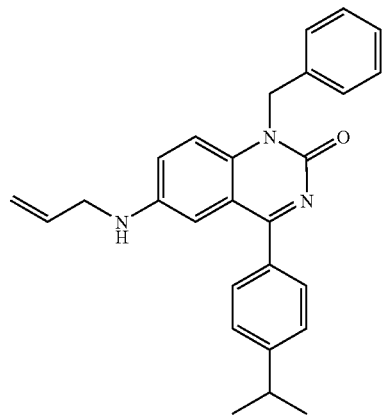 [SMILES: C=CCNc1ccc2c(c1)c(-c1ccc(C(C)C)cc1)nc(=O)n2Cc1ccccc1]

$^1$H-NMR (300 MHz, CDCl$_3$): 7.72 (d, 2H), 7.73 (d, 2H), 7.29-7.33 (m, 5H), 7.14 (d, (1H), 7.03 (d, 1H), 6.98 (dd, 1H), 5.78-5.93 (m, 1H), 5.54 (s, 2H), 5.21 (dd, 1H), 5.16 (dd, 1H), 3.89 (broad s, NH), 3.70 (broad s, 2H), 3.01 (hept, 1H), 1.32 (d, 6H). MS: 410 (M+1)$^+$

Synthesis of 1-isopropyl-4-(4-isopropyl-phenyl)-6,7-dimethoxy-1.H.-quinazolin-2-one and Related Compounds

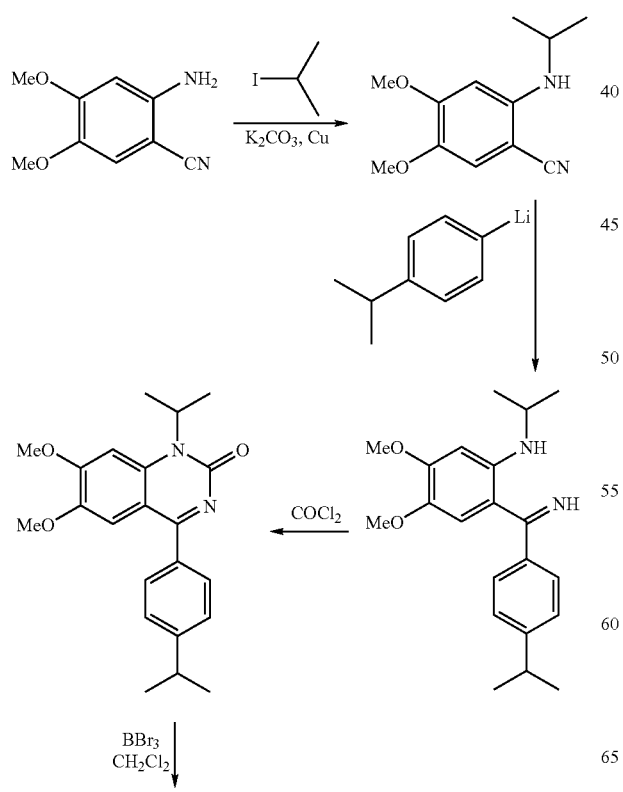

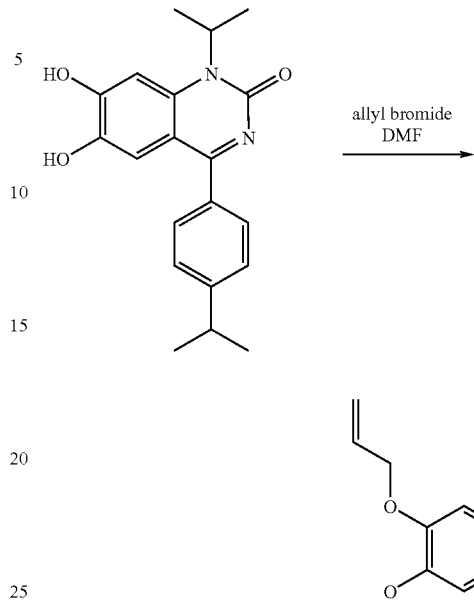

Example 16

1-Isopropyl-4-(4-isopropyl-phenyl)-6,7-dimethoxy-1.H.-quinazolin-2-one

A. Synthesis of 2-isopropylamino-4,5-dimethoxy-benzonitrile

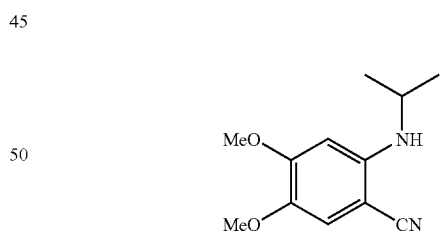

A suspension of 4.52 g (25.4 mmol) 2-amino-4,5-dimethoxy-benzonitrile, 4.38 g (31.7 mmol) potassium carbonate and 100 mg copper powder in 15 ml 2-iodo-propane is stirred at 90° C. for 5 days. Extractive work-up with ethyl acetate/water and concentration i.V. affords a dark oil, which is purified by flash chromatography (ethyl acetate/hexane). yield: 4.15 g (74%) yellow oil.

$^1$H-NMR (300 MHz, CDCl$_3$): 6.81 (s, 1H), 6.16 (s, 1H), 3.89 (s, 3H), 3.78 (s, 3H), 3.67 (8-line system, 1H), 1.26 (d, 6H). MS: 221 (M+1)$^+$ B. Synthesis of {2-[imino-(4-isopropyl-phenyl)-methyl]-4,5-dimethoxy-phenyl}-isopropyl-amine

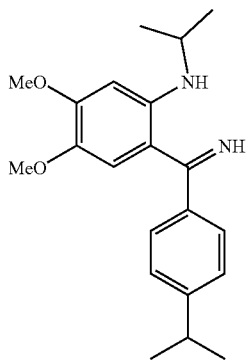 [SMILES: COc1cc(NC(C)C)c(C(=N)c2ccc(C(C)C)cc2)cc1OC]

An ice-cold solution of 1.24 g (6.27 mmol) 4-isopropyl-bromobenzene in 7 ml anhydrous diethyl ether is treated with 4.3 ml 1.6 M (6.87 mmol) butyllithium (in hexane). Upon complete addition, stirring is continued for another 30 minutes. Then 500 mg (2.27 mmol) of the nitrile (diluted with 7 ml diethyl ether) prepared in step A is added dropwise. The cooling bath is removed and the reaction warmed to rt. The orange suspension obtained is poured onto ice and extracted with ethyl acetate. Purification of the crude product by flash chromatography (ethyl acetate/hexane) yields 223 mg (29%) of a yellow oil.

$^1$H-NMR (300 MHz, CDCl$_3$): 9.4 (broad NH), 9.1 (broad NH), 7.24-7.30 (m, 4H), 6.69 (s, 1H), 6.28 (s, 1H), 3.93 (s, 3H), 3.75 (broad m, 1H), 3.59 (s, 3H), 2.96 (hept, 1H), 1.33 (d, 6H), 1.29 (d, 6H). MS: 341 (M+1)$^+$ C. Synthesis of 1-isopropyl-4-(4-isopropyl-phenyl)-6,7-dimethoxy-1.H.-quinazolin-2-one

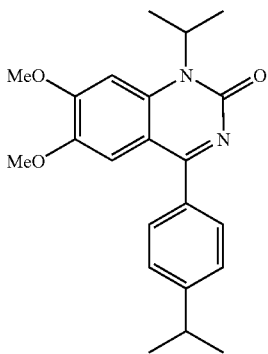 [SMILES: COc1cc2c(-c3ccc(C(C)C)cc3)nc(=O)n(C(C)C)c2cc1OC]

A solution of 200 mg (0.587 mmol) of the imine prepared in step B and 0.24 ml (1.72 mmol) triethylamine in 2 ml toluene is treated dropwise with 0.43 ml (0.82 mmol) of phosgene solution (1.9 M in toluene). The cooling bath is removed and by the time the mixture has reached rt the reaction is complete. Extractive work-up with ethyl acetate/water followed by flash chromatography (ethyl acetate/hexane) of the crude product affords 102 mg (47%) of the quinazolinone. m.p. 160-162° C.

$^1$H-NMR (300 MHz, CDCl$_3$): 7.69 (d, 2H), 7.36 (2, 2H), 7.26 (s, 1H), 6.98 (s, 1H), 5.27 (broad m, 1H), 4.05 (s, 3H), 3.82 (s, 3H), 2.99 (hept, 1H), 1.71 (d, 6H), 1.30 (d, 6H). MS: 367 (M+1)$^+$ The corresponding compound in which R3' is tert.-butyl is analogously prepared:

(4-.tert.-Butyl-phenyl)-(2-isopropylamino-4,5-dimethoxy-phenyl)-methanone

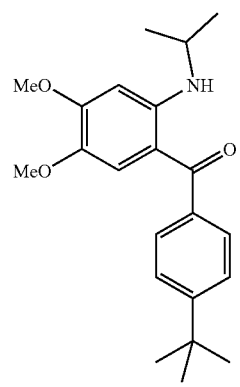 [SMILES: COc1cc(NC(C)C)c(C(=O)c2ccc(C(C)(C)C)cc2)cc1OC]

$^1$H-NMR (300 MHz, CDCl$_3$): 8.9 (broad NH), 7.54 (d, 2H), 7.44 (d, 2H), 7.07 (s, 1H), 6.23 (s, 1H), 3.94 (s, 3H), 3.73 (8-line system, 1H), 3.67 (s, 3H), 1.35 (s, 9H). MS: 356 (M+1)$^+$ Example 17

Synthesis of 6,7-dihydroxy-1-isopropyl-4-(4-isopropyl-phenyl)-1.H.-quinazolin-2-one

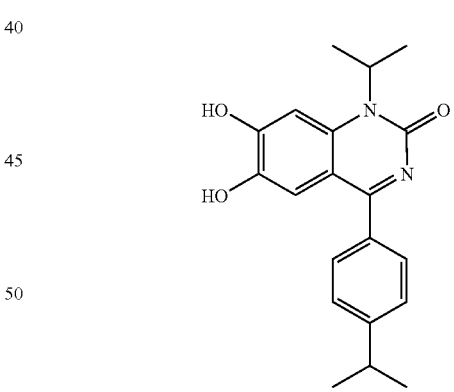

1.1 ml (1.09 mmol) of a solution of BBr$_3$ (1.0 M in dichloromethane) is added to 100 mg (0.272 mmol) 1-isopropyl-4-(4-isopropyl-phenyl)-6,7-dimethoxy-1.H.-quinazolin-2-one. After stirring for 30 min at rt the solution is poured into 100 ml water. The resulting yellow precipitate is filtered off, washed with ether, dried and subjected to chromatography (hexane/ethyl acetate) to give the product as a yellow solid.

$^1$H-NMR (300 MHz, CD$_3$OD): 7.66 (d, 2H), 7.61 (dd, 1H), 7.23 (s, 1H), 7.14 (s, 1H), 5.21 (m, 1H), 3.09 (hept, 1H), 1.71 (d, 6H), 1.34 (d, 6H). MS: 339 (M+1)$^+$

Example 18

6,7-bis-Allyloxy-1-isopropyl-4-(4-isopropyl-phenyl)-1.H.-quinazolin-2-one

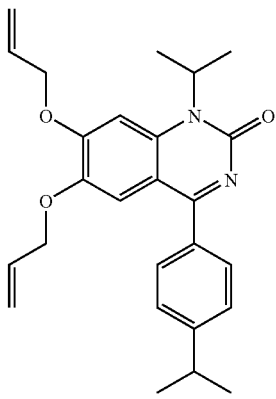 [SMILES: C=CCOc1cc2c(-c3ccc(C(C)C)cc3)nc(=O)n(C(C)C)c2cc1OCC=C]

To a solution of 75 mg (0.204 mmol) 6,7-dihydroxy-1-isopropyl-4-(4-isopropyl-phenyl)-1.H.-quinazolin-2-one in 2 ml DMF is added 0.5 ml allylbromide and 21 mg (0.9 mmol) NaH. The reaction mixture is stirred for 4 h at rt, diluted with dichloromethane and extracted with water. The organic layer is dried and evaporated. After chromatography (dichloromethane/MeOH) the product is obtained as yellow oil.

$^1$H-NMR (300 MHz, CDCl$_3$): 7.65 (d, 2H), 7.36 (d, 2H), 7.28 (s, 1H), 7.00 (s, 1H), 6.19-5.94 (m, 2H), 5.54-5.28 (m, 5H), 4.80 (d, 2H), 4.54 (d, 2H), 3.00 (hept, 1H), 1.67 (d, 6H) 1.31 (d, 6H). MS: 419 (M+1)$^+$ The compounds of the following examples are prepared analogously to example 16:

Example 19

1-Isopropyl-4-(4-isopropyl-phenyl)-5-methyl-1.H.-quinazolin-2-one

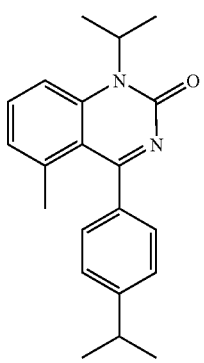 [SMILES: Cc1cccc2c1c(-c1ccc(C(C)C)cc1)nc(=O)n2C(C)C]

m.p. 149° C. $^1$H-NMR (300 MHz, CDCl$_3$): 7.56 (d, 1H), 7.69 (s, 1H), 7.4 (d, 2H), 7.29 (d, 2H), 7.00 (d, 1H), 4.95 (hept, 1H), 2.97 (hept, 1H), 2.04 (s, 3H), 1.69 (d, 6H), 1.30 (d, 6H). MS: 321 (M+1)$^+$

Example 20

1-Isopropyl-4-(4-isopropyl-phenyl)-1.H.-quinazolin-2-one

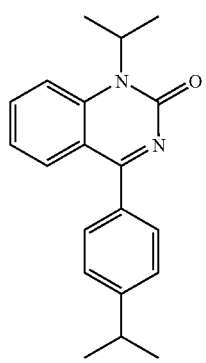

m.p. 128° C. $^1$H-NMR (300 MHz, CDCl$_3$): 7.89 (dd, 1H), 7.66-7.74 (m, 3H), 7.57 (d, 1H), 7.36 (d, 2H), 7.18 (t, 1H), 5.19 (broad hept, 1H), 3.00 hept, 1H), 1.72 (d, 6H), 1.31 (d, 6H). MS: 307 (M+1)$^+$

Example 21

1-Isopropyl-4-(3-isopropyl-phenyl)-6-methoxy-1.H.-quinazolin-2-one

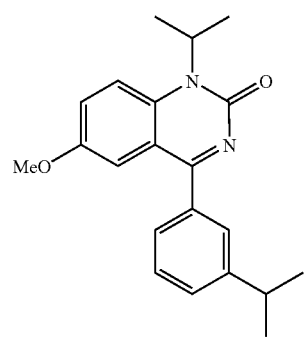 [SMILES: COc1ccc2c(c1)c(-c1cccc(C(C)C)c1)nc(=O)n2C(C)C]

$^1$H-NMR (300 MHz, CDCl$_3$): 7.63 (s, 1H), 7.53-7.59 (m, 2H), 7.39-7.47 (m, 2H), 7.36 (dd, 1H), 7.26 (s, 1H), 5.23 (broad hept, 1H), 3.75 (s, 3H), 3.00 (hept, 1H), 1.68 (d, 6H), 1.30 (d, 6H). MS: 337 (M+1)$^+$

Example 22

1-Isopropyl-4-(4-isopropyl-phenyl)-5-methoxy-1.H.-quinazolin-2-one

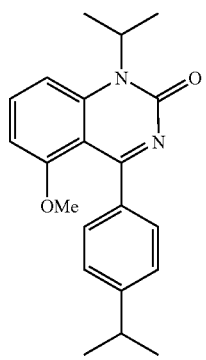 [SMILES: COc1cccc2c1c(-c1ccc(C(C)C)cc1)nc(=O)n2C(C)C]

m.p. 165° C. $^1$H-NMR (300 MHz, CDCl$_3$): 7.61 (t, 1H), 7.51 (d, 2H), 7.24 (d, 2H), 7.12 (d, 1H), 6.63 (d, 1H), 4.96 (broad hept, 1H), 3.57 (s, 3H), 2.96 (hept, 1H), 1.68 (d, 6H), 1.27 (d, 6H). MS: 337 (M+1)$^+$

Example 23

1-Isopropyl-4-(4-isopropyl-phenyl)-6-methyl-1.H.-quinazolin-2-one

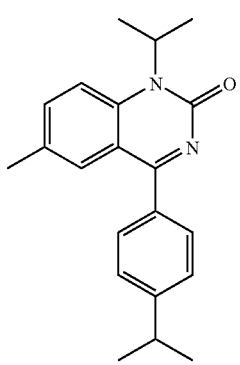 [SMILES: Cc1ccc2c(c1)c(-c1ccc(C(C)C)cc1)nc(=O)n2C(C)C]

m.p. 87-89° C. $^1$H-NMR (300 MHz, CDCl$_3$): 7.68 (d, 2H), 7.66 (s, 1H), 7.46-7.56 (m, 2H), 7.37 (d, 2H), 5.20 (broad hept, 1H), 3.01 (hept, 1H), 2.37 (s, 3H), 1.69 (d, 6H), 1.31 (d, 6H). MS: 321 (M+1)$^+$

Example 24

1-Isopropyl-4-(4-isopropyl-phenyl)-6-methoxy-1.H.-quinazolin-2-one

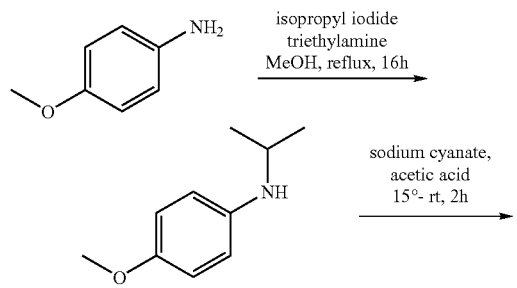

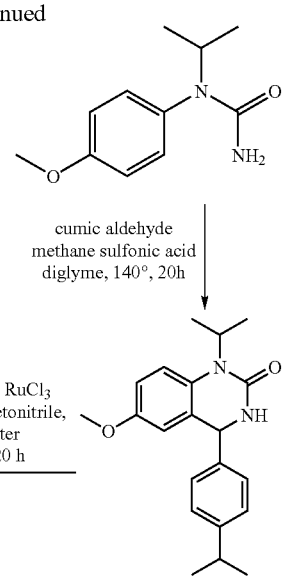

A. Synthesis of isopropyl-(4-methoxy-phenyl)-amine (known)

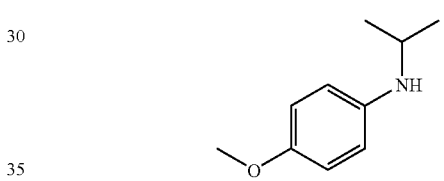

A solution of 5 g (40.6 mmol) p-anisidin, 4.1 ml (40.6 mmol) isopropyl iodide and 5.7 ml (40.6 mmol) triethylamine in 40 ml methanol is refluxed for 18 h. The reaction mixture is extracted with diethyl ether/water and the organic layers are evaporated. The crude product is purified by flash chromatography using dichloromethane/MeOH (98:2) as eluent to yield isopropyl-(4-methoxy-phenyl)-amine.

$^1$H NMR (300 MHz, CDCl$_3$): 6.78 (d, 2H), 6.58 (d, 2H), 3.75 (s, 3H), 3.55 (hept, 1H), 1.09 (d, 6H). MS: 166 (M+1)$^+$ B. Synthesis of 1-isopropyl-1-(4-methoxy-phenyl)-urea (known)

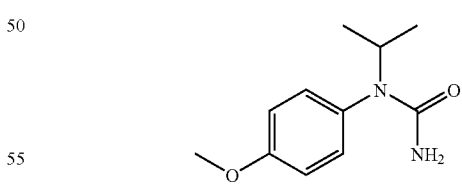

To a solution of 4.47 g (27.1 mmol) isopropyl-(4-methoxy-phenyl)-amine in 70 ml acetic acid are added in small portions 1.72 g (25.4 mmol) sodium cyanate while keeping the temperature below 15° C. by means of an ice bath. After stirring for 2 h at room temperature the acetic acid is evaporated and the residue is taken up in dichloromethane and washed with aqueous sodium hydroxide solution (1M). The organic phase is evaporated and the crude product is purified by recrystallization from dichloromethane/hexanes to yield 1-isopropyl-1-(4-methoxy-phenyl)-urea.

¹H NMR (300 MHz, CDCl₃): 7.10 (d, 2H), 6.94 (d, 2H), 4.85 (hept. 1H), 4.14 (broad, 2H), 3.83 (s, 3H), 1.04 (d, 6H). MS: 209 (M+1)⁺

C. Synthesis of 1-isopropyl-4-(4-isopropyl-phenyl)-6-methoxy-3,4-dihydro-1.H.-quinazolin-2-one

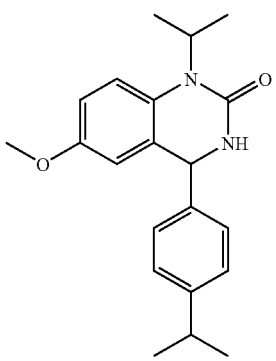 [SMILES: COc1ccc2c(c1)C(c1ccc(C(C)C)cc1)NC(=O)N2C(C)C]

A solution of 1.0 g (4.8 mmol)1-isopropyl-1-(4-methoxyphenyl)-urea, 0.87 ml (5.76 mmol) cumic aldehyde and 156 μl (2.4 mmol) methanesulfonic acid in 10 ml toluene is heated to reflux for 3 d. After extraction with water and ethyl acetate the crude product is purified by flash chromatography using hexanes/ethyl acetate (1:1) as eluent to yield 1-isopropyl-4-(4-isopropyl-phenyl)-6-methoxy-3,4-dihydro-1.H.-quinazolin-2-one.

¹H NMR (300 MHz, DMSO): 7.36 (d, 1H), 7.16 (d, 2H), 7.15 (d, 2H), 7.01 (d, 1H), 6.83 (d, 1H), 6.78 (dd, 1H), 5.13 (d, 1H), 4.32 (hept., 1H), 3.66 (s, 3H), 2.81 (hept., 1H), 1.40 (d, 3H), 1.37 (d, 3H), 1.13 (d, 6H). MS: 339 (M+1)⁺

D. Synthesis of 1-isopropyl-4-(4-isopropyl-phenyl)-6-methoxy-1.H.quinazolin-2-one

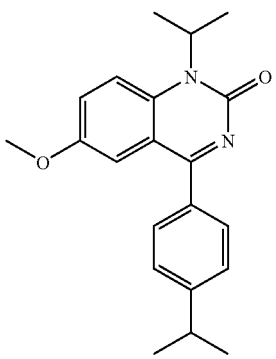 [SMILES: COc1ccc2c(c1)c(-c1ccc(C(C)C)cc1)nc(=O)n2C(C)C]

To a mixture of 3.65 g (10.8 mmol)1-isopropyl-4-(4-isopropyl-phenyl)-6-methoxy-3,4-dihydro-1.H.-quinazolin-2-one, 4 ml CCl₄, 4 ml acetonitrile and 8 ml water are added 3.45 g (16.2 mmol) sodium periodate and a trace of ruthenium trichloride hydrate. After stirring overnight water is added and the reaction mixture is extracted with dichloromethane. The organic layer is dried over MgSO₄ and completely evaporated. The remaining solid is washed with diethyl ether to yield 1-isopropyl-4-(4-isopropyl-phenyl)-6-methoxy-1.H.-quinazolin-2-one.

¹H NMR (CDCl₃, 300 MHz): 7.70 (d, 2H), 7.54 (d, 1H), 7.38-7.31 (m, 4H), 5.21 (hept, 1H), 3.78 (s, 3H), 3.00 (hept, 1H), 1.69 (d, 7.0, 6H), 1.30 (d, 7.0, 6H). MS: 337 (M+1)⁺

The compounds of the following examples are prepared by analogy to the example described immediately above:

Example 25

1-Isopropyl-4-(4-isopropyl-2-methyl-phenyl)-6-methoxy-1.H.-quinazolin-2-one

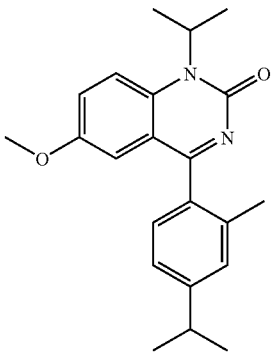

¹H NMR (300 MHz, CDCl₃): 7.54 (d, 1H), 7.33 (dd, 1H), 7.26 (d, 1H), 7.15 (m, 2H), 6.87 (d, 1H), 5.28 (m, 1H), 3.71 (s, 3H), 2.94 (hept, 1H), 2.22 (s, 3H), 1.70 (d, 6H), 1.28 (d, 6H). MS: 351 (M+1)⁺

Example 26

4-(4-Ethyl-phenyl)-1-isopropyl-6-methoxy-1.H.-quinazolin-2-one

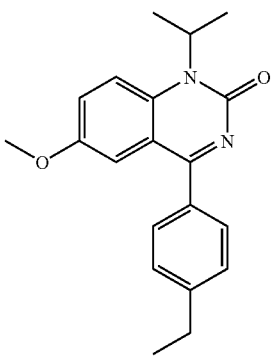 [SMILES: CCc1ccc(-c2nc(=O)n(C(C)C)c3ccc(OC)cc23)cc1]

¹H NMR (300 MHz, CDCl₃): 769 (.d, 2H), 7.54 (d, 1H), 7.36-7.29 (m, 4H), 5.22 (hept, 1H), 3.77 (s, 3H), 2.74 (q, 2H), 1.68 (d, 6H), 1.29, t, 3H).

Example 27

4-(4-tert.-Butyl-phenyl)-1-isopropyl-6-methoxy-1.H.-quinazolin-2-one

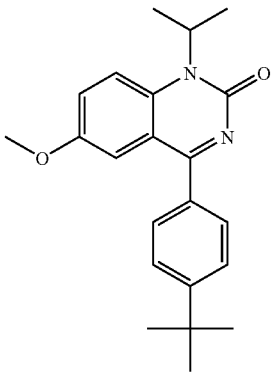 [SMILES: COc1ccc2c(c1)c(-c1ccc(C(C)(C)C)cc1)nc(=O)n2C(C)C]

¹H NMR (300 MHz, CDCl₃): 7.71 (d, 2H), 7.54 (d, 1H), 7.35-7.31 (m, 4H), 5.21 (hept, 1H), 3.79 (s, 3H), 1.69 (d, 6H), 1.38 (s, 9H). MS: 351 (M+1)⁺

Example 28

1-Cyclopentyl-4-(4-isopropyl-phenyl)-6-methoxy-1.H.-quinazolin-2-one

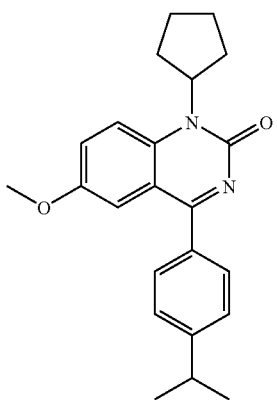 [SMILES: COc1ccc2c(c1)c(-c1ccc(C(C)C)cc1)nc(=O)n2C1CCCC1]

¹H NMR (300 MHz, CD₃OD): 7.78 (d, 1H), 7.68 (d, 2H), 7.51 (dd, 1H), 7.47 (d, 2H), 7.28 (d, 1H), 5.32 (quint, 1H), 3.77 (s, 3H), 3.04 (hept, 1H), 2.41-2.29 (m, 2H), 2.19-2.00 (m, 4H), 1.84-1.73 (m, 2H), 1.33 (d, 6H). MS: 363 (M+1)⁺

Example 29

1-Benzyl-4-(4-isopropyl-phenyl)-6-methoxy-1.H.-quinazolin-2-one

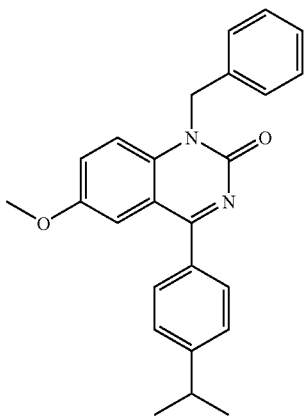 [SMILES: COc1ccc2c(c1)c(-c1ccc(C(C)C)cc1)nc(=O)n2Cc1ccccc1]

¹H NMR (300 MHz, CDCl₃): 7.73 (d, 2H), 7.40 (d, 2H), 7.35 (t, 1H), 7.33-7.24 (m, 7H), 5.56 (s, 2H), 3.76 (s, 3H), 3.02 (hept, 1H), 1.32 (d, 6H). MS: 385 (M+1)⁺

Example 30

1-(3-chloro-propyl)-4-(4-isopropyl-phenyl)-6-methoxy-1.H.-quinazolin-2-one

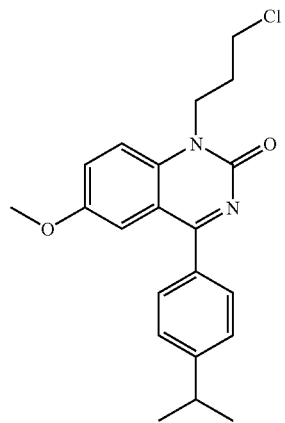 [SMILES: COc1ccc2c(c1)c(-c1ccc(C(C)C)cc1)nc(=O)n2CCCCl]

This compound is prepared analogously to 1-isopropyl-4-(4-isopropyl-phenyl)-6-methoxy-1.H.-quinazolin-2-one starting from 4-methoxy-aniline and 1-bromo-3-chloropropane.

¹H NMR: (300 MHz, CD₃OD): 7.74 (d, 2H), 7.71 (d, 1H), 7.63 (dd, 1H), 7.51 (d, 1H), 7.33 (d, 1H), 4.51 (m, 2H), 3.80 (s, 3H), 3.78 (t, 2H), 3.06 (hept, 1H), 2.29 (m, 2H), 1.34 (d, 6H). MS: 377 (M+1)⁺

Synthesis of 6-hydroxy-1-isopropyl-4-(4-isopropyl-phenyl)-1.H.-quinazolin-2-one and 6-allyloxy-1-isopropyl-4-(4-isopropyl-phenyl)-1.H.-quinazolin-2-one

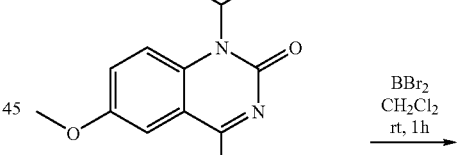

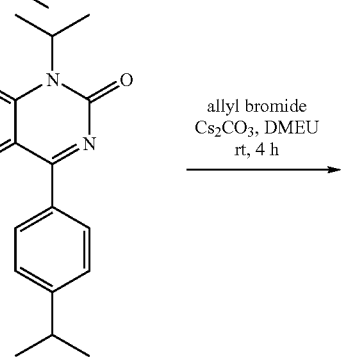

Example 31

Synthesis of 6-hydroxy-1-isopropyl-4-(4-isopropyl-phenyl)-1.H.-quinazolin-2-one

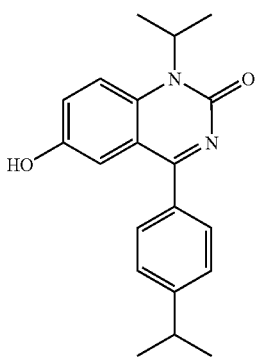 [SMILES: CC(C)c1ccc(-c2nc(=O)n(C(C)C)c3ccc(O)cc23)cc1]

To 4.63 g (13.8 mmol) 1-isopropyl-4-(4-isopropyl-phenyl)-6-methoxy-1.H.-quinazolin-2-one are added first 10 ml dichloromethane followed by 27.6 ml (27.6 mmol) of a 1M solution of BBr$_3$ in dichloromethane. After stirring overnight at room temperature further 14 ml (14 mmol) BBr$_3$ solution are added. One hour later the reaction mixture is poured onto water and extracted with dichloromethane. The organic phase is evaporated and the residue recrystallized from diethyl ether.

$^1$H NMR (CD$_3$OD, 300 MHz): 8.00 (d, 1H), 7.76 (d, 2H), 7.74 (dd, 1H), 7.65 (d, 2H), 7.28 (d, 1H), 5.34 (m, 1H), 3.12 (hept, 1H), 1.72 (d, 6H), 1.36 (d, 6H). MS: 323 (M+1)$^+$

Example 32

Synthesis of 6-allyloxy-1-isopropyl-4-(4-isopropyl-phenyl)-1.H.-quinazolin-2-one

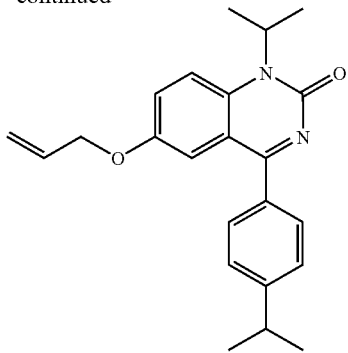

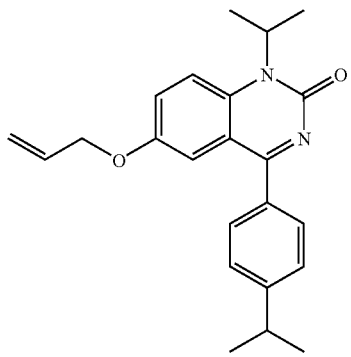

To a solution of 0.2 g (0.62 mmol) 6-hydroxy-1-isopropyl-4-(4-isopropyl-phenyl)-1.H.-quinazolin-2-one in 1 ml DMEU are added 0.303 g (0.93 mmol) cesium carbonate and 78.8 μl (0.93 mmol) allyl bromide. After stirring for 3 days at room temperature the reaction mixture is extracted with water/dichloromethane. Evaporation of the organic phase followed by preparative HPLC yields 6-allyloxy-1-isopropyl-4-isopropyl-phenyl)-1.H.-quinazolin-2-one.

$^1$H NMR (CDCl$_3$, 300MHz): 7.68 (dt, 2H), 7.52 (d, 1H), 7.38-7.32 (m, 4H), 6.00 (ddt, 1H), 5.37 (dq, 1H), 5.31 (dq, 1H), 5.20 (hept, 1H), 4.50 (dt, 1H), 3.00 (hept, (1H), 1.69 (d, 6H), 1.31 (d, 6H). MS: 363 (M+1)$^+$ The compounds of the following examples are prepared by analogy to the example described immediately above:

Example 33

1-Isopropyl-4-(4-isopropyl-phenyl)-6-propoxy-1.H.-quinazolin-2-one

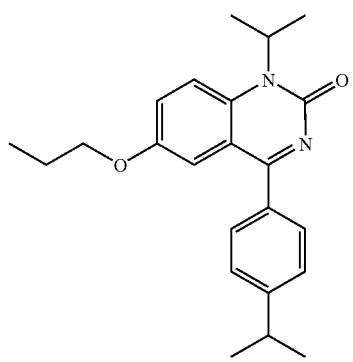 [SMILES: CCCOc1ccc2c(c1)c(-c1ccc(C(C)C)cc1)nc(=O)n2C(C)C]

$^1$H NMR (300 MHz, CDCl$_3$): 7.70 (d, 2H), 7.52 (d, 1H), 7.37 (d, 2H), 7.34 (dd, 1H), 7.31 (d, 1H), 5.21 (hept, 1H), 3.87 (t, 2H), 3.00 (hept, 1H), 1.79 (hex, 2H), 1.71 (d, 6H), 1.31 (d, 6H), 1.02 (t, 3H). MS: 365 (M+1)$^+$

Example 34

6-Ethoxy-1-isopropyl-4-(4-isopropyl-phenyl)-1.H.-quinazolin-2-one

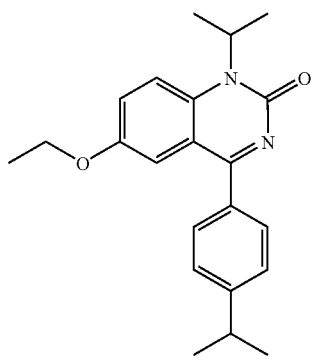 [SMILES: CCOc1ccc2c(c1)c(-c1ccc(C(C)C)cc1)nc(=O)n2C(C)C]

$^1$H NMR (300 MHz, CDCl$_3$): 7.70 (d, 2H), 7.53 (d, 1H), 7.37 (d, 2H), 7.33 (d, 1H), 7.31 (s, 1H), 5.21 (hept, 1H), 3.98 (q, 2H), 3.00 (hept, 1H), 1.69 (d, 6H), 1.40 (t, 3H), 1.31 (d, 6H). MS: 351 (M+1)$^+$

Example 35

6-Isopropoxy-1-isopropyl-4-(4-isopropyl-phenyl)-1.H.-quinazolin-2-one

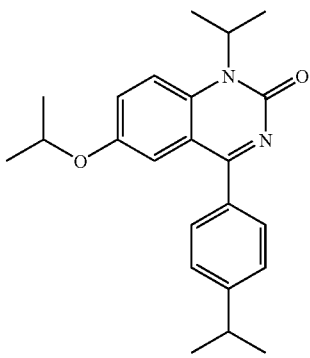 [SMILES: CC(C)Oc1ccc2c(c1)c(-c1ccc(C(C)C)cc1)nc(=O)n2C(C)C]

¹H NMR (300 MHz, CDCl₃): 7.69 (d, 2H), 7.52 (m, 1H), 7.37 (d, 2H), 7.34-7.30 (m, 3H), 5.21 (hept, 1H), 4.45 (hept, 1H), 3.00 (hept, 1H), 1.69 (d, 6H), 1.31 (d, 6H), 1.31 (d, 6H). MS: 365 (M+1)⁺

Example 36

6-Butoxy-1-isopropyl-4-(4-isopropyl-phenyl)-1.H.-quinazolin-2-one

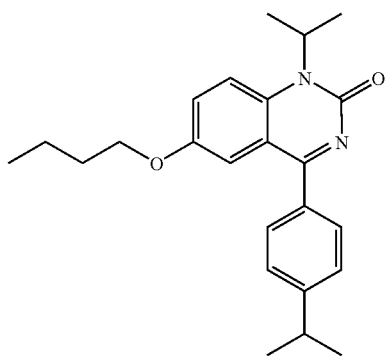 [SMILES: CCCCOc1ccc2c(c1)c(-c1ccc(C(C)C)cc1)nc(=O)n2C(C)C]

¹H NMR (300 MHz, CDCl₃): 7.70 (d, 2H), 7.53 (d, 1H), 7.37 (d, 2H), 7.35-7.30 (m, 2H), 5.21 (hept, 1H), 3.91 (t, 2H), 3.00 (hept, 1H), 1.75 (quint, 2H), 1.69 (d, 6H), 1.47 (hex, 2H), 1.31 (d, 6H), 0.95 (t, 3H). MS: 379 (M+1)⁺

Example 37

1-Isopropyl-4-(4-isopropyl-phenyl)-6-propargyloxy-1.H.-quinazolin-2-one

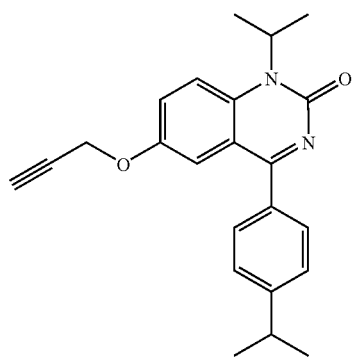 [SMILES: C#CCOc1ccc2c(c1)c(-c1ccc(C(C)C)cc1)nc(=O)n2C(C)C]

¹H NMR (300 MHz, CDCl₃): 7.72 (d, 2H), 7.55 (d, 1H), 7.45 (d, 1H), 7.40 (dd, 1H), 7.36 (d, 2H), 5.20 (hept, 1H), 4.66 (d, 2H), 3.00 (hept, 1H), 2.56 (t, 1H), 1.69 (d, 6H), 1.31 (d, 6H). MS: 361 (M+1)⁺

Example 38

1-Isopropyl-4-(4-isopropyl-phenyl)-6-(2-methyl-allyloxy)-1.H.-quinazolin-2-one

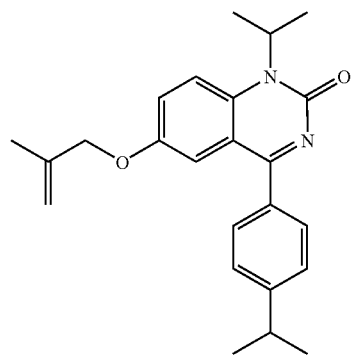 [SMILES: C=C(C)COc1ccc2c(c1)c(-c1ccc(C(C)C)cc1)nc(=O)n2C(C)C]

¹H NMR (300 MHz, CDCl₃): 7.68 (d, 2H), 7.52 (d, 1H), 7.37-7.29 (m, 4H), 5.20 (hept, 1H), 5.01 (s, 2H), 4.40 (s, 2H), 2.99 (hept, 1H), 1.78 (s, 3H), 1.69 (d, 6H), 1.30 (d, 6H). MS: 377 (M+1)⁺

Example 39

6-(2-Chloro-ethoxy)-1-isopropyl-4-(4-isopropyl-phenyl)-1.H.-quinazolin-2-one

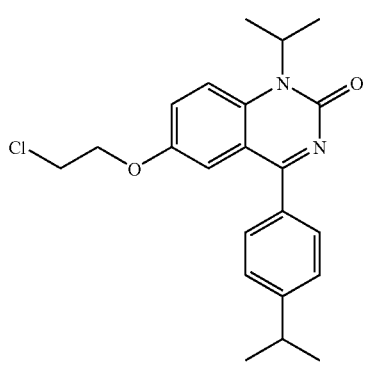 [SMILES: CC(C)c1ccc(-c2nc(=O)n(C(C)C)c3ccc(OCCCl)cc23)cc1]

¹H NMR (300 MHz, CDCl₃): 7.68 (d, 2H), 7.55 (d, 1H), 7.40-7.33 (m, 4H), 5.20 (hept, 1H), 4.19 (t, 2H), 3.81 (t, 2H), 3.01 (hept, 1H), 1.69 (d, 6H), 1.31 (d, 6H). MS: 387 (30), 385 (100) (chloro isotope pattern) (M+1)⁺

Example 40

6-(3-Chloro-propoxy)-1-isopropyl-4-(4-isopropyl-phenyl)-1.H.-quinazolin-2-one

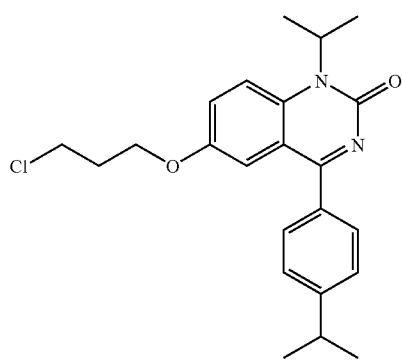 [SMILES: CC(C)c1ccc(-c2nc(=O)n(C(C)C)c3ccc(OCCCCl)cc23)cc1]

$^1$H NMR (300MHz, CDCl$_3$): 7.71 (d, 2H), 7.55 (dd, 1H), 7.39 (d, 2H), 7.37 (m, 1H), 7.34 (m, 1H), 5.21 (hept, 1H), 4.08 (t, 2H), 3.74 (t, 2H), 3.01 (hept, 1H), 2.22 (quint, 2H), 1.69 (d, 6H), 1.31 (d, 6H). MS: 401 (30), 399 (100) (chloro isotope pattern) (M+1)$^+$

Example 41

6-Cyclopropylmethoxy-1-isopropyl-4-(4-isopropyl-phenyl)-1.H.-quinazolin-2-one

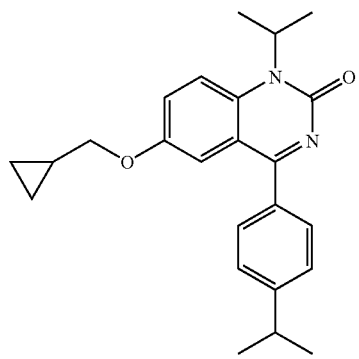 [SMILES: CC(C)c1ccc(-c2nc(=O)n(C(C)C)c3ccc(OCC4CC4)cc23)cc1]

$^1$H NMR (300 MHz, CDCl$_3$): 7.69 (d, 2H), 7.53 (d, 1H), 7.37 (d, 2H), 7.35 (dd, 1H), 7.31 (d, 1H), 5.20 (hept, 1H), 3.76 (d, 2H), 3.00 (hept, 1H), 1.69 (d, 6H), 1.31 (d, 6H), 1.25 (m, 1H), 0.68-0.62 (m, 2H), 0.36-0.31 (m, 2H). MS: 377 (M+1)$^+$

Example 42

Synthesis of 5-allyl-6-hydroxy-1-isopropyl-4-(4-isopropyl-phenyl)-1.H.-quinazolin-2-one

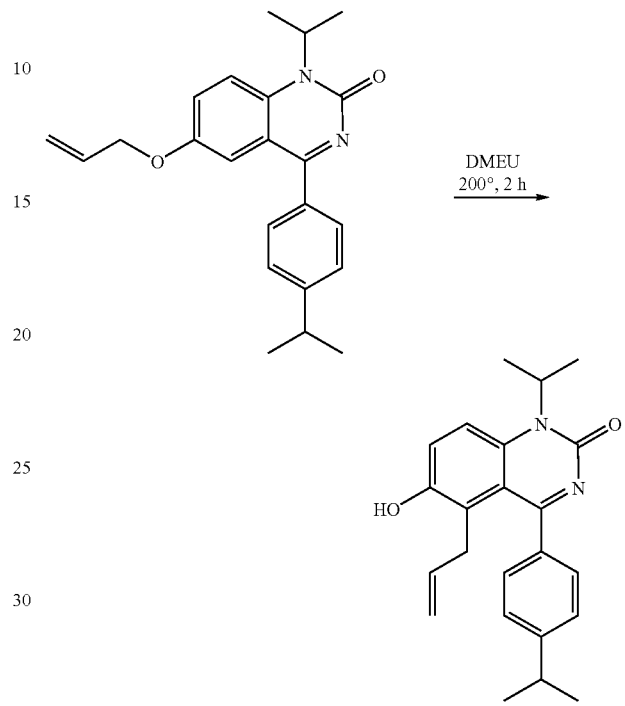

A solution of 40 mg (0.11 mmol) 6-allyloxy-1-isopropyl-4-(4-isopropyl-phenyl)-1.H.-quinazolin-2-one in 4 ml DMEU is heated in an oil bath of 200° C. for 2 h. Preparative HPLC of the reaction mixture affords 5-allyl-6-hydroxy-1-isopropyl-4-(4-isopropyl-phenyl)-1.H.-quinazolin-2-one.

$^1$H NMR (300MHz, CDCl$_3$): 7.51 (d, 1H), 7.48 (d, 2H), 7.39 (d, 1H), 7.25 (d, 2H), 5.63 (ddt, 1H), 5.02 (d, 1H), 4.94 (m, 1H), 4.87 (d, 1H), 3.23 (d, 2H), 2.94 (hept, 1H), 1.69 (d, 6H), 1.26 (d, 6H). MS: 363 (M+1)$^+$

Example 43

Synthesis of 5-allyl-1-isopropyl-4-(4-isopropyl-phenyl-6-methoxy-1.H.-quinazolin-2-one

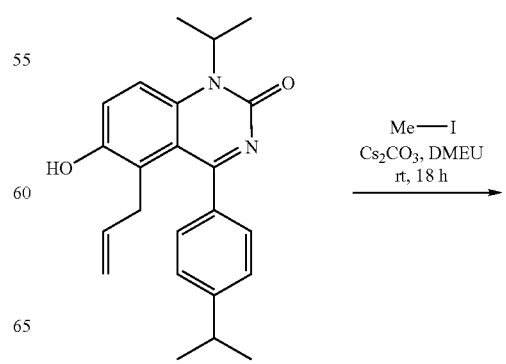

-continued

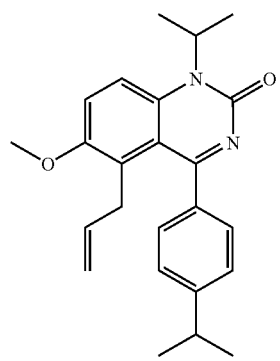

A mixture of 10 mg (27.6 μmol) 5-allyl-6-hydroxy-1-isopropyl-4-(4-isopropyl-phenyl)-1.H.-quinazolin-2-one, 13.5 mg (41.4 μmol) cesium carbonate, 0.3 ml DMEU and 2.6 μl (41.4 μmol) methyl iodide is stirred overnight. After extraction with water/dichloromethane the crude product is purified by preparative HPLC.

$^1$H NMR (300 MHz, CDCl$_3$): 7.49 (d, 2H), 7.42 (d, 1H), 7.35 (d, 1H), 7.26 (d, 2H), 5.51 (ddt, 1H), 4.89 (hept, 1H), 4.74 (d, 1H), 4.47 (d, 1H), 3.87 (s, 3H), 3.26 (d, 2H), 2.95 (hept, 1H), 1.68 (d, 6H), 1.26 (d, 6H). MS: 377 (M+1)$^+$ The compound of the following example is prepared by analogy to the example described immediately above:

Example 44

5-Allyl-1-isopropyl-4-(4-isopropyl-phenyl)-6-propargyloxy-1.H.-quinazolin-2-one

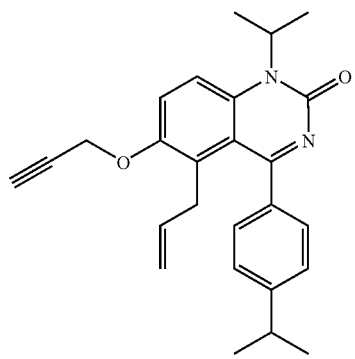 [SMILES: C#CCOc1ccc2c(c(-c3ccc(C(C)C)cc3)nc(=O)n2C(C)C)c1CC=C]

$^1$H NMR (300 MHz, CDCl$_3$): 7.50 (d, 2H), 7.49, (d, 1H), 7.43 (d, 1H), 7.26 (d, 2H), 5.50, (ddt, 1H), 4.88 (hept, 1H), 4.76 (d, 1H), 4.74 (d, 2H), 4.49 (d, 1H), 3.29 (d, 2H), 2.95 (hept, 1H), 2.53 (t, 2H), 1.68 (d, 6H), 1.26 (d, 6H). MS: 401 (M+1)$^+$ Example 45

[1-Benzyl-4-(4-isopropyl-phenyl)-2-oxo-1,2-dihydro-quinazolin-6-yloxy]-acetonitrile A. Synthesis of 1-benzyl-6-hydroxy-4-(4-isopropyl-phenyl)-1H-quinazolin-2-one

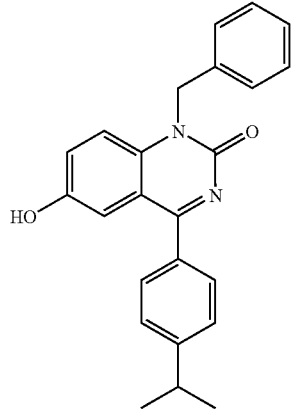 [SMILES: CC(C)c1ccc(-c2nc(=O)n(Cc3ccccc3)c3ccc(O)cc23)cc1]

A solution of 470 mg (1.22 mmol) of 1-benzyl-4-(4-isopropyl-phenyl)-6-methoxy-1H-quinazolin-2-one in 5 ml anhydrous THF is treated at 0° C. dropwise with 2.44 ml 1.0 M (2.44 mmol; 2 eq.) boron tribromide solution (in methylene chloride). After complete addition, the mixture is allowed to come to rt and stirred for 4 h. The yellow-red solution is poured into water and extracted with CH$_2$Cl$_2$. Concentration in vacuo afforded a yellow solid. yield: 360 mg (80%). m.p.>270° C.

$^1$H-NMR (300 MHz, CDCl$_3$): 7.64 (d, 2H), 7.17-7.37 (m, 12H), 5.53 (broad, 1H), 2.94 (hept, 1H), 1.26 (d, 6H). MS: 371 (M+1)$^+$ B. Synthesis of [1-benzyl-4-(4-isopropyl-phenyl)-2-oxo-1,2-dihydro-quinazolin-6-yloxy]-acetonitrile

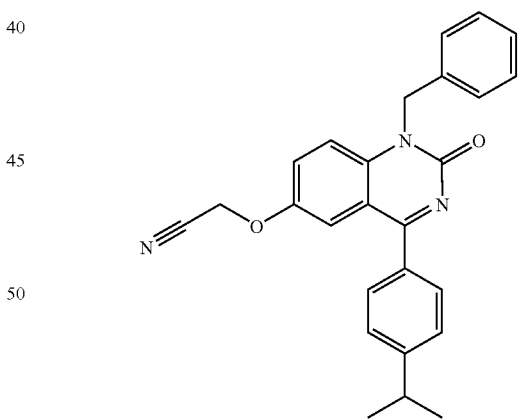

A mixture of 100 mg (0.27 mmol) of the phenol obtained in the previous step, 22 μl (0.35 mmol; 1.3 eq.) chloroacetonitrile and 44.8 mg (0.32 mmol; 1.2 eq.) potassium carbonate was stirred at 60° C. for 6 h. Since TLC showed incomplete reaction, another 1.5 eq. chloro acetonitrile are added and stirring is continued for 4 h. The dark suspension is extracted with ethyl acetate/water. Purification by column chromatography (ethyl acetate/petroleum ether) results in 66 mg (60%) of the title compound. m.p. 139-141° C.

$^1$H-NMR (300 MHz, CDCl$_3$): 7.77 (d, 2H), 7.50 (broad s, 1H), 7.42 (d, 2H), 7.27-7.39 (m, 7H), 5.57 (broad s, 2H), 4.72 (s, 2H); 3.03 (hept, 1H), 1.34 (d, 6H). MS: 410 (M+1)$^+$

Example 46
Synthesis of 1-(3-chloro-benzyl)-4-(4-isopropyl-phenyl)-6-methoxy-1.H.quinazolin-2-one
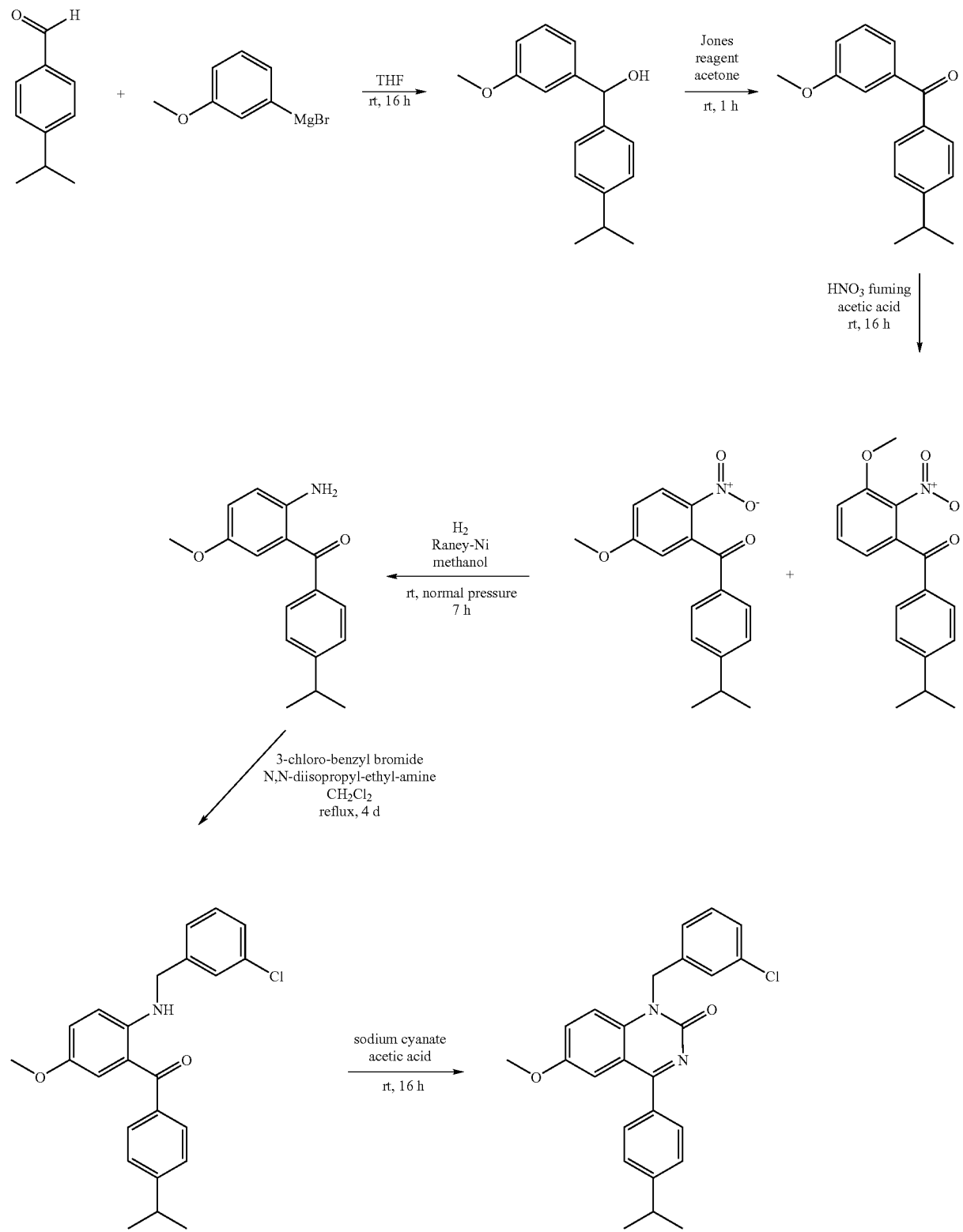

A. Synthesis of (4-isopropyl-phenyl)-(3-methoxy-phenyl)-methanol:

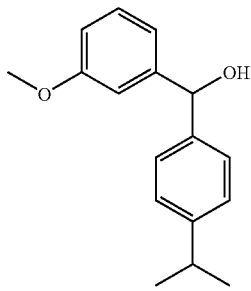 [SMILES: COc1cccc(C(O)c2ccc(C(C)C)cc2)c1]

To 3.4 g (139 mmol) magnesium covered with THF is added a first small portion of a solution of 26 g (139 mmol) 3-bromo-anisol in 150 ml THF. The Grignard reaction is initiated by gentle heating and the rest of the 3-bromoanisol solution is added dropwise. After the reaction had stopped a solution of 20.9 ml (139 mmol) cumic aldehyde in 100 ml THF is added slowly at 20°-30° C. After stirring for 3 h at rt the reaction mixture is poured on saturated aqueous ammonium chloride solution and extracted with diethyl ether. After evaporation of the solvent crude (4-isopropyl-phenyl)-(3-methoxy-phenyl)-methanol is obtained that is directly oxidized in the next step.

MS: 239 (M–OH)$^+$

B. Synthesis of (4-isopropyl-phenyl)-(3-methoxy-phenyl)-methanone

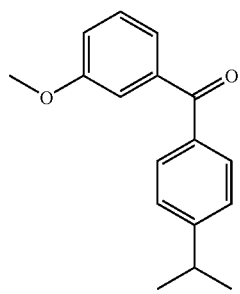 [SMILES: COc1cccc(C(=O)c2ccc(C(C)C)cc2)c1]

To a solution of 34.5 g (134 mmol) (4-isopropyl-phenyl)-(3-methoxy-phenyl)-methanol in 200 ml acetone is added slowly 50 ml Jones reagent (taken from an aqueous stock solution of 100 ml containing 26.7 g CrO$_3$ and 23 ml H$_2$SO$_4$). After 1 h stirring at rt 80 ml isopropanol and 50 ml sodium bisulfite (40% in water) are added.

The reaction mixture is poured on saturated ammonium chloride solution and extracted with dichloromethane. After evaporation of the solvent followed by flash chromatography using a gradient going from hexanes to hexanes/ethyl acetate (9:1) (4-isopropyl-phenyl)-(3-methoxy-phenyl)-methanone is obtained.

$^1$H NMR (300 MHz, CDCl$_3$): 7.77 (d, 2H), 7.40-7.32 (m, 5H), 7.13 (m, 1H), 3.86 (s, 3H), 2.99 (hept, 1H), 1.30 (d, 6H). MS: 255 (M+1)$^+$ C. Synthesis of (4-isopropyl-phenyl)-(5-methoxy-2-nitro-phenyl)-methanone and (4-isopropyl-phenyl)-(3-methoxy-2-nitro-phenyl)-methanone

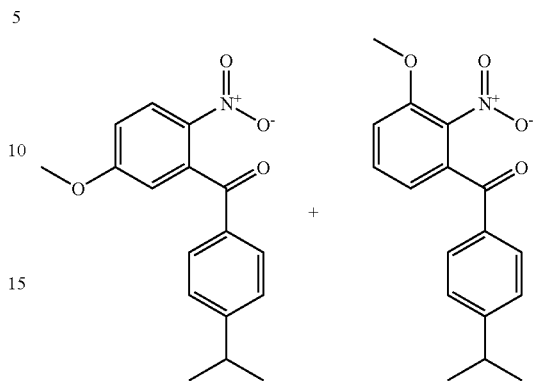

To a solution of 21.6 g (84.9 mmol) (4-isopropyl-phenyl)-(3-methoxy-phenyl)-methanone is added slowly at 5°-10° C. 60 ml nitric acid (100%). After stirring overnight the reaction mixture is neutralized with aqueous sodium hydroxide (20%) and extracted with dichloromethane. The different isomers are separated by means of column chromatography using a gradient going from hexanes to hexanes/ethyl acetate (8:1).

(4-isopropyl-phenyl)-(5-methoxy-2-nitro-phenyl)-methanone:

$^1$H NMR (300 MHz, CDCl$_3$): 8.25 (d, 1H), 7.69 (d, 2H), 7.30 (d, 2H), 7.07 (dd, 1H), 6.87 (d, 1H), 3.91 (s, 3H), 2.96 (hept, 1H), 1.26 (d, 6H). MS: 330 (35) (M+1)$^+$, 270 (100)

(4-isopropyl-phenyl)-(3-methoxy-2-nitro-phenyl)-methanone (RE 1445, unknown):

$^1$H NMR (300 MHz, CDCl$_3$): 7.75 (d, 2H), 7.53 (t, 1H), 7.31 (d, 2H), 7.23 (d, 1H), 7.08 (d, 1H), 3.98 (s, 3H), 2.97 (hept, 1H), 1.27 (d, 6H). MS: 300 (7) (M+1)$^+$, 270 (100).

D. Synthesis of (2-amino-5-methoxy-phenyl)-(4-isopropyl-phenyl)-methanone

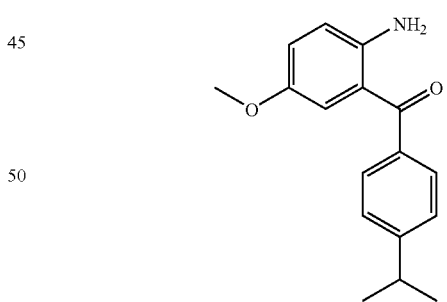

A solution of 5.6 g (18.7 mmol) (4-isopropyl-phenyl)-(5-methoxy-2-nitro-phenyl)-methanone in 100 ml methanol is hydrogenated in the presence of 2 g Raney nickel at 5 bar for 5 h. The reaction mixture is filtered and the filtrate is evaporated. The residue is dissolved in ether and the product is precipitated by the addition of gaseous hydrochloric acid as its hydrochloride.

$^1$HNMR (300 MHz, CDCl$_3$): 8.03 (d, 1H), 7.70 (d, 2H), 7.28 (d, 2H), 7.12 (d, 1H), 7.07 (dd, 1H), 3.77 (s, 3H), 2.96 (hept, 1H), 1.27 (d, 6H). MS: 270 (M+1)$^+$ E. Synthesis of [2-(3-chloro-benzylamino)-5-methoxy-phenyl]-(4-isopropyl-phenyl)-methanone

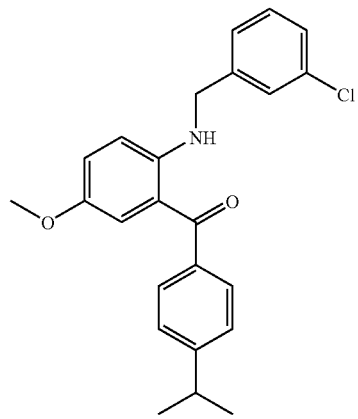 [SMILES: COc1ccc(NCc2cccc(Cl)c2)c(C(=O)c2ccc(C(C)C)cc2)c1]

To a solution of 100 mg (0.327 mmol) (2-amino-5-methoxy-phenyl)-(4-isopropyl-phenyl)-methanone in 1 ml dichloromethane is added 140 µl (0.818 mmol) N,N-diisopropylethylamine and 48.7 µl (0.360 mmol)3-chloro-benzyl bromide. The reaction mixture is heated under reflux for 4 days and extracted with water/dichloromethane. The organic residue is chromatographed. For further purification the corresponding hydrochloride is precipitated form an etheric solution by addition of gaseous hydrochloric acid.

$^1$H NMR (300 MHz, CD$_3$OD): 7.67 (d, 2H), 7.43 (d, 2H), 7.47-7.19 (m, 5H), 7.16 (d, 1H), 7.07 (t, broad, 1H), 4.66 (s, 2H) 3.81 (s, 3H), 3.03 (hept, 1H), 1.31 (d, 6H). MS: 396 (30), 394 (100) (chloro isotope pattern) (M+1)$^+$ F. Synthesis of 1-(3-chloro-benzyl)-4-(4-isopropyl-phenyl)-6-methoxy-1.H.-quinazolin-2-one

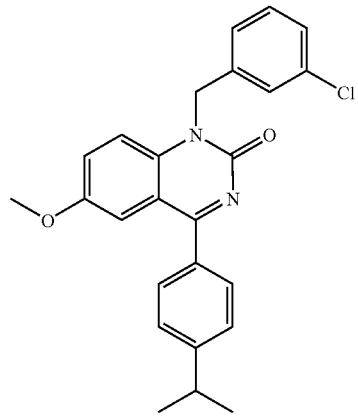 [SMILES: COc1ccc2c(c1)c(-c1ccc(C(C)C)cc1)nc(=O)n2Cc1cccc(Cl)c1]

A solution of 40 mg (102 µmol) [2-(3-chloro-benzylamino)-5-methoxy-phenyl]-(4-isopropyl-phenyl)-methanone as its free base in 0.8 ml acetic acid is treated with 6.6 mg (102 µmol) sodium cyanate and stirred overnight at rt. The reaction mixture is basified with aqueous sodium hydroxide solution (1M), extracted with ethyl acetate and purified by preparative HPLC.

$^1$H NMR (300 MHz, CDCl$_3$): 7.74 (d, 2H), 7.41-7.37 (m, 3H), 7.29-7.16 (m, 6H), 5.52 (s, 2H), 3.77 (s, 3H), 3.01 (hept, 1H), 1.32 (d, 6H). MS: 421 (30), 419 (100) (chloro isotope pattern) (M+1)$^+$ The following methanone is prepared analogously to the steps A to E of the example described immediately above:

(2-Isopropylamino-5-methoxy-phenyl)-(4-isopropyl-phenyl) methanone

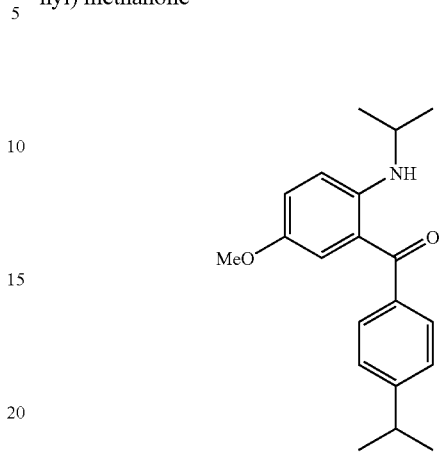

$^1$H-NMR (300 MHz, CDCl$_3$): 8.06 (d, NH), 7.58 (d, 2H), 7.29 (d, 2H), 7.03-7.10 (m, 2H), 4.76 (d, 1H), 5.75 (hept, 1H), 3.67 (s, 3H), 2.97 (hept, 1H), 1.29 (d, 6H), 1.28 (d, 6H). MS: 312 (M+1)$^+$ The compounds of the following examples are prepared by analogy to example 46:

Example 47

1-(3-Fluoro-benzyl)-4-(4-isopropyl-phenyl)-6-methoxy-1.H.-quinazolin-2-one

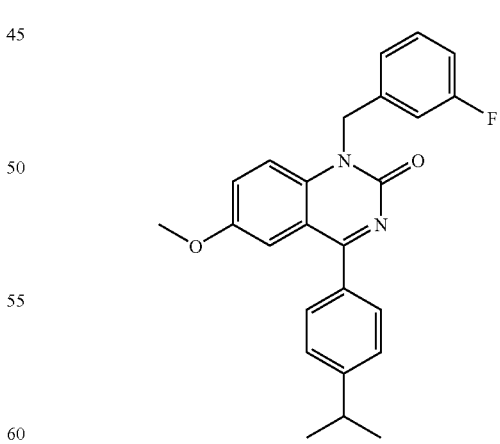

$^1$H NMR (300 MHz, CDCl$_3$): 7.74 (d, 2H), 7.39 (d, 2H), 7.37 (m, 1H), 7.32-7.24 (m, 2H), 7.18 (d, 1H), 7.09 (d, 1H), 7.00-6.92 (m, 2H), 5.53 (s, 2H), 3.76 (s, 3H), 3.01 (hept, 1H), 1.31 (d, 6H). MS: 403 (M+1)$^+$

Example 48

4-(4-Isopropyl-phenyl)-6-methoxy-1-naphthalen-2-ylmethyl-1.H.-quinazolin-2-one

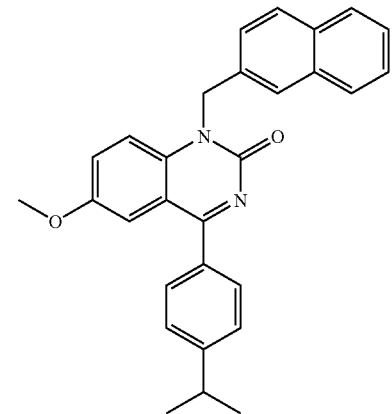 [SMILES: COc1ccc2c(c1)c(-c1ccc(C(C)C)cc1)nc(=O)n2Cc1ccc2ccccc2c1]

¹H NMR (300 MHz, CDCl₃): 7.83-7.72 (m, 6H), 7.49-7.36 (m, 6H), 7.31-7.18 (m, 2H), 5.72 (s, 2H), 3.74 (s, 3H), 3.02 (hept, 1H), 1.32 (d, 6H). MS: 435 (M+1)⁺

Example 49

4-[4-(4-Isopropyl-phenyl)-6-methoxy-2-oxo-2.H.-quinazolin-1-ylmethyl]-benzonitrile

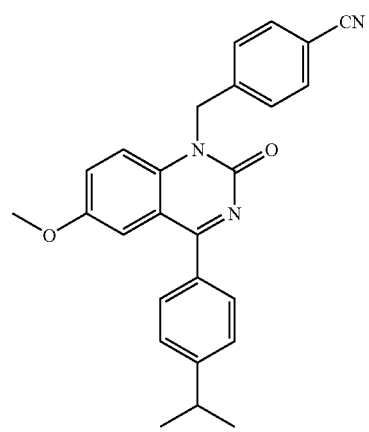 [SMILES: COc1ccc2c(c1)c(-c1ccc(C(C)C)cc1)nc(=O)n2Cc1ccc(C#N)cc1]

¹H NMR (300 MHz, CDCl₃): 7.74 (d, 2H), 7.63 (d, 2H), 7.42-7.39 (m, 5H), 7.27 (m, 1H), 7.09 (d, 1H), 5.59 (s, 2H), 3.77 (s, 3H), 3.02 (hept, 1H), 1.32 (d, 6H). MS: 410 (M+1)⁺

Example 50

4-[4-(4-Isopropyl-phenyl)-6-methoxy-2-oxo-2.H.-quinazolin-1-ylmethyl]-3-methoxy-benzoic acid methyl ester

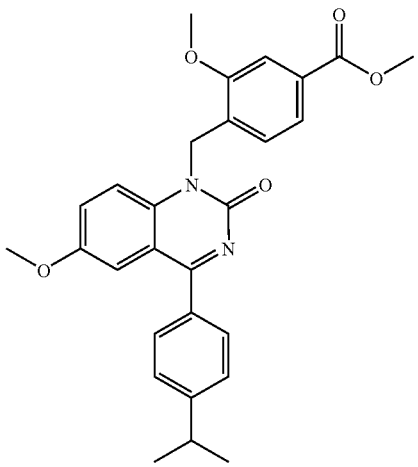

¹H NMR (300 MHz, CDCl₃): 7.75 (d, 2H), 7.59 (s, 1H), 7.50 (d, 1H), 7.40 (d, 2H), 7.37 (d, 1H), 7.23 (dd, 1H), 7.12 (d, 1H), 6.99 (d, 1H), 5.57 (s, 2H), 4.02 (s, 3H), 3.88 (s, 3H), 3.76 (s, 3H), 3.01 (hept, 1H), 1.32 (d, 6H). MS: 473 (M+1)⁺

Example 51

{4-[4-(4-Isopropyl-phenyl)-6-methoxy-2-oxo-2.H.-quinazolin-1-ylmethyl]-phenoxy}-acetonitrile

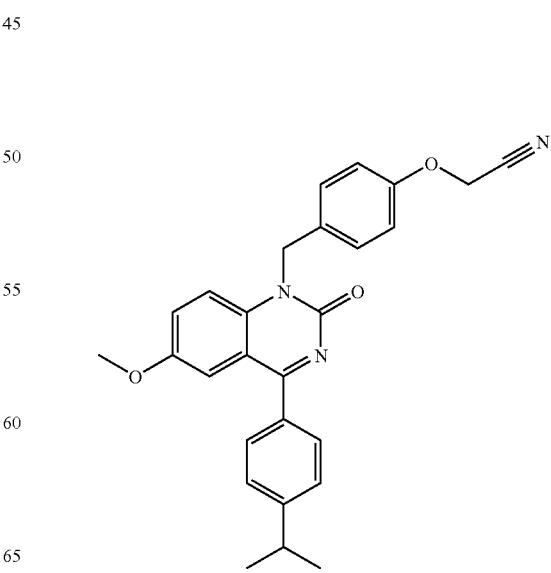

¹H NMR (300 MHz, CDCl₃): 7.73 (d, 2H), 7.40 (d, 2H), 7.36 (d, 1H), 7.33 (d, 2H), 7.27-7.21 (m, 2H), 6.94 (d, 2H), 5.51 (s, 2H), 4.74 (s, 2H), 3.76 (s, 3H), 3.01 (hept, (1H), 1.32 (d, 6H). MS: 440 (M+1)⁺

Example 52

3-[4-(4-Isopropyl-phenyl-6-methoxy-2-oxo-2.H.-quinazolin-1-ylmethyl]-benzoic acid methyl ester

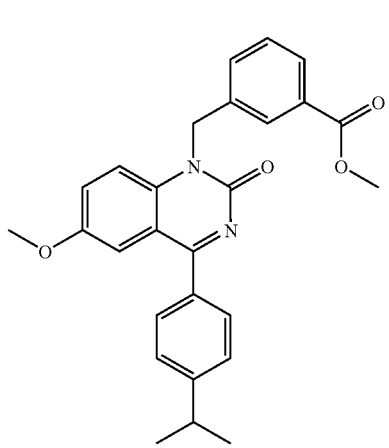

¹H NMR (300 MHz, CDCl₃): 8.02 (s, 1H), 7.95 (d, 1H), 7.75 (d, 2H), 7.50 (d, 1H), 7.40 (d, 2H), 7.39 (m, 1H), 7.37 (d, 1H), 7.25 (dd, 1H), 7.19 (d, 1H), 5.58 (s, 2H), 3.90 (s, 3H), 3.76 (s, 3H), 3.02 (hept, 1H), 1.32 (d, 6H). MS: 443 (M+1)⁺

Example 53

4-(4-Isopropyl-phenyl)-6-methoxy-1-(3-nitro-benzyl)-1.H.-quinazolin-2-one

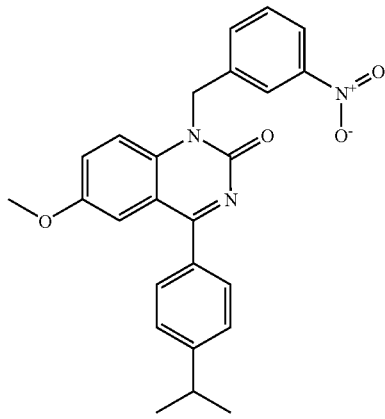 [SMILES: COc1ccc2c(c1)c(-c1ccc(C(C)C)cc1)nc(=O)n2Cc1cccc([N+](=O)[O-])c1]

¹H NMR (300 MHz, CDCl₃): 8.18 (s, 1H), 8.15 (d, 1H), 7.75 (d, 2H), 7.67 (d, 1H), 7.52 (t, 1H), 7.41 (d, 2H), 7.41 (d, 1H), 7.29 (dd, 1H), 7.16 (d, 1H), 5.63 (s, 2H), 3.77 (s, 3H), 3.02 (hept, 1H), 1.32 (d, 6H). MS: 430 (M+1)⁺

Synthesis of 3-[4-(4-isopropyl-phenyl)-6-methoxy-2-oxo-2.H.-quinazolin-1-ylmethyl]-benzoic acid and 3-[4-(4-isopropyl-phenyl)-6-methoxy-2-oxo-2.H.-quinazolin-1-ylmethyl]-benzamide

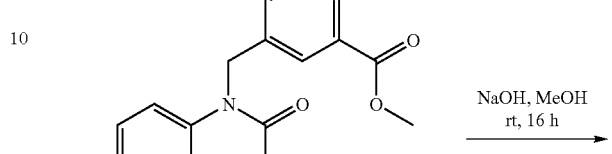

NaOH, MeOH
rt, 16 h

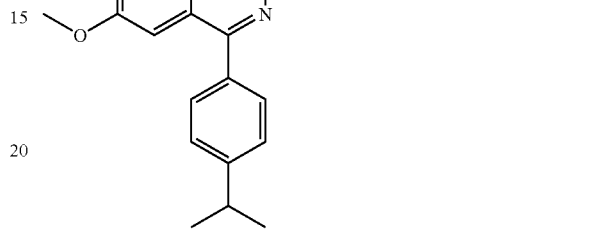

1) (COCl₂), CH₂Cl₂, 16 h, rt
2) ammonia in water/dioxane, 1h, rt

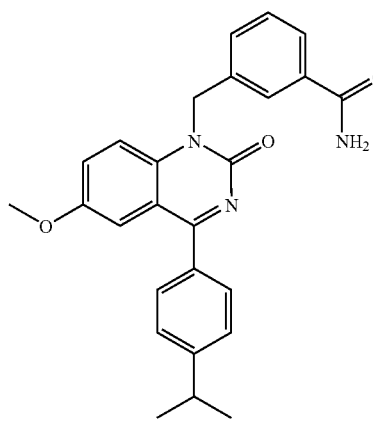

Example 54

3-[4-(4-isopropyl-phenyl)-6-methoxy-2-oxo-2.H.-quinazolin-1-ylmethyl]-benzoic acid

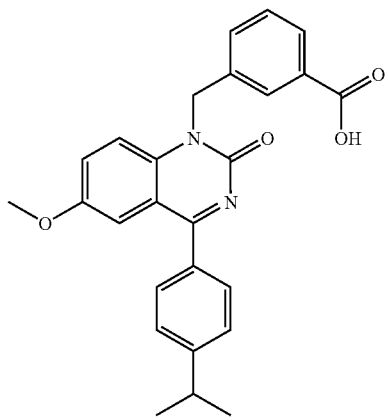 [SMILES: COc1ccc2c(c1)c(-c1ccc(C(C)C)cc1)nc(=O)n2Cc1cccc(C(=O)O)c1]

A solution of 0.67 g (1.51 mmol) 3-[4-(4-isopropyl-phenyl)-6-methoxy-2-oxo-2.H.-quinazolin-1-ylmethyl]-benzoic acid methyl ester 4 ml in methanol is treated with 2.27 ml (2.27 mmol) aqueous sodium hydroxide solution (1M). After stirring overnight the reaction mixture is acidified and extracted with water/dichloromethane. Evaporation of the organic phase affords 3-[4-(4-isopropyl-phenyl)-6-methoxy-2-oxo-2.H.-quinazolin-1-ylmethyl]-benzoic acid.

$^1$H NMR (300 MHz, CDCl$_3$): 8.07 (s, 1H), 8.00 (d, 1H), 7.76 (d, 2H), 7.56 (d, 1H), 7.41 (d, 2H), 7.42 (t, 1H), 7.38 (d, 1H), 7.30 (dd, 1H), 7.24 (d, 1H), 5.61 (s, 2H), 3.76 (s, 3H), 3.01 (hept, 1H), 1.31 (d, 6H). MS: 429 (M+1)$^+$

Example 55

Synthesis of 3-[4-(4-isopropyl-phenyl)-6-methoxy-2-oxo-2.H.-quinazolin-1-ylmethyl]-benzamide

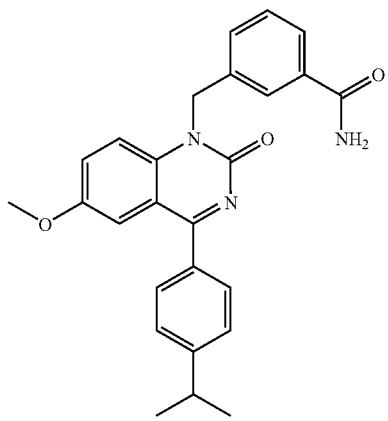

A solution of 0.60 g (1.40 mmol) 3-[4-(4-isopropyl-phenyl)-6-methoxy-2-oxo-2.H.-quinazolin-1-ylmethyl]-benzoic acid in 5 ml dichloromethane is treated with 144 µl (1.68 mmol) oxalyl chloride. After stirring overnight the solvent and the excess of reagent is evaporated and the crude acid chloride is used for the following acylation reaction without purification.

A solution of 30 mg (0.067 mmol) acid chloride in 0.3 ml dioxane is treated with 0.3 ml aqueous ammonia (25%). After stirring for 1 h the reaction mixture is extracted with water/dichloromethane. Evaporation of the organic phase yields 3-[4-(4-isopropyl-phenyl)-6-methoxy-2-oxo-2.H.-quinazolin-1-ylmethyl]-benzamide.

$^1$H NMR (300 MHz, CDCl$_3$): 7.83 (s, 1H), 7.71(d, 2H), 7.71 (d, 1H), 7.42 (d, 1H), 7.38 (d, 2H), 7.35 (t, 1H), 7.35 (d, 1H), 7.25 (dd, 1H), 7.21 (d, 1H), 6.54 (broad, 1H), 5.80 (broad, 1H), 5.54 (s, 2H), 3.74 (s, 3H), 3.00 hept, 1H), 1.30 (d, 6H). MS: 428 (M+1)$^+$ The compounds of the following examples are prepared by analogy to the example described immediately above:

Example 56

3-[4-(4-Isopropyl-phenyl)-6-methoxy-2-oxo-2.H.-quinazolin-1-ylmethyl]-N,N-dimethyl-benzamide

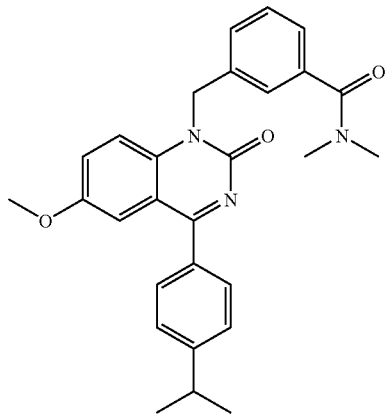

$^1$H NMR (300 MHz, CDCl$_3$): 7.74 (d, 2H), 7.39 (d, 2H), 7.36-7.27 (m, 5H), 7.24 (dd, 1H), 7.18 (d, 1H) 5.56 (s, 2H), 3.75 (s, 3H), 3.07 (s, 3H), 3.01 (hept, 1H), 2.92 (s, 3H), 1.31 (d, 6H). MS: 456 (M+1)$^+$

Example 57

3-[4-(4-Isopropyl-phenyl)-6-methoxy-2-oxo-2.H.-quinazolin-1-ylmethyl]-benzoic acid 2-dimethylamino-ethyl ester

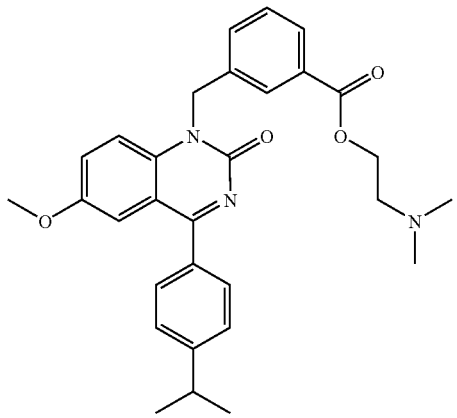

¹H NMR (300 MHz, CDCl₃): 8.01 (s, 1H), 7.94 (d, 1H), 7.73 (d, 2H), 7.47 (d, 1H), 7.39 (d, 2H), 7.36 (d, 1H), 7.40-7.35 (m, 1H), 7.24 (dd, 1H), 7.18 (d, 1H), 5.58 (s, broad, 2H), 4.42 (t, 2H), 3.75 (s, 3H), 3.01 (hept, 1H), 2.72 (t, 2H), 2.33 (s, 6H), 1.31 (d, 6H). MS: 500 (M+1)⁺

Example 58

3-[4-(4-Isopropyl-phenyl)-6-methoxy-2-oxo-2.H.-quinazolin-1-ylmethyl]-N-methyl-benzamide

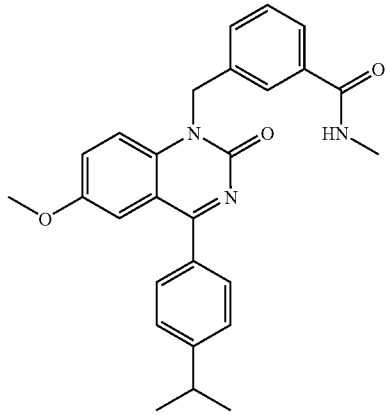

¹H NMR (300 MHz, CDCl₃): 7.74 (s, 1H), 7.73 (d, 2H), 7.67 (d, 1H), 7.45-7.35 (m, 5H), 7.27-7.20 (m, 2H), 6.32 (broad, 1H), 5.55 (broad, 2H), 3.75 (s, 3H), 3.01 (hept, 1H), 2.96 (d, 3H), 1.31 (d, 6H). MS: 442 (M+1)⁺

Example 59

3-[4-(4-Isopropyl-phenyl)-6-methoxy-2-oxo-2.H.-quinazolin-1-ylmethyl]-benzoic acid isopropyl ester

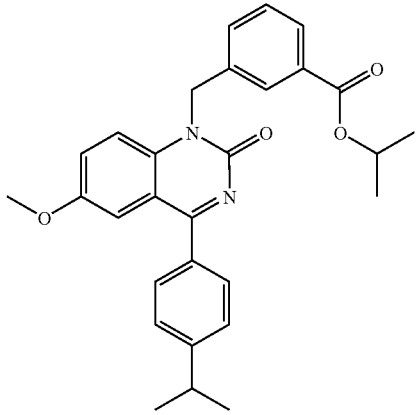 [SMILES: COc1ccc2c(c1)c(-c1ccc(C(C)C)cc1)nc(=O)n2Cc1cccc(C(=O)OC(C)C)c1]

¹H NMR (300 MHz, CDCl₃): 8.03 (s, 1H), 7.93, d, 1H), 7.74, (d, 2H), 7.47-7.35 (m, 5H), 7.28-7.19 (m, 2H), 5.59 (broad, 2H), 5.24 (hept, 1H), 3.76 (s, 3H), 3.01 (hept, 1H), 1.36 (d, 6H), 1.32 (d, 6H). MS: 470 (M+1)⁺

Example 60

3-[4-(4-Isopropyl-phenyl)-6-methoxy-2-oxo-2.H.-quinazolin-1-ylmethyl]-benzoic acid 2-(2-dimethylamino-ethoxy)-ethyl ester

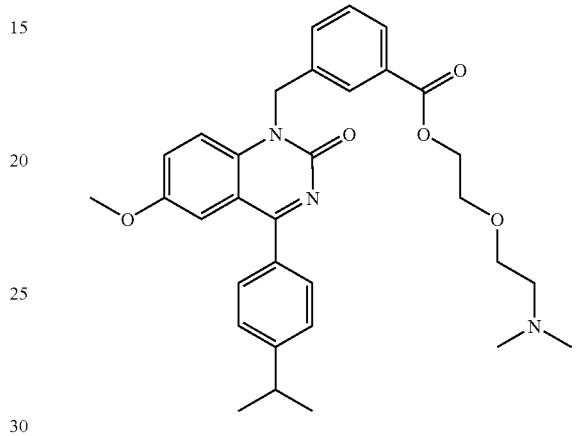

¹H NMR (300 MHz, CDCl₃): 8.04 (s, 1H), 7.96 (d, 1H), 7.74 (d, 2H), 7.47 (d, 1H), 7.40 (d, 2H), 7.41-7.36 (m, 2H), 7.27-7.17 (m, 2H), 5.59 (s, 2H), 4.47 (t, 2H), 3.79 (t, 2H), 3.76 (s, 3H), 3.62 (t, 2H), 3.01 (hept, 1H), 2.52 (t, 2H), 2.26 (s, 6H), 1.32 (d, 6H). MS: 544 (M+1)⁺

Example 61

3-[4-(4-Isopropyl-phenyl)-2-oxo-6-prop-2-ynyloxy-2H-quinazolin-1-ylmethyl]-benzoic acid 2-(2-dimethylamino-ethoxy)-ethyl ester (trifluoroacetic acid salt)

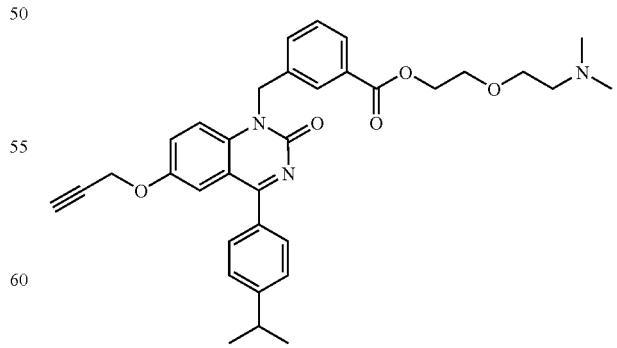

¹H NMR (300 MHz, CDCl₃): 8.07 (s, 1H), 7.99 (d, 1H), 7.73 (d, 2H), 7.61 (d, 1H), 7.54 (s, 1H), 7.50-7.40 (m, 5H), 5.61 (s, 2H), 4.68 (d, 2H), 4.44 (dd, 2H), 3.92 (dd, 2H), 3.79 (dd, 2H), 3.32 (m, 2H), 2.89 (s, 6H), 1.33 (d, 6H). MS: 568 (M+1)⁺

Example 62

3-[4-(4-Isopropyl-phenyl)-6-methoxy-2-oxo-2.H.-quinazolin-1-ylmethyl]-benzoic acid 4-dimethylamino-butyl ester

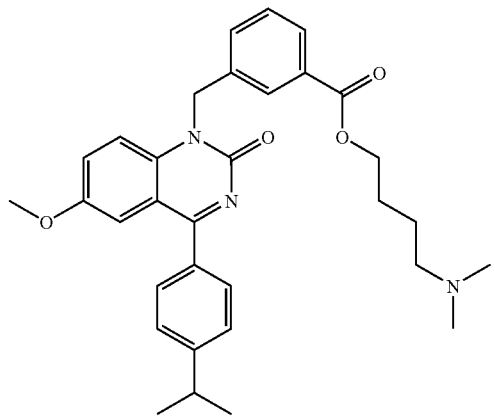

¹H NMR (300 MHz, CDCl₃): 8.03 (s, 1H), 7.94 (d, 1H), 7.75 (d, 2H), 7.48 (d, 1H), 7.40 (d, 2H), 7.41-7.37 (m, 2H), 7.28-7.18 (m, 2H), 5.59 (s, 2H), 4.83 (t, 2H), 3.76 (s, 3H), 3.02 (hept, 1H), 2.84 (t, 2H), 2.24 (s, 6H), 1.80 (quint, 2H), 1.62 (quint, 2H), 1.32 (d, 6H). MS: 528 (M+1)⁺

Example 63

3-[4-(4-Isopropyl-phenyl)-6-methoxy-2-oxo-2.H.-quinazolin-1-ylmethyl]-benzoic acid 3-dimethylamino-propyl ester

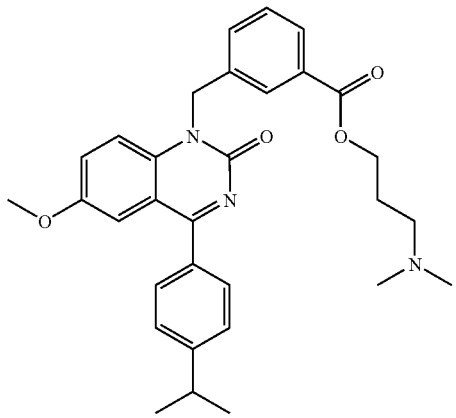

¹H NMR (300 MHz, CDCl₃): 8.02 (s, 1H), 7.94 (d, 1H), 7.74 (d, 2H), 7.49 (d, 1H), 7.40 (d, 2H), 7.41-7.37 (m, 2H), 7.27-7.18 (m, 2H), 5.59 (s, 2H), 4.36 (t, 2H), 3.76 (s, 3H), 3.02 (hept, 1H), 2.42 (t, 2H), 2.25 (s, 6H), 1.94 (quint, 2H), 1.32 (d, 6H). MS: 514 (M+1)⁺

Example 64

3-[4-(4-Isopropyl-phenyl)-6-methoxy-2-oxo-2.H.-quinazolin-1-ylmethyl]-benzoic acid 3-(4-methyl-piperazin-1-yl)-propyl ester

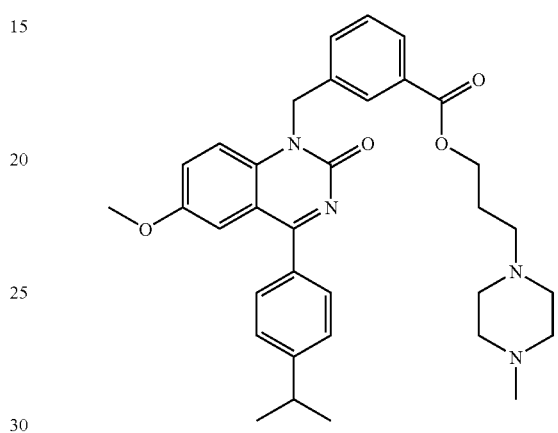

¹H NMR (300 MHz, CDCl₃): 8.01 (s, 1H), 7.93 (d, 1H), 7.75 (d, 2H), 7.49 (d, 1H), 7.41 (d, 2H), 7.42-7.37 (m, 2H), 7.28-7.18 (m, 2H), 5.60 (s, 2H), 4.36 (t, 2H), 3.76 (s, 3H), 3.02 (hept, 1H), 2.52-2.47 (m, 10H), 2.31 (s, 3H), 1.95 (quint, 2H), 1.32 (d, 6H). MS: 569 (M+1)⁺

Example 65

1-(3-amino-benzyl)-4-(4-isopropyl-phenyl)-6-methoxy-1.H.-quinazolin-2-one

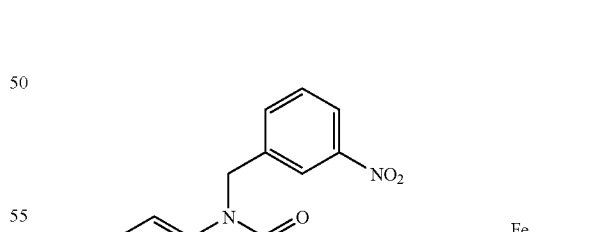
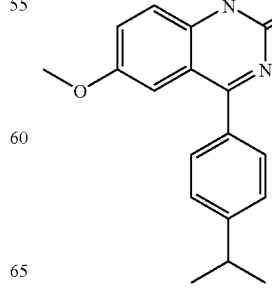

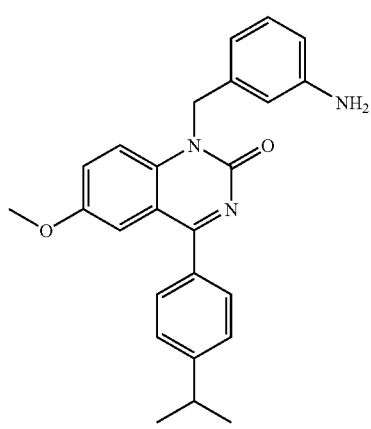

To a solution of 260 mg (0.610 mmol) 4-(4-isopropyl-phenyl)-6-methoxy-1-(3-nitro-benzyl)-1.H.-quinazolin-2-one in 2.5 ml dichloromethane is added 2.5 ml acetic acid and 136 mg (2.44 mmol) iron powder. After stirring overnight the reaction mixture is basified with sodium hydroxide and extracted with water/dichloromethane. The organic layers are evaporated to yield 1-(3-amino-benzyl)-4-(4-isopropyl-phenyl)-6-methoxy-1.H.-quinazolin-2-one.

$^1$H NMR (300 MHz, CDCl$_3$): 7.71 (d, 2H), 7.38 (d, 2H), 7.33 (d, 1H), 7.27-7.25 (m, 2H), 7.13 (t, 1H), 6.91-6.74 (m, 3H), 5.45 (s, 2H), 3.74 (s, 3H), 3.00 (hept, 1H), 1.30 (d, 6H). MS: 400 (M+1)$^+$

Example 66

1-(3-formylamino-benzyl)-4-(4-isopropyl-phenyl)-6-methoxy-1.H.-quinazolin-2-one

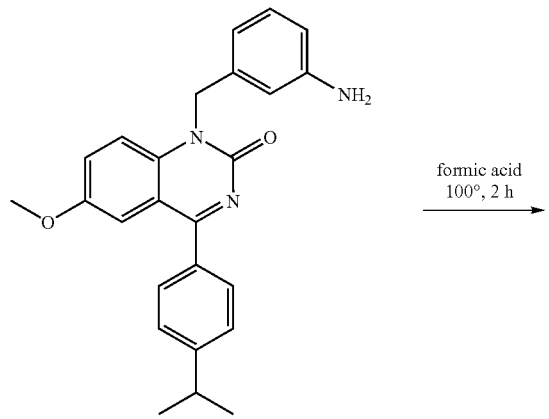

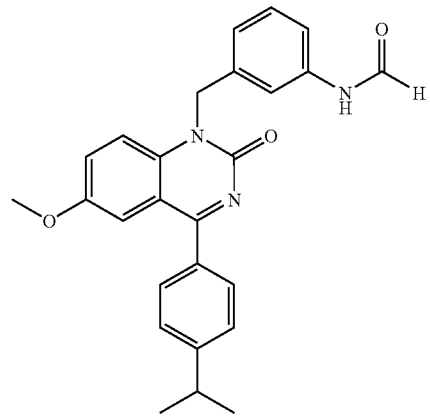

A solution of 20 mg (50 μmol) 1-(3-amino-benzyl)-4-(4-isopropyl-phenyl)-6-methoxy-1.H.-quinazolin-2-one in 1 ml formic acid is heated to 100° for 2 h. After evaporation of the formic acid the residue was washed with ether to give 1-(3-formylamino-benzyl)-4-(4-isopropyl-phenyl)-6-methoxy-1.H.-quinazolin-2-one.

$^1$H NMR (300MHz, CDCl$_3$): Mixture of two rotamers: 8.62 (d, 0.4H), 8.32 (s, 0.6H), 7.74-7.62 (m, 3H), 7.55-7.22 (m, 6.5H), 7.18-7.13 (m, 0.5H), 7.07 (d, 0.5H), 7.00-6.98 (m, 0.5H), 5.33-5.49 (m, 2H), 3.76 (s, 1.2H), 3.75 (s, 1.8H), 3.07-2.94 (m, 1H), 1.32 (d, 2.4H), 1.32 (d, 3.6H). MS: 428 (M+1)$^+$

Example 67

Synthesis of (2-amino-3-methoxy-phenyl)-(4-isopropyl-phenyl)-methanone

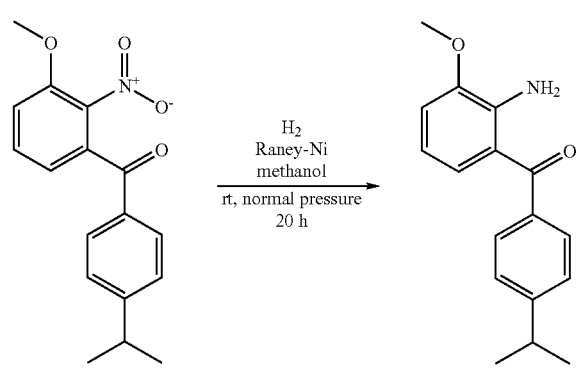 [SMILES: COc1cccc(C(=O)c2ccc(C(C)C)cc2)c1[N+](=O)[O-] ; COc1cccc(C(=O)c2ccc(C(C)C)cc2)c1N]

A solution of 6.8 g (22 mmol) (4-isopropyl-phenyl)-(3-methoxy-2-nitro-phenyl)-methanone in 90 ml methanol and 40 ml THF is hydrogenated at normal pressure and rt during 20 h in the presence of 2 g Raney nickel. After filtration and evaporation of the solvent the residue is taken up in ether and (4-isopropyl-phenyl)-(3-methoxy-2-nitro-phenyl)-methanone precipitates by the addition of saturated etheric hydrochloric acid as its hydrochloride.

$^1$HNMR (300 MHz, CDCl$_3$): 7.72 (d, 2H), 7.31 (d, 2H), 7.24-7.13 (m, 3H), 6.91 (broad, 3H), 4.02 (s, 3H), 2.97 (hept, 1H), 1.28 (d, 6H). MS: 270 (M+1)$^+$ Example 68

Synthesis of (2-amino-3-hydroxy-phenyl)-(4-isopropyl-phenyl)-methanone and (3,4-dihydro-2.H.-benzo[1,4]oxazin-5-yl)-(4-isopropyl-phenyl)-methanone

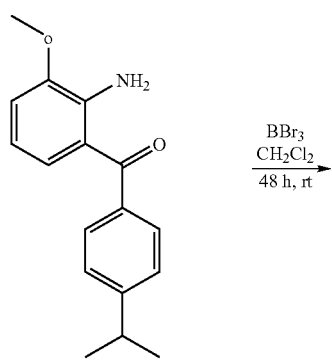

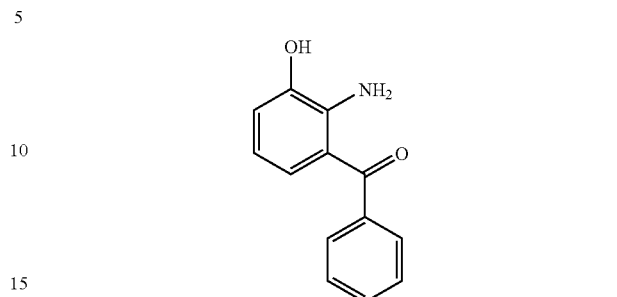

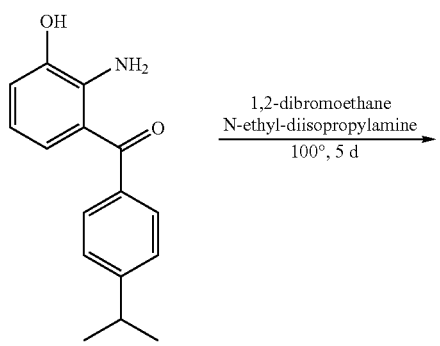

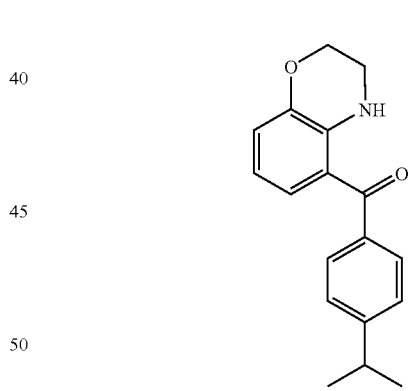

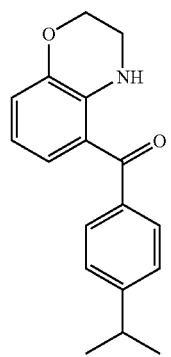 [SMILES: CC(C)c1ccc(C(=O)c2cccc3c2NCCO3)cc1]

A. (2-Amino-3-hydroxy-phenyl)-(4-isopropyl-phenyl)-methanone

To a solution of 0.5 g (1.64 mmol) (2-amino-3-methoxy-phenyl)-(4-isopropyl-phenyl)-methanone in 5 ml dichloromethane is added under inert atmosphere 3.3 ml (3.3 mmol) 1M solution of BBr$_3$ in dichloromethane. After stirring for 48 h the reaction mixture is poured onto 1M aqueous thiosulfate solution and extracted with dichloromethane to yield (2-amino-3-hydroxy-phenyl)-(4-isopropyl-phenyl)-methanone.

$^1$H NMR (300 MHz, CDCl$_3$): 7.61 (d, 2H), 7.30 (d, 2H), 7.13 (d, 1H), 6.86 (d, 1H), 6.48 (t, 1H), 5.0 (broad, 3H), 2.98 (hept, 1H), 1.29 (d, 6H). MS: 256 (M+1)$^+$ B. (3,4-Dihydro-2.H.-benzo[1,4]oxazin-5-yl)-(4-isopropyl-phenyl)-methanone A solution of 0.5 g (1.96 mmol) (2-amino-3-hydroxy-phenyl)-(4-isopropyl-phenyl)-methanone, 0.85 ml (9.8 mmol) dibromoethane and 0.67 ml (3.9 mmol) N-ethyl-diisopropylamine in 3 ml dioxane is heated to 100° for 5 d. After extraction with water/dichloromethane the crude product is purified by flash chromatography using a gradient going from hexanes to hexanes/ethyl acetate 7:1 to yield (3,4-dihydro-2.H.-benzo[1,4]oxazin-5-yl)-(4-isopropyl-phenyl)-methanone.

$^1$H NMR (300 MHz, CDCl$_3$): 7.56 (d, 2H), 7.29 (d, 2H), 7.13 (d, 1H), 6.92 (d, 1H), 6.45 (t, 1H), 4.25 (t, 2H), 3.58 (t, 2H), 2.97 (hept, 1H), 1.28 (d, 6H). MS: 282 (M+1)$^+$ Synthesis of (2-amino-5-methoxy-phenyl)-(4-isopropyl-phenyl)-methanone and (4-isopropyl-phenyl)-{5-methoxy-2-[(pyridin-2-ylmethyl)-amino]-phenyl}-methanone
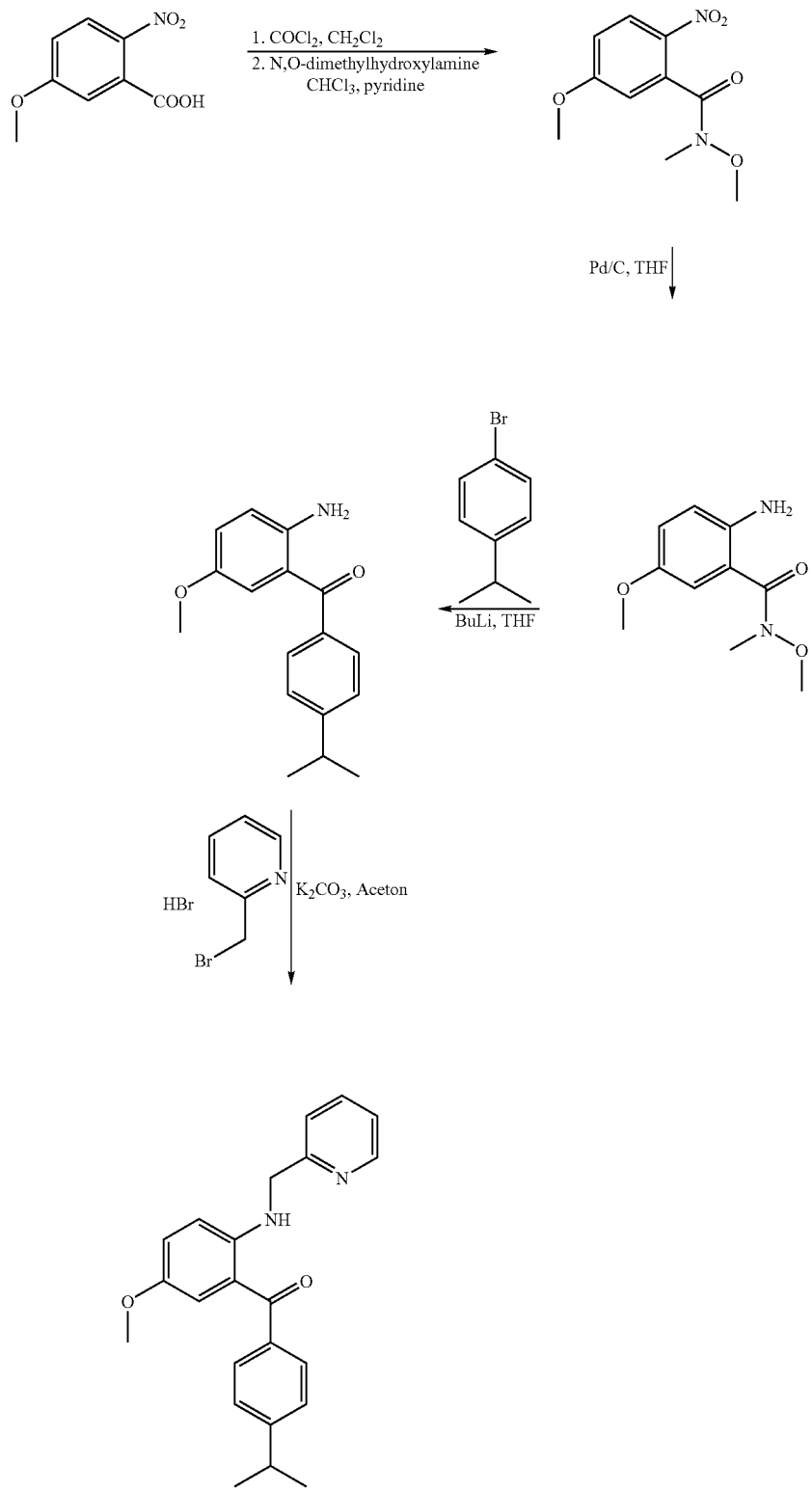

Example 69

(2-Amino-5-methoxy-phenyl)-(4-isopropyl-phenyl)-methanone

A. Synthesis of 5,.N.-dimethoxy-.N.-methyl-2-nitro-benzamide

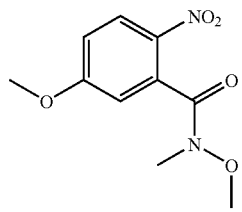

2.4 g (12.2 mmol) of 5-methoxy-2-nitro benzoic acid is dissolved in 50 ml methylene chloride. Oxalyl chloride (1.2 ml, 13.4 mmol) is added and the solution is cooled to 0° C. After addition of two drops of DMF the solution is stirred overnight and evaporated. The crude material is dissolved in 50 ml chloroform, N,O-dimethylhydroxylamine (1.28 g, 13.4 mmol) and pyridine (2.2 ml, 26.8 mmol) is added and the reaction mixture is stirred for two hours.

The reaction mixture is extracted with ether/brine, the organic layer is dried and evaporated. Crystallization from ethyl acetate/hexanes yields 2.1 g (69%) of the product as yellow solid.

$^1$H-NMR (300 MHz, CDCl$_3$): 8.17 (d, 1H), 7.00-6.94 (m, 2H), 3.92 (s, 3H), 3.38 (d, 3H). MS: 241 (M+1)$^+$

B. Synthesis of 2-amino-5,.N.-dimethoxy-.N.-methyl-benzamide

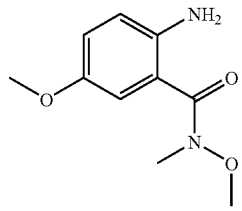

Hydrogenation of a solution of 1.65 g (6.87 mmol) of the material prepared in A over Pd/C yields after filtration 83% of the desired product as yellow oil.

$^1$H-NMR (300 MHz, DMSO-d$_6$): 6.80-6.61 (m, 3H), 4.8 (broad, 2H), 3.63 (s, 3H), 3.54 (s, 3H), 3.20 (s, 3H). MS: 211 (M+1)$^+$ C. Synthesis of (2-amino-5-methoxy-phenyl)-(4-isopropyl-phenyl)-methanone

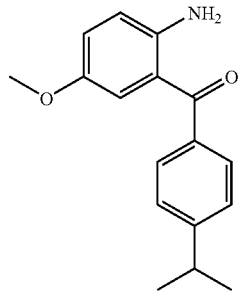 [SMILES: COc1ccc(N)c(C(=O)c2ccc(C(C)C)cc2)c1]

610 mg (2.9 mmol) of the material prepared in B and 578 mg (2.9 mmol) 4-isopropylphenylbromid are dissolved in 11 ml THF. The solution is cooled to −78° C. and BuLi (3.6 ml, 1.6 M in hexanes) is added dropwise. After 30 min the solution is diluted with 1N HCl end extracted with ethyl acetate. The organic layer is dried and evaporated. After chromatography (hexane/ethyl acetate) the product (570 mg, 73% yield) is obtained as yellow oil.

$^1$H-NMR (300 MHz, DMSO-d$_6$): 7.53 (d, 2H), 7.37 (d, 2H), 7.05 (dd, 1H), 6.84-6.75 (m, 2H), 6.58 (broad, 2H), 3.56 (s, 3H), 2.96 (hept, 1H), 1.23 (d, 2H). MS: 270 (M+1)$^+$

Example 70

(4-isopropyl-phenyl)-{5-methoxy-2-[(pyridin-2-ylmethyl)-amino]-phenyl}-methanone

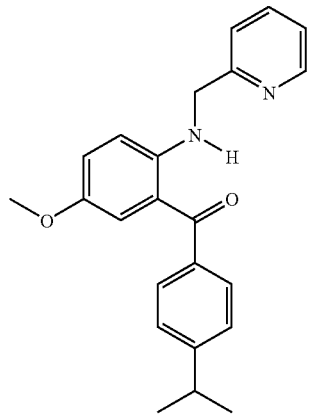 [SMILES: COc1ccc(NCc2ccccn2)c(C(=O)c2ccc(C(C)C)cc2)c1]

410 mg (2.97 mmol) potassium carbonate and 150 mg (0.59 mmol) 2-bromoethylpyridine hydrobromide are added to a solution of 160 mg (0.59 mmol) (2-amino-5-methoxy-phenyl)-(4-isopropyl-phenyl)-methanone in 3 ml acetone. The reaction mixture is stirred for 2 days at 90° C., diluted with ethyl acetate and extracted with brine. The organic layer is dried and evaporated. After chromatography (hexane/ethyl acetate) the product is obtained as yellow oil.

$^1$H-NMR (300 MHz, DMSO-d$_6$): 8.53 (d, 1H), 8.49 (t, 1H), 7.74 (d, 1H), 7.55 (d, 2H), 7.37 (m, 3H), 7.25 (m, 1H), 7.07 (m, 1H), 6.90 (d, 1H), 6.75 (d, 1H) 4.52 (d, 2H), 3.57 (s, 3H), 2.96 (hept, 1H), 1.23 (d, 6H). MS: 361 (M+1)$^+$ The compound of the following example is prepared by analogy to the example described immediately above:

Example 71

(4-Isopropyl-phenyl)-{5-methoxy-2-[(pyridin-3-ylmethyl)-amino]-phenyl}-methanone

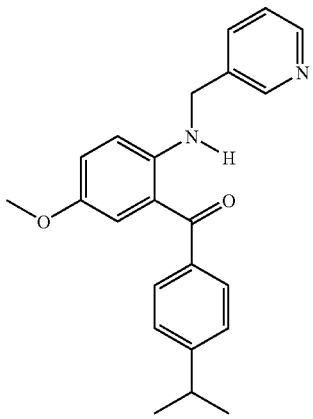 [SMILES: COc1ccc(NCc2cccnc2)c(C(=O)c2ccc(C(C)C)cc2)c1]

$^1$H-NMR (300 MHz, CDCl$_3$): 8.63 (d, 1H), 8.51 (d, 1H), 8.42 (t, 1H), 7.70 (m, 1H), 7.61 (d, 2H), 7.31 (m, 3H), 7.11 (d, 1H), 7.00 (dd, 1H), 6.64 (d, 1H), 4.49 (d, 2H), 3.67 (s, 3H), 2.97 (hept, 1H), 1.29 (d, 6H). MS: 361 (M+1)$^+$

Example 72

1-Benzyl-4-(4-isopropyl-phenyl)-6,7-dimethoxy-1.H.-quinazolin-2-one

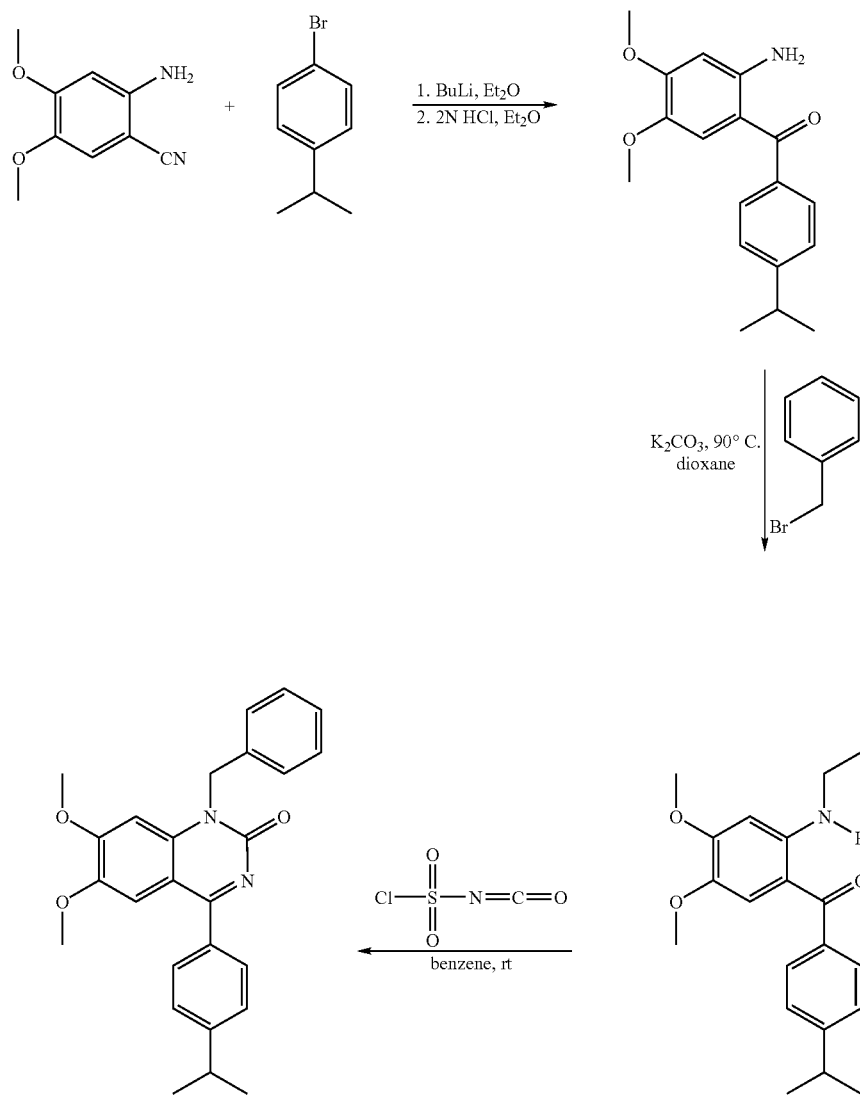

A. Synthesis of (2-amino-4,5-dimethoxy-phenyl)-(4-isopropyl-phenyl)-methanone

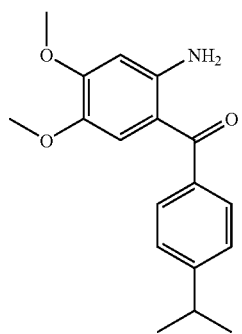 [SMILES: COc1cc(N)c(C(=O)c2ccc(C(C)C)cc2)cc1OC]

18.8 ml (30 mmol) of BuLi (1.6 M in hexane) is added dropwise to a cooled (−5° C.) solution of 6 g (30 mmol) 4-isopropyl-1-bromobenzene in 25 ml ether. The reaction mixture is stirred for 15 min at −5° C. and one additional hour at rt. After that time the solution is cooled to −5° C. and a solution 1.8 g (10 mmol) 2-amino-4,5-dimethoxybenzonitrile in 20 ml ether/THF (1:1) is added dropwise. After 30 min the reaction mixture is poured slowly into water and extracted with ethyl acetate. The organic layer is dried and evaporated. The crude material is dissolved in 200 ml ether and stirred with 100 ml 2N HCl for one hour. After chromatography (DCM/MeOH 15:1) the product is obtained as yellow oil.

$^1$H-NMR (300 MHz, DMSO-d$_6$): 7.47 (d, 2H), 7.37 (d, 2H), 7.11 (broad, 2H), 6.79 (s, 1H), 6.41 (s, 1H), 3.77 (s, 3H), 3.49 (s, 3H), 2.95 (hept, 1H), 1.23 (d, 2H). MS: 300 (M+1)$^+$ B. Synthesis of (2-benzylamino-4,5-dimethoxy-phenyl)-(4-isopropyl-phenyl)-methanone

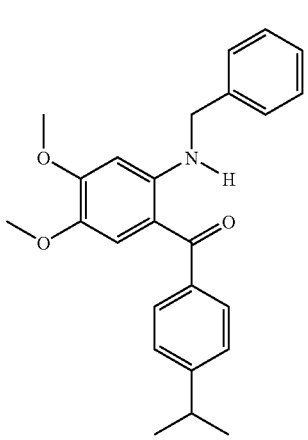 [SMILES: COc1cc(NCc2ccccc2)c(C(=O)c2ccc(C(C)C)cc2)cc1OC]

228 mg (1.65 mmol) potassium carbonate and 43 μl (0.36 mmol) benzylbromide are added to a solution of 100 mg (0.33 mmol) (2-amino-4,5-dimethoxy-phenyl)-(4-isopropyl-phenyl)-methanone in 3 ml dioxane. The reaction mixture is stirred for 3 days at 90° C., diluted with ethyl acetate and extracted with brine. The organic layer is dried and evaporated. After chromatography (hexanelethyl acetate) the product is obtained as yellow oil.

$^1$H-NMR (300 MHz, CDCl$_3$): 9.38 (t, 1H), 7.57 (d, 2H), 7.42-7.20 (m, 7H), 7.15 (s, 1H), 6.17 (s, 1H), 4.49 (d, 2H), 3.78 (s, 3H), 3.64 (s, 3H), 2.97 (hept, 1H), 1.27 (d, 6H). MS: 390 (M+1)$^+$ C. Synthesis of 1-benzyl-4-(4-isopropyl-phenyl)-6,7-dimethoxy-1.H.-quinazolin-2-one

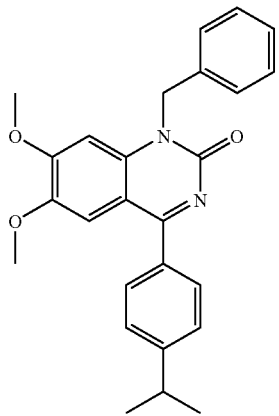 [SMILES: COc1cc2c(-c3ccc(C(C)C)cc3)nc(=O)n(Cc3ccccc3)c2cc1OC]

To a cooled solution of 100 mg (0.26 mmol) (2-amino-4,5-dimethoxy-phenyl)-(4-isopropyl-phenyl)-methanone in 3 ml benzene is added 22 μl (0.26 mmol) chlorosulfonylisocyanate. After 2h the benzene is distilled off and the residue dissolved in 4 ml THF/water (1:1). After stirring for one hour at rt the reaction mixture is diluted with ethyl acetate and extracted with brine. The organic layer is dried, evaporated and the residual oil is crystallized from ether.

$^1$H-NMR (300 MHz, CDCl$_3$): 7.72 (d, 2H), 7.40-7.20 (m, 7H), 7.05 (s, 1H), 6.71 (s, 1H), 5.58 (s, 2H), 3.82 (s, 3H), 3.80 (s, 3H), 3.01 (hept, 1H), 1.31 (d, 6H). MS: 415 (M+1)$^+$ Corresponding methanone compounds listed below are analogously prepared as described above.:

[2-(3-Fluoro-benzylamino)-4,5-dimethoxy-phenyl]-(4-isopropyl-phenyl)-methanone

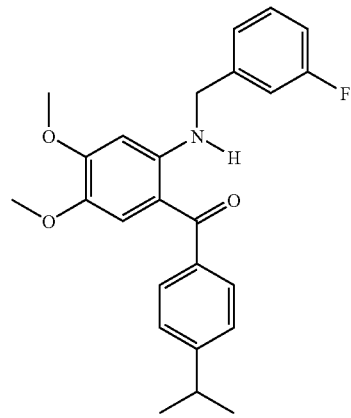 [SMILES: COc1cc(NCc2cccc(F)c2)c(C(=O)c2ccc(C(C)C)cc2)cc1OC]

$^1$H-NMR (300 MHz, DMSO-d$_6$): 9.18 (t, 1H), 7.50-6.98 (m, 8H), 6.90 (s, 1H), 6.29 (s, 1H), 4.50 (d, 2H), 3.71 (s, 3H), 3.48 (s, 3H), 2.94 (hept, 1H), 1.21 (d, 6H). MS: 408 (M+1)$^+$ 4-{[2-(4-Isopropyl-benzoyl)-4,5-dimethoxy-phenylamino]-methyl}-benzonitrile

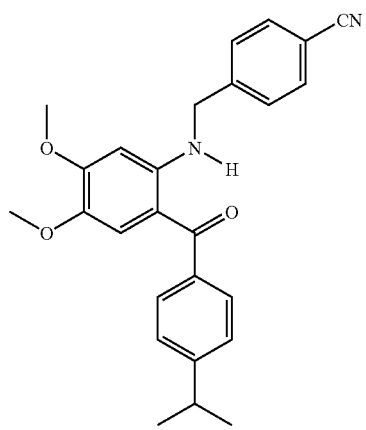 [SMILES: COc1cc(NCc2ccc(C#N)cc2)c(C(=O)c2ccc(C(C)C)cc2)cc1OC]

$^1$H-NMR (300 MHz, DMSO-d$_6$): 9.41 (t, 1H), 7.66-7.28 (m, 8H), 7.11 (s, 1H), 6.02 (s, 1H), 4.58 (d, 2H), 3.75 (s, 3H), 3.68 (s, 3H), 2.99 (hept, 1H), 1.30 (d, 6H). MS: 415 (M+1)$^+$

[2-(3-chloro-benzylamino)-4,5-dimethoxy-phenyl]-(4-isopropyl-phenyl)-methanone

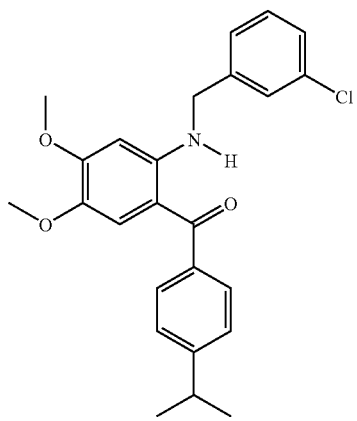 [SMILES: COc1cc(NCc2cccc(Cl)c2)c(C(=O)c2ccc(C(C)C)cc2)cc1OC]

$^1$H-NMR (300 MHz, CDCl$_3$): 9.36 (t, 1H), 7.57 (d, 2H), 7.40-7.22 (m, 6H), 7.10 (s, 1H), 6.10 (s, 1H), 4.48 (d, 2H), 3.78(s, 3H), 3.67 (s, 3H), 2.97 (hept, 1H), 1.32 (d, 6H). MS: 424 (M+1)$^+$ (2-Isopropyl amino-4,5-dimethoxy-phenyl)-(4-isopropyl-phenyl)-methanone

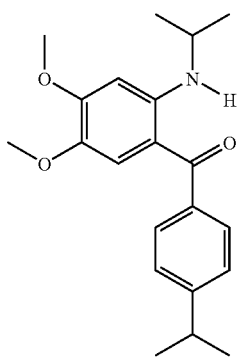 [SMILES: COc1cc(NC(C)C)c(C(=O)c2ccc(C(C)C)cc2)cc1OC]

$^1$H-NMR (300 MHz, CDCl$_3$): 8.96 (d, 1H), 7.52 (d, 2H), 7.31 (d, 2H), 7.06 (s, 1H), 6.27 (s, 1H), 3.94 (s, 3H), 3.76 (hept, 1H), 3.67 (s, 3H), 2.97 (hept, 1H), 1.22-1.34 (m, 12H). MS: 342 (M+1)$^+$ The compounds of the following examples are prepared by analogy to Example 72

Example 73

1-Isobutyl-4-(4-isopropyl-phenyl)-6,7-dimethoxy-1.H.-quinazolin-2-one

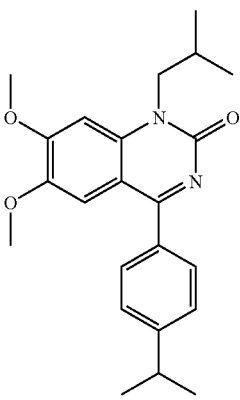 [SMILES: COc1cc2c(-c3ccc(C(C)C)cc3)nc(=O)n(CC(C)C)c2cc1OC]

$^1$H-NMR (300 MHz, CDCl$_3$): 7.70 (d, 2H), 7.39 (d, 2H), 7.29 (s, 1H), 6.78 (s, 1H), 4.21 (d, 2H), 4.06 (s, 3H), 3.84 (s, 3H), 3.01 (hept, 1H), 2.35 (hept, 1H), 1.32 (d, 6H), 1.08 (d, 6H). MS: 381 (M+1)$^+$

Example 74

1-Ethyl-4-(4-isopropyl-phenyl)-6,7-dimethoxy-1.H.-quinazolin-2-one

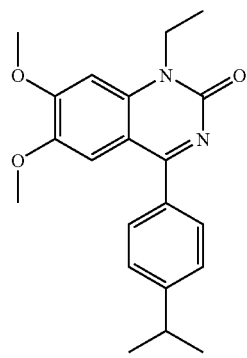 [SMILES: CCn1c(=O)nc(-c2ccc(C(C)C)cc2)c2cc(OC)c(OC)cc21]

$^1$H-NMR (300 MHz, CDCl$_3$): 7.68 (d, 2H), 7.37 (d, 2H), 7.29 (s, 1H), 6.78 (s, 1H), 4.36 (q, 2H), 4.05 (s, 3H), 3.82 (s, 3H), 2.98 (hept, 1H), 1.41 (t, 3H), 1.32 (d, 6H). MS: 353 (M+1)$^+$

Example 75

1-(2-Fluoro-benzyl)-4-(4-isopropyl-phenyl)-6,7-dimethoxy-1H-quinazolin-2-one

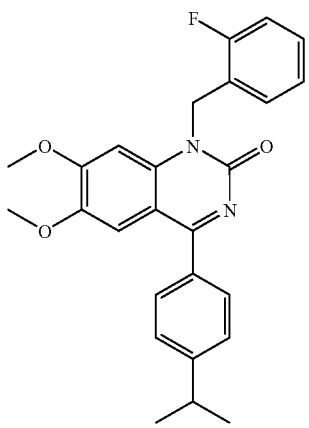 [SMILES: COc1cc2c(-c3ccc(C(C)C)cc3)nc(=O)n(Cc3ccccc3F)c2cc1OC]

$^1$H NMR (300 MHz, CDCl$_3$): 7.71 (d, 2H), 7.47 (td, 1H), 7.38 (d, 2H), 7.30-7.23 (m, 1H), 7.26 (s, 1H), 7.12 (d, 1H), 7.06 (dd, 1H), 6.84 (s, 1H), 5.62 (s, 2H), 3.93 (s, 3H), 3.79 (s, 3H), 3.01 (hept, 1H), 1.31 (d, 6H). MS: 433 (M+1)⁺

Example 76

1-(4-Fluoro-benzyl)-4-(4-isopropyl-phenyl)-6,7-dimethoxy-1H-quinazolin-2-one

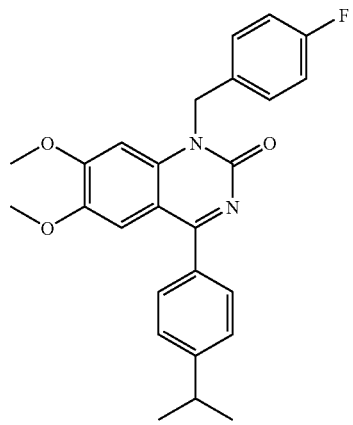 [SMILES: COc1cc2c(-c3ccc(C(C)C)cc3)nc(=O)n(Cc3ccc(F)cc3)c2cc1OC]

¹H NMR (300 MHz, CDCl₃): 7.71 (d, 2H), 7.39 (d, 2H), 7.34 (dd, 2H), 7.27 (s, 1H), 7.02 (t, 2H), 6.66 (s, 1H), 5.53 (s, 2H), 3.84 (s, 3H), 3.80 (s, 3H), 3.01 (hept, 1H), 1.32 (d, 6H). MS: 433 (M+1)⁺

Example 77

4-(4-.tert.-Butyl-phenyl)-1-isopropyl-6,7-dimethoxy-1.H.-quinazolin-2-one

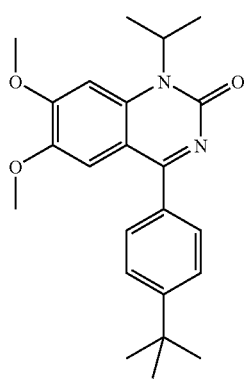 [SMILES: COc1cc2c(-c3ccc(C(C)(C)C)cc3)nc(=O)n(C(C)C)c2cc1OC]

¹H-NMR (300 MHz, DMSO-d₆): 7.64 (d, 2H), 7.58 (d, 2H), 7.14 (s, 1H), 7.13 (s, 1H), 5.11 (hept, 1H), 3.98 (s, 3H), 3.68 (s, 3H), 1.57 (d, 6H) 1.34 (s, 9H). MS: 381 (M+1)⁺

The following alternative methanone compound is prepared as described below.

Synthesis of 2-chloro-.N.-[2-(4-isopropyl-benzoyl)-4,5-dimethoxy-phenyl]-2-phenyl-acetamide

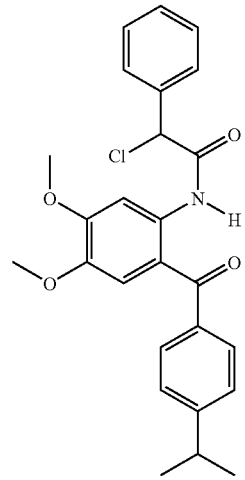 [SMILES: COc1cc(NC(=O)C(Cl)c2ccccc2)c(C(=O)c2ccc(C(C)C)cc2)cc1OC]

To a solution of 50 mg (0.17 mmol) (2-amino-4,5-dimethoxy-phenyl)-(4-isopropyl-phenyl)-methanone in 3 ml dichloromethane is added α-chlorophenyl acetyl chloride (27 µl, 0.18 mmol) and triethylamine (58 µl 0.42 mmol). After stirring for 48 h at rt the solution is extracted with chloroform/brine. The organic layer is dried and evaporated. After chromatography (hexane/ethyl acetate) the product is obtained as yellow oil.

¹H-NMR (300 MHz, CDCl₃): 12.12 (s, 1H), 8.43 (s, 1H), 7.68-7.36 (m, 9H), 7.13 (s, 1H), 5.46 (s, 1H), 3.97 (s, 3H), 3.75 (s, 3H), 3.01 (hept, 1H), 1.31 (d, 6H). MS: 452 (M+1)⁺

Example 78

Synthesis of 1-Isopropyl-4-(4-isopropyl-phenyl)-6,7-dimethoxy-1.H.-quinazoline-2-thione

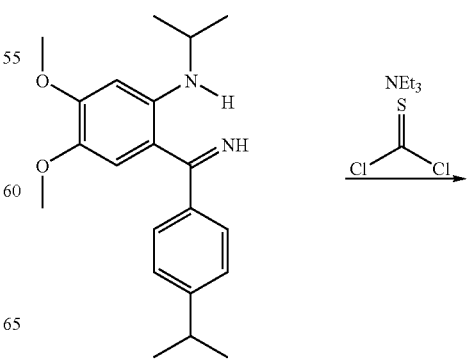

-continued

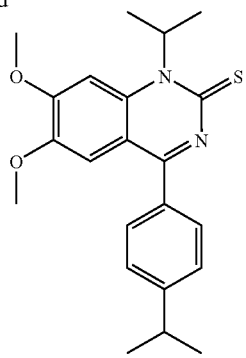

To a solution of 100 mg (2.94 mmol) {2-[Imino-(4-isopropyl-phenyl)-methyl]-4,5-dimethoxy-phenyl}isopropyl-amine (prepared as described in Example 16) in 1 ml dichloromethane is added 164 µl (5.88 mmol) triethylamine and 46 µl (5.88 mmol) thiophosgene. The resulting mixture is stirred at 0° C. for 2 days. After that time the reaction is diluted with water and extracted with dichloromethane. The organic layer is dried and evaporated. Chromatography (hexane/ethyl acetate, 4:1) yields the desired product as a yellow oil.

$^1$H-NMR (300 MHz, DMSO-$d_6$): 7.73 (d, 2H), 7.46 (d, 2H), 7.25-7.20 (m, 2H), 6.49 (hept, 1H), 4.04 (s, 3H), 3.75 (s, 3H), 3.00 (hept, 1H), 1.70 (d, 6H), 1.26 (d, 6H). MS: 383 (M+1)$^+$ Synthesis of 1-benzyl-4-(4-isopropyl-phenyl)-6-propargyloxy-1.H.-quinazolin-2-one

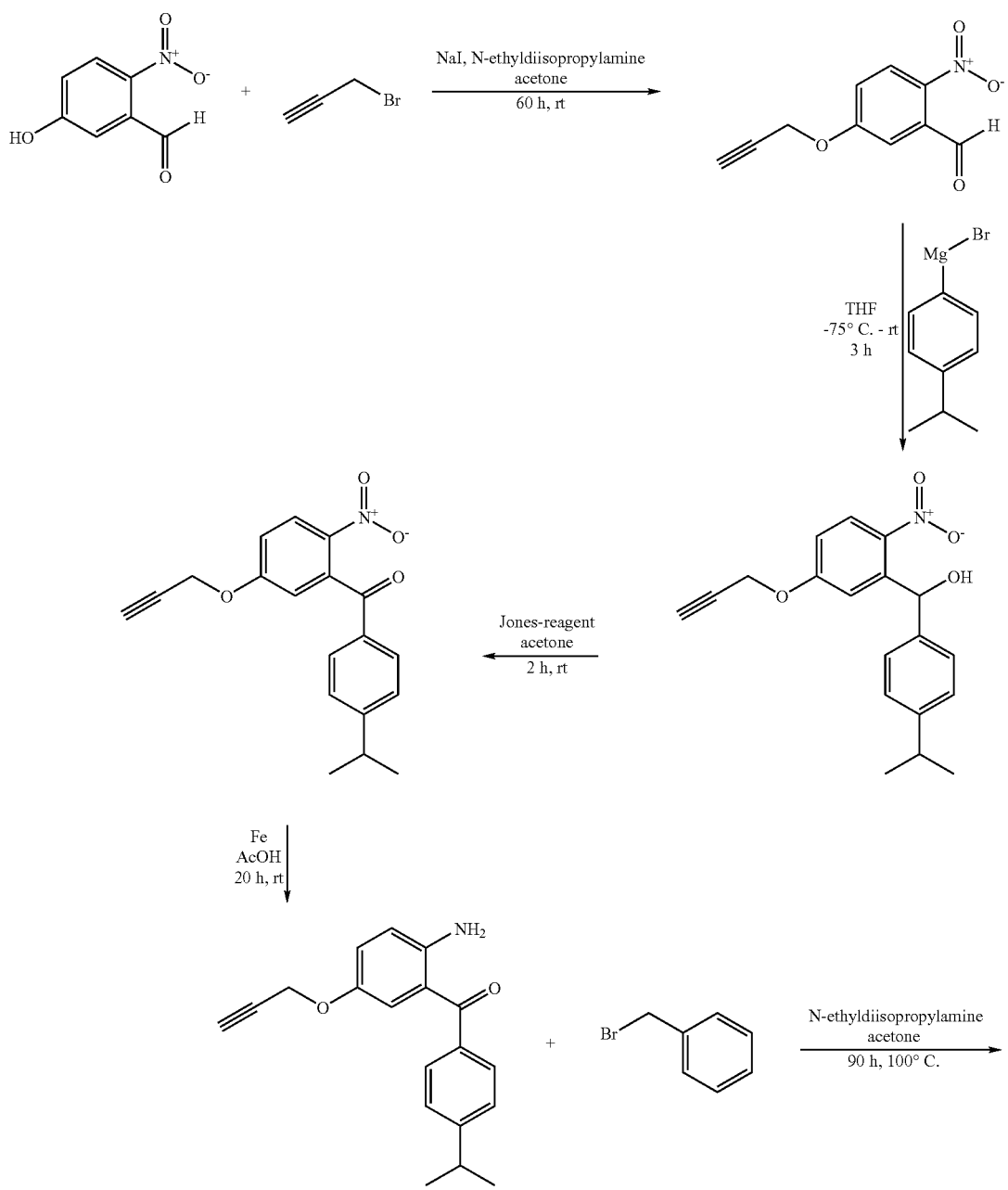

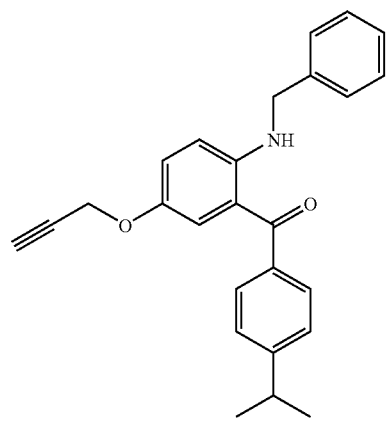

Example 79A (2-amino-5-propargyloxy-phenyl)-(4-isopropyl-phenyl)-methanone

A. Synthesis of 2-nitro-5-propargyloxy-benzaldehyde

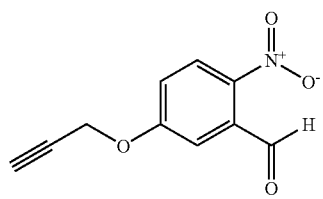

A mixture of 25 g (150 mmol) 5-hydroxy-2-nitro-benzaldehyde, 44.9 g (299 mmol) sodium iodide, 44.5 g propargyl bromide (80% in toluene), 42 ml N-ethyl-diisopropylamine and 400 ml acetone is stirred at rt for 6 d. The reaction mixture is filtered, concentrated, taken up in 1M aqueous hydrochloric acid and extracted with ethyl acetate to yield 2-nitro-5-propargyloxy-benzaldehyde.

$^1$H NMR (300 MHz, CDCl$_3$): 10.49 (s, 1H), 8.19 (d, 1H), 7.43 (s, 1H), 7.25 (d, 2H), 4.85 (s, 2H), 2.60 (s, 1H).

B. Synthesis of (4-isopropyl-phenyl)-(2-nitro-5-propargyloxy-phenyl)-methanol

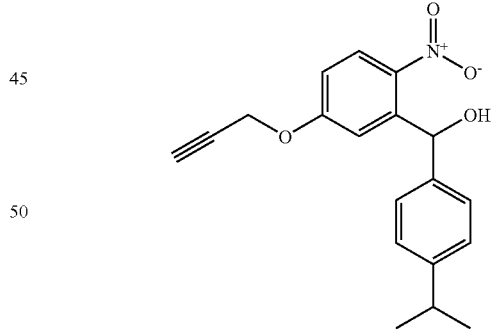

To a solution of 30.7 g (150 mmol) 2-nitro-5-propargyloxy-benzaldehyde in 200 ml THF are added at −75° during 40 min 200 ml (175 mmol) of a 0.88 M solution of 4-isopropyl magnesium bromide in THF. After stirring for 1 h at −75° saturated aqueous ammonium chloride solution is added and the reaction mixture is extracted with portions of ethyl acetate. Evaporation of the organic phases yields (4-isopropyl-phenyl)-(2-nitro-5-propargyloxy-phenyl)-methanol. $^1$H NMR (300 MHz, CDCl$_3$): 8.09 (d, 1H), 7.45 (d, 1H), 7.26 (d, 2H), 7.19 (d, 2H), 6.98 (dd, 1H), 6.52 (broad, 1H), 4.80 (d, 2H), 2.88 (hept, 1H), 2.71 (broad, 1H), 2.56 (t, 1H), 1.23 (d, 6H). MS: 308 (100) (M−OH)$^+$, 294 (50)

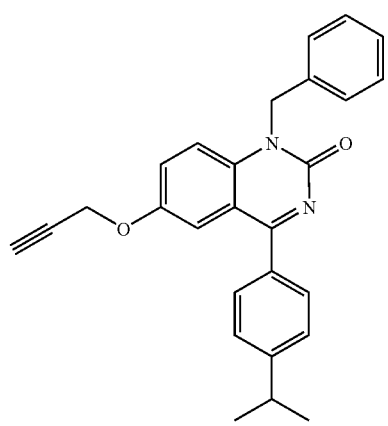

C. Synthesis of (4-isopropyl-phenyl)-(2-nitro-5-propargyloxy-phenyl)-methanone

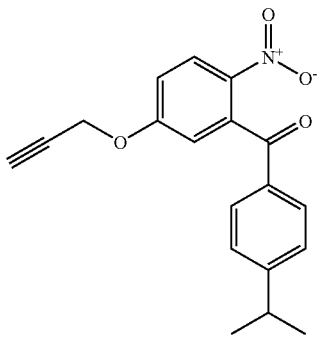 [SMILES: C#CCOc1ccc([N+](=O)[O-])c(C(=O)c2ccc(C(C)C)cc2)c1]

To an ice cold solution of (4-isopropyl-phenyl)-(2-nitro-5-propargyloxy-phenyl)-methanol in 200 ml acetone are added dropwise 60 ml Jones reagent. After stirring for 2 h at rt the reaction is quenched by the addition of isopropanol and sodium bisulfite solution (40%). Extraction with dichloromethane affords (4-isopropyl-phenyl)-(2-nitro-5-propargyloxy-phenyl)-methanone.

$^1$H NMR (300 MHz, CDCl$_3$): 8.27 (d, 1H), 7.70 (d, 2H), 7.30 (d, 2H), 7.18 (dd, 1H), 6.97 (d, 1H), 4.81 (d, 2H), 2.96 (hept, 1H), 2.59 (t, 1H), 1.27 (d, 6H).

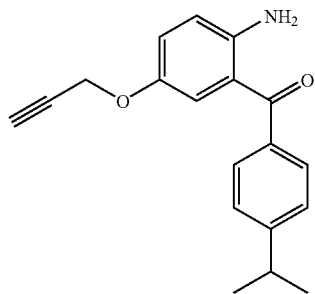 [SMILES: C#CCOc1ccc(N)c(C(=O)c2ccc(C(C)C)cc2)c1]

D. Synthesis of (2-amino-5-propargyloxy-phenyl)-(4-isopropyl-phenyl)-methanone

To a solution of 10.59 g (30.7 mmol) (4-isopropyl-phenyl)-(2-nitro-5-propargyloxy-phenyl)-methanone in 250 ml acetic acid are added 13.6 g (246 mmol) iron powder. After stirring for 20 h at rt the reaction mixture is basified by the addition of 2M sodium hydroxide solution, filtered and extracted with dichloromethane. After purification by chromatography using hexanes/ethyl acetate (7:3) as eluent (2-amino-5-propargyloxy-phenyl)-(4-isopropyl-phenyl)-methanone is obtained.

$^1$H NMR (300 MHz, CDCl$_3$): 7.64 (d, 2H), 7.30 (d, 2H), 7.12 (s, 1H), 7.05 (d, 1H), 6.72 (d, 1H), 5.71 (broad, 2H), 4.64 (s, 2H), 2.98 (hept, 1H), 2.48 (s, 1H), 1.30 (d, 6H). MS: 294 (M+1)$^+$ Example 79B Synthesis of (2-benzylamino-5-propargyloxy-phenyl)-(4-isopropyl-phenyl)-methanone

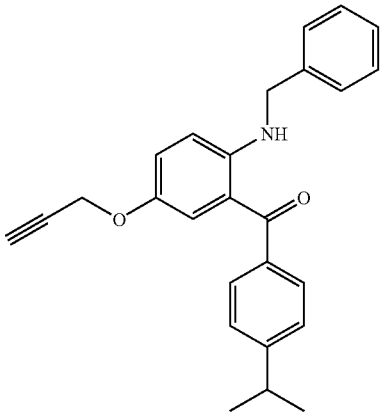 [SMILES: C#CCOc1ccc(NCc2ccccc2)c(C(=O)c2ccc(C(C)C)cc2)c1]

A solution of 100 mg (0.341 mmol) (2-amino-5-propargyloxy-phenyl)-(4-isopropyl-phenyl)-methanone, 44.6 μl (0.375 mmol) benzyl bromide and 32 μl (0.375 mmol) N-ethyl-diisopropylamine in 2 ml dioxane is heated at 100° for 90 h. The reaction mixture is concentrated and the residue taken up in 0.1 M sodium hydroxide solution and extracted with dichloromethane. Preparative HPLC affords (2-benzylamino-5-propargyloxy-phenyl)-(4-isopropyl-phenyl)-methanone.

$^1$H NMR (300 MHz, CD$_3$OD): 7.58 (d, 2H), 7.39-7.31 (m, 6H), 7.27-7.22 (m, 1H), 7.13-7.08 (m, 2H), 6.78 (d, 1H), 4.53 (s, 2H), 4.48 (s, 2H), 3.00 (hept, 1H), 2.91 (s, 1H), 1.30 (d, 6H). MS: 384 (M+1)$^+$ Example 80

1-benzyl-4-(4-isopropyl-phenyl)-6-propargyloxy-1.H.-quinazolin-2-one

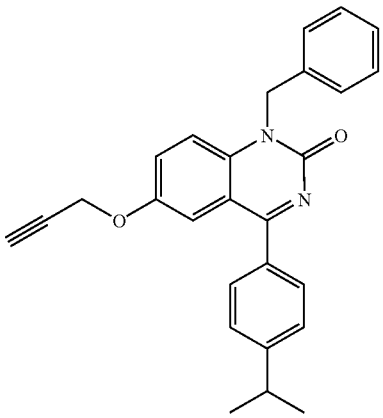 [SMILES: C#CCOc1ccc2c(c1)c(-c1ccc(C(C)C)cc1)nc(=O)n2Cc1ccccc1]

To a solution of 66 mg (0.172 mmol) (2-benzylamino-5-propargyloxy-phenyl)-(4-isopropyl-phenyl)-methanone in 2 ml acetic acid is added 11.7 mg (0.172 mmol) sodium cyanate. After stirring for 3 H the reaction mixture is reduced and the residue is extracted with 1 M sodium hydroxide solution and dichloromethane. After evaporation of the organic phase the crude product is purified by preparative HPLC to yield 1-benzyl-4-(4-isopropyl-phenyl)-6-propargyloxy-1.H.-quinazolin-2-one.

$^1$H NMR (300 MHz, CD$_3$OD): 7.75 (d, 2H), 7.51-7.43 (m, 5H), 7.37-7.23 (m, 5H), 5.61 (s, 2H), 4.71 (s, 2H), 3.07 (s, 1H), 3.05 (hept, 1H), 1.34 (d, 6H). MS: 409 (M+1)$^+$ The following methanone compound is analogously prepared:
Acetic acid 4-{[2-(4-isopropyl-benzoyl)-4-propargyloxy-phenylamino]-methyl}-phenyl ester

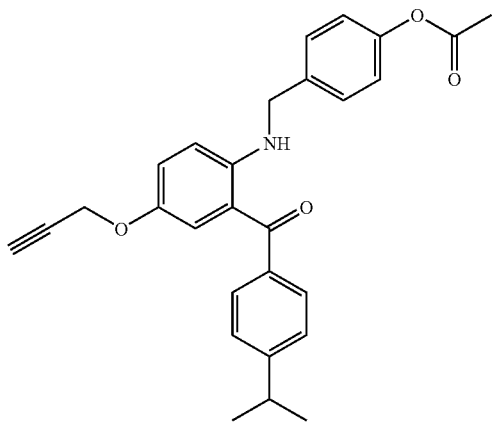 [SMILES: C#CCOc1ccc(NCc2ccc(OC(C)=O)cc2)c(C(=O)c2ccc(C(C)C)cc2)c1]

$^1$H NMR (300 MHz, CD$_3$OD): 7.59 (d, 2H), 7.42-7.36 (m, 4H), 7.13-7.05 (m, 4H), 6.78 (d, 1H), 4.53 (s, 2H), 4.49 (s, 2H), 3.00 hept, 1H), 2.91 (s, 1H), 2.26 (s, 3H), 1.30 (d, 6H). MS: 442 (M+1)$^+$ The compounds of the following examples are prepared by analogy to the example 79:

Example 81

6-Allyloxy-1-benzyl-4-(4-isopropyl-phenyl)-1.H.-quinazolin-2-one

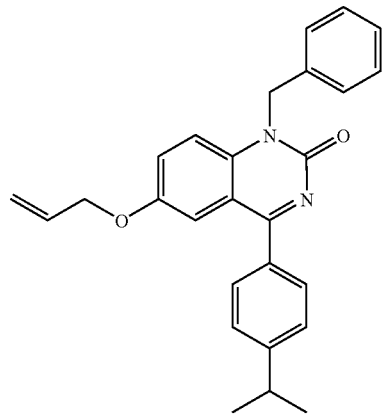 [SMILES: C=CCOc1ccc2c(c1)c(-c1ccc(C(C)C)cc1)nc(=O)n2Cc1ccccc1]

$^1$H NMR (300 MHz, CD$_3$OD): 7.71 (d, 2H); 7.50-7.39 (m, 4H), 7.36-7.23 (m, 6H), 5.98 (ddt, 1H), 5.60 (s, 2H), 5.31 (d, 1H), 5.25 (d, 1H), 4.51 (d, 2H), 3.05 (hept, 1H), 1.34 (d, 6H). MS: 411 (M+1)$^+$ Example 82

Acetic acid 4-[6-allyloxy-4-(4-isopropyl-phenyl)-2-oxo-2.H.-quinazolin-1-ylmethyl]-phenyl ester

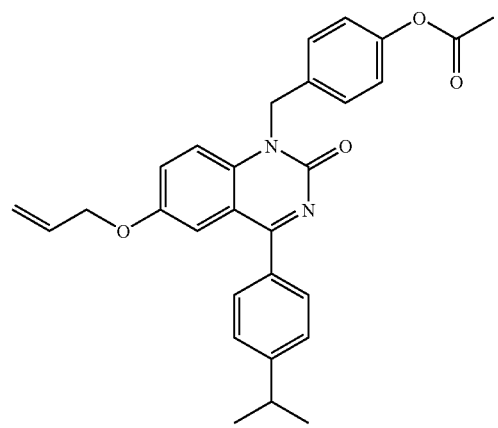 [SMILES: C=CCOc1ccc2c(c1)c(-c1ccc(C(C)C)cc1)nc(=O)n2Cc1ccc(OC(C)=O)cc1]

$^1$H NMR (300 MHz, CD$_3$OD): 7.70 (d, 2H), 7.53-7.41 (m, 4H), 7.37-7.32 (m, 3H), 7.08 (d, 2H), 5.98 (ddt, 1H), 5.59 (s, 2H), 5.31 (d, 1H), 5.25 (d, 1H), 4.52 (d, 2H), 3.05 (hept, 1H), 2.24 (s, 3H) 1.34 (d, 6H). MS: 469 (M+1)$^+$ Example 83

Acetic acid 4-[4-(4-isopropyl-phenyl)-2-oxo-6-propargyloxy-2.H.-quinazolin-1-ylmethyl]-phenyl ester

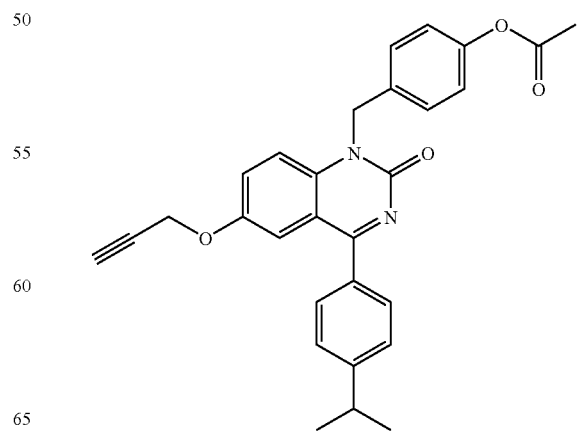

¹H NMR (300 MHz, CDCl₃): 7.75 (d, 2H), 7.50 (s, 1H), 7.40-7.26 (m, 6H), 7.05 (d, 2H), 5.54 (s, 2H), 4.65 (s, 2H), 3.02 (hept, 1H), 2.55 (s, 1H), 2.28 (s, 3H), 1.32 (d, 6H). MS: 467 (M+1)⁺

Example 84

1-Benzo[1,2,5]thiadiazol-5-ylmethyl-4-(4-isopropyl-phenyl)-6-propargyloxy-1H-quinazolin-2-one

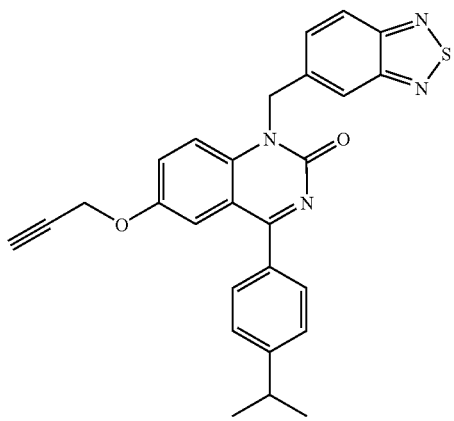 [SMILES: C#CCOc1ccc2c(c1)c(-c1ccc(C(C)C)cc1)nc(=O)n2Cc1ccc2nsnc2c1]

¹H-NMR (300 MHz, CDCl₃): 8.01 (d, 1H), 7.75-7.80 (m, 3H), 7.64 (dd, 1H), 7.53 (d, 1H), 7.41 (d, 2H), 7.21-7.34 (m, 2H+CHCl₃), 5.73 (broad s, 2H), 4.64 (d, 2H), 3.03 (hept, 1H), 2.55 (t, 1H), 1.33 (d, 6H). MS: 467 (M+1)⁺

Example 85

4-(4-Isopropyl-phenyl)-6-propargyloxy-1-thiazol-2-ylmethyl-1H-quinazolin-2-one

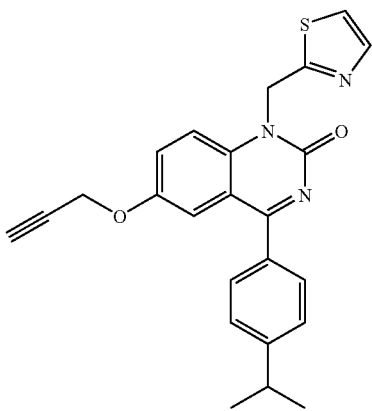 [SMILES: C#CCOc1ccc2c(c1)c(-c1ccc(C(C)C)cc1)nc(=O)n2Cc1nccs1]

¹H-NMR (300 MHz, CDCl₃): 7.78 (d, 1H), 7.70-7.75 (m, 3H), 7.48 (d, 1H), 7.42 (dd, 1H), 7.37 (d, 2H), 7.34 (d, 1H), 5.78 (s, 2H), 4.66 (d, 2H), 3.01 (hept, 1H), 2.55 (t, 1H), 1.31 (d, 6H). MS: 416 (M+1)⁺

The following 1-(hydroxybenzyl)-substituted compounds are prepared substantially as described above in Example 66, with the modification that methoxy-methyl (MOM) is used to protect the benzyl hydroxy group during the synthesis.

Example 86

[2-(2-Hydroxy-benzylamino)-4,5-dimethoxy-phenyl]-(4-isopropyl-phenyl)-methanone

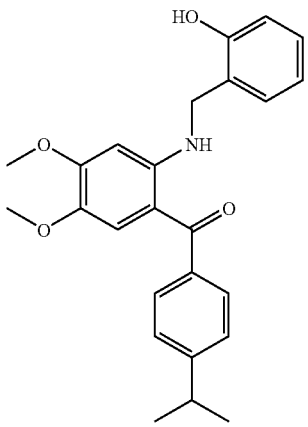 [SMILES: COc1cc(NCc2ccccc2O)c(C(=O)c2ccc(C(C)C)cc2)cc1OC]

¹H NMR (300 MHz, d₆-DMSO): 9.69 (s, 1H), 9.16 (t, 1H), 7.45 (d, 2H), 7.33 (d, 2H), 7.24 (dd, 1H), 7.07 (td, 1H), 6.88 (s, 1H), 6.83 (dd, 1H), 6.75 (td, 1H), 6.43 (s, 1H), 4.40 (d, 2H), 3.80 (s, 3H), 3.48 (s, 3H), 2.94 (hept, 1H), 1.22 (d, 6H). MS: 406 (M+1)⁺

Example 87

1-(2-Hydroxy-benzyl)-4-(4-isopropyl-phenyl)-6-prop-2-ynyloxy-1H-quinazolin-2-one

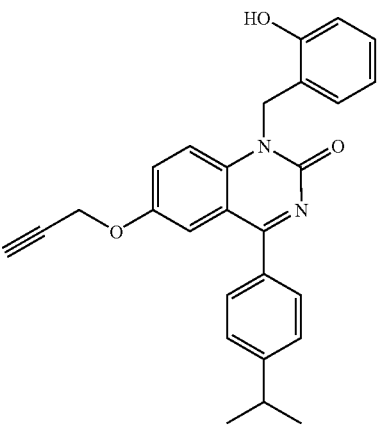 [SMILES: C#CCOc1ccc2c(c1)c(-c1ccc(C(C)C)cc1)nc(=O)n2Cc1ccccc1O]

¹H NMR (300 MHz, CDCl₃): 7.88 (d, 1H), 7.72 (d, 2H), 7.54 (s, 1H), 7.51 (dd, 1H), 7.47 (dd, 1H), 7.38 (d, 2H), 7.23 (ddd, 1H), 6.97 (dd, 1H), 6.86 (td, 1H), 5.48 (s, broad, 2H), 4.69 (d, 2H), 3.01 (hept, 1H), 2.57 (t, 1H), 1.32 (d, 6H). MS: 425 (M+1)⁺

Example 88

1-(2-Hydroxy-benzyl)-4-(4-isopropyl-phenyl)-6,7-dimethoxy-1H-quinazolin-2-one

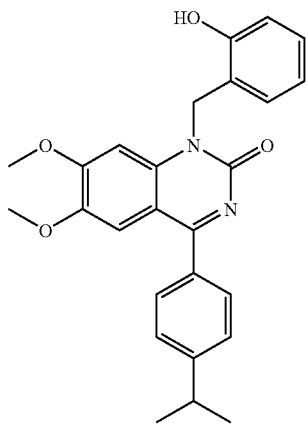 [SMILES: COc1cc2c(-c3ccc(C(C)C)cc3)nc(=O)n(Cc3ccccc3O)c2cc1OC]

$^1$H NMR (300 MHz, CDCl$_3$): 7.69 (d, 2H), 7.46 (d, 1H), 7.39 (d, 2H), 7.31 (s, 1H), 7.30 (s, 1H), 7.23 (t, 1H), 7.01 (d, 1H), 6.85 (t, 1H), 5.48 (s, broad, 2H), 4.10 (s, 3H), 3.82 (s, 3H), 3.01 (hept, 1H), 1.32 (d, 6H). MS: 431 (M+1)$^+$ The following 1-(hydroxybenzyl)-substituted compounds are prepared substantially as described above with the modification that acetyl is used to protect the benzyl hydroxy group during the synthesis.

Example 89

1-(3-Hydroxy-benzyl)-4-(4-isopropyl-phenyl)-6-prop-2-ynyloxy-1H-quinazolin-2-one

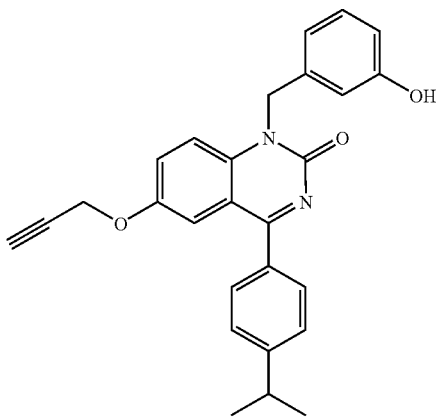 [SMILES: C#CCOc1ccc2c(c1)c(-c1ccc(C(C)C)cc1)nc(=O)n2Cc1cccc(O)c1]

$^1$H NMR: (300 MHz, d$_6$-DMSO): 9.37 (s, 1H), 7.71 (d, 2H), 7.50-7.41 (m, 4H), 7.35 (d, 1H), 7.11 (dd, 1H), 6.72 (d, 1H), 6.63-6.60 (m, 2H), 5.41 (s, 2H), 4.78 (d, 2H), 3.67 (t, 1H), 3.01 (hept, 1H), 1.28 (d, 6H). MS: 425 (M+1)$^+$

Example 90

1-(4-Hydroxy-benzyl)-4-(4-isopropyl-phenyl)-6-prop-2-ynyloxy-1H-quinazolin-2-one

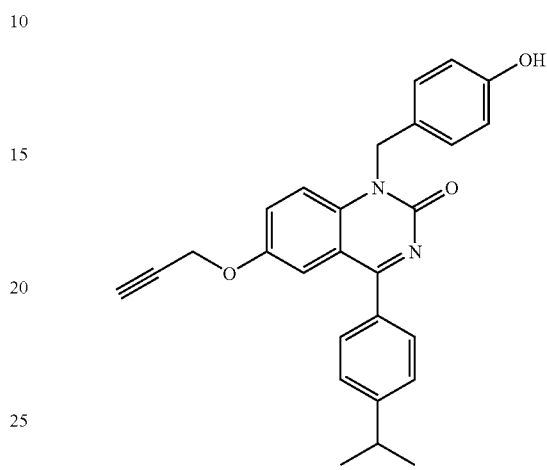

$^1$H-NMR (300 MHz, CDCl$_3$): 7.76 (d, 2H), 7.48 (d, 1H), 7.38 (d, 1H), 7.32 (d, 2H), 7.18 (d, 2H), 6.76 (d, 2H), 5.45 (bs, 3H), 4.65 (d, 2H), 3.02 (hept, 1H), 2.55 (t, 1H), 1.33 (d, 6H). MS: 425 (M+1)$^+$

Example 91

Synthesis of 1-[2-(6-Chloro-hexyloxy)-benzyl]-4-(4-isopropyl-phenyl)-6-prop-2-ynyloxy-1H-quinazolin-2-one

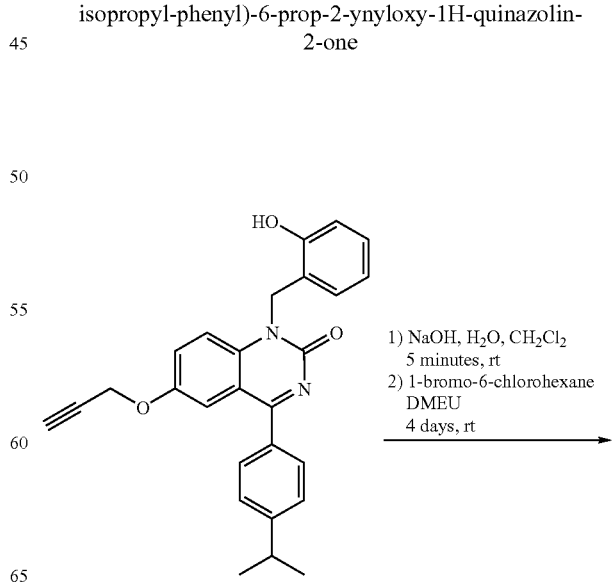

1) NaOH, H$_2$O, CH$_2$Cl$_2$
   5 minutes, rt
2) 1-bromo-6-chlorohexane
   DMEU
   4 days, rt

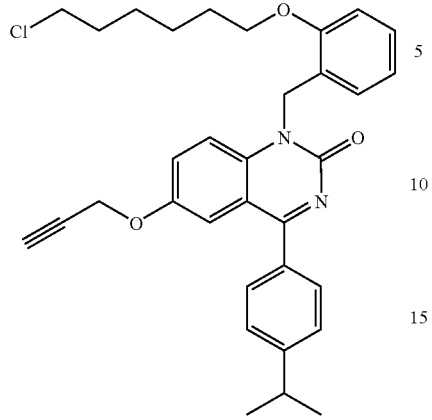

To a solution of 482 mg (1.13 mmol) 1-(2-hydroxy-benzyl)-4-(4-isopropyl-phenyl)-6-prop-2-ynyloxy-1H-quinazolin-2-one in 2 ml dichloromethane is added 1 ml 1M aqueous NaOH. After stirring for 5 minutes the solvents are evaporated. The residue is dissolved in 4.8 ml DMEU and 0.25 ml (1.70 mmol) 1-bromo-6-chlorohexane are added. After stirring for 3 days at rt additional 0.083 ml 1-bromo-6-chlorohexane are added and stirring at rt is continued for 1 day. The reaction mixture is poured onto water, extracted with ethyl acetate and purified by flash chromatography (hexanes/ethyl acetate 6:1).

$^1$H NMR: 7.76 (d, 2H), 7.49 (d, 1H), 7.38 (d, 2H), 7.32-7.26 (m, 2H), 7.21 (ddd, 1H), 6.99 (dd, 1H), 6.90 (d, 1H), 6.80 (t, 1H), 5.56 (s, 2H), 4.43 (d, 2H), 4.10 (t, 2H), 3.56 (t, 2H), 3.02 (hept, 1H), 2.54 (t, 1H), 1.96-1.79 (m, 4H), 1.63-1.56 (m, 4H), 1.33 (d, 6H). MS: 545 (40), 543 (100) (chloro isotope pattern) (M+1)$^+$ Example 92

Synthesis of 1-[2-(6-dimethylamino-hexyloxy)-benzyl]-4-(4-isopropyl-phenyl)-6-prop-2-ynyloxy-1H-quinazolin-2-one

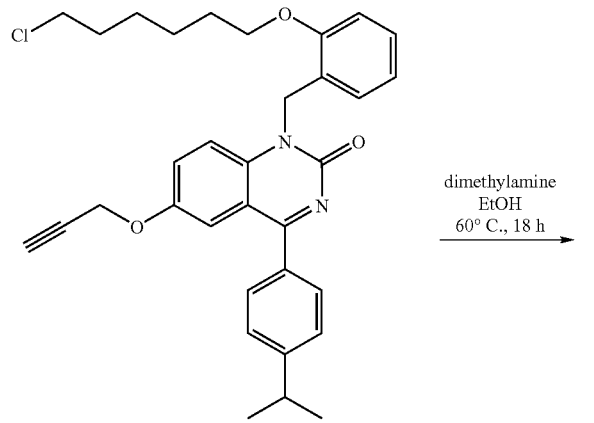

A mixture of 50 mg (92.1 μmol) 1-[2-(6-chloro-hexyloxy)-benzyl]-4-(4-isopropyl-phenyl)-6-prop-2-ynyloxy-1H-quinazolin-2-one and 160 μl ethanolic dimethylamine solution (33%) is heated at 60° C. for 18 h. Extraction with dichloromethane and aqueous 0.1 M NaOH yields the title compound.

$^1$H NMR (300 MHz, CDCl$_3$): 7.75 (d, 2H), 7.48 (d, 1H), 7.38 (d, 2H), 7.27 (m, 2H), 7.10 (td, 1H), 6.98 (dd, 1H), 6.90 (d, 1H), 6.80 (t, 1H), 5.55 (s, 2H), 4.63 (d, 2H), 4.09 (t, 2H), 3.01 (hept, 1H), 2.54 (t, 1H), 2.34 (dd, 2H), 2.27 (s, 6H), 1.90 (quint, 2H), 1.63-1.40 (m, 6H), 1.32 (d, 6H). MS: 552 (M+1)$^+$ The compounds of the following examples are prepared by analogy to the examples described immediately above:

Example 93

1-[2-(6-Imidazol-1-yl-hexyloxy)-benzyl]-4-(4-isopropyl-phenyl)-6-prop-2-ynyloxy-1H-quinazolin-2-one

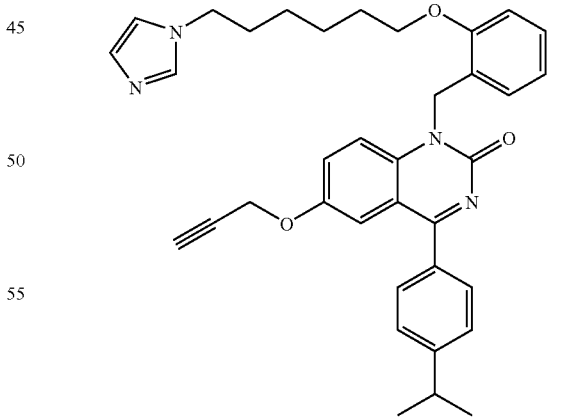

$^1$H NMR: (300 MHz, CDCl$_3$): 7.75 (d, 2H), 7.48-7.45 (m, 2H), 7.38 (d, 2H), 7.27 (dd, 1H), 7.24 (s, 1H), 7.20 (td, 1H), 7.03 (s, 1H), 6.96-6.86 (m, 3H), 6.80 (t, 1H), 5.55 (s, 1H), 4.63 (d, 2H), 4.06 (t, 2H), 3.95 (t, 2H), 3.01 (hept, 1H), 2.54 (t, 1H), 1.88-1.78 (m, 4H), 1.58 (quint, 2H), 1.45-1.37 (m, 2H), 1.32 (d, 6H). MS: 575 (M+1)$^+$

Example 94

4-(4-Isopropyl-phenyl)-1-[3-(7-piperidin-1-yl-heptyloxy)-benzyl]-6-prop-2-ynyloxy-1H-quinazolin-2-one (trifluoroacetic acid salt)

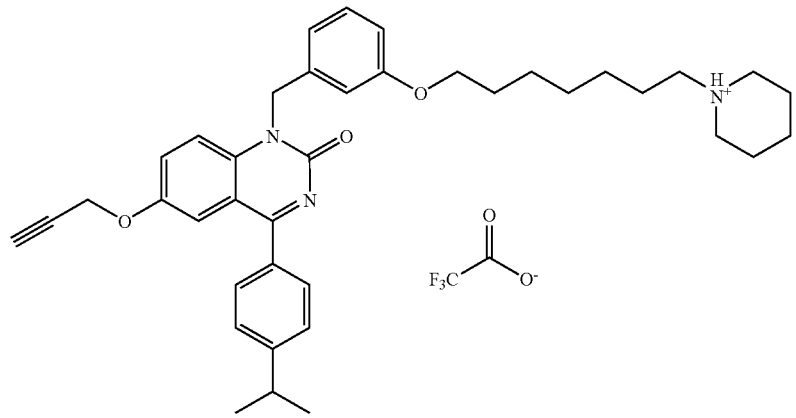

¹H NMR (300 MHz, CDCl3): 7.73 (d, 2H), 7.50 (d, 1H), 7.40 (d, 2H), 7.36 (dd, 1H), 7.32 (d, 1H), 7.24 (t, 1H), 6.90 (d, 1H), 6.82 (s, 1H), 6.79 (d, 1H), 5.52 (s, 2H), 4.65 (d, 2H), 3.90 (t, 2H), 3.61 (d, broad, 2H), 3.03 (hept, 1H), 2.98 (m, broad, 2H), 2.66 (m, broad, 2H), 2.56 (t, 1H), 2.03-1.32 (m, 16H), 1.33 (d, 6H). MS: 606 (M+1)⁺

Example 95

(3-Dimethylamino-propyl)-methyl-carbamic acid 4-[4-(4-isopropyl-phenyl)-2-oxo-6-prop-2-ynyloxy-2H-quinazolin-1-ylmethyl]-phenyl ester (trifluoroacetic acid salt)

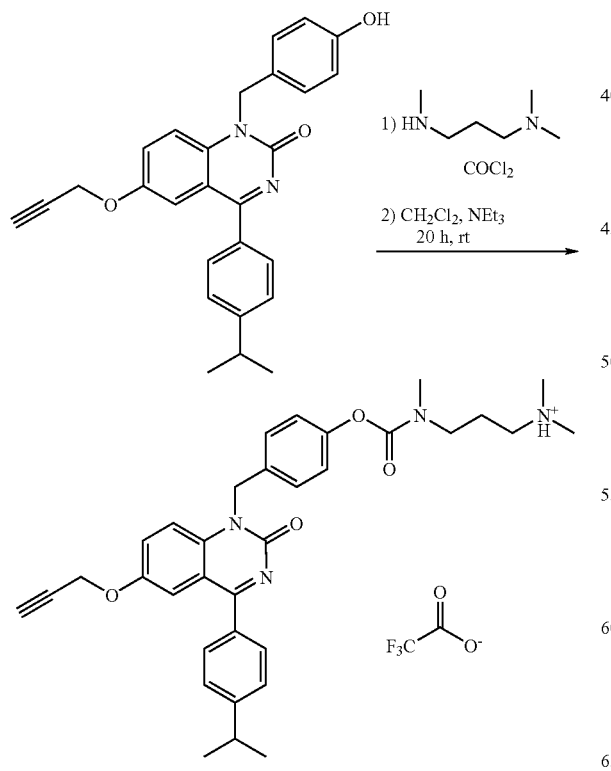

To an excess of phosgene dissolved in toluene are added at 0° C. 41.5 µl (0.283 mmol) N,N,N'-trimethyl-1,3-propanediamine. After 5 minutes the solvent is evaporated and the residue is dissolved in 2 ml dichloromethane. Triethylamine (79.2 µl, 0.566 mmol) and a solution of 100 mg (0.236 mmol) 1-(4-hydroxy-benzyl)-4-(4-isopropyl-phenyl)-6-prop-2-ynyloxy-1H-quinazolin-2-one in 2 ml dichloromethane are added at 0° C. After stirring for 20 h at rt aqueous ammonia and 0.1 M NaOH are added. The title compound is obtained by extraction with dichloromethane followed by reversed phase preparative HPLC.

¹H NMR (300 MHz, CDCl3): 7.73 (d, 2H), 7.54 (d, 1H), 7.45-7.30 (m, 4H), 7.42 (d, 2H), 7.10 d, 2H), 5.56 (s, 2H), 4.68 (d, 2H), 3.44 (t, 2H), 3.20-3.07 (m, 2H), 3.03 (hept, 1H), 2.87 (m, 6H), 2.57 (t, 1H), 2.19 (s, 3H), 2.19-2.07 (m, 2H), 1.33 (d, 6H). MS: 567 (M+1)⁺

Example 96

Synthesis of 4-(4-Isopropyl-phenyl)-1-{3-[2-(2-methoxy-ethoxy)-ethoxy]-benzyl}-6-prop-2-ynyloxy-1H-quinazolin-2-one

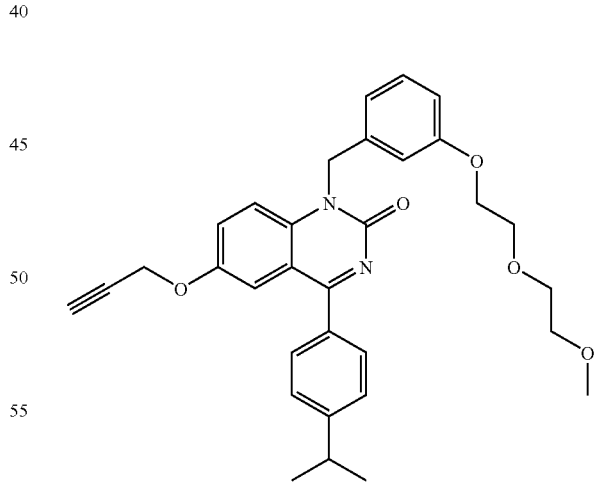

To a solution of 100 mg (0.236 mmol) of 1-(3-hydroxy-benzyl)-4-(4-isopropyl-phenyl)-6-prop-2-ynyloxy-1H-quinazolin-2-one in anhydrous DMF (5 mL) is added NaH (11 mg, 0.471 mmol) and the solution is allowed to stir until evolution of gas ceases. 1-bromo-2-(2-methoxyethoxy)-ethane (34 µl, 0.247 mmol) is added and the mixture is heated for 20 hours at 60° C. After cooling to room temperature, the reaction mixture is quenched with water and extracted with dichloromethane (2×20 ml). The combined organic layers are washed with brine, dried (Na$_2$SO$_4$), filtered and evaporated in vacuo to provide a yellow solid which is purified by flash chromatography on silica gel using petroleum ether/ethyl acetate (1:1) to provide the title compound as a yellow oil. Yield: 111 mg (85%).

$^1$H-NMR (300 MHz, CDCl$_3$): 7.76 (d, 2H), 7.49 (d, 1H), 7.38 (d, 2H), 7.32 (dd, 1H), 7.20-7.28 (m, 2H), 6.90 (dd, 1H), 6.86 (m, 1H), 6.80 (dd, 1H), 5.51 (broad s, 2H), 4.65 (d, 2H), 4.10 (t, 2H), 3.84 (t, 2H), 3.70 (m, 2H), 3.58 (m, 2H), 3.38 (s, 3H), 3.02 (hept, 1H), 2.55 (t, 1H), 1.33 (d, 6H). MS: 527 (M+1)$^+$ Example 97

Synthesis of 4-(4-Isopropyl-phenyl)-1-[3-(2-{2-[2-(2-methoxy-ethoxy)-ethoxy]-ethoxy}-ethoxy)-benzyl]-6-prop-2-ynyloxy-1H-quinazolin-2-one

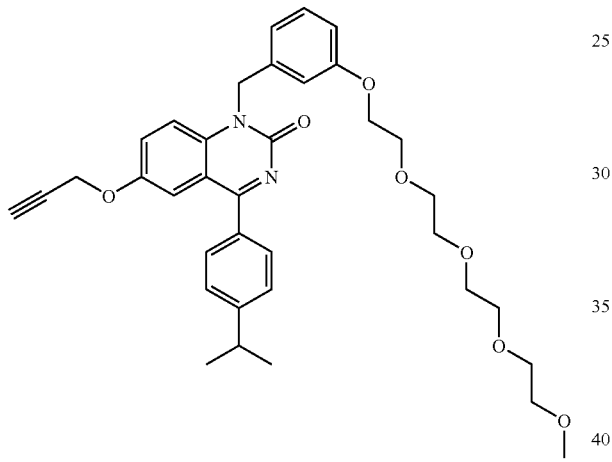

A. Preparation of Mesylate:

To a solution of triethylene glycol monomethyl ether (0.5 ml, 3.1 mmol) in anhydrous THF at room temperature is added triethylamine (516 µM, 3.71 mmol) followed by methanesulfonyl chloride (265 µM, 3.41 mmol). The reaction mixture is allowed to stir for 2.5 hours after which TLC indicates complete conversion. This solution is used as is in Step B.

B. Alkylation of Phenol with the Mesylate:

To a solution of 100 mg (0.236 mmol) of 1-(3-hydroxy-benzyl)-4-(4-isopropyl-phenyl)-6-prop-2-ynyloxy-1H-quinazolin-2-one in acetone (5 ml) is added potassium carbonate (326 mg, 2.36 mmol) followed by the mesylate prepared in Step A (5 ml, 1.18 mmol). The reaction mixture is heated at reflux for 2 days. After cooling to room temperature, the reaction mixture is quenched with water and extracted with EtOAc (2×20 ml). The combined organic layers are washed with brine, dried (Na$_2$SO$_4$), filtered and evaporated in vacuo to provide a yellow oil which is purified by flash chromatography on silica gel using dichloromethane/t-butyl methyl ether (1:1) to provide the title compound as a yellow oil. Yield: 54 mg (35%).

$^1$H-NMR (300 MHz, CDCl$_3$): 7.76 (d, 2H), 7.49 (d, 1H), 7.39 (d, 2H), 7.32 (dd, 1H), 7.20-7.28 (m, 2H), 6.90 (dd, 1H), 6.86 (m, 1H), 6.80 (dd, 1H), 5.52 (broad s, 2H), 4.65 (d, 2H), 4.09 (t, 2H), 3.82 (t, 2H), 3.60-3.72 (m, 10H), 3.55 (m, 2H), 3.37 (s, 3H), 3.03 (hept, 1H), 2.56 (t, 1H), 1.33 (d, 6H). MS: 615 (M+1)$^+$ Example 98

Synthesis of 4-(4-isopropyl-phenyl)-1-[4-(2-{2-[2-(2-methoxy-ethoxy)-ethoxy]-ethoxy}-ethoxy)-benzyl]-6-prop-2-ynyloxy-1H-quinazolin-2-one

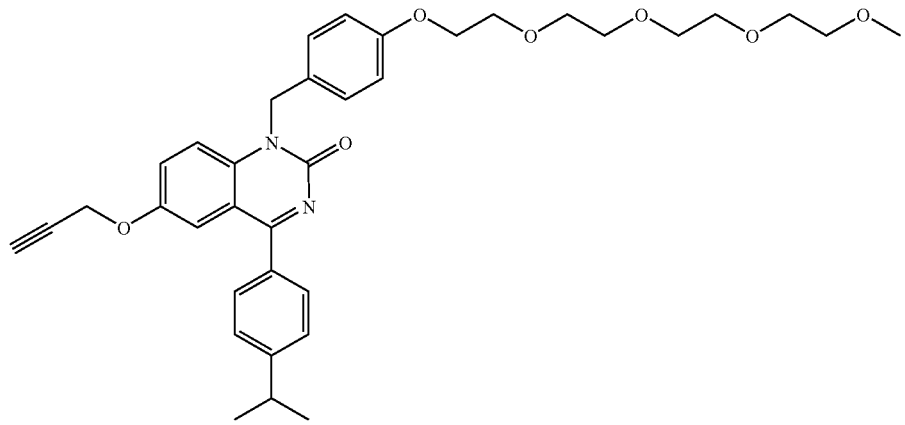 [SMILES: C#CCOc1ccc2c(c1)c(-c1ccc(C(C)C)cc1)nc(=O)n2Cc1ccc(OCCOCCOCCOCCOC)cc1]

To a solution of 100 mg (0.236 mmol) of 1-(4-hydroxy-benzyl)-4-(4-isopropyl-phenyl)-6-prop-2-ynyloxy-1H-quinazolin-2-one in acetone (5 ml) is added potassium carbonate (326 mg, 2.36 mmol) followed by the mesylate (5 ml, 1.18 mmol) prepared in Step A above (see Example RT-3). The reaction mixture is heated at reflux for 2 days. After cooling to room temperature, the reaction mixture is quenched with water and extracted with EtOAc (2×20 ml). The combined organic layers are washed with brine, dried (Na$_2$SO$_4$), filtered and evaporated in vacuo to provide a yellow oil which is purified by flash chromatography on silica gel using dichloromethane/t-butyl methyl ether (1:1) to provide the title compound as a yellow oil. Yield: 44 mg (30%).

$^1$H-NMR (300 MHz, CDCl$_3$): 7.76 (d, 2H), 7.49 (d, 1H), 7.39 (d, 2H), 7.32 (m, 2H), 7.25-7.28 (m, 2H), 6.87 (d, 2H), 5.49 (broad s, 2H), 4.65 (d, 2H), 4.08 (t, 2H), 3.82 (t, 2H), 3.60-3.72 (m, 10H), 3.54 (m, 2H), 3.37 (s, 3H), 3.03 (hept, 1H), 2.55 (t, 1H), 1.33 (d, 6H). MS: 615 (M+1)$^+$ Example 99

Synthesis of 4-(4-isopropyl-phenyl)-1-[3-(2-methoxy-ethoxy)-benzyl]-6-prop-2-ynyloxy-1H-quinazolin-2-one

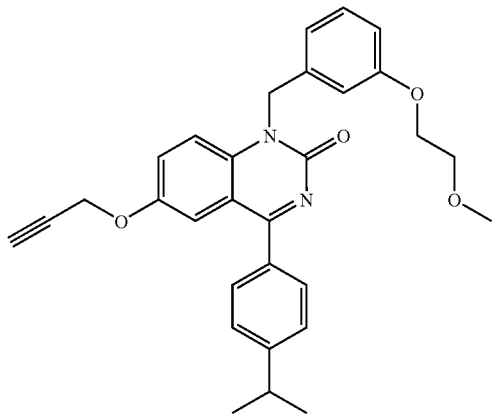 [SMILES: C#CCOc1ccc2c(c1)c(-c1ccc(C(C)C)cc1)nc(=O)n2Cc1cccc(OCCOC)c1]

To a solution of 100 mg (0.236 mmol) of 1-(3-hydroxy-benzyl)-4-(4-isopropyl-phenyl)-6-prop-2-ynyloxy-1H-quinazolin-2-one in anhydrous DMF (5 ml) is added NaH (11 mg, 0.471 mmol) and the solution is allowed to stir until evolution of gas ceases. 1-Bromo-2-methoxy-ethane (34 µl, 0.236 mmol) is added and the mixture is heated for 2 days at 60° C. After cooling to room temperature, the reaction mixture is quenched with water and the mixture is acidified to pH 3 with 10% citric acid. The mixture is extracted with ether (2×20 ml). The combined organic layers are washed with brine, dried (Na$_2$SO$_4$), filtered and evaporated in vacuo to provide a yellow solid which is purified by flash chromatography on silica gel using petroleum ether/ethyl acetate (9:1 to 1:1) to provide the title compound as a yellow oil. Yield:56 mg (49%).

$^1$H-NMR (300 MHz, CDCl$_3$): 7.76 (d, 2H), 7.49 (d, 1H), 7.38 (d, 2H), 7.32 (dd, 1H), 7.20-7.28 (m, 2H), 6.86-6.90 (m, 2H), 6.81 (dd, 1H), 5.52 (broad s, 2H), 4.65 (d, 2H), 4.08 (t, 2H), 3.71 (m, 2H), 3.43 (s, 3H), 3.02 (hept, 1H), 2.55 (t, 1H), 1.33 (d, 6H). MS: 483 (M+1)$^+$ Example 100

Synthesis of 4-(4-isopropyl-phenyl)-1-(3-{2-[2-(2-methoxy-ethoxy)-ethoxy]-ethoxy}-benzyl)-6-prop-2-ynyloxy-1H-quinazolin-2-one

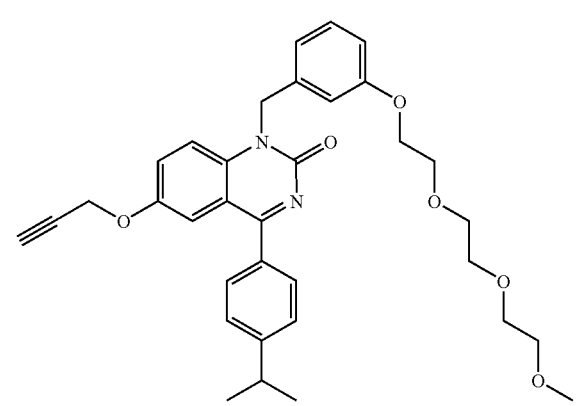 [SMILES: C#CCOc1ccc2c(c1)c(-c1ccc(C(C)C)cc1)nc(=O)n2Cc1cccc(OCCOCCOCCOC)c1]

A. Preparation of Mesylate:

To a solution of triethylene glycol monomethyl ether (0.5 g, 2.35 mmol) in anhydrous THF at room temperature is added triethylamine (392 µl, 2.82 mmol) followed by methanesulfonyl chloride (201 µl, 2.59 mmol). The reaction mixture is allowed to stir for 2.5 hours after which TLC indicates complete conversion. This solution is used as is in Step B.

B. Alkylation of Phenol with the Mesylate:

To a solution of 100 mg (0.236 mmol) of 1-(3-hydroxy-benzyl)-4-(4-isopropyl-phenyl)-6-prop-2-ynyloxy-1H-quinazolin-2-one in acetone (5 ml) is added potassium carbonate (326 mg, 2.36 mmol) followed by the mesylate prepared in Step A (5 ml, 1.18 mmol). The reaction mixture is heated at reflux for 2 days. After cooling to room temperature, the reaction mixture is quenched with water and extracted with EtOAc (2×20 ml). The combined organic layers are washed with brine, dried (Na$_2$SO$_4$), filtered and evaporated in vacuo to provide a yellow oil which is purified by flash chromatography on silica gel using dichloromethane/t-butyl methyl ether (1:1) to provide the title compound as a yellow oil. Yield: 101 mg (75%).

$^1$H-NMR (300 MHz, CDCl$_3$): 7.76 (d, 2H), 7.49 (d, 1H), 7.40 (d, 2H), 7.32 (dd, 1H), 7.20-7.28 (m, 2H), 6.86-6.90 (m, 2H), 6.80 (dd, 1H), 5.52 (broad s, 2H), 4.65 (d, 2H), 4.07 (t, 2H), 3.83 (t, 2H), 3.60-3.72 (m, 6H), 3.55 (m, 2H), 3.37 (s, 3H), 3.03 (hept, 1H), 2.56 (t, 1H), 1.33 (d, 6H). MS: 571 (M+1)$^+$ The compounds of the following examples are prepared by analogy to the example above:

Example 101

4-(4-Isopropyl-phenyl)-1-{2-[2-(2-methoxy-ethoxy)-ethoxy]-benzyl}-6-prop-2-ynyloxy-1H-quinazolin-2-one

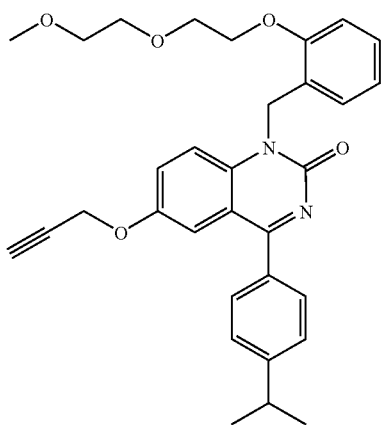 [SMILES: C#CCOc1ccc2c(c1)c(-c1ccc(C(C)C)cc1)nc(=O)n2Cc1ccccc1OCCOCCOC]

$^1$H-NMR (300 MHz, CDCl$_3$): 7.75 (d, 2H), 7.50 (d, 2H), 7.41 (m, 3H), 7.23 (t, 1H), 7.09 (d, 1H), 6.94 (d, 1H), 6.86 (t, 1H), 5.64 (bs, 2H), 4.66 (s, 2H), 4.30 (t, 2H), 3.97 (t, 2H), 3.78 (t, 2H), 3.60 (t, 2H), 3.40 (s, 3H), 3.04 (hept, 1H), 2.56 (t, 1H), 1.34 (d, 6H). MS: 527 (M+1)$^+$

Example 102

Synthesis of 1-[3-(2-hydroxy-ethoxy)-benzyl]-4-(4-isopropyl-phenyl)-6-prop-2-ynyloxy-1H-quinazolin-2-one

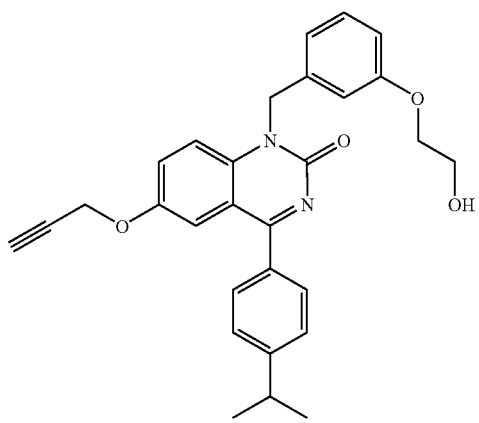 [SMILES: C#CCOc1ccc2c(c1)c(-c1ccc(C(C)C)cc1)nc(=O)n2Cc1cccc(OCCO)c1]

To a solution of 76 mg (0.14 mmol) of 4-(4-isopropyl-phenyl)-6-prop-2-ynyloxy-1-{3-[2-(tetrahydro-pyran-2-yloxy)-ethoxy]-benzyl}-1H-quinazolin-2-one (Example RT-6) in MeOH (10 ml) is added 10 wt % Dowex-50 and the mixture is stirred vigorously for 3 days. The reaction mixture is filtered and the solvent is removed in vacuo. The residue is dissolved in CH$_2$Cl$_2$ and extracted with water and then brine, dried (MgSO$_4$), filtered and evaporated in vacuo to provide a yellow oil which is purified by preparative TLC of silica gel using dichloromethane/ether (1:1) to provide the title compound as a yellow oil. Yield: 11 mg (17%).

$^1$H-NMR (300 MHz, MeOD): 7.75 (d, 2H), 7.45-7.51 (m, 5H), 7.25 (t, 1H), 6.85-6.89 (m, 3H), 5.58 (broad s, 2H), 4.71 (d, 2H), 4.62 (broad s, 1H), 4.01 (t, 2H), 3.83 (t, 2H), 3.04-3.08 (m, 2H), 1.35 (d, 6H). MS: 469 (M+1)$^+$

Example 103

Synthesis of 4-(4-isopropyl-phenyl)-6-prop-2-ynyloxy-1-{3-[2-(tetrahydro-pyran-2-yloxy)-ethoxy]-benzyl}1H-quinazolin-2-one

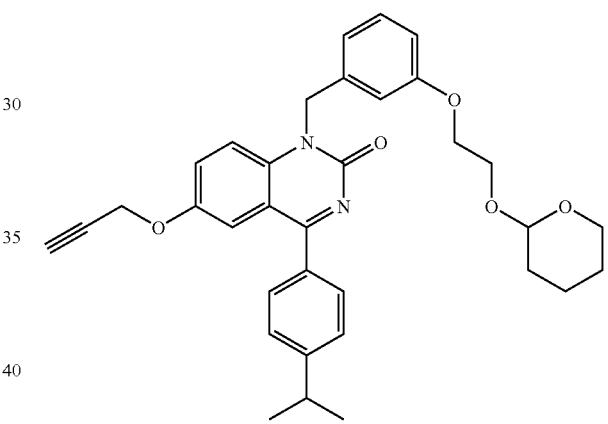

To a solution of 640 mg (1.51 mmol) of 1-(3-hydroxy-benzyl)-4-(4-isopropyl-phenyl)-6-prop-2-ynyloxy-1H-quinazolin-2-one in acetone (20 ml) is added potassium carbonate (2.08 g, 15.1 mmol) followed by 2-(2-bromo-ethoxy)-tetrahydropyran (475 µl, 3.02 mmol). The reaction mixture is heated at reflux for 2 days. After cooling to room temperature, the reaction mixture is quenched with water and extracted with EtOAc (2×20 ml). The combined organic layers are washed with brine, dried (Na$_2$SO$_4$), filtered and evaporated in vacuo to provide a yellow oil which is purified by flash chromatography on silica gel using dichloromethane/t-butyl methyl ether (1:1) to provide the title compound as a yellow oil. Yield: 830 mg (71%).

$^1$H-NMR (300 MHz, CDCl$_3$): 7.75 (d, 2H), 7.49 (d, 1H), 7.40 (d, 2H), 7.32 (dd, 1H), 7.20-7.28 (m, 2H), 6.86-6.90 (m, 2H), 6.80 (dd, 1H), 5.52 (broad s, 2H), 4.68 (m, 1H), 4.65 (d, 2H), 4.07 (m, 2H), 4.00-4.05 (m, 1H), 3.84-3.88 (m, 1H), 3.74-3.81 (m, 1H), 3.49-3.53 (m, 1H), 3.02 (hept, 1H), 2.56 (t, 1H), 1.49-1.72 (m, 6H), 1.33 (d, 6H). MS: 553 (M+1)$^+$, also observed 469 (M−THP+1).

Example 104

Synthesis of 4-(4-isopropyl-phenyl)-1-(2-{2-[2-(2-methoxy-ethoxy)-ethoxy]-ethoxy}-benzyl)-6-prop-2-ynyloxy-1H-quinazolin-2-one

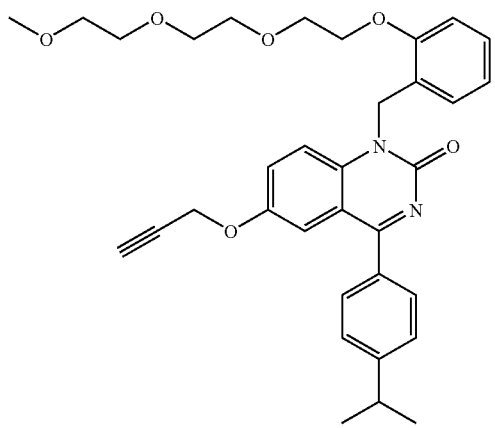 [SMILES: C#CCOc1ccc2c(c1)c(-c1ccc(C(C)C)cc1)nc(=O)n2Cc1ccccc1OCCOCCOCCOC]

To a solution of 125 mg (0.29 mmol) of 1-(2-hydroxybenzyl)-4-(4-isopropyl-phenyl)-6-prop-2-ynyloxy-1H-quinazolin-2-one in acetone (5 ml) is added potassium carbonate (407 mg, 2.94 mmol) followed by 2-[2-(2-methoxyethoxy)-ethoxy]-ethyl-methanesulfonate (as prepared in Step A, Example RT-5) (357 mg, 1.47 mmol). The reaction mixture is heated at reflux overnight. After cooling to room temperature, the reaction mixture is quenched with water and extracted with EtOAc (2×20 ml). The combined organic layers are washed with brine, dried (Na$_2$SO$_4$), filtered and evaporated in vacuo to provide a yellow oil which is purified by preparative TLC chromatography on Silica gel using dichloromethane/ether (1:1) to provide the title compound as a yellow oil. Yield: 29 mg (17%).

$^1$H-NMR (300 MHz, CDCl$_3$): 7.76 (d, 2H), 7.49 (d, 1H), 7.38 (d, 2H), 7.32 (dd, 1H), 7.20-7.28 (m, 2H), 6.86-6.90 (m, 2H), 6.81 (dd, 1H), 5.60 (broad s, 2H), 4.65 (d, 2H), 4.28 (dd, 2H), 3.97 (dd, 2H), 3.78 (m, 2H), 3.63-3.68 (m, 4H), 3.55 (m, 2H), 3.36 (s, 3H), 3.02 (hept, 1H), 2.55 (t, 1H), 1.33 (d, 6H). MS: 571 (M+1)$^+$

Example 105

Methanesulfonic acid 2-[4-(4-isopropyl-phenyl)-2-oxo-6-prop-2-ynyloxy-2H-quinazolin-1-ylmethyl]-phenyl ester

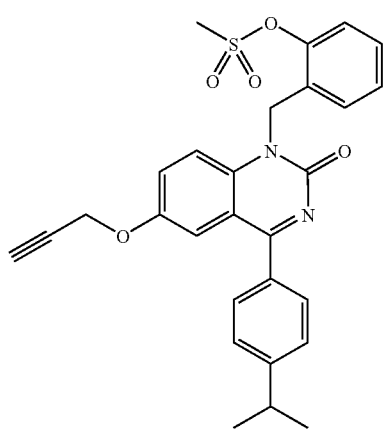 [SMILES: C#CCOc1ccc2c(c1)c(-c1ccc(C(C)C)cc1)nc(=O)n2Cc1ccccc1OS(C)(=O)=O]

In the preparation of example 104, the title compound was isolated as a by-product. Yield: 55 mg (37%).

$^1$H-NMR (300 MHz, CDCl$_3$): 7.77 (d, 2H), 7.49 (d, 1H), 7.17-7.44 (m, 7H), 7.03 (d, 1H), 5.69 (broad s, 2H), 4.66 (d, 2H), 3.36 (s, 3H), 3.03 (hept, 1H), 2.56 (t, 1H), 1.33 (d, 6H). MS: 503 (M+1)$^+$

Example 106

2-[(3-Dimethylamino-propyl)-methyl-amino]-N-{3-[4-(4-isopropyl-phenyl)-2-oxo-6-propargyloxy-2H-quinazolin-1-ylmethyl]-phenyl}-acetamide A. Synthesis of (4-isopropyl-phenyl)-[2-(3-nitro-benzylamino)-5-propargyloxy-phenyl]-methanone

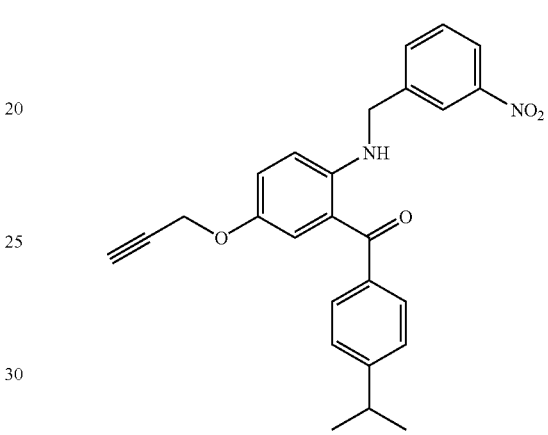

A mixture of 30 g (102 mmol) (2-amino-5-propargyloxyphenyl)-(4-isopropyl-phenyl)-methanone, 23.8 g (110 mmol) 3-nitrobenzylbromide and 21 ml (120 mmol) Hünig's base in 160 ml methylene chloride is stirred overnight at 45° C. The resulting dark solution is washed twice with 200 ml water and with brine. Purification of the crude product by chromatography (CH$_2$Cl$_2$/petroleum ether 1:1) affords 34.4 g (79%) of a viscous red oil.

$^1$H-NMR (300 MHz, CDCl$_3$): 8.60 (broad t, 1H), 8.20 (s, 1H), 8.11 (d, 1H); 7.66 (d, 1H), 7.58 (d, 2H), 7.47 (t, 1H), 7.30 (d, 2H), 7.24 (d, 1H), 7.05 (dd, 1H), 6.55 (d, 1H), 4.57 (d, 2H), 4.51 (d, 2H), 2.99 (hept, 1H), 2.47 (t, 1H), 1.29 (d, 6H). MS: 429 (M+1)$^+$ B. Synthesis of 4-(4-isopropyl-phenyl)-1-(3-nitro-benzyl)-6-propargyloxy-1H-quinazolin-2-one

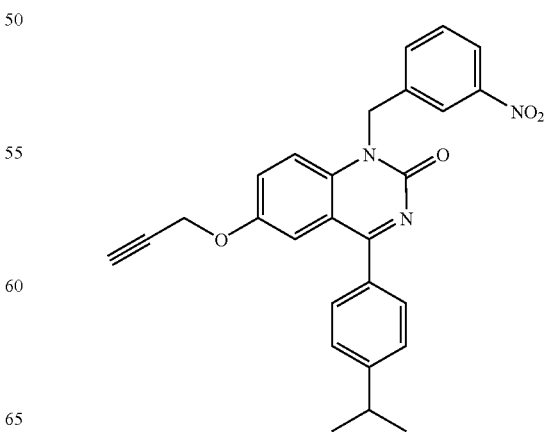

A red solution of 34 g (79.4 mmol) of the benzophenone prepared in step A in 200 ml acetic acid is treated with 6.2 g (95 mmol) sodium cyanate under vigorous stirring which is continued overnight. The mixture is diluted with water and extracted with ethyl acetate. Concentration after washing with bicarbonate solution yields several crops of product. While the initial batches are yellow and pure, the subsequent ones are orange and have to be purified by flash chromatography. Combined yield: 25.9 g (72%). m.p. 167-168° C.

$^1$H-NMR (300 MHz, CDCl$_3$): 8.18 (s, 1H), 8.13 (d, 1H); 7.75 (d, 2H), 7.66 (d, 1H), 7.53 (d, 1H), 7.51 (t, 2H), 7.39 (d, 1H), 7.33 (dd, 1H), 7.16 (d, 1H), 5.62 (broad s, 2H), 4.66 (d, 2H), 3.03 (hept, 1H), 2.57 (t, 1H), 1.33 (d, 6H). MS: 454 (M+1)$^+$ C. Synthesis of 1-(3-amino-benzyl)-4-(4-isopropyl-phenyl)-6-propargyloxy-1H-quinazolin-2-one

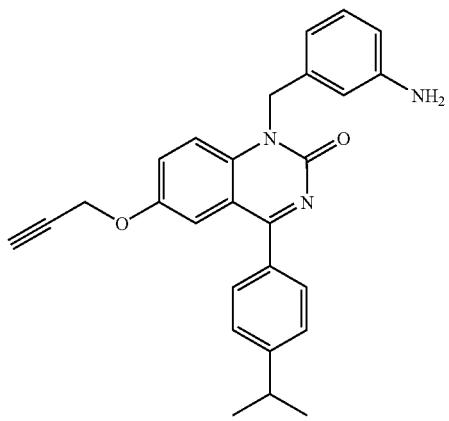 [SMILES: C#CCOc1ccc2c(c1)c(-c1ccc(C(C)C)cc1)nc(=O)n2Cc1cccc([N+](=O)[O-])c1]

A mixture of 5.7 g (12.57 mmol) of the aromatic nitro-compound prepared in step B and 5.7 g (0.10 mol; 8 eq.) iron powder in 85 ml acetic acid is heated to 40° C. and stirred overnight. After 16 h another 3.5 g iron powder is added and stirring continued for 4 h. The brown suspension is distributed between ethyl acetate and water. The organic layer is washed with sodium bicarbonate solution and brine. Concentration in vacuo leaves 5.88 g of yellow foam. Flash chromatography (petroleum ether/ethyl acetate) yields 2.80 g (53%) of a yellow solid. m.p. 186° C.

$^1$H-NMR (300 MHz, CDCl$_3$): 7.76 (d, 2H), 7.48 (s, 1H); 7.39 (d, 2H), 7.30 (s, 2H), 7.11 (t, 1H), 6.73 (d, 1H), 6.62 (s, 1H), 6.57 (d, 1H), 5.46 (broad s, 2H), 4.64 (d, 2H), 3.65 (broad s, NH$_2$), 3.02 (hept, 1H), 2.64 (t, 1H), 1.32 (d, 6H). MS: 424 (M+1)$^+$ D. Synthesis of 4-bromo-N-{3-[4-(4-isopropyl-phenyl)-2-oxo-6-propargyloxy-2H-qunazolin-1-ylmethyl]-phenyl}-butyramide

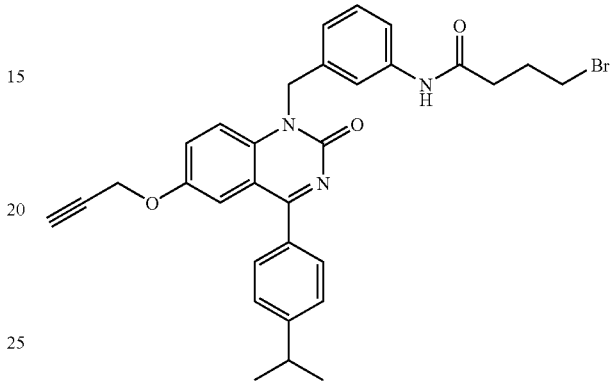

A solution of 5.0 g (11.8 mmol) of the aniline (step C) is taken up in 40 ml CH$_2$Cl$_2$ and cooled with an ice bath. At ca. 3-4° C., 2.3 g (17.7 mmol; 1.5 eq.) Hünig's base is added, followed by the dropwise addition of 2.62 g 4-bromo-butyryl chloride (in 10 ml CH$_2$Cl$_2$). The orange solution is left to stir overnight at rt. The resulting yellow suspension is distributed between methylene chloride and water. The residue obtained after concentration in vacuo is chromatographed (CH$_2$Cl$_2$/MeOH) to yield 2.4 g (53%) of a beige solid. m.p. 121-122° C.

$^1$H-NMR (300 MHz, DMSO): 9.92 (s, NH), 7.71 (d, 2H), 7.60 (d, 1H), 7.30-7.50 (m, 6H), 7.24 (t, 1H), 6.96 (d, 1H), 5.45 (broad s, 2H), 4.79 (d, 2H), 3.66 (t, 2H), 3.02 (hept, 1H), 2.41 (t, 2H), 1.98 (quint, 2H), 1.28 (d, 6H). MS: 492 (M+1-HBr)$^+$ E. Synthesis of N-{3-[4-(4-isopropyl-phenyl)-2-oxo-6-propargyloxy-2H-qunazolin-1-ylmethyl]-phenyl}4-[4-(2-methoxy-ethyl)-piperazin-1-yl]-butyramide

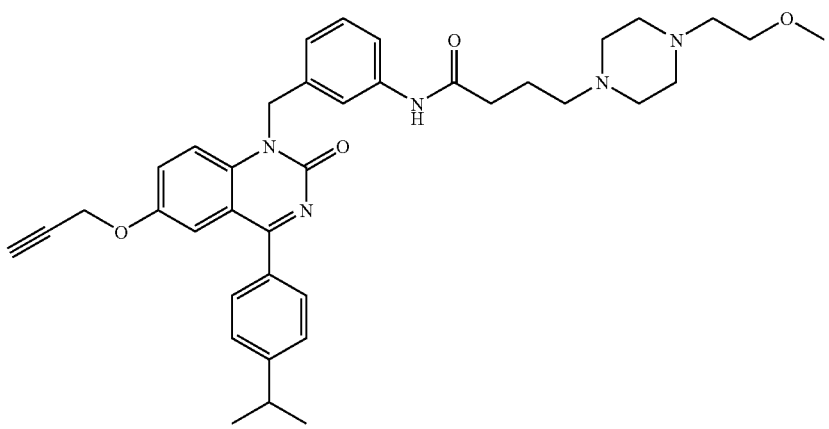 [SMILES: C#CCOc1ccc2c(c1)c(-c1ccc(C(C)C)cc1)nc(=O)n2Cc1cccc(NC(=O)CCCN2CCN(CCOC)CC2)c1]

A solution consisting of 260 mg (0.45 mmol) of the bromide prepared above, 98 mg (0.68 mmol; 1.5 eq.) N-methoxy-ethyl-piperazine and 130 mg (0.94 mmol) potassium carbonate in 1 ml 1,3-dimethyl-2-imidazolidinone (DMEU) is stirred for 90 minutes at 60° C. The mixture is poured into water and extracted with ethyl acetate. Purification by chromatography resulted in 65 mg (24%) of a dark yellow solid. m.p. 140-141° C.

$^1$H-NMR (300 MHz, CDCl$_3$): 8.63 (s, 1H), 7.74 (d, 2H); 7.51 (d, 1H), 7.45-7.49 (m, 2H), 7.36 (d, 2H), 7.24-7.32 (m, 3H), 7.04 (d, 1H), 5.51 (broad s, 2H), 4.62 (d, 2H), 3.47 (t, 2H), 3.33 (s, 3H), 3.01 (hept, 1H), 2.48-2.56 (m, 8H), 2.38-2.48 (m, 6H), 1.88 (quint, 2H), 1.33 (d, 6H). MS: 636 (M+1)$^+$ Example 107

4-(4-Isopropyl-phenyl)-1-[3-(2-oxo-pyrrolidin-1-yl)-benzyl]-6-propargyloxy-1H-quinazolin-2-one

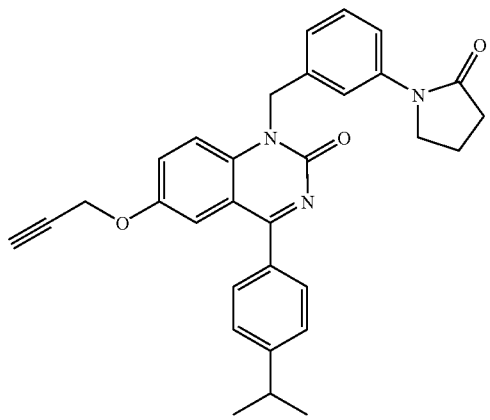 [SMILES: C#CCOc1ccc2c(c1)c(-c1ccc(C(C)C)cc1)nc(=O)n2Cc1cccc(N2CCCC2=O)c1]

A solution of 300 mg (0.52 mmol) 4-bromo-N-{3-[4-(4-isopropyl-phenyl)-2-oxo-6-propargyloxy-2H-qunazolin-1-ylmethyl]-phenyl}-butyramide in 0.5 ml THF is treated with 25 mg sodium hydride (ca. 55% dispersion in mineral oil; 0.57 mmol) at 0° C. The ice bath is removed and the mixture allowed to reach rt. Work-up after 30 minutes with water/ethyl acetate followed by chromatography yields 100 mg (39%) product as a yellow solid. m.p. 68-69° C.

$^1$H-NMR (300 MHz, CDCl$_3$): 7.74 (d, 2H), 7.68-7.71 (m, 1H), 7.47-7.54 (m, 2H), 7.31 (d, 2H), 7.26-7.33 (m, 3H), 7.07 (d, 1H), 5.54 (broad s, 2H), 4.64 (d, 2H), 3.83 (t, 2H), 3.02 (hept, 1H), 2.59 (t, 2H), 2.55 (t, 1H), 2.14 (quint, 2H), 1.32 (d, 6H). MS: 492 (M+1)$^+$ Example 108

2-[(3-Dimethylmino-propyl)-methyl-amino]-N-{3-[4-(4-isopropyl-phenyl)-2-oxo-6-propargyloxy-2H-quinazolin-1-ylmethyl]-phenyl}-acetamide A. Synthesis of 2-chloro-N-{3-[4-(4-isopropyl-phenyl)-2-oxo-6-propargyloxy-2H-quinazolin-1-ylmethyl]-phenyl}-acetamide

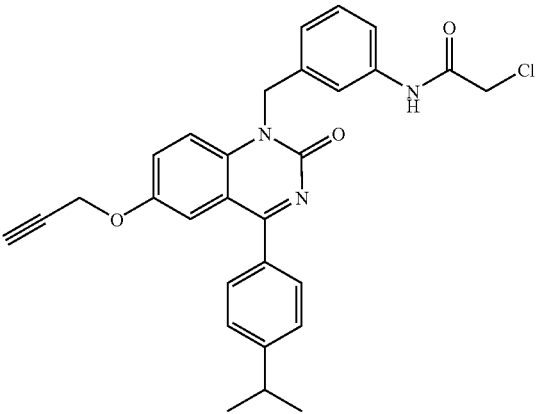 [SMILES: C#CCOc1ccc2c(c1)c(-c1ccc(C(C)C)cc1)nc(=O)n2Cc1cccc(NC(=O)CCl)c1]

A solution of 200 mg (0.47 mmol) 1-(3-amino-benzyl)-4-(4-isopropyl-phenyl)-6-propargyloxy-1H-quinazolin-2-one in 3 ml CH$_2$Cl$_2$ is treated at 0° C. with 41 μl (0.52 mmol; 1.1 eq.) chloroacetyl chloride and 79 μl (0.57 mmol; 1.2 eq.) triethylamine. The mixture is allowed to come to rt. Extractive work-up with water/CH$_2$Cl$_2$ yields 225 mg (95%) of a yellow solid. m.p. 170-172° C.

$^1$H-NMR (300 MHz, CDCl$_3$): 8.31 (s, 1H), 7.75 (d, 2H), 7.61 (d, 1H), 7.51 (d, 1H), 7.47 (s, 1H), 7.39 (d, 2H), 7.27-7.37 (m, 3H), 7.13 (d, 1H), 5.54 (broad s, 2H), 4.65 (d, 2H), 4.17 (s, 2H), 3.02 (hept, 1H), 2.55 (t, 1H), 1.32 (d, 6H). MS: 500 (M+1)$^+$ B. Synthesis of 2-[(3-dimethylmino-propyl)-methyl-amino]-N-{3-[4-(4-isopropyl-phenyl)-2-oxo-6-propargyloxy-2H-quinazolin-1-ylmethyl]-phenyl}-acetamide

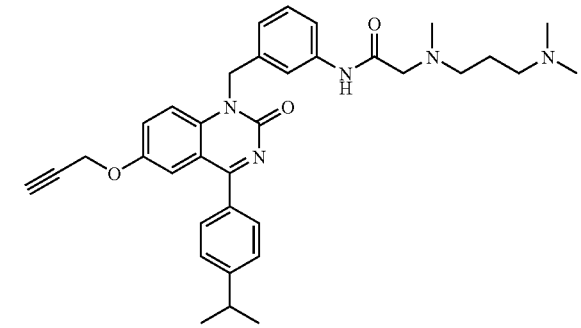 [SMILES: C#CCOc1ccc2c(c1)c(-c1ccc(C(C)C)cc1)nc(=O)n2Cc1cccc(NC(=O)CN(C)CCCN(C)C)c1]

A solution of 100 mg (0.20 mmol) of the chloride prepared in step A in 5 ml CH$_2$Cl$_2$ is treated at rt with 35 μl (0.24 mmol; 1.2 eq.) N,N,N-trimethyl-1,3-propandiamine and 36 mg (0.26 mmol; 1.3 eq) potassium carbonate. After 30 minutes the temperature is raised to 40° C. and stirring continued for 20 h. Aqueous work-up followed by chromatography (CH$_2$Cl$_2$:MeOH:NH$_3$ 100:10:1) afforded 28 mg (24%) of a yellow solid. m.p. 122-124° C.

$^1$H-NMR (300 MHz, CDCl$_3$): 9.31 (s, 1H), 7.76 (d, 2H), 7.57 (s, 2H), 7.50 (s, 1H), 7.39 (d, 2H), 7.27-7.35 (m, 3H), 7.06 (d, 1H), 5.54 (broad s, 2H), 4.65 (s, 2H), 3.13 (s, 2H), 3.02 (hept, 1H), 2.49-2.58 (m, 3H), 2.30-2.40 (m, 5H), 2.21 (s, 6H), 1.57-1.77 (broad quint, 2H), 1.33 (d, 6H). MS: 580 (M+1)$^+$ The compounds of the following examples are prepared by analogy to the example described immediately above:

Example 109

2-(4-Allyl-piperazin-1-yl)-N-{3-[4-(4-isopropyl-phenyl)-2-oxo-6-propargyloxy-2H-quinazolin-1-ylmethyl]-phenyl}-acetamide

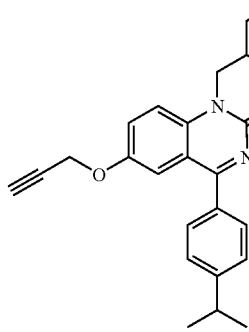

m.p. 203-205° C. $^1$H-NMR (300 MHz, CDCl$_3$): 9.07 (s, NH), 7.76 (d, 2H), 7.47-7.62 (m, 3H), 7.39 (d, 2H), 7.28-7.35 (m, 3H), 7.05 (d, 1H), 5.78-5.96 (m, 1H), 5.54 (broad s, 2H), 5.12-5.26 (m, 2H), 4.65 (d, 2H), 3.13 (s, 2H), 2.96-3.09 (m, 3H), 2.48-2.73 (m, 9H) 1.33 (d, 6H). MS: 590 (M+1)$^+$

Example 110

N-{3-[4-(4-Isopropyl-phenyl)-2-oxo-6-propargyloxy-2H-quinazolin-1-ylmethyl]-phenyl}-2-(4-methyl-piperazin-1-yl)-acetamide

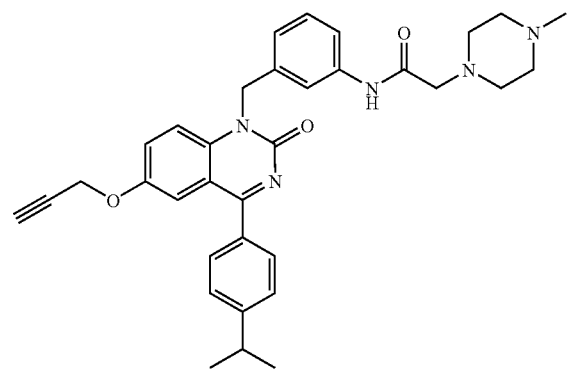 [SMILES: C#CCOc1ccc2c(c1)c(-c1ccc(C(C)C)cc1)nc(=O)n2Cc1cccc(NC(=O)CN2CCN(C)CC2)c1]

m.p. 159-161° C. $^1$H-NMR (300 MHz, CDCl$_3$): 9.06 (s, NH), 7.75 (d, 2H), 7.59 (s, 1H), 7.52 (d, 1H), 7.49 (d, 1H), 7.38 (d, 2H), 7.27-7.33 (m, 3H), 7.05 (d, 1H), 5.54 (broad s, 2H), 4.64 (d, 2H), 3.13 (s, 2H), 3.02 (hept, 1H), 2.60-2.70 (broad, 4H), 2.54 (t, 1H), 2.45-2.57 (broad, 4H), 2.32 (s, 3H), 1.32 (d, 6H). MS: 564 (M+1)$^+$

Example 111

N-{3-[4-(4-Isopropyl-phenyl)-2-oxo-6-propargyloxy-2H-quinazolin-1-ylmethyl]-phenyl}-2-[4-(2-methoxy-ethyl)-piperazin-1-yl]-acetamide

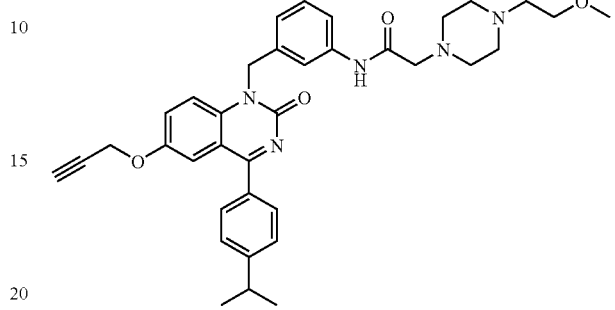

m.p. 198-200° C. $^1$H-NMR (300 MHz, CDCl$_3$): 9.08 (s, NH), 7.75 (d, 2H), 7.69 (s, 1H), 7.46-7.56 (m, 2H), 7.39 (d, 2H), 7.27-7.35 (m, 3H), 7.05 (d, 1H), 5.54 (broad s, 2H), 4.64 (d, 2H), 3.51(t, 2H), 3.36 (s, 3H), 3.12 (s, 2H), 3.02 (hept, 1H), 2.60-2.72 (m, 1H), 1.32 (d, 6H). MS: 608 (M+1)$^+$

Example 112

N-{3-[4-(4-Isopropyl-phenyl)-2-oxo-6-propargyloxy-2H-quinazolin-1-ylmethyl]-phenyl}-2-[4-(2-methoxy-ethyl)-piperazin-1-yl]-N-methyl-acetamide

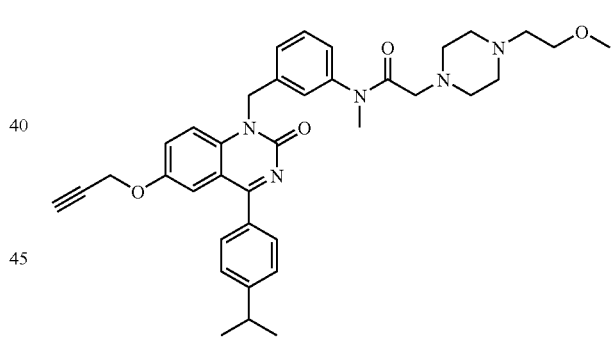

A solution of 1.20 g (2 mmol) of N-{3-[4-(4-isopropyl-phenyl)-2-oxo-6-propargyloxy-2H-quinazolin-1-ylmethyl]-phenyl}-2-[4-(2-methoxy-ethyl)-piperazin-1-yl]-acetamide is treated with 4.1 ml 0.5 M LDA-solution (in THF) and 0.35 ml (2.0 mmol) HMPT at −78° C. The cooling bath is removed and stirring continued for half an hour while the solution turns slowly red. The reaction mixture is cooled down again to −78° C., 284 µl methyl iodide (2 mmol; diluted with 5 ml THF) is added. After stirring overnight at rt, the orange solution is concentrated in vacuo The yellow foamy residue is purified by chromatography (CH$_2$Cl$_2$/MeOH 9:1). Yield: 480 mg (13%) yellow foam.

$^1$H-NMR (300 MHz, CDCl$_3$): 7.74 (d, 2H), 7.51 (d, 1H), 7.37 (d, 2H), 7.27-7.37 (m, 3H), 7.20 (d, 1H), 7.04-7.11 (m, 2H), 5.54 (broad s, 2H), 4.65 (d, 2H), 3.53 (t, 2H), 3.30 (s, 3H), 3.16 (broad s, 3H), 3.03 (hept, 1H), 2.79 (broad s, 2H), 2.57-2.68 (m, 9H), 2.40-2.52 (broad, 2H), 1.31 (d, 6H). MS: 622 (M+1)$^+$

Example 113

N-[4-(3-Dimethylamino-propyl)-piperazin-1-yl]-N-{3-[4-(4-isopropyl-phenyl)-2-oxo-6-propargyloxy-2H-quinazolin-1-ylmethyl]-phenyl}-acetamide

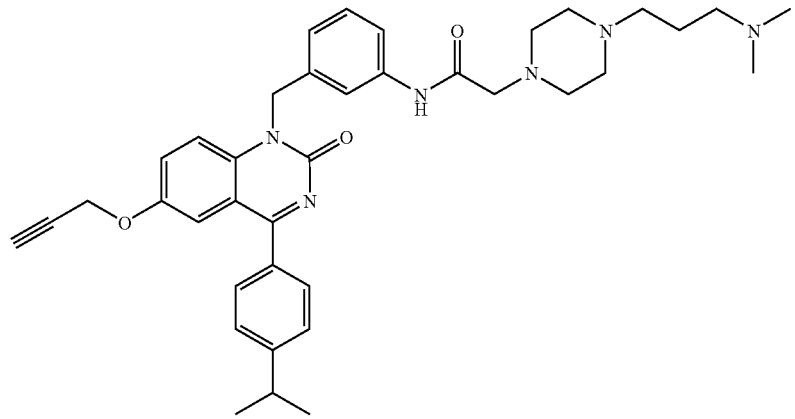 [SMILES: C#CCOc1ccc2c(c1)c(-c1ccc(C(C)C)cc1)nc(=O)n2Cc1cccc(NC(=O)CN2CCN(CCCN(C)C)CC2)c1]

m.p. 170-172° C. $^1$H-NMR (300 MHz, CDCl$_3$): 9.08 (s, NH), 7.76 (d, 2H), 7.60 (s, 1H), 7.48-7.56 (m, 2H), 7.39 (d, 2H), 7.27-7.35 (m, 3H), 7.04 (d, 1H), 5.54 (broad s, 2H), 4.65 (d, 2H), 3.12 (s, 2H), 3.02 (hept, 1H), 2.59-2.70 (broad, 4H), 2.48-2.58 (broad, 4H), 2.41(t, 2H), 2.32 (t, 2H), 2.24 (s, 6H), 1.68 (quint, 2H+H$_2$O), 1.32 (d, 6H). MS: 635 (M+1)$^+$

Example 114

N-{3-[4-(4-Cyclopropyl-phenyl)-2-oxo-6-propargyloxy-2H-quinazolin-1-ylmethyl]-phenyl}-2-(4-methyl-piperazin-1-yl)-acetamide

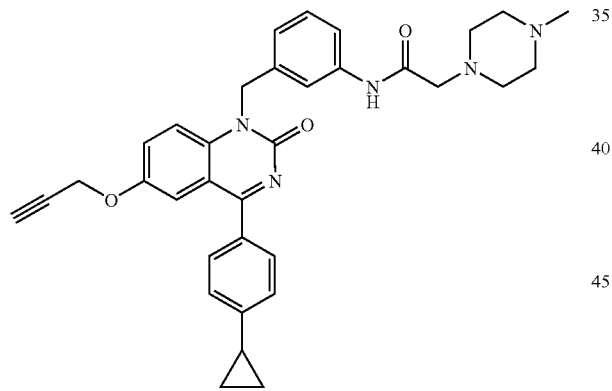

$^1$H-NMR (300 MHz, CDCl$_3$): 9.08 (s, NH), 7.72 (d, 2H), 7.58 (s, 1H), 7.53 (d, 1H), 7.47 (s, 1H), 7.26-7.33 (m, 3H), 7.21 (d, 2H), 7.01 (d, 1H), 5.53 (broad s, 2H), 4.63 (d, 2H), 3.13 (s, 2H), 2.59-2.72 (broad, 4H), 2.55 (t, 1H), 2.46-2.58 (broad, 4H), 2.33 (s, 3H), 2.02 (m, 1H), 1.06-1.13 (m, 2H), 0.80-0.86 (m, 2H). MS: 562 (M+1)$^+$ The following compounds are prepared by analogy to Example 106

Example 115

4-[4-(3-Dimethylamino-propyl)-piperazin-1-yl]-N-{3-[4-(4-isopropyl-phenyl)-2-oxo-6-propargyloxy-2H-quinazolin-1-ylmethyl]-phenyl}-butyramide

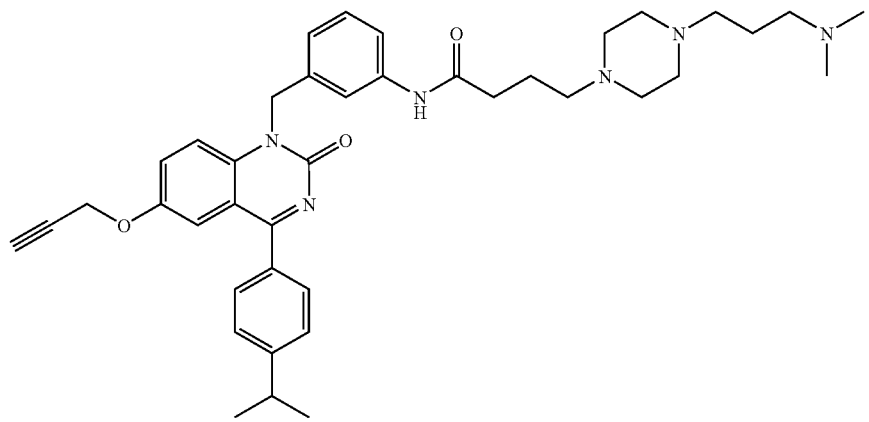 [SMILES: C#CCOc1ccc2c(c1)c(-c1ccc(C(C)C)cc1)nc(=O)n2Cc1cccc(NC(=O)CCCN2CCN(CCCN(C)C)CC2)c1]

m.p. 129-130° C. ¹H-NMR (300 MHz, CDCl₃): 8.66 (s, NH), 7.72 (d, 2H), 7.54 (d, 1H), 7.46 (s, 2H), 7.37 (d, 2H), 7.26-7.32 (m, 3H), 7.01 (d, 1H), 5.53 (broad s, 2H), 4.64 (d, 2H), 3.02 (hept, 1H), 2.34-2.58 (m, 17H), 2.33 (s, 6H), 1.90 (quint, 2H), 1.74 (quint, 2H), 1.33 (d, 6H). MS: 663 (M+1)⁺

Example 116

N-{3-[4-(4-Isopropyl-phenyl)-2-oxo-6-propargyloxy-2H-quinazolin-1-ylmethyl]-phenyl}-4-[(2-methoxy-ethyl)-methyl-amino]-butyramide

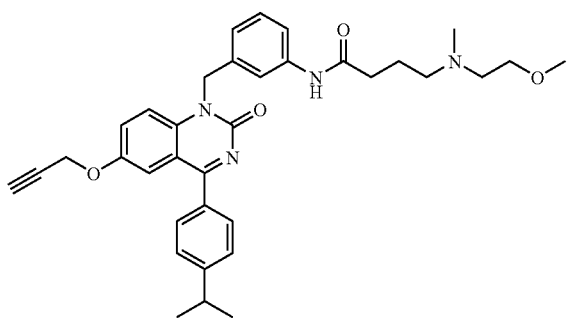 [SMILES: C#CCOc1ccc2c(c1)c(-c1ccc(C(C)C)cc1)nc(=O)n2Cc1cccc(NC(=O)CCCN(C)CCOC)c1]

m.p. 124-125° C. ¹H-NMR (300 MHz, CDCl₃): 9.70 (s, NH), 7.74 (d, 2H), 7.61 (d, 1H), 7.47 (d, 1H), 7.42 (s, 1H), 7.37 (d, 2H), 7.26-7.31 (m, 3H), 7.01 (d, 1H), 5.52 (broad s, 2H), 4.63 (d, 2H), 3.43 (t, 2H), 3.16 (s, 3H), 3.02 (hept, 1H), 2.42-2.76 (m, 7H), 2.23 (s, 3H), 1.84 (quint, 2H), 1.30 (d, 6H). MS: 581 (M+1)⁺

Example 117

N-{3-[4-(4-Isopropyl-phenyl)-2-oxo-6-propargyloxy-2H-quinazolin-1-ylmethyl]-phenyl}-4-morpholin-4-yl-butyramide

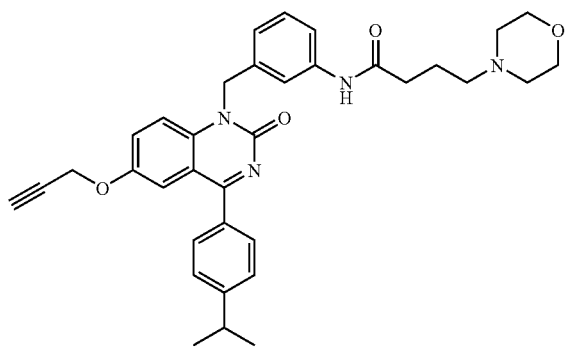 [SMILES: C#CCOc1ccc2c(c1)c(-c1ccc(C(C)C)cc1)nc(=O)n2Cc1cccc(NC(=O)CCCN2CCOCC2)c1]

m.p. 81-82° C. ¹H-NMR (300 MHz, CDCl₃): 8.33 (s, NH), 7.69 (d, 2H), 7.61 (d, 1H), 7.46 (d, 1H), 7.25-7.41 (m, 5H), 7.04 (d, 1H), 5.50 (broad s, 2H), 4.62 (d, 2H), 3.66 (t, 4H), 3.02 (hept, 1H), 2.54 (t, 1H), 2.36-2.46 (m, 8H), 1.87 (quint, 2H), 1.32 (d, 6H). MS: 579 (M+1)⁺

Example 118

N-{3-[6-Allyloxy-4-(4-isopropyl-phenyl)-2-oxo-2H-quinazolin-1-ylmethyl]-phenyl}4-(4-methyl-piperazin-1-yl)-butyramide

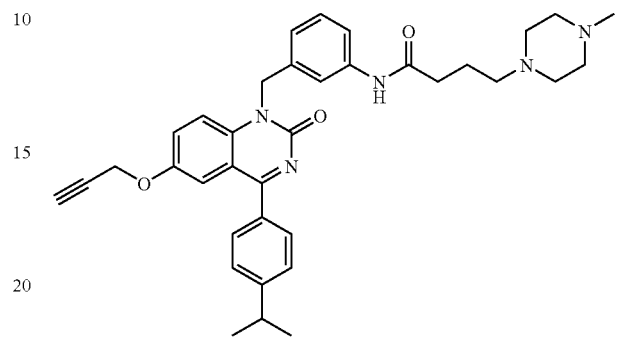

m.p. 152-153° C. ¹H-NMR (300 MHz, CDCl₃): 8.52 (s, NH), 7.70 (d, 2H), 7.55 (d, 1H), 7.32-7.45 (m, 5H), 7.25-7.29 (m, 2H+CHCl₃), 7.03 (d, 1H), 5.90-6.06 (m, 1H), 5.52 (broad s, 2H), 5.26-5.38 (m, 2H), 4.48 (m, 2H), 3.02 (hept, 1H), 2.35-2.57 (m, 12H), 2.24 (s, 3H), 1.89 (quint, 2H), 1.32 (d, 6H). MS: 594 (M+1)⁺

The compounds of the following examples having a nitrogen substituent at R2 in the para or ortho position are prepared in analogy to the examples having such substituents at the meta position described above:

Example 119

4-(4-Isopropyl-phenyl)-1-(4-nitro-benzyl)-6-propargyloxy-1H-quinazolin-2-one m.p. 172° C. ¹H-NMR (300 MHz, CDCl₃): 8.19 (d, 2H), 7.76 (d, 2H), 7.54 (d, 1H), 7.48 (d, 2H), 7.41 (d, 2H), 7.31 (dd, 1H), 7.12 (d, 1H), 5.64 (broad s, 2H), 4.65 (d, 2H), 3.02 (hept, 1H), 2.55 (t, 1H), 1.32 (d, 6H). MS: 454 (M+1)⁺

Example 120

1-(4-Amino-benzyl)-4-(4-isopropyl-phenyl)-6-propargyloxy-1H-quinazolin-2-one

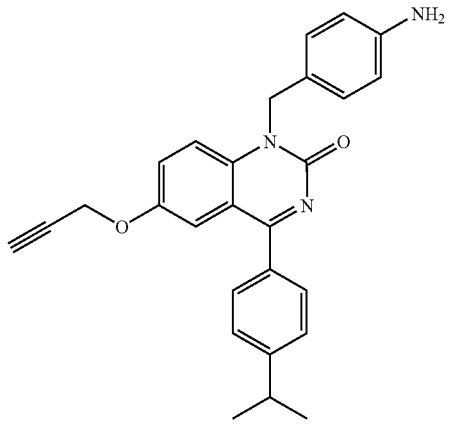 [SMILES: C#CCOc1ccc2c(c1)c(-c1ccc(C(C)C)cc1)nc(=O)n2Cc1ccc(N)cc1]

¹H-NMR (300 MHz, CDCl₃): 8.19 (d, 2H), 7.76 (d, 2H), 7.54 (d, 1H), 7.48 (d, 2H), 7.41 (d, 2H), 7.31 (dd, 1H), 7.12 (d, 1H), 5.64 (broad s, 2H), 4.65 (d, 2H), 3.02 (hept, 1H), 2.55 (t, 1H), 1.32 (d, 6H). MS: 424 (M+1)⁺

Example 121

1-(2-Nitro-benzyl)-4-(4-isopropyl-phenyl)-6-propargyloxy-1H-quinazolin-2-one

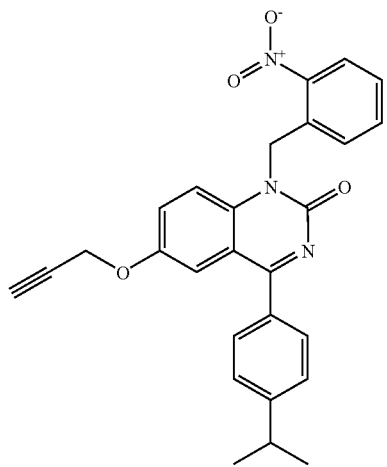 [SMILES: C#CCOc1ccc2c(c1)c(-c1ccc(C(C)C)cc1)nc(=O)n2Cc1ccccc1[N+](=O)[O-]]

¹H-NMR (300 MHz, CDCl₃): 8.24 (d, H), 7.78 (d, 2H), 7.56 (d, 1H), 7.48 (t, 2H), 7.41 (d, 2H), 7.29-7.35 (m, 1H), 7.03 (d, 2H), 5.94 (s, 2H), 4.68 (d, 2H), 3.03 (hept, 1H), 2.57 (t, 1H), 1.35 (d, 6H). MS: 454 (M+1)⁺

Example 122

1-(2-Amino-benzyl)-4-(4-isopropyl-phenyl)-6-propargyloxy-1H-quinazolin-2-one

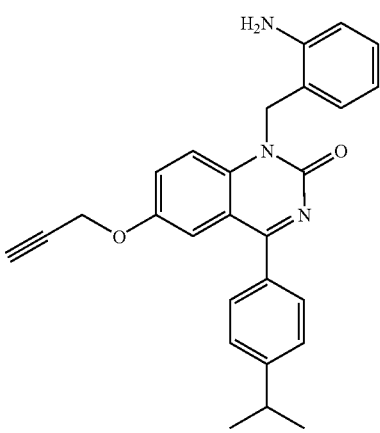

m.p. 74-75° C. ¹H-NMR (300 MHz, CDCl₃): 7.73 (d, 2H), 7.47 (d, 1H), 7.30-7.38 (m, 4H), 7.15 (d, 2H), 6.62 (d, 2H), 5.40 (s, 2H), 4.63 (d, 2H), 3.66 (broad s, NH₂), 3.01 (hept, 1H), 2.55 (t, 1H), 1.33 (d, 6H). MS: 424 (M+1)⁺

Example 123

Synthesis of 1-benzyl-4-(3-chloro-4-isopropyl-phenyl)-6-prop-2-ynyloxy-1H-quinazolin-2-one

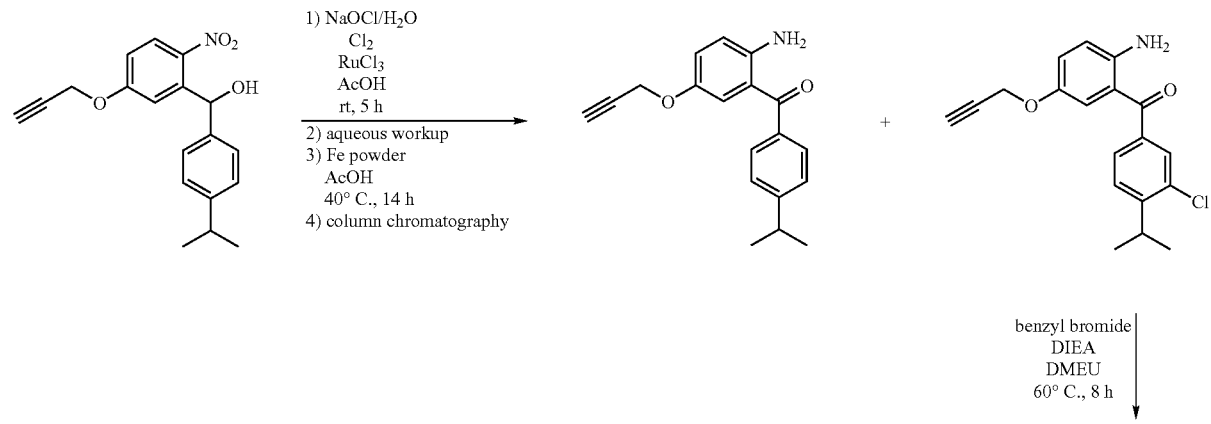

benzyl bromide
DIEA
DMEU
60° C., 8 h

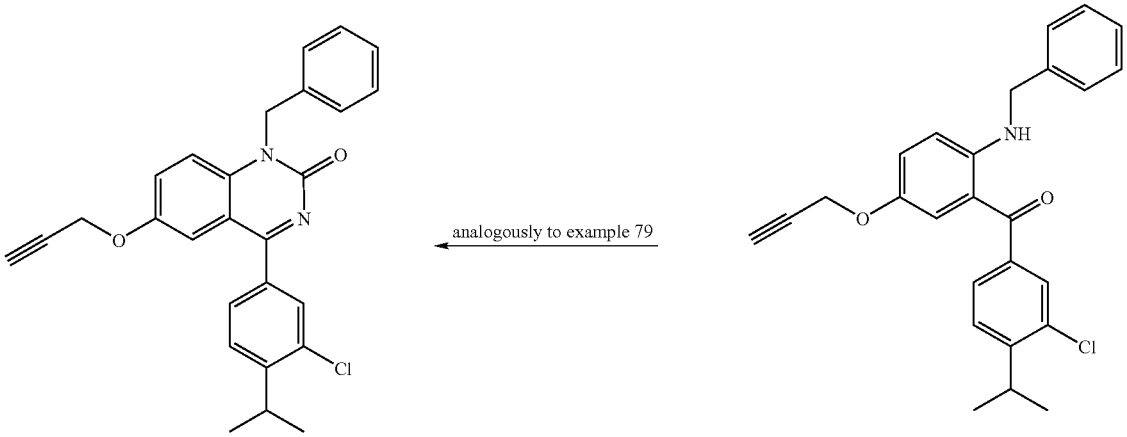

A. Synthesis of (2-amino-5-prop-2-ynyloxy-phenyl)-(3-chloro-4-isopropyl-phenyl)-methanone

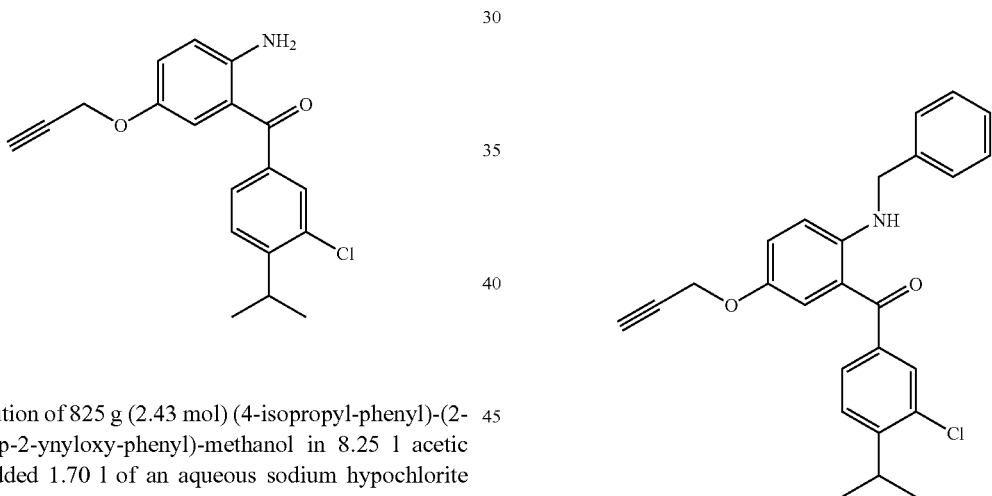

To a solution of 825 g (2.43 mol) (4-isopropyl-phenyl)-(2-nitro-5-prop-2-ynyloxy-phenyl)-methanol in 8.25 l acetic acid are added 1.70 l of an aqueous sodium hypochlorite solution (ca. 15%) containing dissolved chlorine as impurity. In small portions 40 g $RuCl_3$ are added. After 5 h stirring at rt the reaction mixture is extracted with water and tert.-butyl-methylether. The organic layer is evaporated yielding a raw intermediate.

A portion of this (387.3 g) is dissolved in 6.0 l acetic acid before 535 g iron powder are added. After stirring for 14 h at 40° C. the reaction mixture is extracted with water and ethyl acetate. The organic layer is washed with an aqueous sodium bicarbonate solution and evaporated. Column chromatography yields beside (2-amino-5-prop-2-ynyloxy-phenyl)-(4-isopropyl-phenyl)-methanone also (2-amino-5-prop-2-ynyloxy-phenyl)-(3-chloro-4-isopropyl-phenyl)-methanone.

$^1$H NMR (400 MHz, $CDCl_3$): 7.67 (d, 1H), 7.56 (dd, 1H), 7.38 (d, 1H), 7.10 (d, 1H), 7.06 (dd, 1H), 6.72 (d, 1H), 5.78 (s, broad, 2H), 4.55 (d, 2H), 3.47 (hept, 1H), 2.54 (t, 1H), 1.30 (d, 6H). m.p.: 94° C. (hexanes/ether)

B. Synthesis of (2-benzylamino-5-prop-2-ynyloxy-phenyl)-(3-chloro-4-isopropylphenyl)-methanone (hydrochloric acid salt)

To a solution of 100 mg (0.305 mmol) of the amine prepared above in 1 ml DMEU are added 28.5 µl (0.336 µl) DIEA and 40 µl (0.336 µmol) benzyl bromide. After heating for 6 h at 60° C. the reaction mixture is extracted with diluted hydrochloric acid and ether. The crude product is purified by preparative reversed phase HPLC. The hydrochloric acid salt is obtained by treatment of an etheral solution of the free amine with gaseous HCl.

$^1$H NMR (300 MHz, $CDCl_3$): 8.12 (d, 1H), 7.43 (dd, 1H), 7.36 (d, 1H), 7.33 (d, 1H), 7.30-7.22 (m, 3H), 7.17-7.14 (m, 3H), 7.09 (d, 1H), 4.69 (d, 2H), 4.53 (s, 2H), 3.46 (hept, 1H), 2.61 (t, 1H), 1.30 (d, 6H). MS: 420 (30), 418 (100) (M+1)$^+$ (chloro isotope pattern)

C. Synthesis of 1-benzyl-4-(3-chloro-4-isopropyl-phenyl)-6-prop-2-ynyloxy-1H-quinazolin-2-one

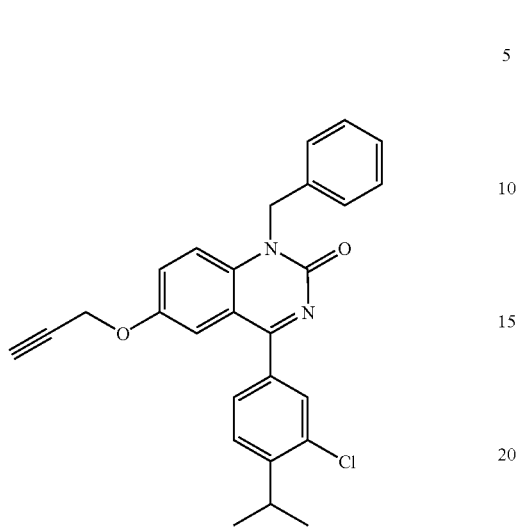

The title compound is prepared from (2-benzylamino-5-prop-2-ynyloxy-phenyl)-(3-chloro-4-isopropylphenyl)-methanone (hydrochloric acid salt) by cyclisation with sodium cyanate analogously to the method described for the preparation of example 62.

$^1$H NMR (300 MHz, CDCl$_3$):7.80 (d, 1H), 7.70 (dd, 1H), 7.49 (s, 1H), 7.48 (d, 1H), 7.37-7.27 (m, 7H), 5.59 (s, 2H), 4.67 (d, 2H), 3.51 (hept, 1H), 2.64 (t, 1H), 1.33 (d, 6H). MS: 445 (30), 443 (100) (M+1)$^+$(chloro isotope pattern)

Example 124

Synthesis of 1-(3-fluoro-benzyl)-4-(4-isopropyl-phenyl)-6-methoxy-1.H.-quinazoline-2-thione

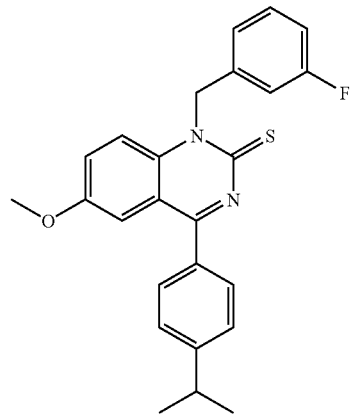

To a solution of 18 mg (47.7 µmol) [2-(3-fluoro-benzylamino)-5-methoxy-phenyl]-(4-isopropyl-phenyl)-methanone in 0.5 ml THF are added 6.9 mg (71.5 µmol) potassium thiocyanate and 0.5 ml acetic acid. After stirring overnight at 60° additional 20.9 mg (215 µmol) potassium cyanate are added and stirring is continued at 80° for additional 24 h. Extraction with aqueous sodium hydroxide and dichloromethane, followed by preparative HPLC affords 1-(3-fluoro-benzyl)-4-(4-isopropyl-phenyl)-6-methoxy-1.H.-quinazoline-2-thione.

$^1$H NMR (300 MHz, CDCl$_3$): 7.78 (d, 2H), 7.40-7.24 (m, 6H), 7.07 (d, 1H), 6.99-6.94 (m, 2H), 6.20 (broad, 2H), 3.78 (s, 3H), 3.01 (hept, 1H), 1.31 (d, 6H). MS: 419 (M+1)$^+$ Example 125

4-(4-isopropyl-phenyl)-6-methoxy-1-(4-methoxy-phenyl)-1.H.-quinazolin-2-one

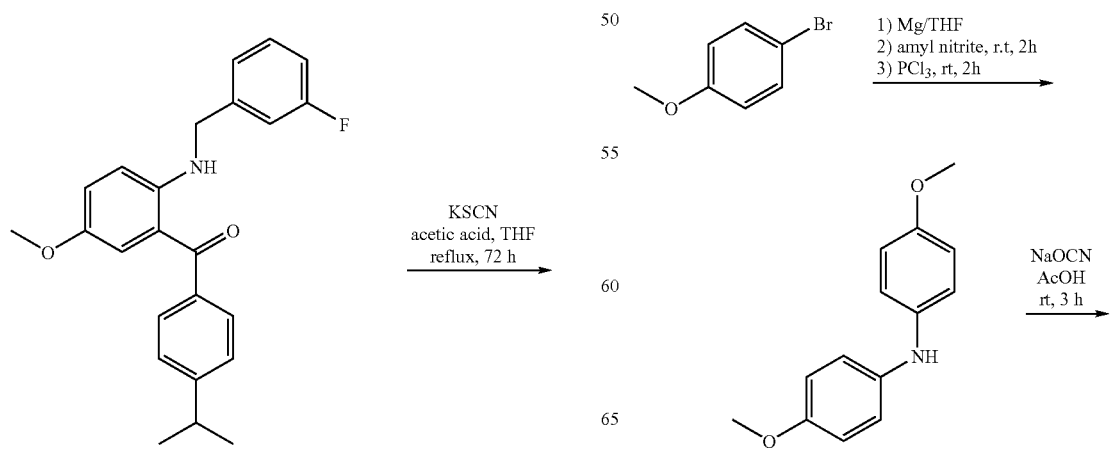

-continued

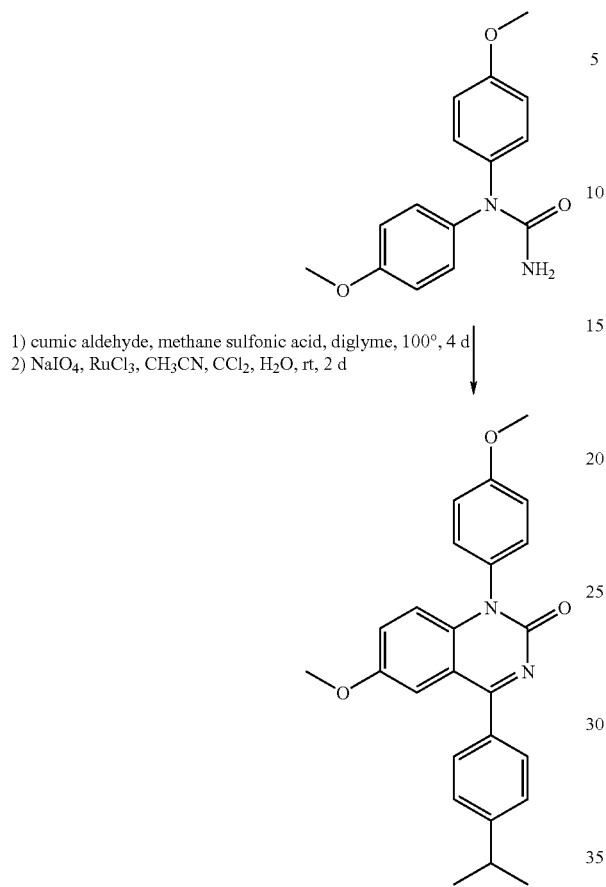

1) cumic aldehyde, methane sulfonic acid, diglyme, 100°, 4 d
2) NaIO₄, RuCl₃, CH₃CN, CCl₂, H₂O, rt, 2 d A. Synthesis of bis-(4-methoxy-phenyl)-amine:

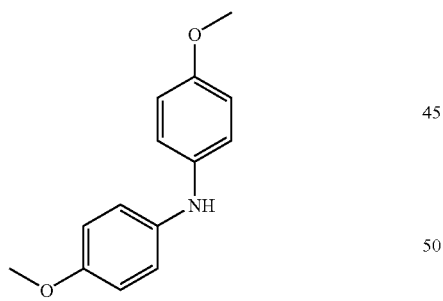

5.61 g (30 mmol) of 4-bromoanisol Grignard reagent is prepared in THF (30 mL) using 0.72 g (30 mmol) magnesium powder. A solution of amyl nitrite (1.33 ml, 10 mmol) in THF (30 ml) is added dropwise to the Grignard reagent whilst maintaining the temperature at about room temperature by cooling in a cold water bath. After 2 h stirring at room temperature 0.873 ml (10 mmol) of phosphorus trichloride dissolved in 10 ml THF is added carefully. After further 2 h 100 ml aqueous sodium hydroxide (1M) is added and the organic solvent is evaporated. Extraction with dichloromethane followed by flash chromatography yields bis-(4-methoxy-phenyl)-amine. ¹H NMR (300 MHz, CDCl₃): 6.83 (broad, 8H), 3.78 (broad, 6H).

B. Synthesis of 1,1-bis-(4-methoxy-phenyl)-urea

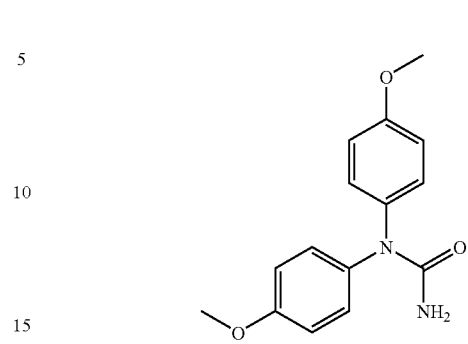

A solution of 423 mg (1.85 mmol) bis-(4-methoxy-phenyl)-amine in 8 ml acetic acid is treated with 120 mg (1.85 mmol) sodium cyanate. After 4.5 h the reaction mixture is poured onto a solution of 8 g sodium hydroxide in 100 ml water. The resultant precipitate is filtered off and dried.

¹H NMR (400 MHz, CDCl₃): 7.26-7.22 (m, 4H), 6.89-6.85 (m, 4H) [non first order spin system], 4.66 (broad, 2H), 3.79 (s, 3H). MS: 273 (M+1)⁺

C. Synthesis of 4-(4-isopropyl-phenyl)-6-methoxy-1-(4-methoxy-phenyl)-1.H.-quinazolin-2-one

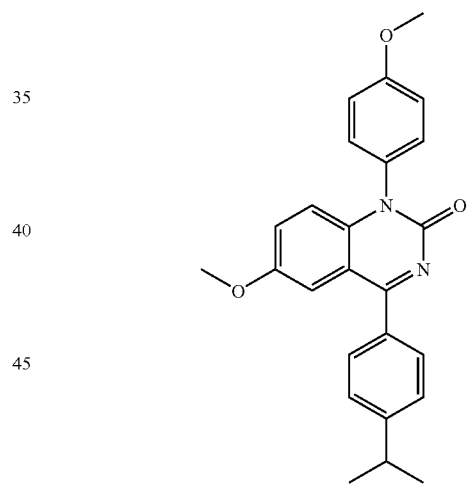

A solution of 144 mg (0.53 mmol) 1,1-bis-(4-methoxy-phenyl)-urea, 160 µl (1.06 mmol) cumic aldehyde and 16 µl (0.27 mmol) methane sulfonic acid in 1 ml diglyme is heated for 4 d at 100°. The reaction mixture is extracted with water/dichloromethane and the intermediate dihydro-quinazolinone is isolated by preparative HPLC. Oxidation with ruthenium trichloride and sodium periodate, as described above, furnishes 4-(4-isopropyl-phenyl)-6-methoxy-1-(4-methoxy-phenyl)-1.H.-quinazolin-2-one.

¹H NMR (300 MHz, CDCl₃): 7.76 (d, 2H), 7.42 (d, 2H), 7.38 (d, 1H), 7.29 (d, 2H), 7.23 (dd, 1H), 7.11 (d, 2H), 6.81 (d, 1H), 3.89 (s, 3H), 3.79 (s, 3H), 3.03 (hept, 1H), 1.33 (d, 6H). MS: 401 (M+1)⁺

Synthesis of 2-chloro-4-(4-isopropyl-phenyl)-6,7-dimethoxy-quinazoline and Related Compounds
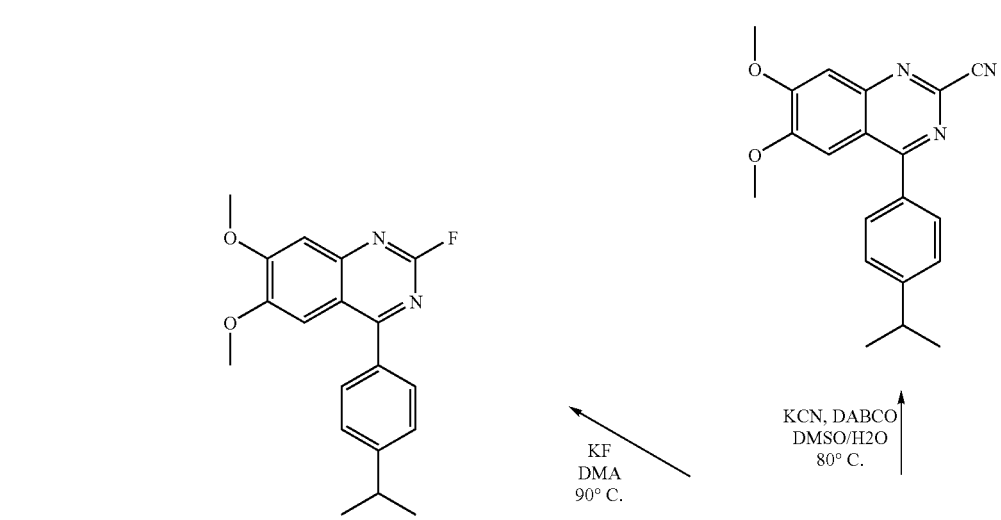
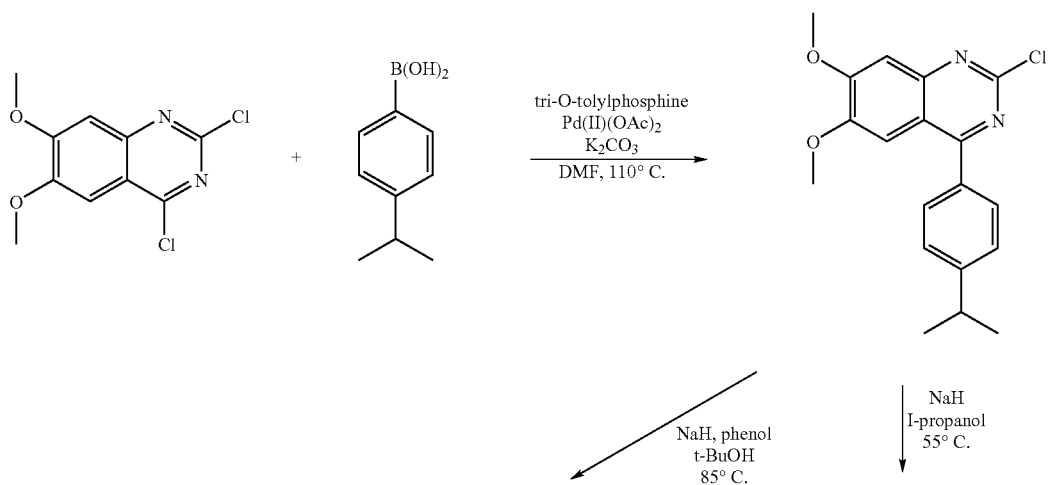
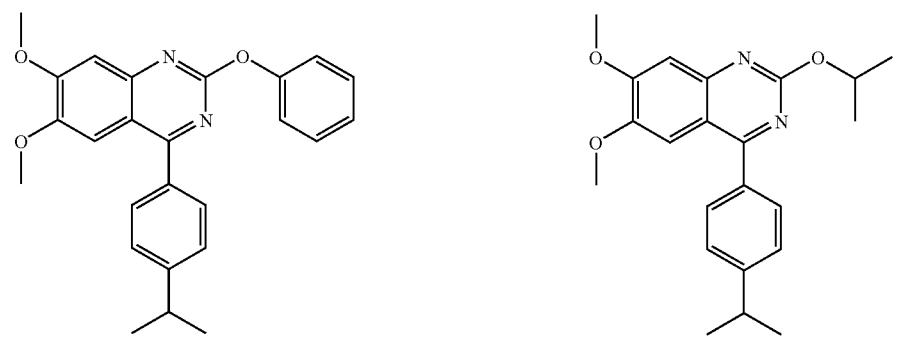

Example 126

2-Chloro-4-(4-isopropyl-phenyl)-6,7-dimethoxy-quinazoline

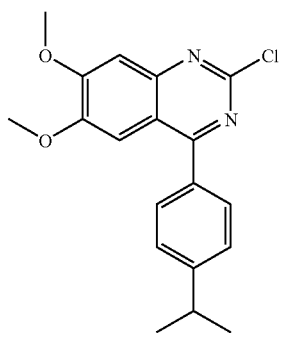 [SMILES: COc1cc2nc(Cl)nc(-c3ccc(C(C)C)cc3)c2cc1OC]

To a solution of 1.4 g (5.5 mmol) 2,4-dichloro-6,7-dimethoxy-quinazoline in 25 ml DMF is added 334 mg (1.1 mmol) tri-O-tolylphosphine, 1.0 g (6.1 mmol) 4-isopropyl-benezeneboronic acid, 142 mg (0.63 mmol) palladium(II) acetate and 5.5 ml of an aqueous 2N $K_2CO_3$ solution. After heating for three hours at 110° C. the mixture is cooled to rt and filtered (Celite). The solution is extracted with ether/brine; the organic layer is dried and evaporated. Crystallisation from ether yields the desired product as yellow solid.

$^1$H-NMR (300 MHz, $CDCl_3$): 7.73 (d, 2H), 7.43 (d, 2H), 7.37 (s, 1H), 7.30 (s, 1H), 4.08 (s, 3H), 3.93 (s, 3H), 3.02 (hept, 1H), 1.32 (d, 6H). MS: 343 $(M+1)^+$

Example 127

2-Isopropoxy-4-(4-isopropyl-phenyl)-6,7-dimethoxy-quinazoline

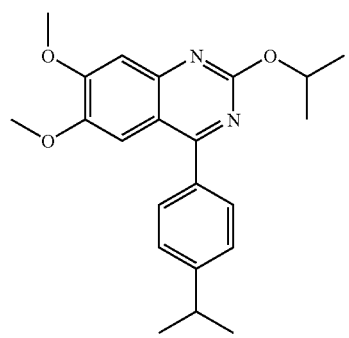

11 mg (0.44 mmol) NaH is dissolved in 2 ml isopropanol and stirred for 2 h at rt. After that time 30 mg (0.088 mmol) 2-chloro-4-(4-isopropyl-phenyl)-6,7-dimethoxy-quinazoline is added and the solution is stirred at 55° C. overnight. The reaction mixture is diluted with ethyl acetate and extracted with brine. The organic layer is dried and evaporated. After chromatography (hexane/ethyl acetate) the product is obtained as yellow oil.

$^1$H-NMR (300 MHz, $CDCl_3$): 7.73 (d, 2H), 7.40 (d, 2H), 7.34 (s, 1H), 7.20 (s, 1H), 5.49 (hept, 1H), 4.06 (s, 3H), 3.89 (s, 3H), 3.02 (hept, 1H), 1.46 (d, 6H), 1.32 (d, 6H). MS: 367 $(M+1)^+$

Example 128

Synthesis of 4-(4-isopropyl-phenyl)-6,7-dimethoxy-2-phenoxy-quinazoline

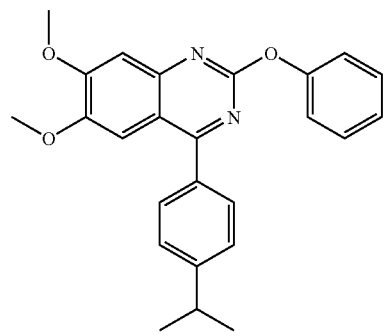 [SMILES: COc1cc2nc(Oc3ccccc3)nc(-c3ccc(C(C)C)cc3)c2cc1OC]

216 mg (2.30 mmol) phenol and 11 mg (0.44 mmol) are dissolved in 2 ml t-butanol and the resulting solution is stirred for 3 h at rt. After that time 80 mg (0.23 mmol) 2-chloro-4-(4-isopropyl-phenyl)-6,7-dimethoxy-quinazoline is added and the solution is stirred at 85° C. overnight. The reaction mixture is diluted with ether and extracted with brine. The organic layer is dried and evaporated. After chromatography (hexane/ethyl acetate the product is obtained as yellow solid.

$^1$H-NMR (300 MHz, $CDCl_3$): 7.75 (d, 2H), 7.46-7.19 (m, 9H), 4.01 (s, 3H), 3.91 (s, 3H), 3.02 (hept, 1H), 1.32 (d, 6H). MS: 401 $(M+1)^+$

Example 129

Synthesis of 2-fluoro-4-(4-isopropyl-phenyl)-6,7-dimethoxy-quinazoline

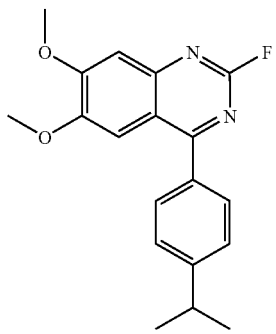 [SMILES: COc1cc2nc(F)nc(-c3ccc(C(C)C)cc3)c2cc1OC]

A solution of 80 mg (0.23 mmol) 2-chloro-4-(4-isopropyl-phenyl)-6,7-dimethoxy-quinazoline and 100 mg (1.70 mmol) KF in 1 ml dimethylacetamide is stirred at 90° C. for 5 days. After extraction (ethyl acetate/brine) the organic layer is dried and evaporated. Flash-chromatography (hexane/ethyl acetate) yields 25 mg (33%) of the product as yellow oil.

$^1$H-NMR (300 MHz, CDCl$_3$): 7.75 (d, 2H), 7.46-7.41 (m, 3H), 7.30 (s, 1H), 4.07 (s, 3H), 3.93 (s, 3H), 3.03 (hept, 1H), 1.33 (d, 6H). MS: 327 (M+1)$^+$ Example 130

Synthesis of 4-4-isopropyl-phenyl)-6,7-dimethoxy-quinazoline-2-carbonitrile

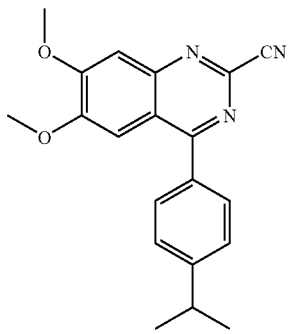 [SMILES: COc1cc2nc(C#N)nc(-c3ccc(C(C)C)cc3)c2cc1OC]

To a solution of 30 mg (0.49 mmol) KCN and 5.7 mg (0.05 mmol) DABCO in 2 ml DMSO is added 1 ml of water. 70 mg (0.20 mmol) of 2-chloro-4-(4-isopropyl-phenyl)-6,7-dimethoxy-quinazoline is added and the resulting mixture is stirred at 80° C. for 4 days. After extraction (ethyl acetate/brine) the organic layer is dried and evaporated. Flash-chromatography (hexane/ethyl acetate) yields 18 mg (27%) of the product as yellow oil.

$^1$H-NMR (300 MHz, CDCl$_3$): 7.74 (d, 2H), 7.48-7.42 (m, 4H), 4.10 (s, 3H), 3.97 (s, 3H), 3.04 (hept, 1H), 1.34 (d, 6H). MS: 334 (M+1)$^+$ The compounds of the following examples are prepared by analogy to the examples described immediately above:

Example 131

4-(4-Isopropyl-phenyl)-6,7-dimethoxy-2-(6-methyl-pyridin-3-yloxy)-quinazoline

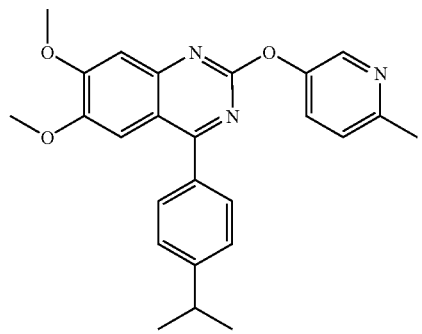

$^1$H-NMR (300 MHz, CDCl$_3$): 8.60 (d, 1H), 7.74 (d, 2H), 7.61 (dd, 1H), 7.43-7.39 (m, 3H), 7.26 (d, 1H), 7.14 (s, 1H), 4.02 (s, 3H), 3.91 (s, 3H), 3.02 (hept, 1H), 2.63 (s, 3H), 1.33 (d, 6H). MS: 416 (M+1)$^+$ Example 132

4-(4-Isopropyl-phenyl)-6,7-dimethoxy-2-(pyridin-3-yloxy)-quinazoline

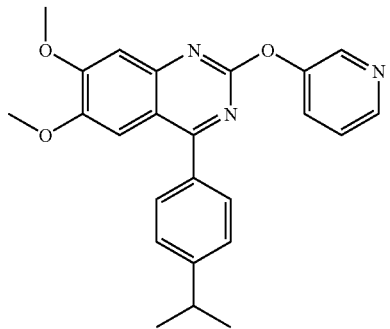 [SMILES: COc1cc2nc(Oc3cccnc3)nc(-c3ccc(C(C)C)cc3)c2cc1OC]

$^1$H-NMR (300 MHz, CDCl$_3$): 8.84 (broad, 1H), 8.54 (d, 1H), 7.92 (broad, 1H), 7.74 (d, 2H), 7.60 (broad, 1H), 7.44-7.40 (m, 3H), 7.17 (s, 1H), 4.05 (s, 3H), 3.92 (s, 3H), 3.03 (hept, 1H), 1.33 (d, 6H). MS: 402 (M+1)$^+$ Example 133

2-Isobutoxy-4-(4-isopropyl-phenyl)-6,7-dimethoxy-quinazoline

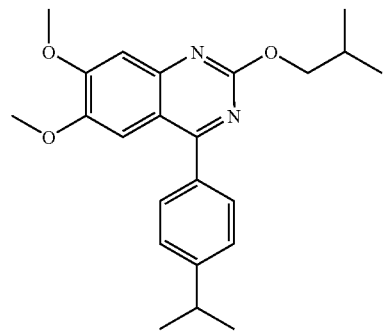 [SMILES: COc1cc2nc(OCC(C)C)nc(-c3ccc(C(C)C)cc3)c2cc1OC]

$^1$H-NMR (300 MHz, CDCl$_3$): 7.72 (d, 2H), 7.42 (d, 2H), 7.34 (s, 1H), 7.26 (s, 1H), 4.29 (d, 2H), 4.08 (s, 3H), 3.90 (s, 3H), 3.03 (hept, 1H), 2.20 (hept, 1H), 1.34 (d, 6H), 1.09 (d, 6H). MS: 381 (M+1)$^+$ Example 134

4-(4-Isopropyl-phenyl)-2,6,7-trimethoxy-quinazoline

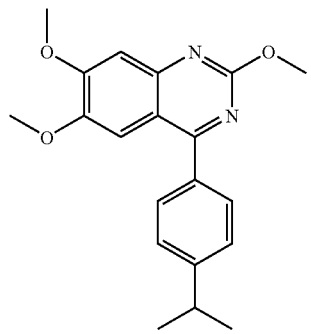

133

¹H-NMR (300 MHz, CDCl₃): 7.76 (d, 2H), 7.41 (d, 2H), 7.37 (s, 1H), 7.22 (s, 1H), 4.18 (s, 3H), 4.07 (s, 3H), 3.88 (s, 3H), 3.01 (hept, 1H), 1.34 (d, 6H). MS: 339 (M+1)⁺

Example 135

4-(4-Isopropyl-phenyl)-2-isopropylsulfanyl-6,7dimethoxy-quinazoline

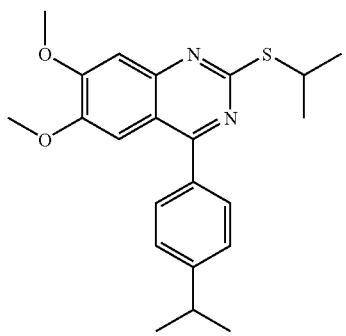

¹H-NMR (300 MHz, CDCl₃): 7.80 (d, 2H), 7.52-7.40 (m, 4H), 4.38 (hept, 1H), 4.18 (s, 3H), 3.94 (s, 3H), 3.07 (hept, 1H), 1.53 (d, 6H), 1.36 (d, 6H). MS: 383 (M+1)⁺

Example 136

2-Azido-4-(4-isopropyl-phenyl)-6,7-dimethoxy-quinazoline

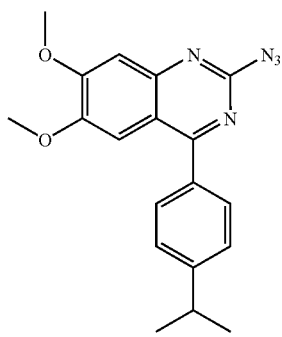 [SMILES: COc1cc2nc(N=[N+]=[N-])nc(-c3ccc(C(C)C)cc3)c2cc1OC]

¹H-NMR (300 MHz, CDCl₃): 8.13 (s, 1H), 7.78 (d, 2H), 7.62 (s, 1H), 7.44 (d, 2H), 4.22 (s, 3H), 3.96 (s, 3H), 3.03 (hept, 1H), 1.36 (d, 6H). MS: 350 (M+1)⁺

134

Example 137

4-(4-tert-Butyl-phenyl)-2-chloro-6,7-dimethoxy-quinazoline

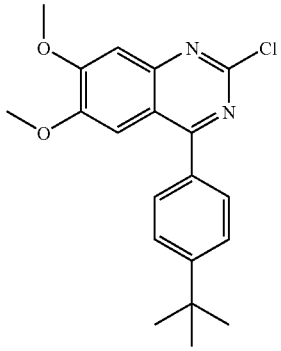 [SMILES: COc1cc2nc(Cl)nc(-c3ccc(C(C)(C)C)cc3)c2cc1OC]

¹H-NMR (300 MHz, DMSO-d₆): 7.78 (d, 2H), 7.63 (d, 2H), 7.42 (s, 1H), 7.33 (s, 1H), 3.98 (s, 3H), 3.83 (s, 3H), 1.37 (s, 9H). MS: 357 (M+1)⁺

Example 138

4-(4-tert.-Butyl-phenyl)-2,6,7-trimethoxy-quinazoline

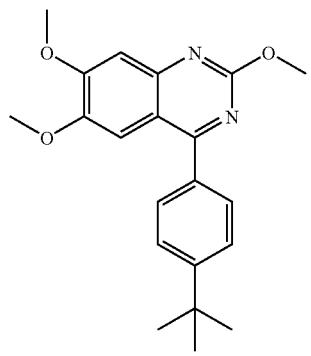

¹H-NMR (300 MHz, CDCl₃): 7.77 (d, 2H), 7.57 (d, 2H), 7.37 (s, 1H), 7.26 (s, 1H), 4.18 (s, 3H), 4.07 (s, 3H), 3.83 (s, 3H), 1.38 (s, 9H). MS: 353 (M+1)⁺

Example 139

2-Chloro-4-(4-isopropyl-phenyl)-6-methoxy-quinazoline

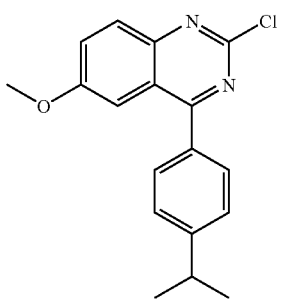 [SMILES: COc1ccc2nc(Cl)nc(-c3ccc(C(C)C)cc3)c2c1]

$^1$H-NMR (300 MHz, CDCl$_3$): 7.96 (d, 1H), 7.75 (d, 2H), 7.56 (dd, 1H), 7.45-7.39 (m, 3H), 3.83 (s, 3H), 3.03 (hept, 1H), 1.35 (d, 6H). MS: 313 (M+1)$^+$ Example 140

4-(4-Isopropyl-phenyl)-6-methoxy-2-(pyridin-3-ylmethoxy)-quinazoline

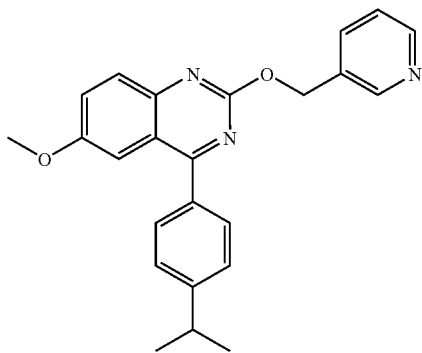 [SMILES: COc1ccc2nc(OCc3cccnc3)nc(-c3ccc(C(C)C)cc3)c2c1]

$^1$H-NMR (300 MHz, CDCl$_3$): 8.92 (broad, 1H), 8.64 (d, 1H), 8.36 (d, 1H), 7.82-7.39 (m, 8H), 5.70 (s, 2H), 3.83 (s, 3H), 3.02 (hept, 1H), 1.33 (d, 6H). MS: 386 (M+1)$^+$ Example 141

4-(4-Isopropyl-phenyl)-6-methoxy-quinazoline-2-carbonitrile

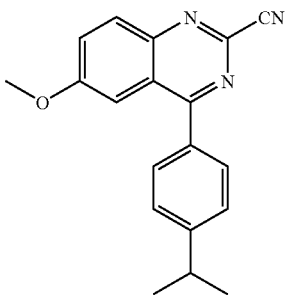 [SMILES: COc1ccc2nc(C#N)nc(-c3ccc(C(C)C)cc3)c2c1]

$^1$H-NMR (300 MHz, CDCl$_3$): 8.08 (d, 1H), 7.76 (d, 2H), 7.65 (dd, 1H), 7.52-7.43 (m, 3H), 3.91 (s, 3H), 3.04 (hept, 1H), 1.34 (d, 6H). MS: 304 (M+1)$^+$ Example 142

4-(4-Isopropyl-phenyl)-6,7-dimethoxy-2-trifluoromethyl-quinazoline

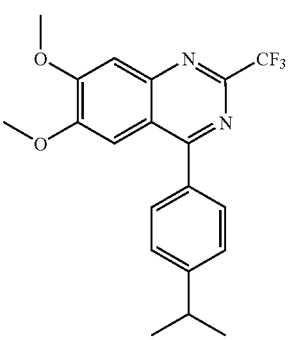 [SMILES: COc1cc2nc(C(F)(F)F)nc(-c3ccc(C(C)C)cc3)c2cc1OC]

A mixture of 100 mg (0.29 mmol) 2-chloro-4-(4-isopropyl-phenyl)-6,7-dimethoxy-quinazoline, 45 mg (1.16 mmol) copper powder and 107 µl (1.16 mmol) CF$_2$Br$_2$ in 2 ml dimethylacetamide is stirred at 150° C. for 2 days. After extraction with water and ethyl acetate the title compound is isolated by flash chromatography.

$^1$H-NMR (300 MHz, CDCl$_3$): 7.77 (d, 2H), 7.53 (s, 1H), 7.49 (s, 1H), 7.45 (d, 2H), 4.10 (s, 3H), 3.97 (s, 3H), 3.03 (hept, 1H), 1.33 (d, 6H). MS: 377 (M+1)$^+$ Example 143

Synthesis of 4-(4-Isopropyl-phenyl)-6,7-dimethoxy-2-methyl-quinazoline

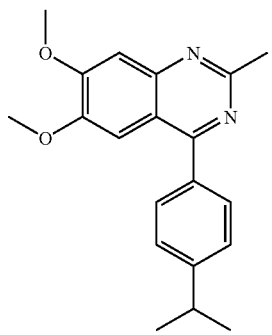

To 166 mg (1.16 mmol) CuBr in 4 ml THF are added dropwise at −78° C. 773 µl (2.32 mmol) of a 3M solution of methylmagnesium iodide. After stirring for 20 minutes 50 mg (0.145 mmol) 2-chloro-4-(4-isopropyl-phenyl)-6,7-dimethoxy-quinazoline are added at the same temperature. After stirring for 1 h the reaction mixture is allowed to reach rt and stirring is continued overnight. After dilution with 50 ml ethyl acetate and filtration the reaction mixture is extracted with brine. Evaporation of the organic phase yields the title compound.

$^1$H-NMR (300 MHz, CDCl$_3$): 7.70 (d, 2H), 7.44-7.33 (m, 4H), 4.07 (s, 3H), 3.91 (s, 3H), 3.02 (hept, 1H), 2.89 (s, 3H), 1.32 (d, 6H). MS: 323 (M+1)$^+$ Example 144

Synthesis of 1-cyclohexylmethyl-4-(4-isopropyl-phenyl)-6,7-dimethoxy-1H-quinazolin-2-one

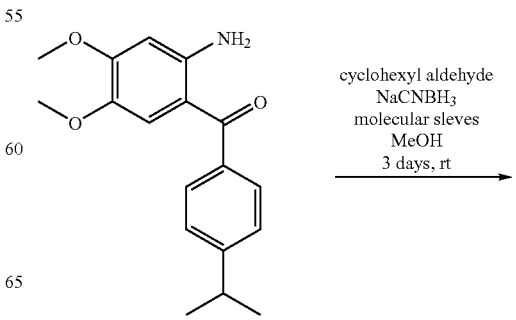

A. Example: Synthesis of [2-(cyclohexylmethyl-amino)-4,5-dimethoxy-phenyl]-(4-isopropyl-phenyl)-methanone

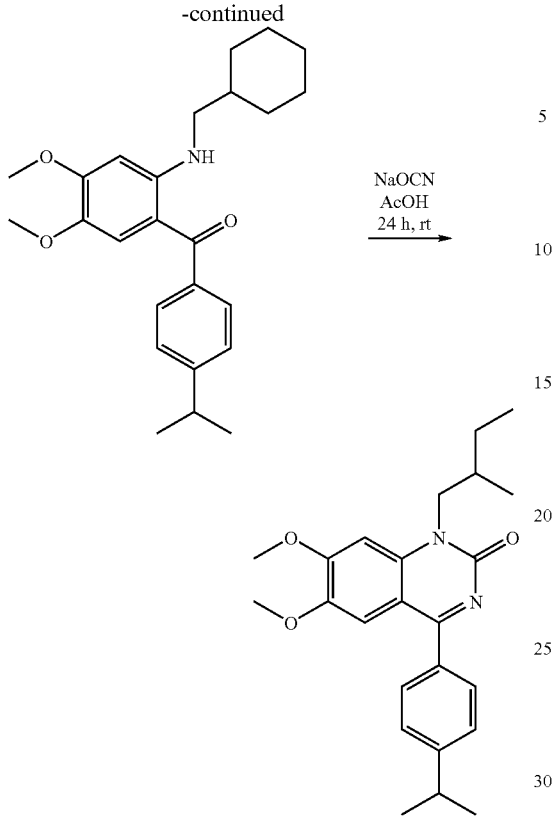

To a mixture of 100 mg (0.334 mmol) (2-amino-4,5-dimethoxy-phenyl)-(4-isopropyl-phenyl)-methanone, 37 µl (0.306 mmol) cyclohexyl aldehyde, 765 mg molecular sieves (3 Å) and 22 µl acetic acid in 2 ml methanol are added after ½ h stirring 21 mg (0.327 mmol) NaCNBH$_3$. After 20 h stirring at rt additional 37 µl (0.306 mmol) cyclohexyl aldehyde and 21 mg (0.327 mmol) NaCNBH$_3$ are added and stirring is continued for further 48 h. After filtration through celite the reaction mixture is extracted with aqueous bicarbonate solution and ethyl acetate. The product is purified by reversed phase preparative HPLC.

$^1$H NMR (300 MHz, CDCl$_3$):7.54 (d, 2H), 7.29 (d, 2H), 7.06 (s, 1H), 6.27 (s, broad, 1H), 3.96 (s, 3H), 3.68 (s, 3H), 3.08 (d, 2H), 2.97 (hept, 1H), 1.94-1.89 (m, 2H), 1.88-1.49 (m, 5H), 1.32-1.01 (m, 4H), 1.29 (d, 6H). MS: 396 (M+1)$^+$

B. Synthesis of 1-cyclohexylmethyl-4-(4-isopropyl-phenyl)-6,7-dimethoxy-1H-quinazolin-2-one

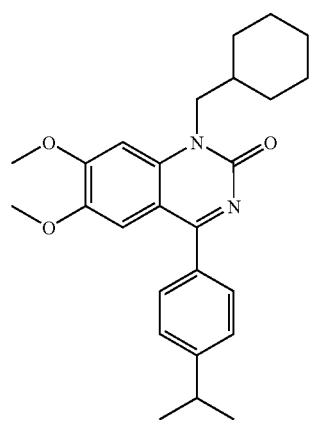 [SMILES: COc1cc2c(-c3ccc(C(C)C)cc3)nc(=O)n(CC3CCCCC3)c2cc1OC]

To a solution of 50 mg (0.126 mmol) (2-amino-4,5-dimethoxy-phenyl)-(4-isopropyl-phenyl)-methanone in 1 ml acetic acid are added 8 mg (0.126 mmol) sodium cyanate. After stirring for 24 h at rt the solvent is evaporated and the residue is extracted with dichloromethane/0.1 M NaOH. Recrystallisation from ether/hexanes yields the title compound.

$^1$H NMR (300 MHz, CDCl$_3$): 7.69 (d, 2H), 7.38 (d, 2H), 7.27 (s, 1H), 6.77 (s, 1H), 4.19 (m, 2H), 4.05 (s, 3H), 3.83 (s, 3H), 3.00 (hept, 1H), 2.04-1.62 (m, 7H), 1.31 (d, 6H), 1.32-1.16 (m, 4H). MS: 421 (M+1)$^+$ The methanone compound of the following example is prepared by analogy to the Example described immediately above:

Example 145

{2-[2-(3,5-Dimethoxy-phenyl)-2-methyl-propylamino]-4,5-dimethoxy-phenyl}-(4-isopropyl-phenyl)-methanone

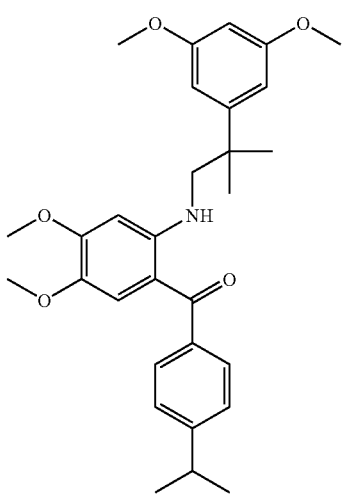

$^1$H NMR (300 MHz, CDCl$_3$): 7.50 (d, 2H), 7.28 (d, 2H), 7.01 (s, 1H), 6.61 (d, 2H), 6.31 (t, 1H), 6.16 (s, 1H), 3.88 (s, 3H), 3.77 (s, 6H), 3.65 (s, 3H), 3.35 (s, 2H), 2.97 (hept, 1H), 1.49 (s, 6H), 1.29 (d, 6H). MS: 492 (M+1)$^+$ Synthesis of 2-chloro-4-(4-isopropyl-phenyl)-6-methoxy-quinazoline and Related Compounds

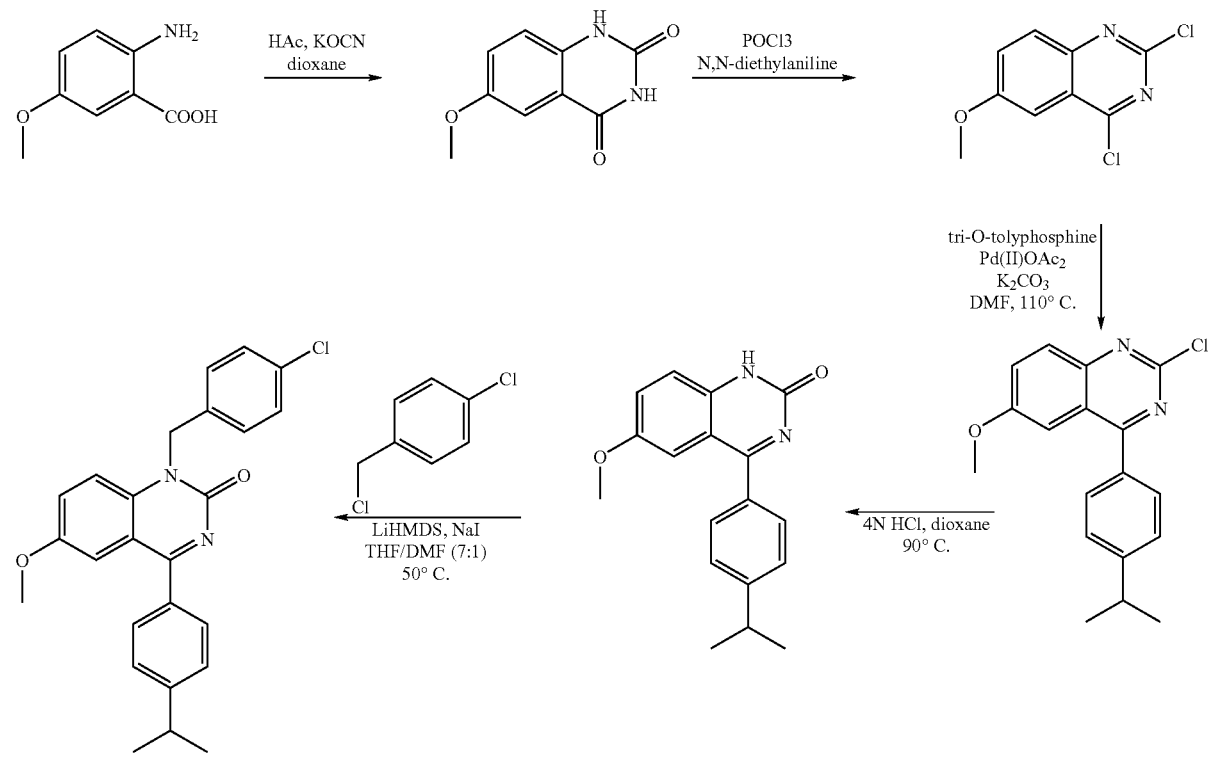

Example 146

Synthesis of 2-Chloro-4-(4-isopropyl-phenyl)-6-methoxy-quinazoline

A. Synthesis of 6-methoxy-1.H.-quinazoline-2,4-dione

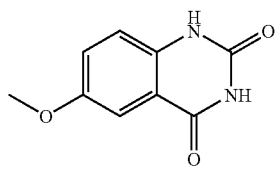

To a solution of 15 g (90 mmol) 2-amino-5-methoxybenzoic acid in 100 ml dioxane is added 6.6 ml (117 mmol) acetic acid. The reaction mixture is cooled (15° C.) and a solution of 9.4 g (117 mmol) potassium cyanate in 22 ml water is added dropwise over two hours. After that time 57.4 g (1.43 mol) NaOH is added and the reaction mixture is refluxed for 90 minutes. After cooling the reaction mixture is slowly acidified with 260 ml 12 N HCl (pH3). The resulting precipitate is filtered off, and washed with water, acetone and finally ether to give slightly brown crystals.

$^1$H-NMR (300 MHz, DMSO-d$_6$): 11.25 (s, 1H), 11.00 (s, 1H), 7.31-7.08 (m, 3H), 3.77 (s, 3H). MS: 193 (M+1)$^+$

B. Synthesis of 2,4-dichloro-6-methoxy-quinazoline

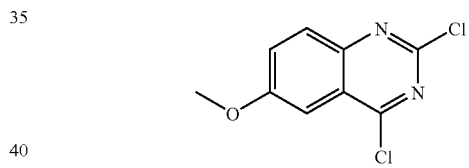

12.4 ml (136.3 mmol) POCl$_3$ and 32.7 ml (204.5 mmol) N,N-diethylaniline are added to a suspension of 13.1 g (68.2 mmol) 6-methoxy-1.H.-quinazoline-2,4-dione and the resulting mixture is heated at reflux for 4 h. After cooling, the reaction mixture is poured into 600 ml water. After extraction with 400 ml ethyl acetate the organic layer is dried and evaporated to a volume of 30 ml to yield an orange precipitate. The precipitate is filtered off, washed with toluene and hexane and dried.

$^1$H-NMR (300 MHz, DMSO-d$_6$): 7.97 (d, 1H), 7.80 (dd, 1H), 7.47 (d, 1H), 3.98 (s, 3H). MS: 229 (M+1)$^+$

C. Synthesis of 2-chloro-4-(4-isopropyl-phenyl)-6-methoxy-quinazoline

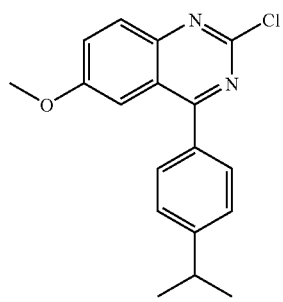 [SMILES: COc1ccc2nc(Cl)nc(-c3ccc(C(C)C)cc3)c2c1]

To a solution of 6.2 g (27 mmol) 2,4-dichloro-6-methoxy-quinazoline in 100 ml DMF is added 1.9 g (6.2 mmol) tri-O-tolylphosphine, 4.2 g, (26 mmol) 4-isopropylbenezeneboronic acid, 620 mg (2.7 mmol) palladium(II)acetate and 24 ml of an aqueous 2N $K_2CO_3$ solution. After heating for three hours at 110° C. the mixture is cooled to rt and filtered (Celite). The solution is extracted with ether/brine the organic layer is dried and evaporated. Chromatography (hexanw/ethyl acetate) yields the desired product as a yellow oil.

$^1$H-NMR (300 MHz, CDCl$_3$): 7.92 (d, 1H), 7.75 (d, 2H), 7.37 (dd, 1H), 7.25-7.21 (m, 3H), 3.93 (s, 3H), 3.02 (hept, 1H), 1.32 (d, 6H). MS: 313 (M+1)$^+$

Example 147

Synthesis of 4-(4-isopropyl-phenyl)-6-methoxy-1.H.-quinazolin-2-one

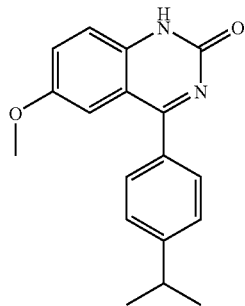 [SMILES: COc1ccc2[nH]c(=O)nc(-c3ccc(C(C)C)cc3)c2c1]

To a suspension of 2.7 g (8.7 mmol) chloro-4-(4-isopropyl-phenyl)-6-methoxy-quinazoline in 20 ml dioxane is added 20 ml 4N HCl. The reaction mixture is stirred at 90° C. overnight. The dioxane is evaporated and the residual aqueous phase is adjusted to pH12 with conc. NaOH. The resulting precipitate is extracted with ethyl acetate, the organic layer is dried and evaporated to yield the desired product as yellow solid.

$^1$H-NMR (300 MHz, DMSO-$_6$): 7.63 (d, 2H), 7.42 (d, 2H), 7.26 (m, 2H), 7.03 (d, 1H), 3.67 (s, 3H), 3.29 (hept, 1H), 1.26 (d, 6H). MS: 295 (M+1)$^+$

Example 148

Synthesis of 1-(4-chloro-benzyl)-4-(4-isopropyl-phenyl)-6-methoxy-1.H.-quinazolin-2-one

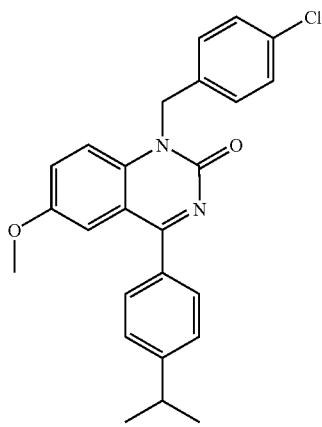

To a solution of 100 mg (0.34 mmol) 4-(4-isopropyl-phenyl)-6-methoxy-1.H.-quinazolin-2-one in 3 ml THF/DMF (7:1) is added LiHMDS (510 µl of a 1M solution in THF), 109 mg (0.68 mmol) 4-chlorobenzyl chloride and 76 mg (0.51 mmol) sodium iodide. The reaction mixture is heated at 50° C. overnight. After extraction with ethyl acetate/brine the organic layer is dried and evaporated. After chromatography (hexane/ethyl acetate) the product is obtained as yellow oil.

$^1$H-NMR (300 MHz, DMSO-d$_6$): 7.70 (d, 2H), 7.48-7.29 (m, 8H), 7.20 (s, 1H), 5.58 (s, 2H), 3.71 (s, 3H), 3.02 (hept, 1H), 1.27 (d, 6H). MS: 419 (M+1)$^+$ The compounds of the following examples are prepared by analogy to the examples described immediately above

Example 149

1-(4-Bromo-benzyl)-4-(4-isopropyl-phenyl)-6-methoxy-1.H.-quinazolin-2-one

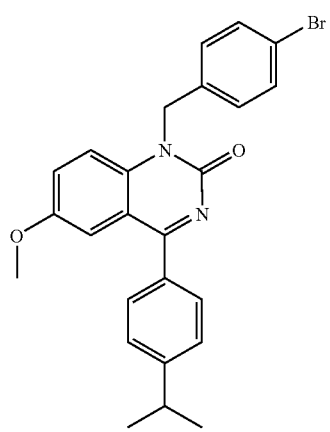 [SMILES: COc1ccc2c(c1)c(-c1ccc(C(C)C)cc1)nc(=O)n2Cc1ccc(Br)cc1]

$^1$H-NMR (300 MHz, CDCl$_3$): 7.72 (d, 2H), 7.46-7.36 (m, 5H), 7.27-7.16 (m, 4H), 5.49 (s, 2H), 3.70 (s, 3H), 3.00 (hept, 1H), 1.32 (d, 6H). MS: 465 (M+1)$^+$

Example 150

1-(4-Fluoro-benzyl)-4-(4-isopropyl-phenyl)-6-methoxy-1.H.-quinazolin-2-one

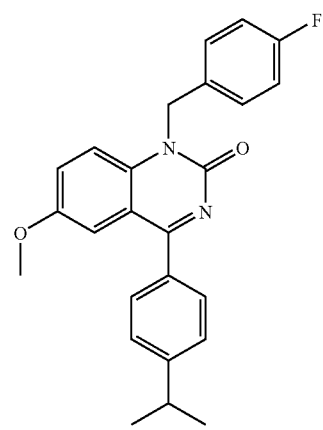 [SMILES: COc1ccc2c(c1)c(-c1ccc(C(C)C)cc1)nc(=O)n2Cc1ccc(F)cc1]

¹H-NMR (300 MHz, CDCl₃): 7.72 (d, 2H), 7.40-7.20 (m, 7H), 7.04-6.98 (m, 2H), 5.51 (s, 2H), 3.76 (s, 3H), 3.01 (hept, 1H), 1.32 (d, 6H). MS: 403 (M+1)⁺

Example 151

Acetic acid 4-[4-(4-isopropyl-phenyl)-6-methoxy-2-oxo-2.H.-quinazolin-1-ylmethyl]-phenyl ester

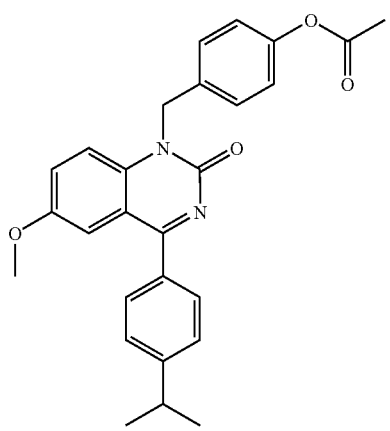 [SMILES: COc1ccc2c(c1)c(-c1ccc(C(C)C)cc1)nc(=O)n2Cc1ccc(OC(C)=O)cc1]

¹H-NMR (300 MHz, CDCl₃): δ: 7.77 (d, 2H), 7.42-7.21 (m, 7H), 7.04 (d, 2H), 5.57 (s, 2H), 3.78 (s, 3H), 3.02 (hept, 1H), 2.25 (s, 3H), 1.35 (d, 6H). MS: 443 (M+1)⁺

Example 152

4-(4-Isopropyl-phenyl)-6-methoxy-1-(4-methoxy-benzyl)-1.H.-quinazolin-2-one

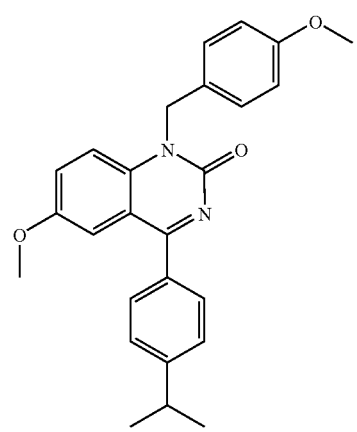

¹H-NMR (300 MHz, DMSO-d₆): 7.68 (d, 2H), 7.50-7.41 (m, 4H), 7.25-7.17 (m, 3H), 6.87 (d, 2H), 5.41 (s, 2H), 3.69 (s, 3H), 3.68 (s, 3H), 3.00 (hept, 1H), 1.26 (d, 6H). MS: 415 (M+1)⁺

Example 153

1-(4-Hydroxy-benzyl)-4-(4-isopropyl-phenyl)-6-methoxy-1.H.-quinazolin-2-one

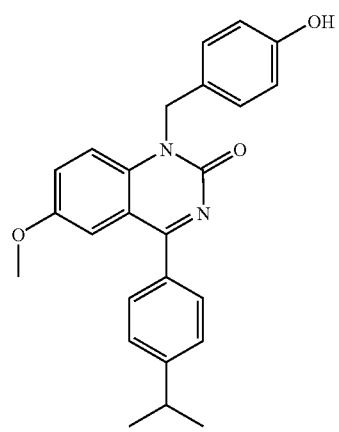 [SMILES: COc1ccc2c(c1)c(-c1ccc(C(C)C)cc1)nc(=O)n2Cc1ccc(O)cc1]

¹H-NMR (300 MHz, CDCl₃): 7.67 (d, 2H), 7.42-7.25 (m, 5H), 7.13 (d, 2H), 6.77 (d, 2H), 5.42 (s, 2H), 3.78 (s, 3H), 2.99 (hept, 1H), 1.26 (d, 6H). MS: 401 (M+1)⁺

Example 154

4-(4-Isopropyl-phenyl)-6-methoxy-1-(4-trifluoromethyl-benzyl)-1.H.-quinazolin-2-one

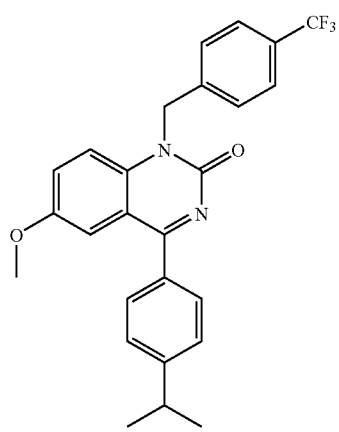 [SMILES: COc1ccc2c(c1)c(-c1ccc(C(C)C)cc1)nc(=O)n2Cc1ccc(C(F)(F)F)cc1]

¹H-NMR (300 MHz, CDCl₃): 7.74 (d, 2H), 7.59 (d, 2H), 7.42-7.20 (m, 6H), 7.15 (d, 1H), 5.60 (s, 2H), 3.77 (s, 3H), 3.02 (hept, 1H), 1.32 (d, 6H). MS: 453 (M+1)⁺

Example 155

4-(4-Isopropyl-phenyl)-6-methoxy-1-(4-nitro-benzyl)-1.H.-quinazolin-2-one

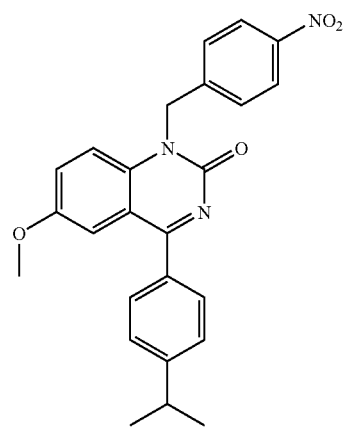

¹H-NMR (300 MHz, DMSO-d₆): 8.18 (d, 2H), 7.71 (d, 2H), 7.55-7.22 (m, 7H), 5.63 (s, 2H), 3.72 (s, 3H), 3.01 (hept, 1H), 1.27 (d, 6H). MS: 430 (M+1)⁺

Example 156

4-(4-Isopropyl-phenyl)-6-methoxy-1-(4-methylsulfanyl-benzyl)-1.H.-quinazolin-2-one

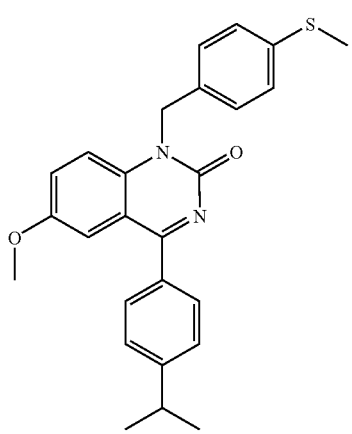 [SMILES: COc1ccc2c(c1)c(-c1ccc(C(C)C)cc1)nc(=O)n2Cc1ccc(SC)cc1]

¹H-NMR (300 MHz, DMSO-d₆): 7.69 (d, 2H), 7.49-7.44 (m, 4H), 7.22-7.17 (m, 5H), 5.44 (s, 2H), 3.70 (s, 3H), 2.41 (s, 3H), 1.27 (d, 6H). MS: 431 (M+1)⁺

Example 157

1-(4-Amino-benzyl)-4-(4-isopropyl-phenyl)-6-methoxy-1.H.-quinazolin-2-one

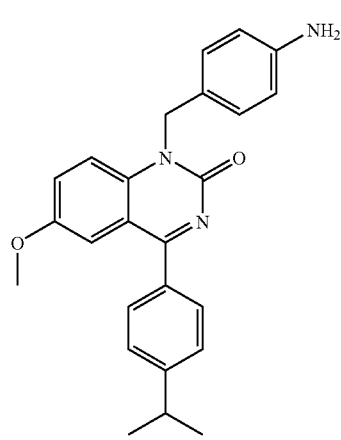 [SMILES: COc1ccc2c(c1)c(-c1ccc(C(C)C)cc1)nc(=O)n2Cc1ccc(N)cc1]

¹H-NMR (300 MHz, CDCl₃): 7.71 (d, 2H), 7.53 (d, 1H), 7.39-7.06 (m, 6H), 6.72-6.64 (m, 2H), 5.48 (s, 2H), 3.75 (s, 3H), 3.00 (hept, 1H), 1.31 (d, 6H). MS: 400 (M+1)⁺

Example 158

4-[4-(4-Isopropyl-phenyl)-6-methoxy-2-oxo-2.H.-quinazolin-1-ylmethyl]-benzoic acid methyl ester

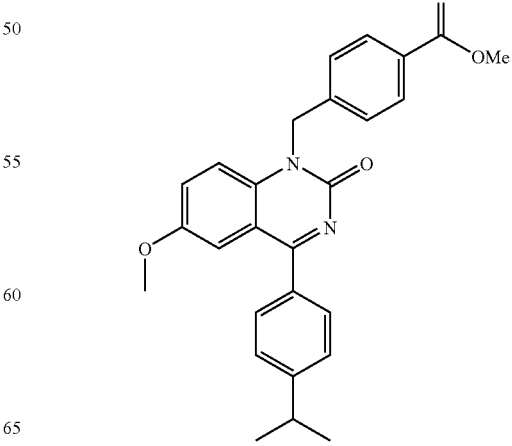

147

¹H-NMR (300 MHz, DMSO-d₆): 7.90 (d, 2H), 7.71 (d, 2H), 7.49-7.36 (m, 6H), 7.20 (d, 1H), 5.56 (s, 2H), 3.81 (s, 3H), 3.70 (s, 3H), 3.01 (hept, 1H), 1.27 (d, 6H). MS: 443 (M+1)⁺

Example 159

4-(4-Isopropyl-phenyl)-1-(4-methanesulfonyl-benzyl)-6-methoxy-1.H.-quinazolin-2-one

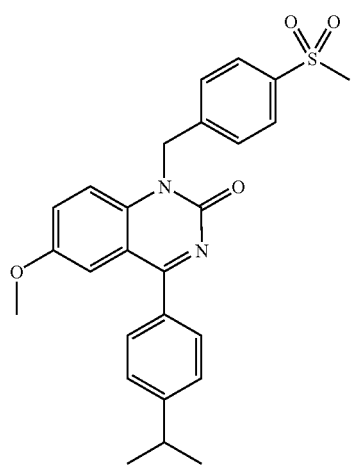 [SMILES: COc1ccc2c(c1)c(-c1ccc(C(C)C)cc1)nc(=O)n2Cc1ccc(S(C)(=O)=O)cc1]

¹H-NMR (300 MHz, DMSO-₆): 7.87 (d, 2H), 7.71 (d, 2H), 7.54-7.42 (m, 6H), 7.21 (d, 1H), 5.60 (s, 2H), 3.71 (s, 3H), 3.01 (hept, 1H), 1.27 (d, 6H). MS: 463 (M+1)⁺

Example 160

1-[4-(2-Chloro-ethoxy)-benzyl]-4-(4-isopropyl-phenyl)-6-methoxy-1.H.-quinazolin-2-one

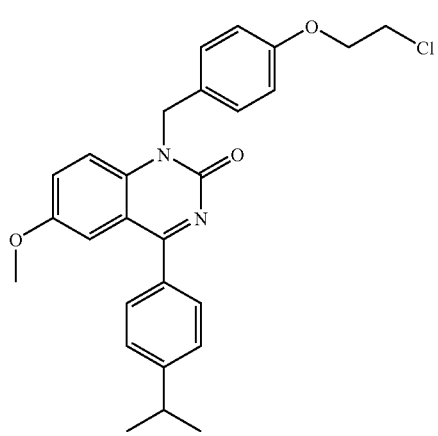 [SMILES: COc1ccc2c(c1)c(-c1ccc(C(C)C)cc1)nc(=O)n2Cc1ccc(OCCCl)cc1]

148

¹H-NMR (300 MHz, CDCl₃): 7.71 (d, 2H), 7.41-7.20 (m, 7H), 6.83 (d, 2H), 5.48 (s, 2H), 4.18 (t, 3H), 3.81-3.73 (m, 5H), 3.01 (hept, 1H), 1.31 (d, 6H). MS: 463 (M+1)⁺

Example 161

N-(2-Dimethylamino-ethyl)-4-[4-(4-isopropyl-phenyl)-6-methoxy-2-oxo-2.H.-quinazolin-1-ylmethyl]-benzamide

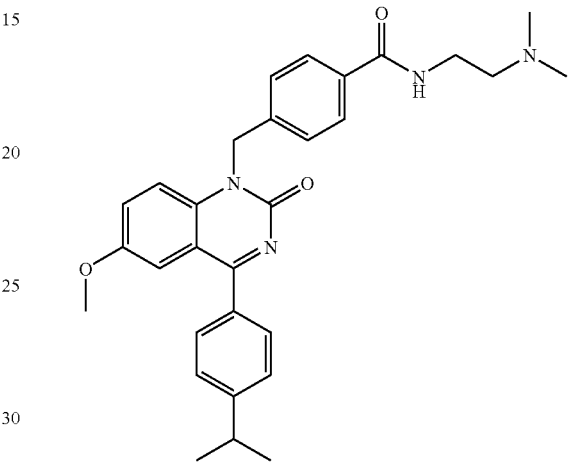

¹H-NMR (300 MHz, CDCl₃): 7.79-7.71 (m, 4H), 7.42-7.13 (m, 7H), 6.85 (broad, 1H), 5.59 (s, 2H), 3.76 (s, 3H), 3.52 (q, 2H), 3.02 (hept, 1H), 2.51 (t, 2H), 2.26 (s, 6H), 1.32 (d, 6H). MS: 499 (M+1)⁺

Example 162

4-[4-(4-Isopropyl-phenyl)-6-methoxy-2-oxo-2.H.-quinazolin-1-ylmethyl]-.N.-(2-pyrrolidin-1-yl-ethyl)-benzamide

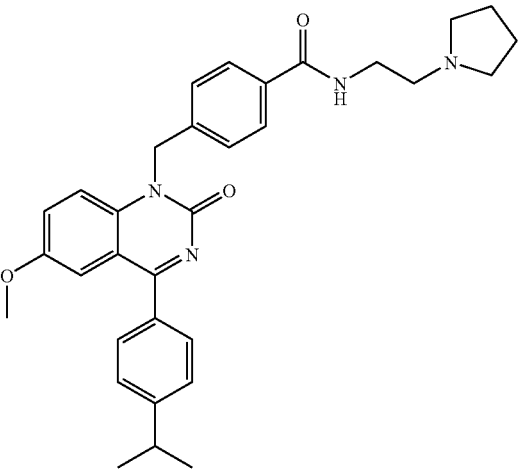 [SMILES: COc1ccc2c(c1)c(-c1ccc(C(C)C)cc1)nc(=O)n2Cc1ccc(C(=O)NCCN2CCCC2)cc1]

¹H-NMR (300 MHz, CDCl₃): 7.79 (d, 2H), 7.71 (d, 2H), 7.42-7.13 (m, 7H), 5.57 (s, 2H), 3.75 (s, 3H), 3.57 (q, 2H), 3.01 (hept, 1H), 2.78 (t, 2H), 2.66 (s, 4H), 1.82 (s, 4H), 1.32 (d, 6H). MS: 525 (M+1)⁺

Example 163

N-(2-Ethylamino-ethyl)-4-[4-(4-isopropyl-phenyl)-6-methoxy-2-oxo-2.H.-quinazolin-1-ylmethyl]-benzamide

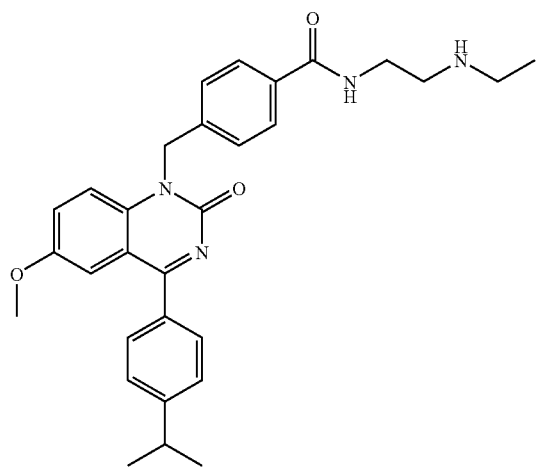 [SMILES: CCNCCNC(=O)c1ccc(Cn2c(=O)nc(-c3ccc(C(C)C)cc3)c3cc(OC)ccc32)cc1]

¹H-NMR (300 MHz, MeOD): 7.81 (d, 2H), 7.72 (d, 2H), 7.52-7.32 (m, 7H), 5.63 (s, 2H), 3.75 (s, 3H), 3.63 (t, 2H), 3.16-2.97 (m, 5H), 1.34 (d, 6H), 1.26 (t, 3H). MS: 499 (M+1)⁺

Example 164

1-(2-Hydroxy-benzyl)-4-(4-isopropyl-phenyl)-6-methoxy-1.H.-quinazolin-2-one

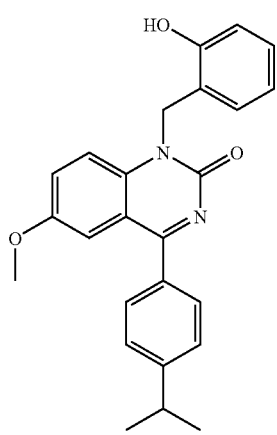

¹H-NMR (300 MHz, CDCl₃): 9.94 (s, 1H), 7.86 (d, 1H), 7.69 (d, 2H), 7.50-7.20 (m, 6H), 6.98 (d, 1H), 6.86 (t, 1H), 5.48 (s, 2H), 3.80 (s, 3H), 3.01 (hept, 1H), 1.31 (d, 6H). MS: 401 (M+1)⁺

Example 165

1-(2-Chloro-benzyl)-4-(4-isopropyl-phenyl)-6-methoxy-1.H.-quinazolin-2-one

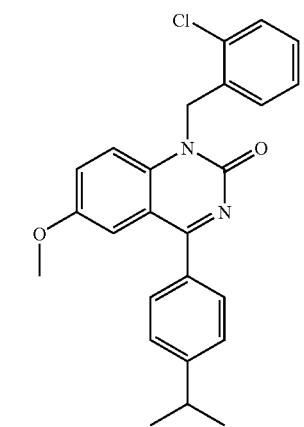

¹H-NMR (300 MHz, CDCl₃): 7.75 (d, 2H), 7.45-6.93 (m, 9H), 5.63 (s, 2H), 3.76 (s, 3H), 3.02 (hept, 1H), 1.32 (d, 6H). MS: 419 (M+1)⁺

Example 166

4-(4-Isopropyl-phenyl)-6-methoxy-1-(2-methyl-benzyl)-1.H.-quinazolin-2-one

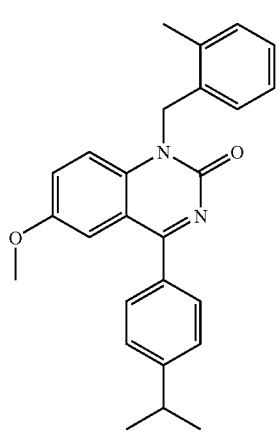 [SMILES: COc1ccc2c(c1)c(-c1ccc(C(C)C)cc1)nc(=O)n2Cc1ccccc1C]

¹H-NMR (300 MHz, DMSO-d₆): 7.73 (d, 2H), 7.50-6.88 (m, 8H), 6.53 (d, 1H), 5.40 (s, 2H), 3.72 (s, 3H), 3.03 (hept, 1H), 2.41 (s, 3H), 1.28 (d, 6H). MS: 399 (M+1)⁺

Example 167

4-(4-Isopropyl-phenyl)-6-methoxy-1-(2-nitro-benzyl)-1.H.-quinazolin-2-one

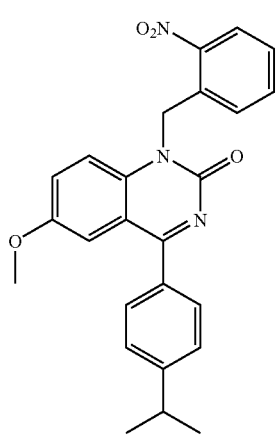 [SMILES: COc1ccc2c(c1)c(-c1ccc(C(C)C)cc1)nc(=O)n2Cc1ccccc1[N+](=O)[O-]]

¹H-NMR (300 MHz, DMSO-d₆): 8.24 (dd, 1H), 7.60-7.39 (m, 8H), 6.92 (dd, 1H), 5.79 (s, 2H), 3.73 (s, 3H), 3.03 (hept, 1H), 1.28 (d, 6H). MS: 430 (M+1)⁺

Example 168

2-[4-(4-Isopropyl-phenyl)-6-methoxy-2-oxo-2.H.-quinazolin-1-ylmethyl]-benzonitrile

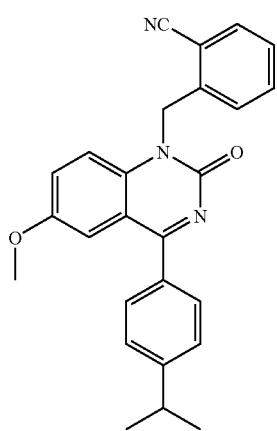

¹H-NMR (300 MHz, DMSO-d₆): 7.92 (d, 1H), 7.71 (d, 2H), 7.61-7.39 (m, 6H), 7.23 (d, 1H), 7.00 (d, 1H), 5.63 (s, 2H), 3.73 (s, 3H), 3.03 (hept, 1H), 1.27 (d, 6H). MS: 410 (M+1)⁺

Example 169

4-(4-Isopropyl-phenyl)-6-methoxy-1-(3-methoxy-benzyl)-1.H.-quinazolin-2-one

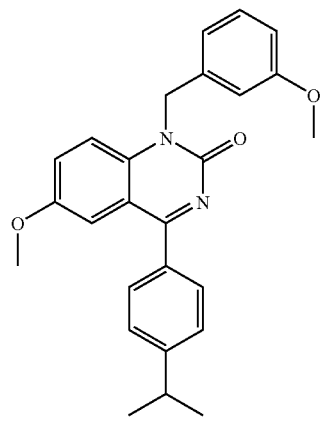 [SMILES: COc1cccc(Cn2c(=O)nc(-c3ccc(C(C)C)cc3)c3cc(OC)ccc32)c1]

¹H-NMR (300 MHz, DMSO-d₆): 7.70 (d, 2H), 7.49-7.44 (m, 4H), 7.26-7.18 (m, 2H), 6.89-6.75 (m, 3H), 5.46 (s, 2H), 3.71 (s, 6H), 3.01 (hept, 1H), 1.27 (d, 6H). MS: 415 (M+1)⁺

Example 170

3-[4-(4-Isopropyl-phenyl)-6-methoxy-2-oxo-2.H.-quinazolin-1-ylmethyl]-benzonitrile

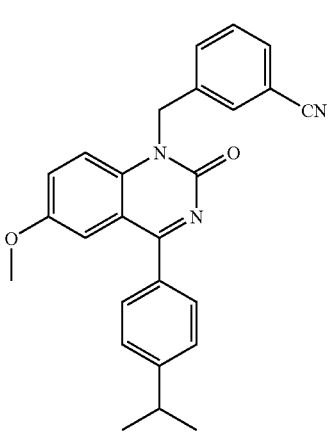 [SMILES: COc1ccc2c(c1)c(-c1ccc(C(C)C)cc1)nc(=O)n2Cc1cccc(C#N)c1]

153

¹H-NMR (300 MHz, DMSO-d₆): 7.82-7.42 (m, 1OH), 7.20 (s, 1H), 5.53 (s, 2H), 3.71 (s, 3H), 3.01 (hept, 1H), 1.27 (d, 6H). MS: 410 (M+1)⁺

Example 171

1-(2,6-Difluoro-benzyl)-4-(4-isopropyl-phenyl)-6-methoxy-1.H.-quinazolin-2-one

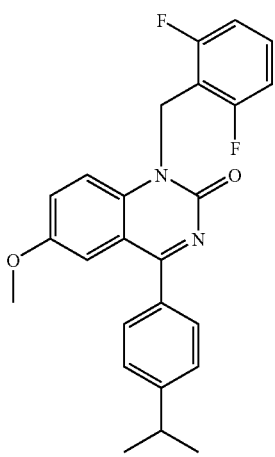 [SMILES: COc1ccc2c(c1)c(-c1ccc(C(C)C)cc1)nc(=O)n2Cc1c(F)cccc1F]

¹H-NMR (300 MHz, CDCl₃): 7.72 (d, 2H), 7.40-7.23 (m, 6H), 6.87 (t, 2H), 5.71 (s, 2H), 3.75 (s, 3H), 3.00 (hept, 1H), 1.31 (d, 6H). MS: 421 (M+1)⁺

Example 172

1-(2,4-Difluoro-benzyl)-4-(4-isopropyl-phenyl)-6-methoxy-1.H.-quinazolin-2-one

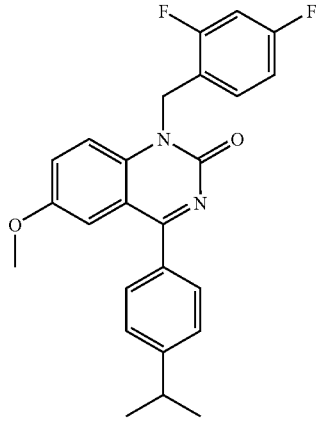 [SMILES: COc1ccc2c(c1)c(-c1ccc(C(C)C)cc1)nc(=O)n2Cc1ccc(F)cc1F]

154

¹H-NMR (300 MHz, CDCl₃): 7.72 (d, 2H), 7.43-7.20 (m, 6H), 6.62-6.73 (m, 2H), 5.54 (s, 2H), 3.77 (s, 3H), 3.01 (hept, 1H), 1.31 (d, 6H). MS: 421 (M+1)⁺

Example 173

1-(3,4-Difluoro-benzyl)-4-(4-isopropyl-phenyl)-6-methoxy-1.H.-quinazolin-2-one

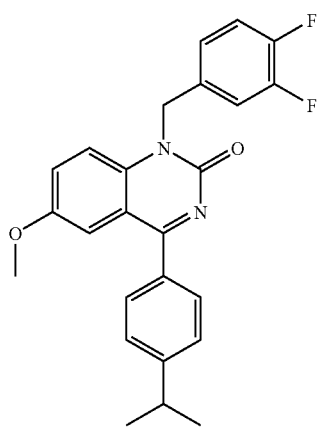 [SMILES: COc1ccc2c(c1)c(-c1ccc(C(C)C)cc1)nc(=O)n2Cc1ccc(F)c(F)c1]

¹H-NMR (300 MHz, CDCl₃): 7.73 (d, 2H), 7.42-7.05 (m, 8H), 5.49 (s, 2H), 3.77 (s, 3H), 3.02 (hept, 1H), 1.32 (d, 6H). MS: 421 (M+1)⁺

Example 174

1-(3,4-Dichloro-benzyl)-4-(4-isopropyl-phenyl)-6-methoxy1-.H.-quinazolin-2-one

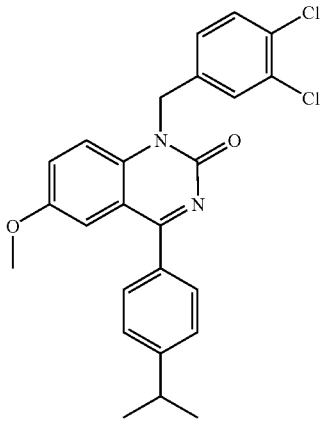 [SMILES: COc1ccc2c(c1)c(-c1ccc(C(C)C)cc1)nc(=O)n2Cc1ccc(Cl)c(Cl)c1]

¹H-NMR (300 MHz, CDCl₃): 7.71 (d, 2H), 7.42-7.13 (m, 8H), 5.49 (s, 2H), 3.77 (s, 3H), 3.02 (hept, 1H), 1.32 (d, 6H). MS: 453 (M+1)⁺

Example 175

4-(4-Isopropyl-phenyl)-6-methoxy-1-(2,4,6-trifluoro-benzyl)-1.H.-quinazolin-2-one

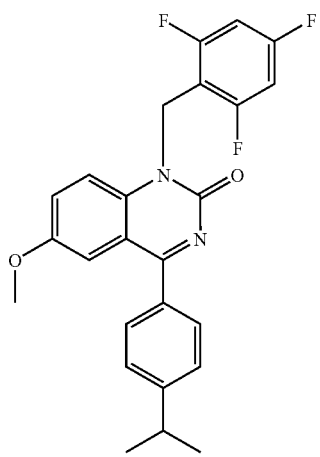 [SMILES: COc1ccc2c(c1)c(-c1ccc(C(C)C)cc1)nc(=O)n2Cc1c(F)cc(F)cc1F]

¹H-NMR (300 MHz, CDCl₃): 7.72 (d, 2H), 7.40-7.25 (m, 5H), 6.66 (t, 2H), 5.64 (s, 2H), 3.76 (s, 3H), 3.00 (hept, 1H), 1.31 (d, 6H). MS: 439 (M+1)⁺

Example 176

4-(4-Isopropyl-phenyl)-6-methoxy-1-pentafluorophenylmethyl-1.H.-quinazolin-2-one

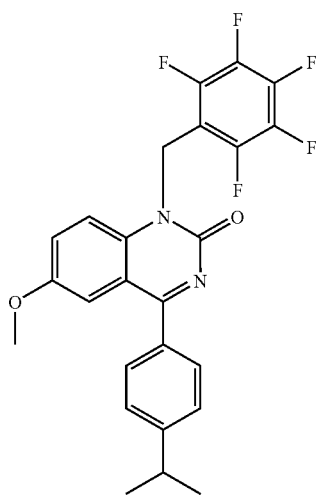 [SMILES: COc1ccc2c(c1)c(-c1ccc(C(C)C)cc1)nc(=O)n2Cc1c(F)c(F)c(F)c(F)c1F]

¹H-NMR (300 MHz, CDCl₃): 7.71 (d, 21), 7.42-7.20 (m, 5H), 5.68 (s, 2H), 3.78 (s, 3H), 3.01 (hept, 1H), 1.31 (d, 6H). MS: 475 (M+1)⁺

Example 177

4-(4-Isopropyl-phenyl)-6-methoxy-1-pyridin-3-ylmethyl-1.H.-quinazolin-2-one

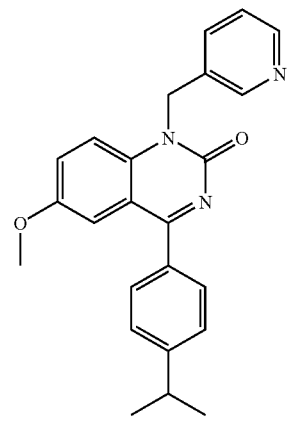 [SMILES: COc1ccc2c(c1)c(-c1ccc(C(C)C)cc1)nc(=O)n2Cc1cccnc1]

¹H-NMR (300 MHz, CDCl₃): 9.17 (s, 1H), 8.74 (d, 1H), 8.58 (d, 1H), 7.90 (t, 1H), 7.73 (d, 2H), 7.46-7.35 (m, 4H), 5.78 (s, 2H), 3.79 (s, 3H), 3.02 (hept, 1H), 1.33 (d, 6H). MS: 386 (M+1)⁺

Example 178

4-(4-Isopropyl-phenyl)-6-methoxy-1-pyridin-2-ylmethyl-1.H.-quinazolin-2-one

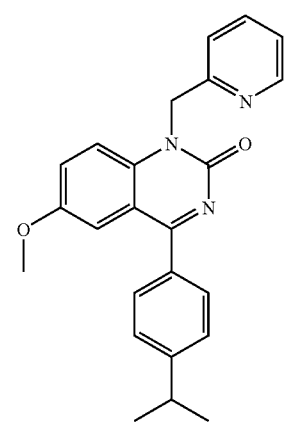 [SMILES: COc1ccc2c(c1)c(-c1ccc(C(C)C)cc1)nc(=O)n2Cc1ccccn1]

¹H-NMR (300 MHz, CDCl₃): 8.57 (s, 1H), 7.71 (d, 2H), 7.62 (t, 1H), 7.53 (d, 1H), 7.41-7.175 (m, 6H), 5.65 (s, 2H), 3.75 (s, 3H), 3.01 (hept, 1H), 1.31 (d, 6H). MS: 386 (M+1)⁺

Example 179

1-(6-Chloro-pyridin-3-ylmethyl)-4-(4-isopropyl-phenyl)-6-methoxy-1.H.-quinazolin-2-one

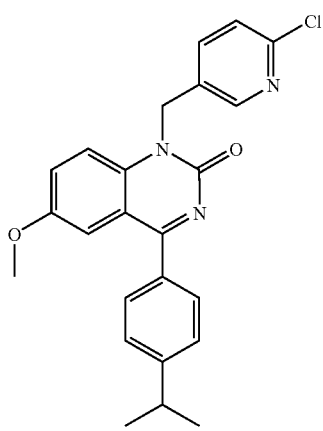 [SMILES: COc1ccc2c(c1)c(-c1ccc(C(C)C)cc1)nc(=O)n2Cc1ccc(Cl)nc1]

¹H-NMR (300 MHz, CDCl₃): 8.46 (d, 1H), 7.74-7.65 (m, 3H), 7.41-7.16 (m, 6H), 5.52 (s, 2H), 3.77 (s, 3H), 3.01 (hept, 1H), 1.31 (d, 6H). MS: 420 (M+1)⁺

Example 180

4-(4-Isopropyl-phenyl)-6-methoxy-1-(5-nitro-furan-2-ylmethyl)-1.H.-quinazolin-2-one

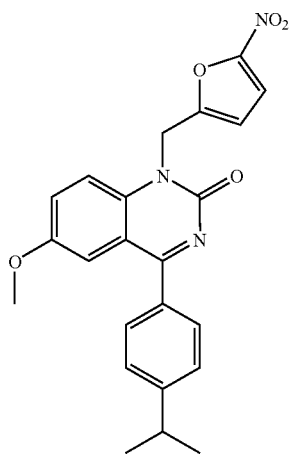 [SMILES: COc1ccc2c(c1)c(-c1ccc(C(C)C)cc1)nc(=O)n2Cc1ccc([N+](=O)[O-])o1]

¹H-NMR (300 MHz, CDCl₃): 7.69 (d, 2H), 7.56-7.37 (m, 6H), 6.70 (d, 1H), 5.53 (s, 2H), 3.80 (s, 3H), 3.01 (hept, 1H), 1.31 (d, 6H). MS: 420 (M+1)⁺

Example 181

4-(4-Isopropyl-phenyl)-6-methoxy-1-(2-oxo-2-phenyl-ethyl)-1.H.-quinazolin-2-one

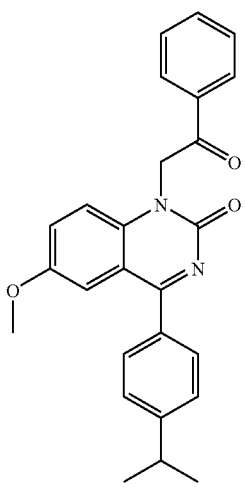 [SMILES: COc1ccc2c(c1)c(-c1ccc(C(C)C)cc1)nc(=O)n2CC(=O)c1ccccc1]

¹H-NMR (300 MHz, CDCl₃): 8.09 (d, 2H), 7.75-7.22 (m, 9H), 6.97 (d, 1H), 5.82 (s, 2H), 3.78 (s, 3H), 3.01 (hept, 1H), 1.32 (d, 6H). MS: 413 (M+1)⁺

Example 182

1-Isobutyl-4-(4-isopropyl-phenyl)-6-methoxy-1.H.-quinazolin-2-one

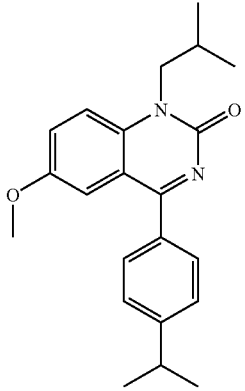 [SMILES: COc1ccc2c(c1)c(-c1ccc(C(C)C)cc1)nc(=O)n2CC(C)C]

¹H-NMR (300 MHz, DMSO-d₆): 7.72-7.40 (m, 6H), 7.18 (d, 1H), 4.08 (d, 2H), 3.75 (s, 3H), 3.00 (hept, 1H), 2.15 (hept, 1H), 1.23 (d, 6H) 0.95 (d, 6H). MS: 351 (M+1)⁺

Example 183

1-[2-(1.H.-Indol-2-yl)-ethyl]-4-(4-isopropyl-phenyl)-6-methoxy-1.H.-quinazolin-2-one

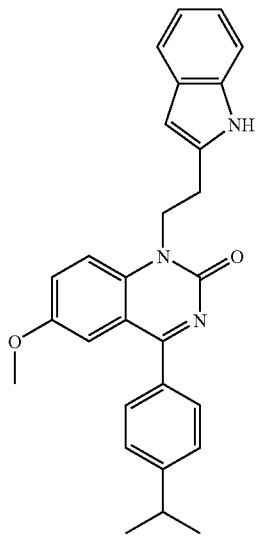 [SMILES: COc1ccc2c(c1)c(-c1ccc(C(C)C)cc1)nc(=O)n2CCc1cc2ccccc2[nH]1]

¹H-NMR (300 MHz, CDCl₃): 8.12 (broad, 1H), 7.75-7.67 (m, 3H), 7.42-7.12 (m, 9H), 4.58 (t, 2H), 3.78 (s, 3H), 3.30 (t, 3H), 3.01 (hept, 1H), 1.31 (d, 6H). MS: 438 (M+1)⁺

Example 184

4-(4-Isopropyl-phenyl)-6-methoxy-1-phenethyl-1H-quinazolin-2-one

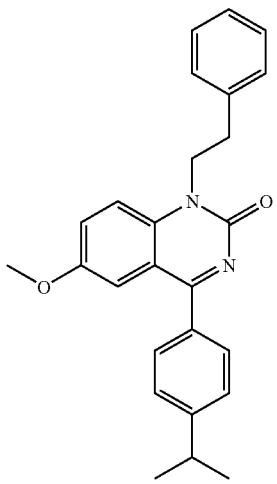 [SMILES: COc1ccc2c(c1)c(-c1ccc(C(C)C)cc1)nc(=O)n2CCc1ccccc1]

m.p. 133-135° C.

¹H-NMR (300 MHz, CDCl₃): 7.70 (d, 2H), 7.20-7.45 (m, 10H), 4.49 (t, 2H), 3.79 (s, 3H), 3.12 (t, 2H), 3.01 (hept, 1H), 1.33 (d, 6H). MS: 399 (M+1)⁺

Example 185

[4-(4-Isopropyl-phenyl)-6-methoxy-2-oxo-2.H.-quinazolin-1-yl]-acetic acid ethyl ester

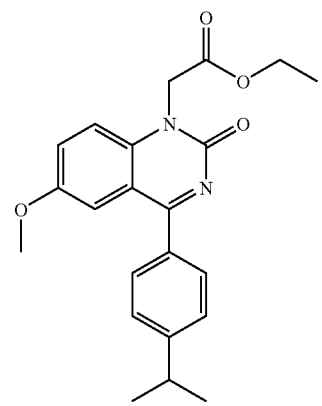 [SMILES: CCOC(=O)Cn1c(=O)nc(-c2ccc(C(C)C)cc2)c2cc(OC)ccc21]

¹H-NMR (300 MHz, CDCl₃): 7.70 (d, 2H), 7.40-7.31 (m, 4H), 7.08 (d, 1H), 5.08 (d, 2H), 4.25 (q, 2H), 3.78 (s, 3H), 3.00 (hept, 1H), 2.15 (hept, 1H), 1.32-1.26 (m, 9H). MS: 381 (M+1)⁺

Example 186

[4-(4-Isopropyl-phenyl)-6-methoxy-2-oxo-2.H.-quinazolin-1-yl]-acetonitrile

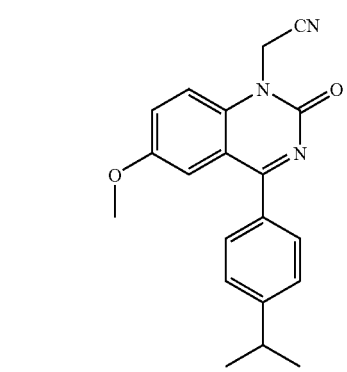 [SMILES: COc1ccc2c(c1)c(-c1ccc(C(C)C)cc1)nc(=O)n2CC#N]

¹H-NMR (300 MHz, CDCL₃): 7.69 (d, 2H), 7.51-7.20 (m, 5H), 5.26 (d, 2H), 3.81 (s, 3H), 3.01 (hept, 1H), 1.31 (d, 6H). MS: 334 (M+1)⁺

Example 187

1-(2-Hydroxy-2-phenyl-ethyl)-4-(4-isopropyl-phenyl)-6-prop-2-ynyloxy-1H-quinazolin-2-one Example 188

Acetic acid 2-[4-(4-isopropyl-phenyl)-2-oxo-6-prop-2-ynyloxy-2H-quinazolin-1-yl]-1-phenyl-ethyl ester

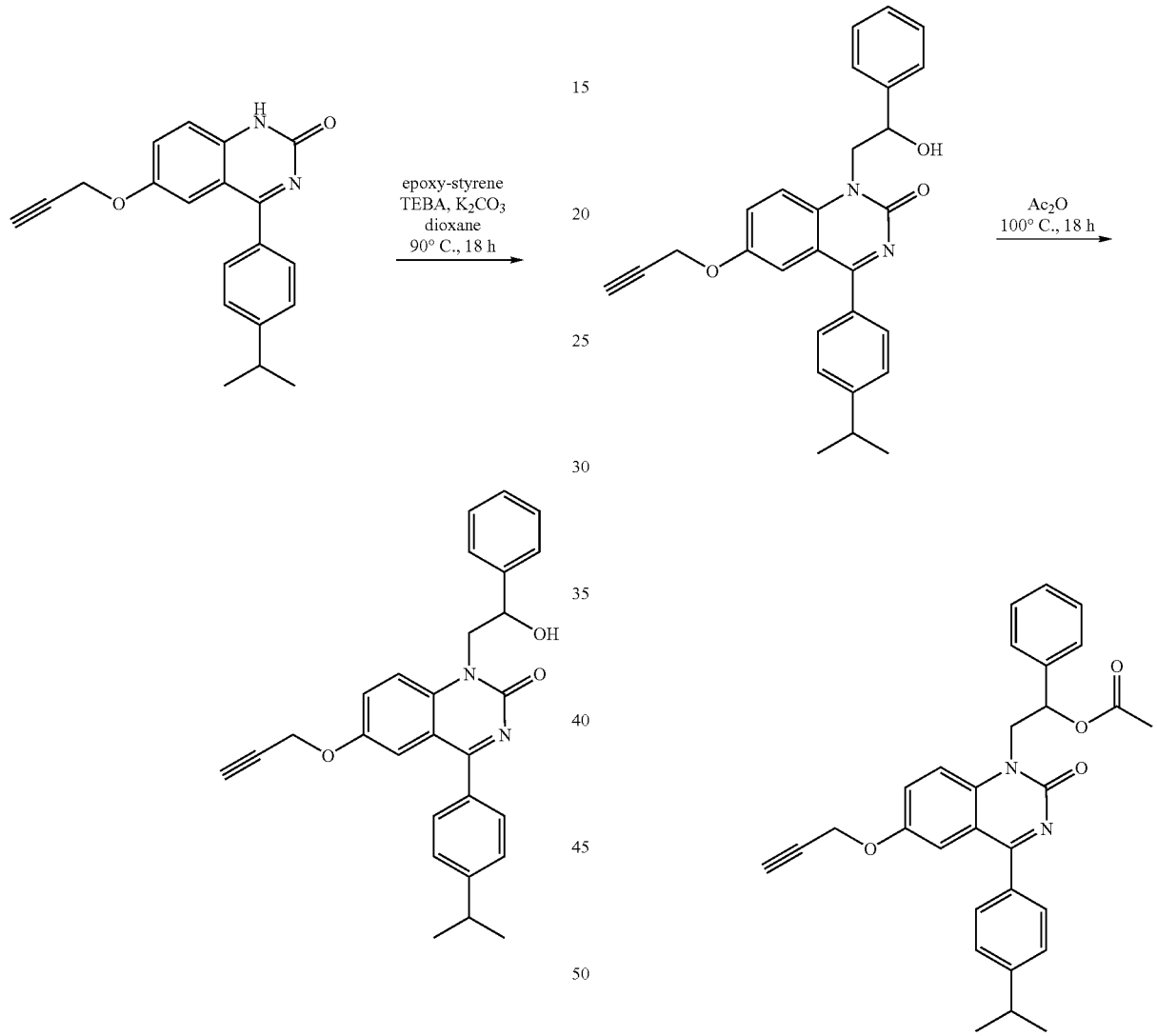

A mixture of 2.00 g (6.28 mmol) 4-(4-isopropyl-phenyl)-6-prop-2-ynyloxy-1H-quinazolin-2-one, 0.72 ml (6.28 mmol) epoxy-styrene, 0.143 g (0.628 mmol) benzyl-triethylammonium chloride (TEBA), 0.086 g (0.628 mmol) potassium carbonate and 5 ml dioxane is heated at 90° C. for 18 h. Aqueous work up followed by chromatography on silica gives 1-(2-hydroxy-2-phenyl-ethyl)-4-(4-isopropyl-phenyl)-6-prop-2-ynyloxy-1H-quinazolin-2-one.

¹H NMR (300 MHz, CDCl₃): 7.72 (d, 2H), 7.56 (d, 2H), 7.49 (m, 1H), 7.43-7.30 (m, 7H), 5.31 (dd, 1H), 4.68 (d, 2H), 4.66 (dd, 1H), 4.39 (dd, 1H)) 3.02 (hept, 1H), 2.55 (t, 1H), 1.32 (d, 6H). MS: 439 (M+1)⁺

A solution of 100 mg (0.228 mmol) 1-(2-hydroxy-2-phenyl-ethyl)-4-(4-isopropyl-phenyl)-6-prop-2-ynyloxy-1H-quinazolin-2-one in 1 ml acetic anhydride is heated at 100° C. for 18 h. The reaction mixture is poured onto 1 M aqueous NaOH and extracted with ether. The product is purified by preparative reversed phase HPLC.

¹H NMR (300 MHz, CDCl₃): 7.71 (d, 2H), 7.60-7.33 (m, 10H), 6.31 (dd, 1H), 4.72 (dd, 1H), 4.68 (d, 2H), 4.59 (dd, 1H), 3.01 (hept, 1H), 2.58 (t, 1H), 1.93 (s, 3H), 1.32 (d, 6H). MS: 481 (M+1)⁺

Example 189

4-(4-Isopropyl-phenyl)-1-(2-oxo-2-phenyl-ethyl)-6-prop-2-ynyloxy-1H-quinazolin-2-one

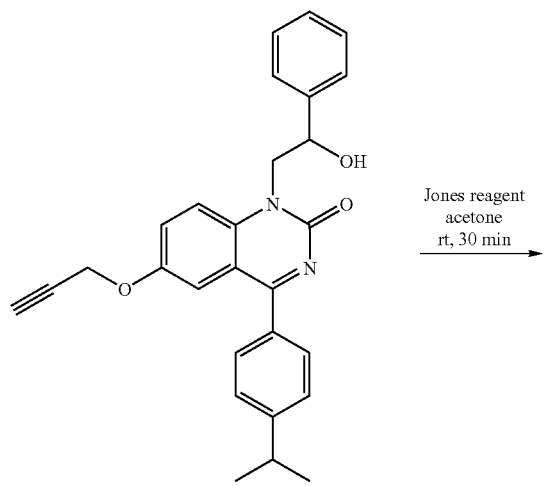

Jones reagent
acetone
rt, 30 min

To a solution of 200 mg (0.456 mmol) 1-(2-hydroxy-2-phenyl-ethyl)-4-(4-isopropyl-phenyl)-6-prop-2-ynyloxy-1H-quinazolin-2-one in 2 ml acetone are added 0.17 ml (0.45 mmol) Jones reagent. After stirring for 30 minutes at rt aqueous work up followed by recrystallisation from ethyl acetate yields 4-(4-isopropyl-phenyl)-1-(2-oxo-2-phenyl-ethyl)-6-prop-2-ynyloxy-1H-quinazolin-2-one.

$^1$H NMR (300 MHz, CDCl$_3$): 8.09 (d, 2H), 7.75 (d, 2H), 7.67 (t, 1H), 7.54 (t, 2H), 7.52 (d, 1H), 7.38 (d, 2H), 7.34 (dd, 1H), 6.98 (d, 1H), 5.82 (s, 2H), 4.66 (d, 2H), 3.02 (hept, 1H), 2.56 (t, 1H), 1.33 (d, 6H). MS: 437 (M+1)$^+$

Example 190

1-[2-(4-Fluoro-phenyl)-2-oxo-ethyl]-4-(4-isopropyl-phenyl)-6-prop-2-ynyloxy-1H-quinazolin-2-one

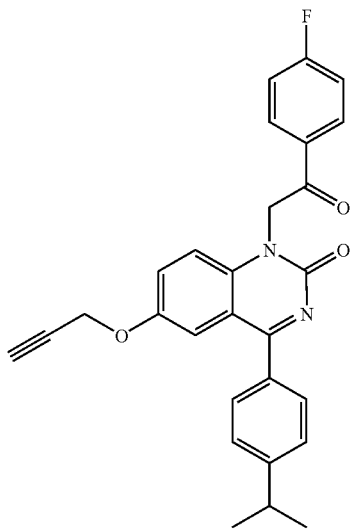 [SMILES: C#CCOc1ccc2c(c1)c(-c1ccc(C(C)C)cc1)nc(=O)n2CC(=O)c1ccc(F)cc1]

$^1$H NMR (300 MHz, CDCl3): 8.13 (dd, 2H), 7.76 (d, 2H), 7.53 (d, 1H), 7.39 (d, 2H), 7.36 (dd, 1H), 7.22 (t, 2H), 7.00 (d, 1H), 5.78 (s, 2H), 4.67 (d, 2H), 3.02 (hept, 1H), 2.56 (t, 1H), 1.33 (d, 6H). MS: 455 (M+1)$^+$ The Agents of the Invention, as defined above, e.g., of formula I, particularly as exemplified, in free or pharmaceutically acceptable acid addition salt form, exhibit pharmacological activity and are useful as pharmaceuticals, e.g. for therapy, in the treatment of diseases and conditions as hereinafter set forth.

Inositol Phosphate Formation Assay:

To determine antagonistic activity at the human parathyroid calcium-sensing receptor (PCaR), compounds were tested in functional assays measuring the inhibition of calcium-induced inositol phosphate formation in CCL39 fibroblasts stably transfected with human PCaR.

Cells were seeded into 24 well plates and grown to confluence. Cultures were then labeled with [$^3$H]inositol (74 Mbq/ml) in serum-free medium for 24 h. After labeling, cells were washed once with a modified Hepes-buffered salt solution (mHBS: 130 mM NaCl, 5.4 mM KCl, 0.5 mM CaCl$_2$, 0.9 mM MgSO$_4$, 10 mM glucose, 20 mM HEPES, pH 7.4). and incubated with mHBS at 37° C. in the presence of 20 mM LiCl to block inositol monophosphatase activity. Test compounds were added 3 minutes before stimulating PCaR with 5.5 mM calcium and incubations continued for further 20 min. Thereafter, cells were extracted with 10 mM ice-cold formic acid and inositol phosphates formed were determined using anion exchange chromatography and liquid scintillation counting.

Assay for Intracellular Free Calcium:

An alternative method to determine antagonism at the PCaR consists in measuring the inhibition of intracellular calcium transients stimulated by extracellular calcium. CCL39 fibroblasts stably transfected with human PCaR were seeded at 40,000 cells/well into 96-well Viewplates and incubated for 24 hours. Medium was then removed and replaced with fresh medium containing 2 microM Fluo-3 AM (Molecular Probes, Leiden, The Netherlands), In routine experiments, cells were incubated at 37° C., 5% $CO_2$ for 1 h. Afterwards, plates were washed twice with mHBS and wells were refilled with 100 microl mHBS containing the test compounds. Incubation was continued at room temperature for 15 minutes. To record changes of intracellular free calcium, plates were transferred to fluorescence-imaging plate reader (Molecular Devices, Sunnyvale, Calif., USA). A baseline consisting in 5 measurements of 0.4 seconds each (laser excitation 488 nm) was recorded. Cells were then stimulated with calcium (2.5 mM final), and fluorescence changes recorded over a period of 3 minutes.

When measured in the above assays, Agents of the Invention typically have $IC_{50}$s in the range from about 50 μM down to about 10 nM or less.

Agents of the Invention are accordingly indicated for preventing or treating all bone conditions which are associated with increased calcium depletion or resorption or in which stimulation of bone formation and calcium fixation in the bone is desirable, e.g. osteoporosis of various genesis (e.g. juvenile, menopausal, post-menopausal, post-traumatic, caused by old age or by cortico-steroid therapy or inactivity), fractures, osteopathy, including acute and chronic states associated with skeletal demineralisation, osteo-malacia, periodontal bone loss or bone loss due to arthritis or osteoarthritis or for treating hypoparathyroidism.

Further diseases and disorders which might be prevented or treated include e.g. seizures, stroke, head trauma, spinal cord injury, hypoxia-induced nerve cell damage such as in cardiac arrest or neonatal distress, epilepsy, neurodegenerative diseases such as Alzheimer's disease, Huntington's disease and Parkinson's disease, dementia, muscle tension, depression, anxiety, panic disorder, obsessive-compulsive disorder, post-traumatic stress disorder, schizophrenia, neuroleptic malignant syndrome, congestive heart failure; hypertension; gut motility disorders such as diarrhea, and spastic colon and dermatological disorders, e.g. in tissue healing, for example burns, ulcerations and wounds.

The Agents of the Invention are particularly indicated for preventing or treating osteoporosis of various genesis.

For all the above uses, an indicated daily dosage is in the range from about 0.03 to about 300 mg preferably 0.03 to 30, more preferably 0.1 to 10 mg of a compound of the invention. Agents of the Invention may be administered twice a day or up to twice a week.

The Agents of the Invention may be administered in free form or in pharmaceutically acceptable salt form. Such salts may be prepared in conventional manner and exhibit the same order of activity as the free compounds. The present invention also provides a pharmaceutical composition comprising an Agent of the Invention in free base form or in pharmaceutically acceptable salt form in association with a pharmaceutically acceptable diluent or carrier. Such compositions may be formulated in conventional manner. The Agents of the Invention may be administered by any conventional route, for example parenterally e.g. in form of injectable solutions or suspensions, enterally, e.g. orally, for example in the form of tablets or capsules or in a transdermal, nasal or a suppository form.

In accordance with the foregoing the present invention further provides:

a) an Agent of the Invention or a pharmaceutically acceptable salt thereof for use as a pharmaceutical;

b) a method for preventing or treating above mentioned disorders and diseases in a subject in need of such treatment, which method comprises administering to said subject an effective amount of an Agent of the Invention or a pharmaceutically acceptable salt thereof;

c) an Agent of the Invention or a pharmaceutically acceptable salt thereof for use in the preparation of a pharmaceutical composition e.g. for use in the method as in b) above.

According to a further embodiment of the invention, the Agents of the Invention may be employed as adjunct or adjuvant to other therapy, e.g. a therapy using a bone resorption inhibitor, for example as in osteoporosis therapy, in particular a therapy employing calcium, a calcitonin or an analogue or derivative thereof, e.g. salmon, eel or human calcitonin, a steroid hormone, e.g. an estrogen, a partial estrogen agonist or estrogen-gestagen combination, a SERM (Selective Estrogen Receptor Modulator) e.g. raloxifene, lasofoxifene, TSE-424, FC1271, Tibolone (Livial®), vitamin D or an analog thereof or PTH, a PTH fragment or a PTH derivative e.g. PTH (1-84), PTH (1-34), PTH (1-36), PTH (1-38), PTH (1-31) $NH_2$ or PTS 893.

When the Agents of the Invention are administered in conjunction with, e.g. as an adjuvant to bone resorption inhibition therapy, dosages for the co-administered inhibitor will of course vary depending on the type of inhibitor drug employed, e.g. whether it is a steroid or a calcitonin, on the condition to be treated, whether it is a curative or preventive therapy, on the regimen and so forth.

The invention claimed is:

1. A compound of formula IV

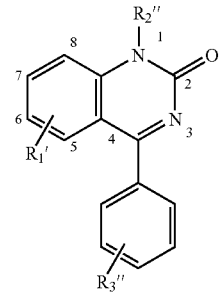

wherein $R_1'$ represents 1 to 2 substituents independently selected from optionally substituted C2-C7 alkenyl, optionally substituted C2-C7 alkenyloxy, optionally substituted C2-C7 alkynyl, or optionally substituted C2-C7 alkynyloxy, wherein the optional substituents are 1 or 2 substituents independently selected from halo, C1-C7 alkyl, C2-C7 alkenyl, C2-C7 alkynyl, cycloalkyl, or cyano;

$R_2''$ is aryl-methyl, substituted with 1, 2, or 3 substituents independently selected from C1-C7alkyl, C1-C7alkoxy, hydroxyl, halogen, cyano, trifluoromethyl, methylenedioxy, ethylenedioxy, oxyethylene, and oxypropylene;

$R_3''$ is C1-C7 alkyl;

or an acid addition salt thereof.

2. A pharmaceutical composition comprising a compound defined in claim 1, or addition salt thereof and a pharmaceutically acceptable excipient, diluent or carrier.

3. A compound selected from:
3-[4-(4-isopropyl-phenyl)-2-oxo-6-prop-2-ynyloxy-2H-quinazolin-1-ylmethyl]-benzoic acid 2-(2-dimethylamino-ethoxy)-ethyl ester (trifluoroacetic acid salt);
(2-benzylamino-5-propargyloxy-phenyl)-(4-isopropyl-phenyl)-methanone;
1-benzyl-4-(4-isopropyl-phenyl)-6-propargyloxy-1-H-quinazolin-2-one;
6-allyloxy-1-benzyl-4-(4-isopropyl-phenyl)-1-H-quinazolin-2-one;

acetic acid 4-[6-allyloxy-4-(4-isopropyl-phenyl)-2-oxo-2-H-quinazolin-1-ylmethyl]-phenyl ester;
acetic acid 4-[4-(4-isopropyl-phenyl)-2-oxo-6-propargyloxy-2-H-quinazolin-1-ylmethyl]-phenyl ester;
1-benzo[1,2,5]thiadiazol-5-ylmethyl-4-(4-isopropyl-phenyl)-6-propargyloxy-1H-quinazolin-2-one;
1-(2-hydroxy-benzyl)-4-(4-isopropyl-phenyl)-6-prop-2-ynyloxy-1H-quinazolin-2-one;
1-(3-Hydroxy-benzyl)-4-(4-isopropyl-phenyl)-6-prop-2-ynyloxy-1H-quinazolin-2-one;
1-(4-hydroxy-benzyl)-4-(4-isopropyl-phenyl)-6-prop-2-ynyloxy-1H-quinazolin-2-one;
1-[2-(6-chloro-hexyloxy)-benzyl]-4-(4-isopropyl-phenyl)-6-prop-2-ynyloxy-1H-quinazolin-2-one;
1-[2-(6-dimethylamino-hexyloxy)-benzyl]-4-(4-isopropyl-phenyl)-6-prop-2-ynyloxy-1H-quinazolin-2-one;
1-[2-(6-imidazol-1-yl-hexyloxy)-benzyl]-4-(4-isopropyl-phenyl)-6-prop-2-ynyloxy-1H-quinazolin-2-one;
4-(4-isopropyl-phenyl)-1-[3-(7-piperidin-1-yl-heptyloxy)-benzyl]-6-prop-2-ynyloxy-1H-quinazolin-2-one (trifluoroacetic acid salt);
(3-dimethylamino-propyl)-methyl-carbamic acid 4-[4-(4-isopropyl-phenyl)-2-oxo-6-prop-2-ynyloxy-2H-quinazolin-1-ylmethyl]-phenyl ester (trifluoroacetic acid salt);
4-(4-isopropyl-phenyl)-1-{3-[2-(2-methoxy-ethoxy)-ethoxy]-benzyl}-6-prop-2-ynyloxy-1H-quinazolin-2-one;
4-(4-isopropyl-phenyl)-1-[3-(2-{2-[2-(2-methoxy-ethoxy)-ethoxy]-ethoxy}-ethoxy)-benzyl]-6-prop-2-ynyloxy-1H-quinazolin-2-one;
4-(4-isopropyl-phenyl)-1-[4-(2-{2-[2-(2-methoxy-ethoxy)-ethoxy]-ethoxy}-ethoxy)-benzyl]-6-prop-2-ynyloxy-1H-quinazolin-2-one;
4-(4-isopropyl-phenyl)-1-[3-(2-methoxy-ethoxy)-benzyl]-6-prop-2-ynyloxy-1H-quinazolin-2-one;
4-(4-isopropyl-phenyl)-1-(3-{2-[2-(2-methoxy-ethoxy)-ethoxy]-ethoxy}-benzyl)-6-prop-2-ynyloxy-1H-quinazolin-2-one;
4-(4-isopropyl-phenyl)-1-{2-[2-(2-methoxy-ethoxy)-ethoxy]-benzyl}-6-prop-2-ynyloxy-1H-quinazolin-2-one;
1-[3-(2-hydroxy-ethoxy)-benzyl]-4-(4-isopropyl-phenyl)-6-prop-2-ynyloxy-1H-quinazolin-2-one;
4-(4-isopropyl-phenyl)-6-prop-2-ynyloxy-1-{3-[2-(tetrahydro-pyran-2-yloxy)-ethoxy]-benzyl}-1H-quinazolin-2-one;
4-(4-isopropyl-phenyl)-1-(2-{2-[2-(2-methoxy-ethoxy)-ethoxy]-ethoxy}-benzyl)-6-prop-2-ynyloxy-1H-quinazolin-2-one;
methanesulfonic acid 2-[4-(4-isopropyl-phenyl)-2-oxo-6-prop-2-ynyloxy-2H-quinazolin-1-ylmethyl]-phenyl ester;
2-[(3-dimethylamino-propyl)-methyl-amino]-N-{3-[4-(4-isopropyl-phenyl)-2-oxo-6-propargyloxy-2H-quinazolin-1-ylmethy]-phenyl}-acetamide;
4-(4-isopropyl-phenyl)-1-(3-nitro-benzyl)-6-propargyloxy-1H-quinazolin-2-one;
1-(3-amino-benzyl)-4-(4-isopropyl-phenyl)-6-propargyloxy-1H-quinazolin-2-one;
4-bromo-N-{3-[4-(4-isopropyl-phenyl)-2-oxo-6-propargyloxy-2H-qunazolin-1-ylmethyl]-phenyl}-butyramide;
N-{3-[4-(4-isopropyl-phenyl)-2-oxo-6-propargyloxy-2H-quinazolin-1-ylmethyl]-phenyl}-4-[4-(2-methoxy-ethyl)-piperazin-1-yl]-butyramide;
4-(4-isopropyl-phenyl)-1-[3-(2-oxo-pyrrolidin-1-yl)-benzyl]-6-propargyloxy-1H-quinazolin-2-one;
2-[(3-dimethylmino-propyl)-methyl-amino]-N-{3-[4-(4-isopropyl-phenyl)-2-oxo-6-propargyloxy-2H-quinazolin-1-ylmethyl]-phenyl}-acetamide;
2-chloro-N-{3-[4-(4-isopropyl-phenyl)-2-oxo-6-propargyloxy-2H-quinazolin-1-ylmethyl]-phenyl}-acetamide;
2-[(3-dimethylmino-propyl)-methyl-amino]-N-{3-[4-(4-isopropyl-phenyl)-2-oxo-6-propargyloxy-2H-quinazolin-1-ylmethyl]-phenyl}-acetamide;
2-(4-allyl-piperazin-1-yl)-N-{3-[4-(4-isopropyl-phenyl)-2-oxo-6-propargyloxy-2H-quinazolin-1-ylmethyl]-phenyl}-acetamide;
N-{3-[4-(4-isopropyl-phenyl)-2-oxo-6-propargyloxy-2H-quinazolin-1-ylmethyl]-phenyl}-2-(4-methyl-piperazin-1-yl)-acetamide;
N-{3-[4-(4-isopropyl-phenyl)-2-oxo-6-propargyloxy-2H-quinazolin-1-ylmethyl]-phenyl}-2-[4-(2-methoxy-ethyl)-piperazin-1-yl]-acetamide;
N-{3-[4-(4-isopropyl-phenyl)-2-oxo-6-propargyloxy-2H-quinazolin-1-ylmethyl]-phenyl}-2-[4-(2-methoxy-ethyl)-piperazin-1-yl]-N-methyl-acetamide;
N-[4-(3-dimethylamino-propyl)-piperazin-1-yl]-N -{3-[4-(4-isopropyl-phenyl)-2-oxo-6-propargyloxy-2H-quinazolin-1-ylmethyl]-phenyl}-acetamide;
N-{3-[4-(4-cyclopropyl-phenyl)-2-oxo-6-propargyloxy-2H-quinazolin-1-ylmethyl]-phenyl}-2-(4-methyl-piperazin-1-yl)-acetamide;
4-[4-(3-dimethylamino-propyl)-piperazin-1-yl]-N-{3-[4-(4-isopropyl-phenyl)-2-oxo-6-propargyloxy-2H-quinazolin-1-ylmethy]-phenyl}-butyramide;
N-{3-[4-(4-isopropyl-phenyl)-2-oxo-6-propargyloxy-2H-quinazolin-1-ylmethyl]-phenyl}-4-[(2-methoy-ethyl)-methyl-amino]-butyramide;
N-{3-[4-(4-isopropyl-phenyl)-2-oxo-6-propargyloxy-2H-quinazolin-1-ylmethyl]-phenyl}-4-morpholin-4-yl-butyramide;
N-{3-[6-allyloxy-4-(4-isopropyl-phenyl)-2-oxo-2H-quinazolin-1-ylmethyl]-phenyl}-4-(4-methyl-piperazin-1-yl)-butyramide;
4-(4-isopropyl-phenyl)-1-(4-nitro-benzyl)-6-propargyloxy-1H-quinazolin-2-one;
1-(4-amino-benzyl)-4-(4-isopropyl-phenyl)-6-prapargyloxy-1H-quinazolin-2-one;
1-(2-nitro-benzyl)-4-(4-isopropyl-phenyl)-6-propargyloxy-1H-quinazolin-2-one;
1-(2-amino-benzyl)-4-(4-isopropyl-phenyl)-6-propargyloxy-1H-quinazolin-2-one;
1-benzyl-4-(3-chloro-4-isopropyl-phenyl)-6-prop-2-ynyloxy-1H-quinazolin-2-one;
(2-benzylamino-5-prop-2-ynyloxy-phenyl)-(3-chloro-4-isopropylphenyl)-methanone (hydrochloric acid salt); and
1-benzyl-4-(3-chloro-4-isopropyl-phenyl)-6-prop-2-ynyloxy-1H-quinazolin-2-one;
or an acid addition salt thereof.

\* \* \* \* \*